US008889150B2

(12) United States Patent
Malouin et al.

(10) Patent No.: US 8,889,150 B2
(45) Date of Patent: Nov. 18, 2014

(54) **BACTERIAL VACCINE COMPONENTS FROM *STAPHYLOCOCCUS AUREUS* AND USES THEREOF**

(75) Inventors: Francois Malouin, Eastman (CA); Marianne Allard, Sherbrooke (CA); Christian Lebeau Jacob, Sherbrooke (CA); Brian Geoffrey Talbot, Sherbrooke (CA); Daniel Scholl, Brookings, SD (US); Pierre Lacasse, Sherbrooke (CA); Moussa Sory Diarra, Agassiz (CA); Celine Ster, Compton (CA)

(73) Assignee: SOCPRA—Sciences et Génie, s.e.c., Sherbrooke (CA)

( * ) Notice: Subject to any disclaimer, the term of this patent is extended or adjusted under 35 U.S.C. 154(b) by 0 days.

(21) Appl. No.: 13/583,054

(22) PCT Filed: Mar. 17, 2011

(86) PCT No.: PCT/CA2011/050145
§ 371 (c)(1), (2), (4) Date: Nov. 15, 2012

(87) PCT Pub. No.: WO2011/113160
PCT Pub. Date: Sep. 22, 2011

(65) Prior Publication Data

US 2013/0064845 A1 Mar. 14, 2013

Related U.S. Application Data

(60) Provisional application No. 61/314,670, filed on Mar. 17, 2010.

(51) Int. Cl.

| | |
|---|---|
| ***A61K 39/085*** | (2006.01) |
| ***C07K 14/31*** | (2006.01) |
| ***C12Q 1/68*** | (2006.01) |
| ***G01N 33/569*** | (2006.01) |
| *A61K 39/00* | (2006.01) |

(52) U.S. Cl.
CPC ....... *C12Q 1/689* (2013.01); *A61K 2039/55566* (2013.01); *C12Q 2600/158* (2013.01); *G01N 33/56938* (2013.01); *A61K 2039/552* (2013.01); *A61K 39/085* (2013.01); *A61K 39/00* (2013.01)
USPC ...................... 424/243.1; 424/190.1; 530/350

(58) Field of Classification Search
CPC ............... A61K 2039/552; A61K 2039/55566
USPC ........................................... 424/243.1, 190.1
See application file for complete search history.

(56) References Cited

U.S. PATENT DOCUMENTS

| | | | | |
|---|---|---|---|---|
| 6,228,844 | B1 | 5/2001 | Wolff et al. | |
| 7,060,458 | B1 * | 6/2006 | Doucette-Stamm et al. | 435/69.1 |
| 8,110,198 | B2 * | 2/2012 | Doucette-Stamm et al. | 424/243.1 |
| 2004/0147734 | A1 | 7/2004 | Doucette-Stamm | |

FOREIGN PATENT DOCUMENTS

| | | |
|---|---|---|
| EP | 0187702 | 2/1991 |
| EP | 1719520 | 1/2005 |
| EP | 11755607 | 2/2014 |
| WO | 02/094868 A2 | 11/2002 |
| WO | 03091279 | 11/2003 |
| WO | 2004043405 | 5/2004 |
| WO | 2005007683 | 1/2005 |
| WO | 2006059846 | 6/2006 |
| WO | 2008152447 | 12/2008 |
| WO | CA2011050145 | 6/2011 |
| WO | CA2011050145 | 9/2012 |

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Accession : B1GVC1 (Apr. 29, 2008) and Accession: D2G4X5 (Feb. 9, 2010).*
Sandholm et al., "Bovine mastitis—why does antibiotic therapy not always work? An overview", J Vet Phamacol Therap., 1990, 13:248-260.
Schaffer et al., "Staphylococcal vaccines and immunotherapies", Infect Dis Clin North Am., 2009, 23:153-171.
Sears et al., "Management and treatment of staphylococcal mastitis ", Vet Clin North Am Food Anim Pract, 2003, 19:171-185.
Sibbald et al., "Mapping the pathways to staphylococcal pathogenesis by comparative secretomics", Microbial Mol Biol Rev., 2006, 70:755-788.
Silanikove et al., "Posttranslational ruling of xanthine oxidase activity in bovine milk by its substrates", Biochem Biophys Res Commun., 2007, 363:561-565.
Somerville et al., "At the crossroads of bacterial metabolism and virulence factor synthesis in Staphylococci", Microbiol Mol Biol Rev., 2009, 73:233-248.
Spickler et al., "Adjuvants in veterinary vaccines: mode of action and adverse effects", J Vet Intern Med, 2003, 17:273-281.

(Continued)

*Primary Examiner* — Padma V Baskar
(74) *Attorney, Agent, or Firm* — Julie Gauvreau; Goudreau Gage Dubuc

(57) ABSTRACT

Agents, compositions, methods and kits useful for the treatment and diagnosis of Staphylococcal intramammary infection are disclosed. The agents, compositions, methods and kits are derived from genes expressed during Staphylococcal intramammary infection, and more particularly genes SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome.

19 Claims, 37 Drawing Sheets

(56) References Cited

OTHER PUBLICATIONS

Srinivasan et al., "Prevalence of enterotoxin and toxic shock syndrome toxin genes in *Staphylococcus aureus* isolated from milk of cows with mastitis", Foodborne Pathog Dis., 2006, 3:274-83.
Srivastava et al., "Identification of regulatory elements in 16S rRNA gene of *Acinetobacter* species isolated from water sample", Bioinformation, 2008, 3(4):173-6. (Epub Dec. 6, 2008).
Taverna et al., "Characterization of cell wall associated proteins of a *Staphylococcus aureus* isolated from bovine mastitis case by a proteomic approach", Vet Microbiol., 2007, 119:240-247.
Tollersrud et al., "*Staphylococcus aureus* enterotoxin D is secreted in milk and stimulates specific antibody responses in cows in the course of experimental intramammary infection", Infect Immun., 2006, 74:3507-3512.
Tuchscherr et al., "Antibodies to capsular polysaccharide and clumping factor A prevent mastitis and the emergence of unencapsulated and small-colony variants of *Staphylococcus aureus* in mice", Infect Immun., 2008, 76:5738-5744.
Tusnady et al., "The HMMTOP transmembrane topology prediction server", Bioinformatics, 2001, 17, 849-850.
Voyich et al., "Insights into mechanisms used by *Staphylococcus aureus* to avoid destruction by human neutrophils", J Immunol., 2005, 175:3907-3919.
Ziebandt et al., "Proteomics uncovers extreme heterogeneity in the *Staphylococcus aureus* exoproteome due to genomic plasticity and variant gene regulation", Proteomics, 2010, 285(47): 36794-36803.
Saha et al., "Prediction of Continuous B-Cell Epitopes in Antigenic Sequences Using Physico-chemical Properties", In G.Nicosia, V.Cutello, P.J. Bentley and J.Timis (Eds.) ICARIS 2004, LNCS 3239, Springer, 2004, 197-204.
Saha et al., "Prediction of Continuous B-cell Epitopes in an Antigen Using Recurrent Neural Network", Proteins, 2006, 65(1):40-48.
Allard et al., "Transcriptional modulation of *Staphlococcus aureus* iron-regulated genes during growth in vitro and in a tissue cage model in vivo", Microbes Infect., 2006, 7:1679-1690.
Allard et al., "Transcriptional Analysis of In Vivo-Expressed Genes in *Staphylococcus aureus* During Bovine Mastitis",American Society for Microbiology General Meeting. Boston, USA. Jun. 1-5, 2008 (Poster).
Atalla et al., "Characterization of a *Staphylococcus aureus* small colony variant (SCV) associated with persistent bovine mastitis", Foodborne Pathog, 2008, 5:785-799.
Barkema et al., "Invited Review: The role of cow, pathogen, and treatment regimen in the therapeutic success of bovine *Staphylococcus aureus* mastitis", J Dairy Sci. 2006, 89:1877-1895.
Bradley A., "Bovine mastitis: an evolving disease", Vet J. 2002, 164:116-128.
Barrio et al., "Assessment of the opsonic activity of purified bovine sIgA following intramammary immunization of cows with *Staphylococcus aureus*", J. Dairy Sci., 2003, 86 :2884-2894.
Brouillette et al., "3',5'-cyclic diguanylic acid reduces the virulence of biofilm-forming *Staphylococcus aureus* strains in a mouse model of mastitis infection", Antimicrob. Agents Chemother, 2005, 49:3109-3113.
Burlak et al., "Global analysis of community-associated methicillin-resistant *Staphylococcus aureus* exoproteins reveals molecules produced in vitro and during infection", Cell Microbiol., 2007, 9:1172-1190.
Chang et al., "Protective effects of recombinant staphylococcal enterotoxin type C mutant vaccine against experimental bovine infection by a strain of *Staphylococcus aureus* isolated from subclinical mastitis in dairy cattle", Vaccine, 2008, 26:2081-2091.
Chen et al., "Prediction of linear B-cell epitopes using amino acid pair antigenicity scale", Amino Acids, 2007, 33: 423-428.
Chen et al., "Disruption of a toxin by introduction of a foreign gene into the chromosome of *Clostridium perfringens* using targetron induced mutagenesis", Plasmid., 2007, 58:182-189.
De Groot et al., "Prediction of immunogenicity: in silico paradigms, ex vivo and in vivo correlates", Curr Opinion in Pharmacol, 2008, 8:620-626.
Dehal et al., MicrobesOnline: an integrated portal for comparative and functional genomics. Nucleic Acids Res. Jan. 2010; 38(Database issue): D396-400. Epub Nov. 11, 2009.
Diarra et al., "Response of *Staphylococcus aureus* isolates from bovine mastitis to exogenous iron sources", J. Dairy Sci. ,2002, 85:2141-2148.
El-Manzalawy et al., "Predicting linear B-cell epitopes using string kernels" J Mol Recognit, 2008a, 21: 243-255.
El-Manzalawy et al., "Predicting flexible length linear B-cell epitopes. 7th International Conference on Computational Systems Bioinformatics", Stanford, CA. 2008b., pp. 121-131.
Eng et al., "The Potential of Polyphosphazenes for Delivery of Vaccine Antigens and Immunotherapeutic Agents", Curr Drug Deliv. 2010, 7(1):13-30.
Gardy et al., "PSORTb v.2.0: Expanded prediction of bacterial protein subcellular localization and insights gained from comparative proteome analysis", Bioinformatics, 2005, 21(5):617-623; doi:10.1093/bioinformatics/bti057.
Garzoni et al., "A global view of *Staphylococcus aureus* whole genome expression upon internalization in human epithelial cells", BMC Genomics. 2007, 8:171.
Goerke et al., "Direct quantitative transcript analysis of the agr regulon of *Staphylococcus aureus* during human infection in comparison to the expression profile in vitro", Infect Immun. 2000, 68:1304-1311.
Guidry et al., "Opsonization of *Staphylococcus aureus* by bovine immunoglobulin isotypes", J. of Dairy Sci., 1993. 76:1285-1289.
Haveri et al., "Virulence genes of bovine *Staphylococcus aureus* from persistent and nonpersistent intramammary infections with different clinical characteristics", J Appl Microbiol., 2007, 103:993-1000.
Hogarth et al., "Differential protein composition of bovine whey: a comparison of whey from healthy animals and from those with clinical mastitis", Proteomics, 2004, 4:2094-2100.
Jayarao et al., "Prevalence of foodborne pathogens in bulk tank milk", J Dairy Sci., 2001, 84:2157-2162.
Karaolis et al., Bacterial c-di-GMP is an immunostimulatory molecule. J Immunol., 2007, 178:2171-2181.
Kasturi et al. "Programming the magnitude and persistence of antibody responses with innate immunity", Nature, 2011, 470:543-547.
Lammers et al., "Identification of *Staphylococcus aureus* genes expressed during growth in milk: a useful model for selection of genes important in bovine mastitis?", Microbiology, 2000, 146:981-987.
Larkin et al., "ClustalW and ClustalX version 2. Bioinformatics", 2007, 23(21): 2947-2948.
Linghua et al., "The efficacy of CpG oligodinucleotides, in combination with conventional adjuvants, as immunological adjuvants to swine streptococcic septicemia vaccine in piglets in vivo", Int Immunopharmacol., 2006, 6:1267-76.
Loiselle et al., "Impact of postpartum milking frequency on the immune system and the blood metabolite concentration of dairy cows", J Dairy Sci. ,2009, 92:1900-1912.
Lowe et al. "Identification of novel staphylococcal virulence genes by in vivo expression technology", Mol Microbiol, 1998, 27:967-976.
Mamo et al., "Vaccination with *Staphylococcus aureus* fibrinogen binding protein (FgBPs) reduces colonisation of *S. aureus* in a mouse mastitis model", FEMS Immunology and Medical Microbiology, 1994, 10:47-54.
Maresso et al., "Iron acquisition and transport in *Staphylococcus aureus*", Biometals, 2006, 19:193-203.
Mayer et al., "Oxygen concentration in milk of healthy and mastitic cows and implications of low oxygen tension for the killing of *Staphylococcus aureus* by bovine neutrophils", J Dairy Res, 1988, 55:513-519.
Melchior et al., "Biofilm formation and genotyping of *Staphylococcus aureus* bovine mastitis isolates: evidence for lack of penicillin-resistance in Agr-type II strains", Vet. Microbiol., 2009, 137:83-89.
Middleton J.R., "*Staphylococcus aureus* antigens and challenges in vaccine development", Expert Rev Vaccines, 2008, 7:805-815.

(56) References Cited

OTHER PUBLICATIONS

Moisan et al., "Transcription of virulence factors in *Staphylococcus aureus* small-colony variants isolated from cystic fibrosis patients is influenced by SigB", J Bacteriol., 2006, 188:64-76.

Mitchell et al., "*Staphylococcus aureus* SigB activity promotes a strong fibronectin-bacterium interaction which may sustain host tissue colonization by small-colony variants isolated from cystic fibrosis patients", Mol Microbiol, 2008, 70:1540-1555.

Myllys et al., "Persistence in bovine mastitis of Staphylococcus aureus clones as assessed by random amplified polymorphic DNA analysis, ribotyping and biotyping", Vet Microbiol.,1997, 57:245-251.

National Mastitis Council 1996. Current Concept of Bovine Mastitis. 4 ed. National Mastitis Council, Madison, WI.

Nickerson et al., "Comparison of tilmicosin and cephapirin as therapeutics for Staphylococcus aureus mastitis at dry-off", J Dairy Sci., 1999, 82:696-703.

Owens et al., "Comparison of success of antibiotic therapy during lactation and results of antimicrobial susceptibility tests for bovine mastitis", J Dairy Sci., 1997, 80:313-317.

Park et al., "The analysis of milk components and pathogenic bacteria isolated from bovine raw milk in Korea", J Dairy Sci., 1997, 90:5405-5414.

Peles et al., "Characterization of *Staphylococcus aureus* strains isolated from bovine milk in Hungary", Int J Food Microbiol., 2007, 118:186-93.

Peterson et al., "The Comprehensive Microbial Resource", Nucleic Acids Res., 2001, 29(1): 123-5.

Petitclerc et al., "Efficacy of a lactoferrin-penicillin combination to treat {beta}-lactam-resistant *Staphylococcus aureus* mastitis", J Dairy Sci., 2007, 90:2778-2787.

Pragman et al., "Virulence regulation in *Staphylococcus aureus*: the need for in vivo analysis of virulence factor regulation", FEMS Immunol Med Microbiol., 2004, 42:147-154.

Reinoso et al., "Bovine and rabbit models for the study of a *Staphylococcus aureus* a virulent mutant strain, RC122", Canadian Journal of Veterinary Research, 2002, 66:285-288.

* cited by examiner

*In vitro* growth in milk

Multiple sequence alignment: SACOL0442
Nucleic acid

```
MW0345 (MW2)                      ATGTTCAAAAAAAATGACTCGAAAAATTCAATTCTATTAAAATCTATTCT 50
SAS0347 (MSSA476)                 ATGTTCAAAAAAAATGACTCGAAAAATTCAATTCTATTAAAATCTATTCT 50
SACOL0442 (COL)                   ATGTTCAAAAAATATGACTCAAAAAATTCAATCGTATTAAAATCTATTCT 50
SAOUHSC_00354 (NCTC8325)          ATGTTCAAAAAATATGACTCAAAAAATTCAATCGTATTAAAATCTATTCT 50
NWMN_0362 (Newman)                ATGTTCAAAAAATATGACTCAAAAAATTCAATCGTATTAAAATCTATTCT 50
SAUSA300_0370 (USA300-FPR3757)    ATGTTCAAAAAATATGACTCAAAAAATTCAATCGTATTAAAATCTATTCT 50
SaurJH1_0429 (JH1)                ATGTTCAAAAAATATGACTCAAAAAATTCAATCGTATTAAAATCTATTCT 50
SAHV_0367 (Mu3)                   ATGTTCAAAAAATATGACTCAAAAAATTCAATCGTATTAAAATCTATTCT 50
SaurJH9_0419 (JH9)                ATGTTCAAAAAATATGACTCAAAAAATTCAATCGTATTAAAATCTATTCT 50
SAV0370 (Mu50)                    ATGTTCAAAAAATATGACTCAAAAAATTCAATCGTATTAAAATCTATTCT 50
SA0357 (N315)                     ATGTTCAAAAAATATGACTCAAAAAATTCAATCGTATTAAAATCTATTCT 50
SAB0321 (RF122)                   ATGTTCAAAAAATATGACTCAAAAAATTCAATCGTATTAAAATCTATTCT 50
                                  ************ ******* ***********  ****************

MW0345 (MW2)                      ATCGCTAGGTATCATCTATGGGGGAACATTTGGAATATATCCAAAAGCAG 100
SAS0347 (MSSA476)                 ATCGCTAGGTATCATCTATGGGGGAACATTTGGAATATATCCAAAAGCAG 100
SACOL0442 (COL)                   ATCGCTAGGTATCATCTATGGGGGAACATTTGGAATATATCCAAAAGCAG 100
SAOUHSC_00354 (NCTC8325)          ATCGCTAGGTATCATCTATGGGGGAACATTTGGAATATATCCAAAAGCAG 100
NWMN_0362 (Newman)                ATCGCTAGGTATCATCTATGGGGGAACATTTGGAATATATCCAAAAGCAG 100
SAUSA300_0370 (USA300-FPR3757)    ATCGCTAGGTATCATCTATGGGGGAACATTTGGAATATATCCAAAAGCAG 100
SaurJH1_0429 (JH1)                ATCGCTAGGTATCATCTATGGGGGAACATTTGGAATATATCCAAAAGCAG 100
SAHV_0367 (Mu3)                   ATCGCTAGGTATCATCTATGGGGGAACATTTGGAATATATCCAAAAGCAG 100
SaurJH9_0419 (JH9)                ATCGCTAGGTATCATCTATGGGGGAACATTTGGAATATATCCAAAAGCAG 100
SAV0370 (Mu50)                    ATCGCTAGGTATCATCTATGGGGGAACATTTGGAATATATCCAAAAGCAG 100
SA0357 (N315)                     ATCGCTAGGTATCATCTATGGGGGAACATTTGGAATATATCCAAAAGCAG 100
SAB0321 (RF122)                   ATCGCTAGGTATCATCTATGGGGGAACATTTGGAATATATCCAAAAGCAG 100
                                  **************************************************

MW0345 (MW2)                      ACGCGTCAACACAAAATTCCCCAAGTGTACAAGATAAACAATTCCAAAAA 150
SAS0347 (MSSA476)                 ACGCGTCAACACAAAATTCCCCAAGTGTACAAGATAAACAATTCCAAAAA 150
SACOL0442 (COL)                   ACGCGTCAACACAAAATTCCTCAAGTGTACAAGATAAACAATTACAAAAA 150
SAOUHSC_00354 (NCTC8325)          ACGCGTCAACACAAAATTCCTCAAGTGTACAAGATAAACAATTACAAAAA 150
NWMN_0362 (Newman)                ACGCGTCAACACAAAATTCCTCAAGTGTACAAGATAAACAATTACAAAAA 150
SAUSA300_0370 (USA300-FPR3757)    ACGCGTCAACACAAAATTCCTCAAGTGTACAAGATAAACAATTACAAAAA 150
SaurJH1_0429 (JH1)                ACGCGTCAACACAAAATTCCTCAAGTGTACAAGATAAACAATTACAAAAA 150
SAHV_0367 (Mu3)                   ACGCGTCAACACAAAATTCCTCAAGTGTACAAGATAAACAATTACAAAAA 150
SaurJH9_0419 (JH9)                ACGCGTCAACACAAAATTCCTCAAGTGTACAAGATAAACAATTACAAAAA 150
SAV0370 (Mu50)                    ACGCGTCAACACAAAATTCCTCAAGTGTACAAGATAAACAATTACAAAAA 150
SA0357 (N315)                     ACGCGTCAACACAAAATTCCTCAAGTGTACAAGATAAACAATTACAAAAA 150
SAB0321 (RF122)                   ACGCGTCAACACAAAATTCCTCAAGTGTACAAGATAAACAATTCCAAAAA 150
                                  ******************** ********************** ******

MW0345 (MW2)                      GTTGAAGAAGTACCAAATAATTCAGAAAAAGCTTTGGTTAAAAAACTTTA 200
SAS0347 (MSSA476)                 GTTGAAGAAGTACCAAATAATTCAGAAAAAGCTTTGGTTAAAAAACTTTA 200
SACOL0442 (COL)                   GTTGAAGAAGTACCAAATAATTCAGAAAAAGCTTTGGTTAAAAAACTTTA 200
SAOUHSC_00354 (NCTC8325)          GTTGAAGAAGTACCAAATAATTCAGAAAAAGCTTTGGTTAAAAAACTTTA 200
NWMN_0362 (Newman)                GTTGAAGAAGTACCAAATAATTCAGAAAAAGCTTTGGTTAAAAAACTTTA 200
SAUSA300_0370 (USA300-FPR3757)    GTTGAAGAAGTACCAAATAATTCAGAAAAAGCTTTGGTTAAAAAACTTTA 200
SaurJH1_0429 (JH1)                GTTGAAGAAGTACCAAATAATTCAGAAAAAGCTTTGGTTAAAAAACTTTA 200
SAHV_0367 (Mu3)                   GTTGAAGAAGTACCAAATAATTCAGAAAAAGCTTTGGTTAAAAAACTTTA 200
SaurJH9_0419 (JH9)                GTTGAAGAAGTACCAAATAATTCAGAAAAAGCTTTGGTTAAAAAACTTTA 200
SAV0370 (Mu50)                    GTTGAAGAAGTACCAAATAATTCAGAAAAAGCTTTGGTTAAAAAACTTTA 200
SA0357 (N315)                     GTTGAAGAAGTACCAAATAATTCAGAAAAAGCTTTGGTTAAAAAACTTTA 200
SAB0321 (RF122)                   GTTGAAGAAGTACCAAATAATTCAGAAAAAGCTTTGGTTAAAAAACTGTA 200
                                  *********************************************** **
```

FIG. 11A

```
MW0343 (MW2)                          CGATAGATACAGCCAAAATACAATAAACGGAAAATCTAATAAATCTAGGA 250
SAS0347 (MSSA476)                     CGATAGATACAGCCAAAATACAATAAACGGAAAATCTAATAAATCTAGGA 250
SACOL0442 (COL)                       CGATAGATACAGCAAGGATACAATAAATGGAAAATCTAATAAATCTAGGA 250
SAOUHSC_00354 (NCTC8325)              CGATAGATACAGCAAGGATACAATAAATGGAAAATCTAATAAATCTAGGA 250
NWMN_0362 (Newman)                    CGATAGATACAGCAAGGATACAATAAATGGAAAATCTAATAAATCTAGGA 250
SAUSA300_0370 (USA300-FPR3757)        CGATAGATACAGCAAGGATACAATAAATGGAAAATCTAATAAATCTAGGA 250
SaurJH1_0429 (JH1)                    CGATAGATACAGCAAGGATACAATAAATGGAAAATCTAATAAATCTAGGA 250
SAHV_0367 (Mu3)                       CGATAGATACAGCAAGGATACAATAAATGGAAAATCTAATAAATCTAGGA 250
SaurJH9_0419 (JH9)                    CGATAGATACAGCAAGGATACAATAAATGGAAAATCTAATAAATCTAGGA 250
SAV0370 (Mu50)                        CGATAGATACAGCAAGGATACAATAAATGGAAAATCTAATAAATCTAGGA 250
SA0357 (N315)                         CGATAGATACAGCAAGGATACAATAAATGGAAAATCTAATAAATCTAGGA 250
SAB0321 (RF122)                       CGATAGATACAGCCAAAATACAATAAACGGAAAATCTAATAAAGCTAGGA 250
                                      ************* *  ********** **************** *****

MW0343 (MW2)                          ATTGGGTTTATTCAGAGAGACCTTTAAATGAAAACCAAGTTCGTATAAAT 300
SAS0347 (MSSA476)                     ATTGGGTTTATTCAGAGAGACCTTTAAATGAAAACCAAGTTCGTATAAAT 300
SACOL0442 (COL)                       ATTGGGTTTATTCAGAGAGACCTTTAAATGAAAACCAAGTTCGTATACAT 300
SAOUHSC_00354 (NCTC8325)              ATTGGGTTTATTCAGAGAGACCTTTAAATGAAAACCAAGTTCGTATACAT 300
NWMN_0362 (Newman)                    ATTGGGTTTATTCAGAGAGACCTTTAAATGAAAACCAAGTTCGTATACAT 300
SAUSA300_0370 (USA300-FPR3757)        ATTGGGTTTATTCAGAGAGACCTTTAAATGAAAACCAAGTTCGTATACAT 300
SaurJH1_0429 (JH1)                    ATTGGGTTTATTCAGAGAGACCTTTAAATGAAAACCAAGTTCGTATACAT 300
SAHV_0367 (Mu3)                       ATTGGGTTTATTCAGAGAGACCTTTAAATGAAAACCAAGTTCGTATACAT 300
SaurJH9_0419 (JH9)                    ATTGGGTTTATTCAGAGAGACCTTTAAATGAAAACCAAGTTCGTATACAT 300
SAV0370 (Mu50)                        ATTGGGTTTATTCAGAGAGACCTTTAAATGAAAACCAAGTTCGTATACAT 300
SA0357 (N315)                         ATTGGGTTTATTCAGAGAGACCTTTAAATGAAAACCAAGTTCGTATACAT 300
SAB0321 (RF122)                       ATTGGGTTTATTCAGAGAGACCTTTAAATGAAAATCAAGTTCGCATACAT 300
                                      ********************************** ******** *** **

MW0343 (MW2)                          TTAGAAGGAACATACAGAGTTGCTGATAGAGTATATACACCTAAGAGAAA 350
SAS0347 (MSSA476)                     TTAGAAGGAACATACAGAGTTGCTGATAGAGTATATACACCTAAGAGAAA 350
SACOL0442 (COL)                       TTAGAAGGAACATACACAGTTGCTGGCAGAGTGTATACACCTAAGAGGAA 350
SAOUHSC_00354 (NCTC8325)              TTAGAAGGAACATACACAGTTGCTGGCAGAGTGTATACACCTAAGAGGAA 350
NWMN_0362 (Newman)                    TTAGAAGGAACATACACAGTTGCTGGCAGAGTGTATACACCTAAGAGGAA 350
SAUSA300_0370 (USA300-FPR3757)        TTAGAAGGAACATACACAGTTGCTGGCAGAGTGTATACACCTAAGAGGAA 350
SaurJH1_0429 (JH1)                    TTAGAAGGAACATACACAGTTGCTGATAGAGTATATACACCTAAGAGAAA 350
SAHV_0367 (Mu3)                       TTAGAAGGAACATACACAGTTGCTGATAGAGTATATACACCTAAGAGAAA 350
SaurJH9_0419 (JH9)                    TTAGAAGGAACATACACAGTTGCTGATAGAGTATATACACCTAAGAGAAA 350
SAV0370 (Mu50)                        TTAGAAGGAACATACACAGTTGCTGATAGAGTATATACACCTAAGAGAAA 350
SA0357 (N315)                         TTAGAAGGAACATACACAGTTGCTGATAGAGTATATACACCTAAGAGAAA 350
SAB0321 (RF122)                       TTAGAAGGTACATACAGAGTTGCTGATAGAGTGTATACACCTAAGAGGAA 350
                                      ******** ****** *********  ***** ************** **

MW0343 (MW2)                          TATTACTCTTAATAAAGAAGTTGTCACTTTAAAGGAATTGGATCATATCA 400
SAS0347 (MSSA476)                     TATTACTCTTAATAAAGAAGTTGTCACTTTAAAGGAATTGGATCATATCA 400
SACOL0442 (COL)                       TATTACTCTTAATAAAGAAGTTGTCACTTTAAAAGAATTGGATCATATCA 400
SAOUHSC_00354 (NCTC8325)              TATTACTCTTAATAAAGAAGTTGTCACTTTAAAAGAATTGGATCATATCA 400
NWMN_0362 (Newman)                    TATTACTCTTAATAAAGAAGTTGTCACTTTAAAAGAATTGGATCATATCA 400
SAUSA300_0370 (USA300-FPR3757)        TATTACTCTTAATAAAGAAGTTGTCACTTTAAAAGAATTGGATCATATCA 400
SaurJH1_0429 (JH1)                    TATTACTCTTAATAAAGAAGTTGTCACTTTAAAGGAATTGGATCATATCA 400
SAHV_0367 (Mu3)                       TATTACTCTTAATAAAGAAGTTGTCACTTTAAAGGAATTGGATCATATCA 400
SaurJH9_0419 (JH9)                    TATTACTCTTAATAAAGAAGTTGTCACTTTAAAGGAATTGGATCATATCA 400
SAV0370 (Mu50)                        TATTACTCTTAATAAAGAAGTTGTCACTTTAAAGGAATTGGATCATATCA 400
SA0357 (N315)                         TATTACTCTTAATAAAGAAGTTGTCACTTTAAAGGAATTGGATCATATCA 400
SAB0321 (RF122)                       CATTACTCTTAATAAAGAAGTTGTCACTTTAAAAGAATTGGATCATATCA 400
                                       ******************************** ****************

MW0343 (MW2)                          TAAGATTTGCTCATATTTCTTATGGCTTATATATGGGAGAACATTTGCCT 450
SAS0347 (MSSA476)                     TAAGATTTGCTCATATTTCTTATGGCTTATATATGGGAGAACATTTGCCT 450
SACOL0442 (COL)                       TAAGATTTGCTCATATTTCCTATGGCTTGTATATGGGAGAACATTTGCCT 450
SAOUHSC_00354 (NCTC8325)              TAAGATTTGCTCATATTTCCTATGGCTTGTATATGGGAGAACATTTGCCT 450
NWMN_0362 (Newman)                    TAAGATTTGCTCATATTTCCTATGGCTTGTATATGGGAGAACATTTGCCT 450
SAUSA300_0370 (USA300-FPR3757)        TAAGATTTGCTCATATTTCCTATGGCTTGTATATGGGAGAACATTTGCCT 450
SaurJH1_0429 (JH1)                    TAAGATTTGCTCATATTTCTTATGGCTTATATATGGGAGAACATTTGCCT 450
SAHV_0367 (Mu3)                       TAAGATTTGCTCATATTTCTTATGGCTTATATATGGGAGAACATTTGCCT 450
SaurJH9_0419 (JH9)                    TAAGATTTGCTCATATTTCTTATGGCTTATATATGGGAGAACATTTGCCT 450
SAV0370 (Mu50)                        TAAGATTTGCTCATATTTCTTATGGCTTATATATGGGAGAACATTTGCCT 450
SA0357 (N315)                         TAAGATTTGCTCATATTTCTTATGGCTTATATATGGGAGAACATTTGCCT 450
SAB0321 (RF122)                       TAAGATTTGCTCATATTTCTTATGGCTTATATATGGGAGAACATTTGCCT 450
                                      ******************* ******** *********************
```

FIG. 11B

```
MW0345 (MW2)                          AAAGGTAACATCGTCATAAATACAAAAGATGGCGGTAAATATACATTAGA 500
SAS0347 (MSSA476)                     AAAGGTAACATCGTCATAAATACAAAAGATGGCGGTAAATATACATTAGA 500
SACOL0442 (COL)                       AAAGGTAACATCGTCATAAATACAAAAGATGGTGGTAAATATACATTAGA 500
SAOUHSC_00354 (NCTC8325)              AAAGGTAACATCGTCATAAATACAAAAGATGGTGGTAAATATACATTAGA 500
NWMN_0362 (Newman)                    AAAGGTAACATCGTCATAAATACAAAAGATGGTGGTAAATATACATTAGA 500
SAUSA300_0370 (USA300-FPR3757)        AAAGGTAACATCGTCATAAATACAAAAGATGGTGGTAAATATACATTAGA 500
SaurJH1_0429 (JH1)                    AAAGGTAACATCGTCATAAATACAAAAGATGGCGGTAAATATACATTAGA 500
SAHV_0367 (Mu3)                       AAAGGTAACATCGTCATAAATACAAAAGATGGCGGTAAATATACATTAGA 500
SaurJH9_0419 (JH9)                    AAAGGTAACATCGTCATAAATACAAAAGATGGCGGTAAATATACATTAGA 500
SAV0370 (Mu50)                        AAAGGTAACATCGTCATAAATACAAAAGATGGCGGTAAATATACATTAGA 500
SA0357 (N315)                         AAAGGTAACATCGTCATAAATACAAAAGATGGCGGTAAATATACATTAGA 500
SAB0321 (RF122)                       AAAGGTAACATCGTCATAAATACAAAGAATGGCGGTAAATATACATTAGA 500
                                      **************************  ***** ****************

MW0345 (MW2)                          GTCGCATAAAGAGCTACAAAAAGATAGGGAAAATGTAAAAATTAATACAG 550
SAS0347 (MSSA476)                     GTCGCATAAAGAGCTACAAAAAGATAGGGAAAATGTAAAAATTAATACAG 550
SACOL0442 (COL)                       GTCGCATAAAGAGCTACAAAAAGATAGGGAAAATGTAAAAATTAATACAG 550
SAOUHSC_00354 (NCTC8325)              GTCGCATAAAGAGCTACAAAAAGATAGGGAAAATGTAAAAATTAATACAG 550
NWMN_0362 (Newman)                    GTCGCATAAAGAGCTACAAAAAGATAGGGAAAATGTAAAAATTAATACAG 550
SAUSA300_0370 (USA300-FPR3757)        GTCGCATAAAGAGCTACAAAAAGATAGGGAAAATGTAAAAATTAATACAG 550
SaurJH1_0429 (JH1)                    GTCGCATAAAGAGCTACAAAAAGATAGGGAAAATGTAAAAATTAATACAG 550
SAHV_0367 (Mu3)                       GTCGCATAAAGAGCTACAAAAAGATAGGGAAAATGTAAAAATTAATACAG 550
SaurJH9_0419 (JH9)                    GTCGCATAAAGAGCTACAAAAAGATAGGGAAAATGTAAAAATTAATACAG 550
SAV0370 (Mu50)                        GTCGCATAAAGAGCTACAAAAAGATAGGGAAAATGTAAAAATTAATACAG 550
SA0357 (N315)                         GTCGCATAAAGAGCTACAAAAAGATAGGGAAAATGTAAAAATTAATACAG 550
SAB0321 (RF122)                       GTCGCACAAAGAGTTACAAAAGAATAGGGAAAATGTAGAAATTAATACTG 550
                                      ****** ****** *******  ************** ********** *

MW0345 (MW2)                          CCGATATAAAAAATGTAACTTTCAAACTTGTGAAAAGTGTTAATGACATT 600
SAS0347 (MSSA476)                     CCGATATAAAAAATGTAACTTTCAAACTTGTGAAAAGTGTTAATGACATT 600
SACOL0442 (COL)                       CCGATATAAAAAATGTAACTTTCAAACTTGTGAAAAGTGTTAATGACATT 600
SAOUHSC_00354 (NCTC8325)              CCGATATAAAAAATGTAACTTTCAAACTTGTGAAAAGTGTTAATGACATT 600
NWMN_0362 (Newman)                    CCGATATAAAAAATGTAACTTTCAAACTTGTGAAAAGTGTTAATGACATT 600
SAUSA300_0370 (USA300-FPR3757)        CCGATATAAAAAATGTAACTTTCAAACTTGTGAAAAGTGTTAATGACATT 600
SaurJH1_0429 (JH1)                    CCGATATAAAAAATGTAACTTTCAAACTTGTGAAAAGTGTTAATGACATT 600
SAHV_0367 (Mu3)                       CCGATATAAAAAATGTAACTTTCAAACTTGTGAAAAGTGTTAATGACATT 600
SaurJH9_0419 (JH9)                    CCGATATAAAAAATGTAACTTTCAAACTTGTGAAAAGTGTTAATGACATT 600
SAV0370 (Mu50)                        CCGATATAAAAAATGTAACTTTCAAACTTGTGAAAAGTGTTAATGACATT 600
SA0357 (N315)                         CCGATATAAAAAATGTAACTTTCAAACTTGTGAAAAGTGTTAATGACATT 600
SAB0321 (RF122)                       ATGATATAAAAAATGTAACTTTCGAACTTGTGAAAAGTGTTAATGACATT 600
                                        ********************* **************************

MW0345 (MW2)                          GAACAAGTTTGA 612
SAS0347 (MSSA476)                     GAACAAGTTTGA 612
SACOL0442 (COL)                       GAACAAGTTTGA 612
SAOUHSC_00354 (NCTC8325)              GAACAAGTTTGA 612
NWMN_0362 (Newman)                    GAACAAGTTTGA 612
SAUSA300_0370 (USA300-FPR3757)        GAACAAGTTTGA 612
SaurJH1_0429 (JH1)                    GAACAAGTTTGA 612
SAHV_0367 (Mu3)                       GAACAAGTTTGA 612
SaurJH9_0419 (JH9)                    GAACAAGTTTGA 612
SAV0370 (Mu50)                        GAACAAGTTTGA 612
SA0357 (N315)                         GAACAAGTTTGA 612
SAB0321 (RF122)                       GAACAAGTTTGA 612
                                      ************
```

FIG. 11C

Multiple sequence alignment: SACOL0442
Amino acids

```
SACOL0442 (COL)                     MFKKYDSKNSIVLKSILSLGIIYGGTFGIYPKADASTQNSSSVQDKQLQK 50
SAOUHSC_00354 (NCTC8325)            MFKKYDSKNSIVLKSILSLGIIYGGTFGIYPKADASTQNSSSVQDKQLQK 50
NWMN_0362 (Newman)                  MFKKYDSKNSIVLKSILSLGIIYGGTFGIYPKADASTQNSSSVQDKQLQK 50
SAUSA300_0370 (USA300-FPR3757)      MFKKYDSKNSIVLKSILSLGIIYGGTFGIYPKADASTQNSSSVQDKQLQK 50
SaurJH1_0429 (JH1)                  MFKKYDSKNSIVLKSILSLGIIYGGTFGIYPKADASTQNSSSVQDKQLQK 50
SAHV_0367 (Mu3)                     MFKKYDSKNSIVLKSILSLGIIYGGTFGIYPKADASTQNSSSVQDKQLQK 50
SaurJH9_0419 (JH9)                  MFKKYDSKNSIVLKSILSLGIIYGGTFGIYPKADASTQNSSSVQDKQLQK 50
SAV0370 (Mu50)                      MFKKYDSKNSIVLKSILSLGIIYGGTFGIYPKADASTQNSSSVQDKQLQK 50
SA0357 (N315)                       MFKKYDSKNSIVLKSILSLGIIYGGTFGIYPKADASTQNSSSVQDKQLQK 50
SAS0347 (MSSA476)                   MFKKNDSKNSILLKSILSLGIIYGGTFGIYPKADASTQNSPSVQDKQFQK 50
SAB0321 (RF122)                     MFKKYDSKNSIVLKSILSLGIIYGGTFGIYPKADASTQNSSSVQDKQFQK 50
                                    **** ******:*****************************.*****:**

SACOL0442 (COL)                     VEEVPNNSEKALVKKLYDRYSKDTINGKSNKSRNWVYSERPLNENQVRIH 100
SAOUHSC_00354 (NCTC8325)            VEEVPNNSEKALVKKLYDRYSKDTINGKSNKSRNWVYSERPLNENQVRIH 100
NWMN_0362 (Newman)                  VEEVPNNSEKALVKKLYDRYSKDTINGKSNKSRNWVYSERPLNENQVRIH 100
SAUSA300_0370 (USA300-FPR3757)      VEEVPNNSEKALVKKLYDRYSKDTINGKSNKSRNWVYSERPLNENQVRIH 100
SaurJH1_0429 (JH1)                  VEEVPNNSEKALVKKLYDRYSKDTINGKSNKSRNWVYSERPLNENQVRIH 100
SAHV_0367 (Mu3)                     VEEVPNNSEKALVKKLYDRYSKDTINGKSNKSRNWVYSERPLNENQVRIH 100
SaurJH9_0419 (JH9)                  VEEVPNNSEKALVKKLYDRYSKDTINGKSNKSRNWVYSERPLNENQVRIH 100
SAV0370 (Mu50)                      VEEVPNNSEKALVKKLYDRYSKDTINGKSNKSRNWVYSERPLNENQVRIH 100
SA0357 (N315)                       VEEVPNNSEKALVKKLYDRYSKDTINGKSNKSRNWVYSERPLNENQVRIH 100
SAS0347 (MSSA476)                   VEEVPNNSEKALVKKLYDRYSQNTINGKSNKSRNWVYSERPLNENQVRIN 100
SAB0321 (RF122)                     VEEVPNNSEKALVKKLYDRYSQNTINGKSNKARNWVYSERPLNENQVRIH 100
                                    *********************::*********:****************:

SACOL0442 (COL)                     LEGTYTVAGRVYTPKRNITLNKEVVTLKELDHIIRFAHISYGLYMGEHLP 150
SAOUHSC_00354 (NCTC8325)            LEGTYTVAGRVYTPKRNITLNKEVVTLKELDHIIRFAHISYGLYMGEHLP 150
NWMN_0362 (Newman)                  LEGTYTVAGRVYTPKRNITLNKEVVTLKELDHIIRFAHISYGLYMGEHLP 150
SAUSA300_0370 (USA300-FPR3757)      LEGTYTVAGRVYTPKRNITLNKEVVTLKELDHIIRFAHISYGLYMGEHLP 150
SaurJH1_0429 (JH1)                  LEGTYTVADRVYTPKRNITLNKEVVTLKELDHIIRFAHISYGLYMGEHLP 150
SAHV_0367 (Mu3)                     LEGTYTVADRVYTPKRNITLNKEVVTLKELDHIIRFAHISYGLYMGEHLP 150
SaurJH9_0419 (JH9)                  LEGTYTVADRVYTPKRNITLNKEVVTLKELDHIIRFAHISYGLYMGEHLP 150
SAV0370 (Mu50)                      LEGTYTVADRVYTPKRNITLNKEVVTLKELDHIIRFAHISYGLYMGEHLP 150
SA0357 (N315)                       LEGTYTVADRVYTPKRNITLNKEVVTLKELDHIIRFAHISYGLYMGEHLP 150
SAS0347 (MSSA476)                   LEGTYRVADRVYTPKRNITLNKEVVTLKELDHIIRFAHISYGLYMGEHLP 150
SAB0321 (RF122)                     LEGTYRVADRVYTPKRNITLNKEVVTLKELDHIIRFAHISYGLYMGEHLP 150
                                    ***** **.*****************************************

SACOL0442 (COL)                     KGNIVINTKDGGKYTLESHKELQKDRENVKINTADIKNVTFKLVKSVNDI 200
SAOUHSC_00354 (NCTC8325)            KGNIVINTKDGGKYTLESHKELQKDRENVKINTADIKNVTFKLVKSVNDI 200
NWMN_0362 (Newman)                  KGNIVINTKDGGKYTLESHKELQKDRENVKINTADIKNVTFKLVKSVNDI 200
SAUSA300_0370 (USA300-FPR3757)      KGNIVINTKDGGKYTLESHKELQKDRENVKINTADIKNVTFKLVKSVNDI 200
SaurJH1_0429 (JH1)                  KGNIVINTKDGGKYTLESHKELQKDRENVKINTADIKNVTFKLVKSVNDI 200
SAHV_0367 (Mu3)                     KGNIVINTKDGGKYTLESHKELQKDRENVKINTADIKNVTFKLVKSVNDI 200
SaurJH9_0419 (JH9)                  KGNIVINTKDGGKYTLESHKELQKDRENVKINTADIKNVTFKLVKSVNDI 200
SAV0370 (Mu50)                      KGNIVINTKDGGKYTLESHKELQKDRENVKINTADIKNVTFKLVKSVNDI 200
SA0357 (N315)                       KGNIVINTKDGGKYTLESHKELQKDRENVKINTADIKNVTFKLVKSVNDI 200
SAS0347 (MSSA476)                   KGNIVINTKDGGKYTLESHKELQKDRENVKINTADIKNVTFKLVKSVNDI 200
SAB0321 (RF122)                     KGNIVINTKNGGKYTLESHKELQKNRENVEINTDDIKNVTFELVKSVNDI 200
                                    *********:**************:****:*** *******:********

SACOL0442 (COL)                     EQV 203
SAOUHSC_00354 (NCTC8325)            EQV 203
NWMN_0362 (Newman)                  EQV 203
SAUSA300_0370 (USA300-FPR3757)      EQV 203
SaurJH1_0429 (JH1)                  EQV 203
SAHV_0367 (Mu3)                     EQV 203
SaurJH9_0419 (JH9)                  EQV 203
SAV0370 (Mu50)                      EQV 203
SA0357 (N315)                       EQV 203
SAS0347 (MSSA476)                   EQV 203
SAB0321 (RF122)                     EQV 203
                                    ***
```

FIG. 11D

Multiple sequence alignment: SACOL0720
Nucleic acid

```
SaurJH1_0700 (JH1)                  --------------------------------------------------
SaurJH9_0685 (JH9)                  --------------------------------------------------
SAHV_0659 (Mu3)                     --------------------------------------------------
SAV0662 (Mu50)                      ATGACCTTTAACGAGATAATATTTAAAAATTTCCGTCAAAATTTATCACA 50
SA0617 (N315)                       ATGACCTTTAACGAGATAATATTTAAAAATTTCCGTCAAAATTTATCACA 50
MW0624 (MW2)                        ATGACCTTTAACGAGATAATATTTAAAAATTTCCGTCAAAATTTATCACA 50
SAS0627 (MSSA476)                   ATGACCTTTAACGAGATAATATTTAAAAATTTCCGTCAAAATTTATCACA 50
SACOL0720                           ATGACCTTTAACGAGATAATATTTAAAAATTTCCGTCAAAATTTATCACA 50
SAUSA300_0648 (USA300-FPR3757)      ATGACCTTTAACGAGATAATATTTAAAAATTTCCGTCAAAATTTATCACA 50
SAOUHSC_00668 (NCTC8325)            --------------------------------------------------
NWMN_0631 (Newman)                  --------------------------------------------------
SAB0611 (RF122)                     ATGACCTTTAACGAGATAATATTTAAAAATTTCCGTCAAAATTTATCACA 50

SaurJH1_0700 (JH1)                  --------------------------------------------------
SaurJH9_0685 (JH9)                  --------------------------------------------------
SAHV_0659 (Mu3)                     --------------------------------------------------
SAV0662 (Mu50)                      TTATGCCATCTATCTTTTTTCATTAATTACGAGTGTAGTATTGTATTTTA 100
SA0617 (N315)                       TTATGCCATCTATCTTTTTTCATTAATTACGAGTGTAGTATTGTATTTTA 100
MW0624 (MW2)                        TTATGCCATCTATCTTTTTTCATTAATTACGAGTGTAGTATTGTATTTTA 100
SAS0627 (MSSA476)                   TTATGCCATCTATCTTTTTTCATTAATTACGAGTGTAGTATTGTATTTTA 100
SACOL0720_                          TTATGCCATCTATCTTTTTTCGTTAATTACGAGTGTAGTATTGTATTTTA 100
SAUSA300_0648 (USA300-FPR3757)      TTATGCCATCTATCTTTTTTCGTTAATTACGAGTGTAGTATTGTATTTTA 100
SAOUHSC_00668 (NCTC8325)            ----------------------------------------TTCTATTTTA 10
NWMN_0631 (Newman)                  --------------------------------------------------
SAB0611 (RF122)                     TTATGCCATCTATCTTTTTTCATTAATTACGACTGTACTATTCTATTTTA 100

SaurJH1_0700 (JH1)                  -----------------------------------ATGACAGAGTCATAT 15
SaurJH9_0685 (JH9)                  -----------------------------------ATGACAGAGTCATAT 15
SAHV_0659 (Mu3)                     -----------------------------------ATGACAGAGTCATAT 15
SAV0662 (Mu50)                      GCTTTGTAGCATTAAAATACGCGCATAAACTAAACATGACAGAGTCATAT 150
SA0617 (N315)                       GCTTTGTAGCATTAAAATACGCGCATAAACTAAACATGACAGAGTCATAT 150
MW0624 (MW2)                        GCTTTGTAGCATTAAAATACGCGCATAAACTAAACATGACAGAGTCATAT 150
SAS0627 (MSSA476)                   GCTTTGTAGCATTAAAATACGCGCATAAACTAAACATGACAGAGTCATAT 150
SACOL0720_                          GCTTTGTAGCATTAAAATACGCTCATAAACTAAACATGACAGAGTCATAT 150
SAUSA300_0648 (USA300-FPR3757)      GCTTTGTAGCATTAAAATACGCTCATAAACTAAACATGACAGAGTCATAT 150
SAOUHSC_00668 (NCTC8325)            GCTTTGTAGCATTAAAATACGCTCATAAACTAAACATGACAGAGTCATAT 60
NWMN_0631 (Newman)                  -----------------------------------ATGACAGAGTCATAT 15
SAB0611 (RF122)                     GCTTTGTAGCATTAAAATACGCTCATAAACTAAACATGACAGAGTCATAT 150
                                                                       ***************

SaurJH1_0700 (JH1)                  CCAATTATTAAGGAAGGCTCACAAGTCGGAAGCTACTTTCTATTTTTCAT 65
SaurJH9_0685 (JH9)                  CCAATTATTAAGGAAGGCTCACAAGTCGGAAGCTACTTTCTATTTTTCAT 65
SAHV_0659 (Mu3)                     CCAATTATTAAGGAAGGCTCACAAGTCGGAAGCTACTTTCTATTTTTCAT 65
SAV0662 (Mu50)                      CCAATTATTAAGGAAGGCTCACAAGTCGGAAGCTACTTTCTATTTTTCAT 200
SA0617 (N315)                       CCAATTATTAAGGAAGGCTCACAAGTCGGAAGCTACTTTCTATTTTTCAT 200
MW0624 (MW2)                        CCAATTATTAAGGAAGGCTCACAAGTCGGAAGCTACTTTCTATTTTTCAT 200
SAS0627 (MSSA476)                   CCAATTATTAAGGAAGGCTCACAAGTCGGAAGCTACTTTCTATTTTTCAT 200
SACOL0720_                          CCAATTATAAAGGAAGGCTCACAAGTCGGAAGCTACTTTCTATTTTTCAT 200
SAUSA300_0648 (USA300-FPR3757)      CCAATTATAAAGGAAGGCTCACAAGTCGGAAGCTACTTTCTATTTTTCAT 200
SAOUHSC_00668 (NCTC8325)            CCAATTATAAAGGAAGGCTCACAAGTCGGAAGCTACTTTCTATTTTTCAT 110
NWMN_0631 (Newman)                  CCAATTATAAAGGAAGGCTCACAAGTCGGAAGCTACTTTCTATTTTTCAT 65
SAB0611 (RF122)                     CCAATTATAAAGGAAGGCTCACAAGTCGGAAGCTACTTTCTATTTTTCAT 200
                                    ******** *****************************************
```

FIG. 12A

```
SaurJH1_0700 (JH1)                    CATAATTGCATTTTTGTTATATGCCAATGTGTTATTTATTAAACGACGAA 115
SaurJH9_0685 (JH9)                    CATAATTGCATTTTTGTTATATGCCAATGTGTTATTTATTAAACGACGAA 115
SAHV_0659 (Mu3)                       CATAATTGCATTTTTGTTATATGCCAATGTGTTATTTATTAAACGACGAA 115
SAV0662 (Mu50)                        CATAATTGCATTTTTGTTATATGCCAATGTGTTATTTATTAAACGACGAA 250
SA0617 (N315)                         CATAATTGCATTTTTGTTATATGCCAATGTGTTATTTATTAAACGACGAA 250
MW0624 (MW2)                          CATAATTGCATTTTTGTTATATGCCAATGTGTTATTTATTAAACGACGAA 250
SAS0627 (MSSA476)                     CATAATTGCATTTTTGTTATATGCCAATGTGTTATTTATTAAACGACGAA 250
SACOL0720_                            CATAATTGCATTTTTGTTATATGCCAATGTGTTATTTATTAAACGACGAA 250
SAUSA300_0648 (USA300-FPR3757)        CATAATTGCATTTTTGTTATATGCCAATGTGTTATTTATTAAACGACGAA 250
SAOUHSC_00668 (NCTC8325)              CATAATTGCATTTTTGTTATATGCCAATGTGTTATTTATTAAACGACGAA 160
NWMN_0631 (Newman)                    CATAATTGCATTTTTGTTATATGCCAATGTGTTATTTATTAAACGACGAA 115
SAB0611 (RF122)                       CATAATTGCATTTTTGTTATATGCCAATGTGTTATTTATTAAACGACGAA 250
                                      **************************************************

SaurJH1_0700 (JH1)                    GTTATGAGCTTGCATTATATCAAACATTAGGTTTATCTAAATTCAACATT 165
SaurJH9_0685 (JH9)                    GTTATGAGCTTGCATTATATCAAACATTAGGTTTATCTAAATTCAACATT 165
SAHV_0659 (Mu3)                       GTTATGAGCTTGCATTATATCAAACATTAGGTTTATCTAAATTCAACATT 165
SAV0662 (Mu50)                        GTTATGAGCTTGCATTATATCAAACATTAGGTTTATCTAAATTCAACATT 300
SA0617 (N315)                         GTTATGAGCTTGCATTATATCAAACATTAGGTTTATCTAAATTCAACATT 300
MW0624 (MW2)                          GTTATGAGCTTGCATTATATCAAACATTAGGTTTATCTAAATTCAACATT 300
SAS0627 (MSSA476)                     GTTATGAGCTTGCATTATATCAAACATTAGGTTTATCTAAATTCAACATT 300
SACOL0720_                            GTTATGAGCTTGCATTATATCAAACATTAGGTTTATCTAAATTCAACATT 300
SAUSA300_0648 (USA300-FPR3757)        GTTATGAGCTTGCATTATATCAAACATTAGGTTTATCTAAATTCAACATT 300
SAOUHSC_00668 (NCTC8325)              GTTATGAGCTTGCATTATATCAAACATTAGGTTTATCTAAATTCAACATT 210
NWMN_0631 (Newman)                    GTTATGAGCTTGCATTATATCAAACATTAGGTTTATCTAAATTCAACATT 165
SAB0611 (RF122)                       GTTATGAGCTTGCATTATATCAAACATTAGGTTTATCTAAATTCAACATT 300
                                      **************************************************

SaurJH1_0700 (JH1)                    ATTTATATACTAATGCTCGAACAATTACTAATATTTATAATTACGGCAAT 215
SaurJH9_0685 (JH9)                    ATTTATATACTAATGCTCGAACAATTACTAATATTTATAATTACGGCAAT 215
SAHV_0659 (Mu3)                       ATTTATATACTAATGCTCGAACAATTACTAATATTTATAATTACGGCAAT 215
SAV0662 (Mu50)                        ATTTATATACTAATGCTCGAACAATTACTAATATTTATAATTACGGCAAT 350
SA0617 (N315)                         ATTTATATACTAATGCTCGAACAATTACTAATATTTATAATTACGGCAAT 350
MW0624 (MW2)                          ATTTATATACTAATGCTCGAACAATTACTAATATTTATAATTACGGCAAT 350
SAS0627 (MSSA476)                     ATTTATATACTAATGCTCGAACAATTACTAATATTTATAATTACGGCAAT 350
SACOL0720                             ATTTATATACTAATGCTCGAACAATTACTAATATTTATAATTACGGCAAT 350
SAUSA300_0648 (USA300-FPR3757)        ATTTATATACTAATGCTCGAACAATTACTAATATTTATAATTACGGCAAT 350
SAOUHSC_00668 (NCTC8325)              ATTTATATACTAATGCTCGAACAATTACTAATATTTATAATTACGGCAAT 260
NWMN_0631 (Newman)                    ATTTATATACTAATGCTCGAACAATTACTAATATTTATAATTACGGCAAT 215
SAB0611 (RF122)                       ATTTATATACTAATGCTCGAACAATTACTAATATTTATAATTACGGCAAT 350
                                      **************************************************

SaurJH1_0700 (JH1)                    ATTAGGTATTATTATTGGTATTTTTGGTTCAAAACTGTTATTAATGATTG 265
SaurJH9_0685 (JH9)                    ATTAGGTATTATTATTGGTATTTTTGGTTCAAAACTGTTATTAATGATTG 265
SAHV_0659 (Mu3)                       ATTAGGTATTATTATTGGTATTTTTGGTTCAAAACTGTTATTAATGATTG 265
SAV0662 (Mu50)                        ATTAGGTATTATTATTGGTATTTTTGGTTCAAAACTGTTATTAATGATTG 400
SA0617 (N315)                         ATTAGGTATTATTATTGGTATTTTTGGTTCAAAACTGTTATTAATGATTG 400
MW0624 (MW2)                          ATTAGGTATTATTATTGGTATTTTTGGTTCAAAACTGTTATTAATGATTG 400
SAS0627 (MSSA476)                     ATTAGGTATTATTATTGGTATTTTTGGTTCAAAACTGTTATTAATGATTG 400
SACOL0720_                            ATTAGGTATTATTATTGGTATTTTTGGTTCGAAACTGTTATTAATGATTG 400
SAUSA300_0648 (USA300-FPR3757)        ATTAGGTATTATTATTGGTATTTTTGGTTCGAAACTGTTATTAATGATTG 400
SAOUHSC_00668 (NCTC8325)              ATTAGGTATTATTATTGGTATTTTTGGTTCGAAACTGTTATTAATGATTG 310
NWMN_0631 (Newman)                    ATTAGGTATTATTATTGGTATTTTTGGTTCGAAACTGTTATTAATGATTG 265
SAB0611 (RF122)                       ATTAGGTATTATTATTGGTATTTTTGGTTCGAAACTGTTATTAATGATTG 400
                                      ****************************** *******************

SaurJH1_0700 (JH1)                    TCTTTACATTATTAGGAATTAAAGAAAAGGTTCCAATTATTTTTAGTTTG 315
SaurJH9_0685 (JH9)                    TCTTTACATTATTAGGAATTAAAGAAAAGGTTCCAATTATTTTTAGTTTG 315
SAHV_0659 (Mu3)                       TCTTTACATTATTAGGAATTAAAGAAAAGGTTCCAATTATTTTTAGTTTG 315
SAV0662 (Mu50)                        TCTTTACATTATTAGGAATTAAAGAAAAGGTTCCAATTATTTTTAGTTTG 450
SA0617 (N315)                         TCTTTACATTATTAGGAATTAAAGAAAAGGTTCCAATTATTTTTAGTTTG 450
MW0624 (MW2)                          TCTTTACATTATTAGGAATTAAAGAAAAGGTTCCAATTATTTTTAGTTTG 450
SAS0627 (MSSA476)                     TCTTTACATTATTAGGAATTAAAGAAAAGGTTCCAATTATTTTTAGTTTG 450
SACOL0720_                            TCTTTACATTATTAGGAATTAAAGAAAAGGTTCCAATTATTTTTAGTTTG 450
SAUSA300_0648 (USA300-FPR3757)        TCTTTACATTATTAGGAATTAAAGAAAAGGTTCCAATTATTTTTAGTTTG 450
SAOUHSC_00668 (NCTC8325)              TCTTTACATTATTAGGAATTAAAGAAAAGGTTCCAATTATTTTTAGTTTG 360
NWMN_0631 (Newman)                    TCTTTACATTATTAGGAATTAAAGAAAAGGTTCCAATTATTTTTAGTTTG 315
SAB0611 (RF122)                       TCTTTACATTATTAGGAATTAAAGAAAAGGTTCCAATTATTTTTAGTTTG 450
                                      **************************************************
```

FIG. 12B

```
SaurJH1_0700 (JH1)              AGGGCGGTATTTGAAACATTAATGTTAATCGGTGTCGCTTATTTTTTAAC 365
SaurJH9_0685 (JH9)              AGGGCGGTATTTGAAACATTAATGTTAATCGGTGTCGCTTATTTTTTAAC 365
SAHV_0659 (Mu3)                 AGGGCGGTATTTGAAACATTAATGTTAATCGGTGTCGCTTATTTTTTAAC 365
SAV0662 (Mu50)                  AGGGCGGTATTTGAAACATTAATGTTAATCGGTGTCGCTTATTTTTTAAC 500
SA0617 (N315)                   AGGGCGGTATTTGAAACATTAATGTTAATCGGTGTCGCTTATTTTTTAAC 500
MW0624 (MW2)                    AGGGCGGTATTTGAAACATTAATGTTAATCGGTGTCGCTTATTTTTTAAC 500
SAS0627 (MSSA476)               AGGGCGGTATTTGAAACATTAATGTTAATCGGTGTCGCTTATTTTTTAAC 500
SACOL0720                       AGGGCGGTATTTGAAACATTAATGTTAATCGGTGTCGCTTATTTTTTAAC 500
SAUSA300_0648 (USA300-FPR3757)  AGGGCGGTATTTGAAACATTAATGTTAATCGGTGTCGCTTATTTTTTAAC 500
SAOUHSC_00668 (NCTC8325)        AGGGCGGTATTTGAAACATTAATGTTAATCGGTGTCGCTTATTTTTTAAC 410
NWMN_0631 (Newman)              AGGGCGGTATTTGAAACATTAATGTTAATCGGTGTCGCTTATTTTTTAAC 365
SAB0611 (RF122)                 AGGGCGGTATTTGAAACATTAATGTTAATCGGTGTCGCTTATTTTTTAAC 500
                                **************************************************

SaurJH1_0700 (JH1)              CTCTGCTCAAAATTTTATATTAGTGTTCAAACAATCTATTTCACAGATGT 415
SaurJH9_0685 (JH9)              CTCTGCTCAAAATTTTATATTAGTGTTCAAACAATCTATTTCACAGATGT 415
SAHV_0659 (Mu3)                 CTCTGCTCAAAATTTTATATTACTGTTCAAACAATCTATTTCACAGATGT 415
SAV0662 (Mu50)                  CTCTGCTCAAAATTTTATATTAGTGTTCAAACAATCTATTTCACAGATGT 550
SA0617 (N315)                   CTCTGCTCAAAATTTTATATTAGTGTTCAAACAATCTATTTCACAGATGT 550
MW0624 (MW2)                    CTCTGCTCAAAATTTTATATTAGTGTTCAAACAATCTATTTCACAGATGT 550
SAS0627 (MSSA476)               CTCTGCTCAAAATTTTATATTAGTGTTCAAACAATCTATTTCACAGATGT 550
SACOL0720_                      ATCTGCTCAAAATTTTATATTAGTGTTCAAACAATCTATTTCACAGATGT 550
SAUSA300_0648 (USA300-FPR3757)  ATCTGCTCAAAATTTTATATTAGTGTTCAAACAATCTATTTCACAGATGT 550
SAOUHSC_00668 (NCTC8325)        ATCTGCTCAAAATTTTATATTAGTGTTCAAACAATCTATTTCACAGATGT 460
NWMN_0631 (Newman)              ATCTGCTCAAAATTTTATATTAGTGTTCAAACAATCTATTTCACAGATGT 415
SAB0611 (RF122)                 ATCTGCTCAAAATTTTATATTAGTGTTCAAACAATCTATTTCACAGATGT 550
                                 *************************************************

SaurJH1_0700 (JH1)              CAAAGAATAACCAGGTTAAAGAAACAAATCATAATAAAATTACATTTGAA 465
SaurJH9_0685 (JH9)              CAAAGAATAACCAGGTTAAAGAAACAAATCATAATAAAATTACATTTGAA 465
SAHV_0659 (Mu3)                 CAAAGAATAACCAGGTTAAAGAAACAAATCATAATAAAATTACATTTGAA 465
SAV0662 (Mu50)                  CAAAGAATAACCAGGTTAAAGAAACAAATCATAATAAAATTACATTTGAA 600
SA0617 (N315)                   CAAAGAATAACCAGGTTAAAGAAACAAATCATAATAAAATTACATTTGAA 600
MW0624 (MW2)                    CAAAGAATAACCAGGTTAAAGAAACAAATCATAATAAAATTACATTTGAA 600
SAS0627 (MSSA476)               CAAAGAATAACCAGGTTAAAGAAACAAATCATAATAAAATTACATTTGAA 600
SACOL0720_                      CAAAGAATAACCAGGTTAAAGAAACAAATCATAATAAAATTACATTTGAA 600
SAUSA300_0648 (USA300-FPR3757)  CAAAGAATAACCAGGTTAAAGAAACAAATCATAATAAAATTACATTTGAA 600
SAOUHSC_00668 (NCTC8325)        CAAAGAATAACCAGGTTAAAGAAACAAATCATAATAAAATTACATTTGAA 510
NWMN_0631 (Newman)              CAAAGAATAACCAGGTTAAAGAAACAAATCATAATAAAATTACATTTGAA 465
SAB0611 (RF122)                 CAAAGAATAACCAGGTTAAAGAAACAAATCATAATAAAATTACATTTGAA 600
                                **************************************************

SaurJH1_0700 (JH1)              GAGGTTGTTTTAGGCATCTTAGGTATAGTATTGATTATCACAGGATACTA 515
SaurJH9_0685 (JH9)              GAGGTTGTTTTAGGCATCTTAGGTATAGTATTGATTATCACAGGATACTA 515
SAHV_0659 (Mu3)                 GAGGTTGTTTTAGGCATCTTAGGTATAGTATTGATTACCACAGGATACTA 515
SAV0662 (Mu50)                  GAGGTTGTTTTAGGCATCTTAGGTATAGTATTGATTACCACAGGATACTA 650
SA0617 (N315)                   GAGGTTGTTTTAGGCATCTTAGGTATAGTATTGATTACCACAGGATACTA 650
MW0624 (MW2)                    GAGGTTGTTTTAGGCATCTTAGGTATAGTATTGATTACCACAGGATACTA 650
SAS0627 (MSSA476)               GAGGTTGTTTTAGGCATCTTAGGTATAGTATTGATTACCACAGGATACTA 650
SACOL0720_                      GAGGTTGTTTTAGGCATCTTAGGTATAGTATTGATTACCACAGGATACTA 650
SAUSA300_0648 (USA300-FPR3757)  GAGGTTGTTTTAGGCATCTTAGGTATAGTATTGATTACCACAGGATACTA 650
SAOUHSC_00668 (NCTC8325)        GAGGTTGTTTTAGGCATCTTAGGTATAGTATTGATTACCACAGGATACTA 560
NWMN_0631 (Newman)              GAGGTTGTTTTAGGCATCTTAGGTATAGTATTGATTACCACAGGATACTA 515
SAB0611 (RF122)                 GAGGTTGTTTTAGGCATCTTAGGTATAGTATTGATTACCACAGGATACTA 650
                                ************************************* ************

SaurJH1_0700 (JH1)              TCTATCTTTGAACATTGTTCAATATTATGATTCTATCGGTATACTTATGT 565
SaurJH9_0685 (JH9)              TCTATCTTTGAACATTGTTCAATATTATGATTCTATCGGTATACTTATGT 565
SAHV_0659 (Mu3)                 TCTATCTTTGAACATTGTTCAATATTATGATTCTATCGGTATACTTATGT 565
SAV0662 (Mu50)                  TCTATCTTTGAACATTGTTCAATATTATGATTCTATCGGTATACTTATGT 700
SA0617 (N315)                   TCTATCTTTGAACATTGTTCAATATTATGATTCTATCGGTATACTTATGT 700
MW0624 (MW2)                    TCTATCTTTGAACATTGTTCAATATTATGATTCTATCGGTATACTTATGT 700
SAS0627 (MSSA476)               TCTATCTTTGAACATTGTTCAATATTATGATTCTATCGGTATACTTATGT 700
SACOL0720_                      TCTATCTTTGAACATTGTTCAATATTATGATTCTATCGGTACACTTATGT 700
SAUSA300_0648 (USA300-FPR3757)  TCTATCTTTGAACATTGTTCAATATTATGATTCTATCGGTACACTTATGT 700
SAOUHSC_00668 (NCTC8325)        TCTATCTTTGAACATTGTTCAATATTATGATTCTATCGGTACACTTATGT 610
NWMN_0631 (Newman)              TCTATCTTTGAACATTGTTCAATATTATGATTCTATCGGTACACTTATGT 565
SAB0611 (RF122)                 TCTATCTTTGAACATTGTTCAATATTATGATTCTATCGGTACACTTATGT 700
                                ***************************************** ********
```

FIG. 12C

```
SaurJH1_0700 (JH1)              TTATTTTATTGTCAACTGTGATTGGGGCATACTTATTTTTTAAAAGCTCT 615
SaurJH9_0685 (JH9)              TTATTTTATTGTCAACTGTGATTGGGGCATACTTATTTTTTAAAAGCTCT 615
SAHV_0659 (Mu3)                 TTATTTTATTGTCAACTGTGATTGGGGCATACTTATTTTTTAAAAGCTCT 615
SAV0662 (Mu50)                  TTATTTTATTGTCAACTGTGATTGGGGCATACTTATTTTTTAAAAGCTCT 750
SA0617 (N315)                   TTATTTTATTGTCAACTGTGATTGGGGCATACTTATTTTTTAAAAGCTCT 750
MW0624 (MW2)                    TTATTTTATTGTCAACTGTGATTGGGGCATACTTATTTTTTAAAAGCTCT 750
SAS0627 (MSSA476)               TTATTTTATTGTCAACTGTGATTGGGGCATACTTATTTTTTAAAAGCTCT 750
SACOL0720_                      TTATTTTATTGTCAACTGTGATTGGGGCATACTTATTTTTTAAAAGCTCT 750
SAUSA300_0648 (USA300-FPR3757)  TTATTTTATTGTCAACTGTGATTGGGGCATACTTATTTTTTAAAAGCTCT 750
SAOUHSC_00668 (NCTC8325)        TTATTTTATTGTCAACTGTGATTGGGGCATACTTATTTTTTAAAAGCTCT 660
NWMN_0631 (Newman)              TTATTTTATTGTCAACTGTGATTGGGGCATACTTATTTTTTAAAAGCTCT 615
SAB0611 (RF122)                 TTATTTTATTGTCAACTGTGATTGGGGCATACTTATTTTTTAAAAGCTCT 750
                                **************************************************

SaurJH1_0700 (JH1)              GTTTCTCTAGTTTTTAAAATGGTGAAGAAGTTTAGAAAAGGTGTTATAAG 665
SaurJH9_0685 (JH9)              GTTTCTCTAGTTTTTAAAATGGTGAAGAAGTTTAGAAAAGGTGTTATAAG 665
SAHV_0659 (Mu3)                 GTTTCTCTAGTTTTTAAAATGGTGAAGAAGTTTAGAAAAGGTGTTATAAG 665
SAV0662 (Mu50)                  GTTTCTCTAGTTTTTAAAATGGTGAAGAAGTTTAGAAAAGGTGTTATAAG 800
SA0617 (N315)                   GTTTCTCTAGTTTTTAAAATGGTGAAGAAGTTTAGAAAAGGTGTTATAAG 800
MW0624 (MW2)                    GTTTCTCTAGTTTTTAAAATGGTGAAGAAGTTTAGAAAAGGTGTTATAAG 800
SAS0627 (MSSA476)               GTTTCTCTAGTTTTTAAAATGGTGAAGAAGTTTAGAAAAGGTGTTATAAG 800
SACOL0720_                      GTTTCTCTAGTTTTTAAAATGGTGAAGAAGTTTAGAAAAGGTGTTATAAG 800
SAUSA300_0648 (USA300-FPR3757)  GTTTCTCTAGTTTTTAAAATGGTGAAGAAGTTTAGAAAAGGTGTTATAAG 800
SAOUHSC_00668 (NCTC8325)        GTTTCTCTAGTTTTTAAAATGGTGAAGAAGTTTAGAAAAGGTGTTATAAG 710
NWMN_0631 (Newman)              GTTTCTCTAGTTTTTAAAATGGTGAAGAAGTTTAGAAAAGGTGTTATAAG 665
SAB0611 (RF122)                 GTTTCTCTAGTTTTTAAAATGGTGAAGAAGTTTAGAAAAGGTGTTATAAG 800
                                **************************************************

SaurJH1_0700 (JH1)              TGTAAATGATGTCATGTTCTCATCATCTATTATGTATCGTATTAAGAAAA 715
SaurJH9_0685 (JH9)              TGTAAATGATGTCATGTTCTCATCATCTATTATGTATCGTATTAAGAAAA 715
SAHV_0659 (Mu3)                 TGTAAATGATGTCATGTTCTCATCATCTATTATGTATCGTATTAAGAAAA 715
SAV0662 (Mu50)                  TGTAAATGATGTCATGTTCTCATCATCTATTATGTATCGTATTAAGAAAA 850
SA0617 (N315)                   TGTAAATGATGTCATGTTCTCATCATCTATTATGTATCGTATTAAGAAAA 850
MW0624 (MW2)                    TGTAAATGATGTCATGTTCTCATCATCTATTATGTATCGTATTAAGAAAA 850
SAS0627 (MSSA476)               TGTAAATGATGTCATGTTCTCATCATCTATTATGTATCGTATTAAGAAAA 850
SACOL0720                       TGTAAATGATGTCATGTTCTCATCATCTATTATGTATCGTATTAAGAAAA 850
SAUSA300_0648 (USA300-FPR3757)  TGTAAATGATGTCATGTTCTCATCATCTATTATGTATCGTATTAAGAAAA 850
SAOUHSC_00668 (NCTC8325)        TGTAAATGATGTCATGTTCTCATCATCTATTATGTATCGTATTAAGAAAA 760
NWMN_0631 (Newman)              TGTAAATGATGTCATGTTCTCATCATCTATTATGTATCGTATTAAGAAAA 715
SAB0611 (RF122)                 TGTAAATGATGTCATGTTCTCATCATCTATTATGTATCGTATTAAGAAAA 850
                                **************************************************

SaurJH1_0700 (JH1)              ATGCTTTTTCACTTACGGTCATGGCAATCATTTCAGCGATTACTGTTTCA 765
SaurJH9_0685 (JH9)              ATGCTTTTTCACTTACGGTCATGGCAATCATTTCAGCGATTACTGTTTCA 765
SAHV_0659 (Mu3)                 ATGCTTTTTCACTTACGGTCATGGCAATCATTTCAGCGATTACTGTTTCA 765
SAV0662 (Mu50)                  ATGCTTTTTCACTTACGGTCATGGCAATCATTTCAGCGATTACTGTTTCA 900
SA0617 (N315)                   ATGCTTTTTCACTTACGGTCATGGCAATCATTTCAGCGATTACTGTTTCA 900
MW0624 (MW2)                    ATGCTTTTTCACTTACGGTCATGGCAATCATTTCAGCGATTACTGTTTCA 900
SAS0627 (MSSA476)               ATGCTTTTTCACTTACGGTCATGGCAATCATTTCAGCGATTACTGTTTCA 900
SACOL0720_                      ATGCTTTTTCACTTACGGTCATGGCAATCATTTCAGCGATTACTGTTTCA 900
SAUSA300_0648 (USA300-FPR3757)  ATGCTTTTTCACTTACGGTCATGGCAATCATTTCAGCGATTACTGTTTCA 900
SAOUHSC_00668 (NCTC8325)        ATGCTTTTTCACTTACGGTCATGGCAATCATTTCAGCGATTACTGTTTCA 810
NWMN_0631 (Newman)              ATGCTTTTTCACTTACGGTCATGGCAATCATTTCAGCGATTACTGTTTCA 765
SAB0611 (RF122)                 ATGCTTTTTCACTTACGGTCATGGCAATCATTTCAGCGATTACTGTTTCA 900
                                **************************************************

SaurJH1_0700 (JH1)              GTTCTTTGCTTTGCTGCTATAAGTAGAGCGTCCTTATCAAGTGAAATAAA 815
SaurJH9_0685 (JH9)              GTTCTTTGCTTTGCTGCTATAAGTAGAGCGTCCTTATCAAGTGAAATAAA 815
SAHV_0659 (Mu3)                 GTTCTTTGCTTTGCTGCTATAAGTAGAGCGTCCTTATCAAGTGAAATAAA 815
SAV0662 (Mu50)                  GTTCTTTGCTTTGCTGCTATAAGTAGAGCGTCCTTATCAAGTGAAATAAA 950
SA0617 (N315)                   GTTCTTTGCTTTGCTGCTATAAGTAGAGCGTCCTTATCAAGTGAAATAAA 950
MW0624 (MW2)                    GTTCTTTGCTTTGCTGCTATAAGTAGAGCGTCCTTATCAAGTGAAATAAA 950
SAS0627 (MSSA476)               GTTCTTTGCTTTGCTGCTATAAGTAGAGCGTCCTTATCAAGTGAAATAAA 950
SACOL0720_                      GTTCTTTGCTTTGCTGCTATAAGTAGAGCGTCCTTATCAAGTGAAATAAA 950
SAUSA300_0648 (USA300-FPR3757)  GTTCTTTGCTTTGCTGCTATAAGTAGAGCGTCCTTATCAAGTGAAATAAA 950
SAOUHSC_00668 (NCTC8325)        GTTCTTTGCTTTGCTGCTATAAGTAGAGCGTCCTTATCAAGTGAAATAAA 860
NWMN_0631 (Newman)              GTTCTTTGCTTTGCTGCTATAAGTAGAGCGTCCTTATCAAGTGAAATAAA 815
SAB0611 (RF122)                 GTTCTTTGCTTTGCTGCTATAAGTAGAGCGTCCTTATCAAGTGAAATAAA 950
                                **************************************************
```

FIG. 12D

```
SaurJH1_0700 (JH1)                ATATACTGCACCACACGACGTTACAATTAAAGACCAACAAAAAGCTAATC 865
SaurJH9_0685 (JH9)                ATATACTGCACCACACGACGTTACAATTAAAGACCAACAAAAAGCTAATC 865
SAHV_0659 (Mu3)                   ATATACTGCACCACACGACGTTACAATTAAAGACCAACAAAAAGCTAATC 865
SAV0662 (Mu50)                    ATATACTGCACCACACGACGTTACAATTAAAGACCAACAAAAAGCTAATC 1000
SA0617 (N315)                     ATATACTGCACCACACGACGTTACAATTAAAGACCAACAAAAAGCTAATC 1000
MW0624 (MW2)                      ATATACTGCACCACACGACGTTACAATTAAAGACCAACAAAAAGCTAATC 1000
SAS0627 (MSSA476)                 ATATACTGCACCACACGACGTTACAATTAAAGACCAACAAAAAGCTAATC 1000
SACOL0720_                        ATATACTGCACCACACGACGTTACAATTAAAGACCAACAAAAAGCTAATC 1000
SAUSA300_0648 (USA300-FPR3757)    ATATACTGCACCACACGACGTTACAATTAAAGACCAACAAAAAGCTAATC 1000
SAOUHSC_00668 (NCTC8325)          ATATACTGCACCACACGACGTTACAATTAAAGACCAACAAAAAGCTAATC 910
NWMN_0631 (Newman)                ATATACTGCACCACACGACGTTACAATTAAAGACCAACAAAAAGCTAATC 865
SAB0611 (RF122)                   ATATACTGCACCACACGACGTTACAATTAAAGACCAACAAAAAGCTAATC 1000
                                  **************************************************

SaurJH1_0700 (JH1)                AATTAGCAAGTGAATTAAACAATCAAAAAATTCCTCATTTTTATAATTAT 915
SaurJH9_0685 (JH9)                AATTAGCAAGTGAATTAAACAATCAAAAAATTCCTCATTTTTATAATTAT 915
SAHV_0659 (Mu3)                   AATTAGCAAGTGAATTAAACAATCAAAAAATTCCTCATTTTTATAATTAT 915
SAV0662 (Mu50)                    AATTAGCAAGTGAATTAAACAATCAAAAAATTCCTCATTTTTATAATTAT 1050
SA0617 (N315)                     AATTAGCAAGTGAATTAAACAATCAAAAAATTCCTCATTTTTATAATTAT 1050
MW0624 (MW2)                      AATTAGCAAGTGAATTAAACAATCAAAAAATTCCTCATTTTTATAATTAT 1050
SAS0627 (MSSA476)                 AATTAGCAAGTGAATTAAACAATCAAAAAATTCCTCATTTTTATAATTAT 1050
SACOL0720_                        AATTAGCAAGTGAATTAAACAATCAAAAAATTCCTCATTTTTATAATTAT 1050
SAUSA300_0648 (USA300-FPR3757)    AATTAGCAAGTGAATTAAACAATCAAAAAATTCCTCATTTTTATAATTAT 1050
SAOUHSC_00668 (NCTC8325)          AATTAGCAAGTGAATTAAACAATCAAAAAATTCCTCATTTTTATAATTAT 960
NWMN_0631 (Newman)                AATTAGCAAGTGAATTAAACAATCAAAAAATTCCTCATTTTTATAATTAT 915
SAB0611 (RF122)                   AATTAGCAAGTGAATTAAACAATCAAAAAATTCCTCATTTTTATAATTAT 1050
                                  **************************************************

SaurJH1_0700 (JH1)                AAAGAAGTAATTCATACGAAATTGTATAAAGATAATTTATTTGATGTAAA 965
SaurJH9_0685 (JH9)                AAAGAAGTAATTCATACGAAATTGTATAAAGATAATTTATTTGATGTAAA 965
SAHV_0659 (Mu3)                   AAAGAAGTAATTCATACGAAATTGTATAAAGATAATTTATTTGATGTAAA 965
SAV0662 (Mu50)                    AAAGAAGTAATTCATACGAAATTGTATAAAGATAATTTATTTGATGTAAA 1100
SA0617 (N315)                     AAAGAAGTAATTCATACGAAATTGTATAAAGATAATTTATTTGATGTAAA 1100
MW0624 (MW2)                      AAAGAAGTAATTCATACGAAATTGTATAAAGATAATTTATTTGATGTAAA 1100
SAS0627 (MSSA476)                 AAAGAAGTAATTCATACGAAATTGTATAAAGATAATTTATTTGATGTAAA 1100
SACOL0720_                        AAAGAAGTAATTCATACGAAATTGTATAAAGATAATTTATTTGATGTAAA 1100
SAUSA300_0648 (USA300-FPR3757)    AAAGAAGTAATTCATACGAAATTGTATAAAGATAATTTATTTGATGTAAA 1100
SAOUHSC_00668 (NCTC8325)          AAAGAAGTAATTCATACGAAATTGTATAAAGATAATTTATTTGATGTAAA 1010
NWMN_0631 (Newman)                AAAGAAGTAATTCATACGAAATTGTATAAAGATAATTTATTTGATGTAAA 965
SAB0611 (RF122)                   AAAGAAGTAATTCATACGAAATTGTATAAAGATAATTTATTTGATGTAAA 1100
                                  **************************************************

SaurJH1_0700 (JH1)                AGCGAAAGAACCATACAATGTAACAATTACTAGTGATAAATATATCCCTA 1015
SaurJH9_0685 (JH9)                AGCGAAAGAACCATACAATGTAACAATTACTAGTGATAAATATATCCCTA 1015
SAHV_0659 (Mu3)                   AGCGAAAGAACCATACAATGTAACAATTACTAGTGATAAATATATCCCTA 1015
SAV0662 (Mu50)                    AGCGAAAGAACCATACAATGTAACAATTACTAGTGATAAATATATCCCTA 1150
SA0617 (N315)                     AGCGAAAGAACCATACAATGTAACAATTACTAGTGATAAATATATCCCTA 1150
MW0624 (MW2)                      AGCGAAAGAACCATACAATGTAACAATTACTAGTGATAAATATATCCCTA 1150
SAS0627 (MSSA476)                 AGCGAAAGAACCATACAATGTAACAATTACTAGTGATAAATATATCCCTA 1150
SACOL0720_                        AGCGAAAGAACCATACAATGTAACAATTACTAGTGATAAATACATCCCTA 1150
SAUSA300_0648 (USA300-FPR3757)    AGCGAAAGAACCATACAATGTAACAATTACTAGTGATAAATACATCCCTA 1150
SAOUHSC_00668 (NCTC8325)          AGCGAAAGAACCATACAATGTAACAATTACTAGTGATAAATACATCCCTA 1060
NWMN_0631 (Newman)                AGCGAAAGAACCATACAATGTAACAATTACTAGTGATAAATACATCCCTA 1015
SAB0611 (RF122)                   ATCGAAACAACCATACAATGTAACAATTACTAGTGATAAATACATCCCTA 1150
                                  * ***** ********************************** *******

SaurJH1_0700 (JH1)                ATACTGATTTGAAACGTGGACAAGCTGATTTGTTTGTAGCGGAAGGTTCT 1065
SaurJH9_0685 (JH9)                ATACTGATTTGAAACGTGGACAAGCTGATTTGTTTGTAGCGGAAGGTTCT 1065
SAHV_0659 (Mu3)                   ATACTGATTTGAAACGTGGACAAGCTGATTTGTTTGTAGCGGAAGGTTCT 1065
SAV0662 (Mu50)                    ATACTGATTTGAAACGTGGACAAGCTGATTTGTTTGTAGCGGAAGGTTCT 1200
SA0617 (N315)                     ATACTGATTTGAAACGTGGACAAGCTGATTTGTTTGTAGCGGAAGGTTCT 1200
MW0624 (MW2)                      ATACTGATTTGAAACGTGGACAAGCTGATTTGTTTGTAGCGGAAGGTTCT 1200
SAS0627 (MSSA476)                 ATACTGATTTGAAACGTGGACAAGCTGATTTGTTTGTAGCGGAAGGTTCT 1200
SACOL0720_                        ATACTGATTTGAAACGTGGGCAAGCTGATTTATTTGTAGCGGAAGGTTCT 1200
SAUSA300_0648 (USA300-FPR3757)    ATACTGATTTGAAACGTGGGCAAGCTGATTTATTTGTAGCGGAAGGTTCT 1200
SAOUHSC_00668 (NCTC8325)          ATACTGATTTGAAACGTGGGCAAGCTGATTTATTTGTAGCGGAAGGTTCT 1110
NWMN_0631 (Newman)                ATACTGATTTGAAACGTGGGCAAGCTGATTTATTTGTAGCGGAAGGTTCT 1065
SAB0611 (RF122)                   GTACTGATTTGAAACGTGGGCAAGCTGATTTGTTTGTAGCGGAAGGTTCT 1200
                                   ****************** *********** ******************
```

FIG. 12E

| Strain | Sequence | Position |
|---|---|---|
| SaurJH1_0700 (JH1) | ATCAAAGATTTAGTGAAACATAAGAAGCATGGTAAGGCAATTATAGGAAC | 1115 |
| SaurJH9_0685 (JH9) | ATCAAAGATTTAGTGAAACATAAGAAGCATGGTAAGGCAATTATAGGAAC | 1115 |
| SAHV_0659 (Mu3) | ATCAAAGATTTAGTGAAACATAAGAAGCATGGTAAGGCAATTATAGGAAC | 1115 |
| SAV0662 (Mu50) | ATCAAAGATTTAGTGAAACATAAGAAGCATGGTAAGGCAATTATAGGAAC | 1250 |
| SA0617 (N315) | ATCAAAGATTTAGTGAAACATAAGAAGCATGGTAAGGCAATTATAGGAAC | 1250 |
| MW0624 (MW2) | ATCAAAGATTTAGTGAAACATAAGAAGCATGGTAAAGCAGTTATAGGAAC | 1250 |
| SAS0627 (MSSA476) | ATCAAAGATTTAGTGAAACATAAGAAGCATGGTAAAGCAGTTATAGGAAC | 1250 |
| SACOL0720_ | ATCAAAGATTTAGTGAAACATAAGAAGCATGGTAAGGCAATTATAGGAAC | 1250 |
| SAUSA300_0648 (USA300-FPR3757) | ATCAAAGATTTAGTGAAACATAAGAAGCATGGTAAGGCAATTATAGGAAC | 1250 |
| SAOUHSC_00668 (NCTC8325) | ATCAAAGATTTAGTGAAACATAAGAAGCATGGTAAGGCAATTATAGGAAC | 1160 |
| NWMN_0631 (Newman) | ATCAAAGATTTAGTGAAACATAAGAAGCATGGTAAGGCAATTATAGGAAC | 1115 |
| SAB0611 (RF122) | ATCAAAGATTTAGTGAAACATAAGAAGCATGGTAAAGCAGTTATAGGAAC | 1250 |
| | *********************************** *** ********** | |

| Strain | Sequence | Position |
|---|---|---|
| SaurJH1_0700 (JH1) | GAAAAAACATCATGTTAATATTAAGTTACGGAAAGATATTAATAAAATCT | 1165 |
| SaurJH9_0685 (JH9) | GAAAAAACATCATGTTAATATTAAGTTACGGAAAGATATTAATAAAATCT | 1165 |
| SAHV_0659 (Mu3) | GAAAAAACATCATGTTAATATTAAGTTACGGAAAGATATTAATAAAATCT | 1165 |
| SAV0662 (Mu50) | GAAAAAACATCATGTTAATATTAAGTTACGGAAAGATATTAATAAAATCT | 1300 |
| SA0617 (N315) | GAAAAAACATCATGTTAATATTAAGTTACGGAAAGATATTAATAAAATCT | 1300 |
| MW0624 (MW2) | GAAAAAACATCATGTTAATATTAAGTTGCGGAAAGATATTAATAAAATCT | 1300 |
| SAS0627 (MSSA476) | GAAAAAACATCATGTTAATATTAAGTTGCGGAAAGATATTAATAAAATCT | 1300 |
| SACOL0720_ | GAAAAAACATCATGTTAATATTAAGTTACGTAAAGATATTAATAAAATCT | 1300 |
| SAUSA300_0648 (USA300-FPR3757) | GAAAAAACATCATGTTAATATTAAGTTACGTAAAGATATTAATAAAATCT | 1300 |
| SAOUHSC_00668 (NCTC8325) | GAAAAAACATCATGTTAATATTAAGTTACGTAAAGATATTAATAAAATCT | 1210 |
| NWMN_0631 (Newman) | GAAAAAACATCATGTTAATATTAAGTTACGTAAAGATATTAATAAAATCT | 1165 |
| SAB0611 (RF122) | GAAAAAACATCATGTTAATATTAAGTTACGTAAAGATATTAATAAAATCT | 1300 |
| | *************************** ** ******************* | |

| Strain | Sequence | Position |
|---|---|---|
| SaurJH1_0700 (JH1) | ATTTTATGACAGATGTTGATTTAGGTGGACCAACGTTTGTCTTAAATGAC | 1215 |
| SaurJH9_0685 (JH9) | ATTTTATGACAGATGTTGATTTAGGTGGACCAACGTTTGTCTTAAATGAC | 1215 |
| SAHV_0659 (Mu3) | ATTTTATGACAGATGTTGATTTAGGTGGACCAACGTTTGTCTTAAATGAC | 1215 |
| SAV0662 (Mu50) | ATTTTATGACAGATGTTGATTTAGGTGGACCAACGTTTGTCTTAAATGAC | 1350 |
| SA0617 (N315) | ATTTTATGACAGATGTTGATTTAGGTGGACCAACGTTTGTCTTAAATGAC | 1350 |
| MW0624 (MW2) | ATTTTATGACAGATGTTGATTTAGGTGGACCAACGTTTGTCTTAAATGAC | 1350 |
| SAS0627 (MSSA476) | ATTTTATGACAGATGTTGATTTAGGTGGACCAACGTTTGTCTTAAATGAC | 1350 |
| SACOL0720_ | ATTTTATGACAGATGTTGATTTAGGTGGACCAACGTTTGTCTTAAATGAC | 1350 |
| SAUSA300_0648 (USA300-FPR3757) | ATTTTATGACAGATGTTGATTTAGGTGGACCAACGTTTGTCTTAAATGAC | 1350 |
| SAOUHSC_00668 (NCTC8325) | ATTTTATGACAGATGTTGATTTAGGTGGACCAACGTTTGTCTTAAATGAC | 1260 |
| NWMN_0631 (Newman) | ATTTTATGACAGATGTTGATTTAGGTGGACCAACGTTTGTCTTAAATGAC | 1215 |
| SAB0611 (RF122) | ATTTTATGACAGATGTTGATTTAGGTGGACCAACGTTTGTCTTAAATGAC | 1350 |
| | ************************************************** | |

| Strain | Sequence | Position |
|---|---|---|
| SaurJH1_0700 (JH1) | AAAGACTATCAAGAAATAAGAAAGTATACAAAAGCAAAGCATATCGTCTC | 1265 |
| SaurJH9_0685 (JH9) | AAAGACTATCAAGAAATAAGAAAGTATACAAAAGCAAAGCATATCGTCTC | 1265 |
| SAHV_0659 (Mu3) | AAAGACTATCAAGAAATAAGAAAGTATACAAAAGCAAAGCATATCGTCTC | 1265 |
| SAV0662 (Mu50) | AAAGACTATCAAGAAATAAGAAAGTATACAAAAGCAAAGCATATCGTCTC | 1400 |
| SA0617 (N315) | AAAGACTATCAAGAAATAAGAAAGTATACAAAAGCAAAGCATATCGTCTC | 1400 |
| MW0624 (MW2) | AAAGACTATCAAGAAATAAGAAAGTATACAAAAGCAAAGCATATCGTCTC | 1400 |
| SAS0627 (MSSA476) | AAAGACTATCAAGAAATAAGAAAGTATACAAAAGCAAAGCATATCGTCTC | 1400 |
| SACOL0720_ | AAAGACTATCAAGAAATAAGAAAGTATACAAAGGCAAAGCATATCGTCTC | 1400 |
| SAUSA300_0648 (USA300-FPR3757) | AAAGACTATCAAGAAATAAGAAAGTATACAAAGGCAAAGCATATCGTCTC | 1400 |
| SAOUHSC_00668 (NCTC8325) | AAAGACTATCAAGAAATAAGAAAGTATACAAAGGCAAAGCATATCGTCTC | 1310 |
| NWMN_0631 (Newman) | AAAGACTATCAAGAAATAAGAAAGTATACAAAGGCAAAGCATATCGTCTC | 1265 |
| SAB0611 (RF122) | AAAGACTATCAAGAAATAAGAAAGTATACAAAGGCAAAGCATATCGTCTC | 1400 |
| | ********************************* **************** | |

| Strain | Sequence | Position |
|---|---|---|
| SaurJH1_0700 (JH1) | TCAATTTGGATTCGATTTGAAACATAAAAAAGATGCTTTAGCATTAGAAA | 1315 |
| SaurJH9_0685 (JH9) | TCAATTTGGATTCGATTTGAAACATAAAAAAGATGCTTTAGCATTAGAAA | 1315 |
| SAHV_0659 (Mu3) | TCAATTTGGATTCGATTTGAAACATAAAAAAGATGCTTTAGCATTAGAAA | 1315 |
| SAV0662 (Mu50) | TCAATTTGGATTCGATTTGAAACATAAAAAAGATGCTTTAGCATTAGAAA | 1450 |
| SA0617 (N315) | TCAATTTGGATTCGATTTGAAACATAAAAAAGATGCTTTAGCATTAGAAA | 1450 |
| MW0624 (MW2) | TCAATTTGGATTCGATTTGAAACATAAAAAAGATGCTTTAGCATTAGAAA | 1450 |
| SAS0627 (MSSA476) | TCAATTTGGATTCGATTTGAAACATAAAAAAGATGCTTTAGCATTAGAAA | 1450 |
| SACOL0720_ | TCAATTTGGATTCGATTTGAAACATAAAAAAGATGCTTTAGCATTAGAAA | 1450 |
| SAUSA300_0648 (USA300-FPR3757) | TCAATTTGGATTCGATTTGAAACATAAAAAAGATGCTTTAGCATTAGAAA | 1450 |
| SAOUHSC_00668 (NCTC8325) | TCAATTTGGATTCGATTTGAAACATAAAAAAGATGCTTTAGCATTAGAAA | 1360 |
| NWMN_0631 (Newman) | TCAATTTGGATTCGATTTGAAACATAAAAAAGATGCTTTAGCATTAGAAA | 1315 |
| SAB0611 (RF122) | TCAATTTGGATTCGATTTGAAACATAAAAAAGATGCTTTAGCATTAGAAA | 1450 |
| | ************************************************** | |

FIG. 12F

```
SaurJH1_0700 (JH1)                  AAGTGAAAAATAAAGTTGATAAATCTATTAAAACAAGAAGTGAAGCGATA 1365
SaurJH9_0685 (JH9)                  AAGTGAAAAATAAAGTTGATAAATCTATTAAAACAAGAAGTGAAGCGATA 1365
SAHV_0659 (Mu3)                     AAGTGAAAAATAAAGTTGATAAATCTATTAAAACAAGAAGTGAAGCGATA 1365
SAV0662 (Mu50)                      AAGTGAAAAATAAAGTTGATAAATCTATTAAAACAAGAAGTGAAGCGATA 1500
SA0617 (N315)                       AAGTGAAAAATAAAGTTGATAAATCTATTAAAACAAGAAGTGAAGCGATA 1500
MW0624 (MW2)                        AAGTGAAAAATAAAGTTGATAAATCTATTAAAACAAGAAGTGAAGCGATA 1500
SAS0627 (MSSA476)                   AAGTGAAAAATAAAGTTGATAAATCTATTAAAACAAGAAGTGAAGCGATA 1500
SACOL0720                           AAGCGAAAAATAAAGTTGATAAATCTATTGAAACAAGAAGTGAAGCGATA 1500
SAUSA300_0648 (USA300-FPR3757)      AAGCGAAAAATAAAGTTGATAAATCTATTGAAACAAGAAGTGAAGCGATA 1500
SAOUHSC_00668 (NCTC8325)            AAGCGAAAAATAAAGTTGATAAATCTATTGAAACAAGAAGTGAAGCGATA 1410
NWMN_0631 (Newman)                  AAGCGAAAAATAAAGTTGATAAATCTATTGAAACAAGAAGTGAAGCGATA 1365
SAB0611 (RF122)                     AAGCGAAAAATAAAGTTGATAAATCTATTGAGACAAGAAGTGAAGCGATA 1500
                                    *** ************************* * ******************

SaurJH1_0700 (JH1)                  AGCTCAATATCAAGTTTAACCGGAATATTATTATTTGTAACATCATTTTT 1415
SaurJH9_0685 (JH9)                  AGCTCAATATCAAGTTTAACCGGAATATTATTATTTGTAACATCATTTTT 1415
SAHV_0659 (Mu3)                     AGCTCAATATCAAGTTTAACCGGAATATTATTATTTGTAACATCATTTTT 1415
SAV0662 (Mu50)                      AGCTCAATATCAAGTTTAACCGGAATATTATTATTTGTAACATCATTTTT 1550
SA0617 (N315)                       AGCTCAATATCAAGTTTAACCGGAATATTATTATTTGTAACATCATTTTT 1550
MW0624 (MW2)                        AGCTCAATATCAAGTTTAACCGGAATATTATTATTTGTAACATCATTTTT 1550
SAS0627 (MSSA476)                   AGCTCAATATCAAGTTTAACCGGAATATTATTATTTGTAACATCATTTTT 1550
SACOL0720_                          AGCTCAATATCAAGTTTAACCGGAATATTATTATTTGTAACATCATTTTT 1550
SAUSA300_0648 (USA300-FPR3757)      AGCTCAATATCAAGTTTAACCGGAATATTATTATTTGTAACATCATTTTT 1550
SAOUHSC_00668 (NCTC8325)            AGCTCAATATCAAGTTTAACCGGAATATTATTATTTGTAACATCATTTTT 1460
NWMN_0631 (Newman)                  AGCTCAATATCAAGTTTAACCGGAATATTATTATTTGTAACATCATTTTT 1415
SAB0611 (RF122)                     AGCTCAATATCAAGTTTAACCGGAATATTATTATTTGTAACATCATTTTT 1550
                                    **************************************************

SaurJH1_0700 (JH1)                  AGGTATTACATTCTTGATTGCTGTATGTTGCATTATATACATTAAGCAAA 1465
SaurJH9_0685 (JH9)                  AGGTATTACATTCTTGATTGCTGTATGTTGCATTATATACATTAAGCAAA 1465
SAHV_0659 (Mu3)                     AGGTATTACATTCTTGATTGCTGTATGTTGCATTATATACATTAAGCAAA 1465
SAV0662 (Mu50)                      AGGTATTACATTCTTGATTGCTGTATGTTGCATTATATACATTAAGCAAA 1600
SA0617 (N315)                       AGGTATTACATTCTTGATTGCTGTATGTTGCATTATATACATTAAGCAAA 1600
MW0624 (MW2)                        AGGTATTACATTCTTGATTGCTGTATGTTGCATTATATACATAAAGCAAA 1600
SAS0627 (MSSA476)                   AGGTATTACATTCTTGATTGCTGTATGTTGCATTATATACATAAAGCAAA 1600
SACOL0720_                          AGGTATTACATTCTTGATTGCTGTATGTTGCATTATATACATAAAGCAAA 1600
SAUSA300_0648 (USA300-FPR3757)      AGGTATTACATTCTTGATTGCTGTATGTTGCATTATATACATAAAGCAAA 1600
SAOUHSC_00668 (NCTC8325)            AGGTATTACATTCTTGATTGCTGTATGTTGCATTATATACATAAAGCAAA 1510
NWMN_0631 (Newman)                  AGGTATTACATTCTTGATTGCTGTATGTTGCATTATATACATAAAGCAAA 1465
SAB0611 (RF122)                     AGGTATTACATTCTTGATTGCTGTATGTTGCATTATATACATTAAGCAAA 1600
                                    ***************************************** ********

SaurJH1_0700 (JH1)                  TAGATGAAACCGAAGATGAGTTAGAGAATTATAGTATATTGAGAAAGCTT 1515
SaurJH9_0685 (JH9)                  TAGATGAAACCGAAGATGAGTTAGAGAATTATAGTATATTGAGAAAGCTT 1515
SAHV_0659 (Mu3)                     TAGATGAAACCGAAGATGAGTTAGAGAATTATAGTATATTGAGAAAGCTT 1515
SAV0662 (Mu50)                      TAGATGAAACCGAAGATGAGTTAGAGAATTATAGTATATTGAGAAAGCTT 1650
SA0617 (N315)                       TAGATGAAACCGAAGATGAGTTAGAGAATTATAGTATATTGAGAAAGCTT 1650
MW0624 (MW2)                        TAGATGAAACCGAAGATGAGTTAGAGAATTATAGTATTTTGAGAAAGCTT 1650
SAS0627 (MSSA476)                   TAGATGAAACCGAAGATGAGTTAGAGAATTATAGTATTTTGAGAAAGCTT 1650
SACOL0720_                          TAGATGAAACCGAAGATGAGTTAGAGAATTATAGTATTTTGAGAAAGCTT 1650
SAUSA300_0648 (USA300-FPR3757)      TAGATGAAACCGAAGATGAGTTAGAGAATTATAGTATTTTGAGAAAGCTT 1650
SAOUHSC_00668 (NCTC8325)            TAGATGAAACCGAAGATGAGTTAGAGAATTATAGTATTTTGAGAAAGCTT 1560
NWMN_0631 (Newman)                  TAGATGAAACCGAAGATGAGTTAGAGAATTATAGTATTTTGAGAAAGCTT 1515
SAB0611 (RF122)                     TAGATGAAACCGAAGATGAGTTAGAGAATTATAGTATATTGAGAAAGCTT 1650
                                    ************************************* ************

SaurJH1_0700 (JH1)                  GGATTTACACAAAAAGATATGGCAAGGGGACTAAAGTTTAAAATTATGTT 1565
SaurJH9_0685 (JH9)                  GGATTTACACAAAAAGATATGGCAAGGGGACTAAAGTTTAAAATTATGTT 1565
SAHV_0659 (Mu3)                     GGATTTACACAAAAAGATATGGCAAGGGGACTAAAGTTTAAAATTATGTT 1565
SAV0662 (Mu50)                      GGATTTACACAAAAAGATATGGCAAGGGGACTAAAGTTTAAAATTATGTT 1700
SA0617 (N315)                       GGATTTACACAAAAAGATATGGCAAGGGGACTAAAGTTTAAAATTATGTT 1700
MW0624 (MW2)                        GGATTTACACAAAAAGATATGGCAAGGGGACTAAAGTTTAAAATTATGTT 1700
SAS0627 (MSSA476)                   GGATTTACACAAAAAGATATGGCAAGGGGACTAAAGTTTAAAATTATGTT 1700
SACOL0720                           GGATTTACACAAAAAGATATGGCAAGGGGACTAAAGTTTAAAATTATGTT 1700
SAUSA300_0648 (USA300-FPR3757)      GGATTTACACAAAAAGATATGGCAAGGGGACTAAAGTTTAAAATTATGTT 1700
SAOUHSC_00668 (NCTC8325)            GGATTTACACAAAAAGATATGGCAAGGGGACTAAAGTTTAAAATTATGTT 1610
NWMN_0631 (Newman)                  GGATTTACACAAAAAGATATGGCAAGGGGACTAAAGTTTAAAATTATGTT 1565
SAB0611 (RF122)                     GGATTTACACAAAAAGATATGGCAAGGGGACTAAAGTTTAAAATTATGTT 1700
                                    **************************************************
```

FIG. 12G

```
SaurJH1_0700 (JH1)                TAATTTTGGGTTACCTTTAGTTATTGCACTATCACATGCATATTTTACAT 1615
SaurJH9_0685 (JH9)                TAATTTTGGGTTACCTTTAGTTATTGTACTATCACATGCATATTTTACAT 1615
SAHV_0659 (Mu3)                   TAATTTTGGGTTACCTTTAGTTATTGCACTATCACATGCATATTTTACAT 1615
SAV0662 (Mu50)                    TAATTTTGGGTTACCTTTAGTTATTGCACTATCACATGCATATTTTACAT 1750
SA0617 (N315)                     TAATTTTGGGTTACCTTTAGTTATTGCACTATCACATGCATATTTTACAT 1750
MW0624 (MW2)                      TAATTTTGGGTTACCTTTAGTTATTGCACTATCACATGCATATTTTACAT 1750
SAS0627 (MSSA476)                 TAATTTTGGGTTACCTTTAGTTATTGCACTATCACATGCATATTTTACAT 1750
SACOLC720_                        TAATTTTGGGTTACCTTTAGTTATTGCACTATCACATGCATATTTTACAT 1750
SAUSA300_0648 (USA300-FPR3757)    TAATTTTGGGTTACCTTTAGTTATTGCACTATCACATGCATATTTTACAT 1750
SAOUHSC_00668 (NCTC8325)          TAATTTTGGGTTACCTTTAGTTATTGCACTATCACATGCATATTTTACAT 1660
NWMN_0631 (Newman)                TAATTTTGGGTTACCTTTAGTTATTGCACTATCACATGCATATTTTACAT 1615
SAB0611 (RF122)                   TAATTTTGGGTTACCTTTAGTTATTGCACTATCACATGCATATTTTACAT 1750
                                  ************************** ***********************

SaurJH1_0700 (JH1)                CATTAGCATATATGAAATTAATGGGTACAACGAATCAAATACCGGTTTTC 1665
SaurJH9_0685 (JH9)                CATTAGCATATATGAAATTAATGGGTACAACGAATCAAATACCGGTTTTC 1665
SAHV_0659 (Mu3)                   CATTAGCATATATGAAATTAATGGGTACAACGAATCAAATACCGGTTTTC 1665
SAV0662 (Mu50)                    CATTAGCATATATGAAATTAATGGGTACAACGAATCAAATACCGGTTTTC 1800
SA0617 (N315)                     CATTAGCATATATGAAATTAATGGGTACAACGAATCAAATACCGGTTTTC 1800
MW0624 (MW2)                      CATTAGCATATATGAAATTAATGGGTACAACGAATCAAATACCGGTTTTC 1800
SAS0627 (MSSA476)                 CATTAGCATATATGAAATTAATGGGTACAACGAATCAAATACCGGTTTTC 1800
SACOLC720_                        CATTAGCATATATGAAATTAATGGGTACAACGAATCAAATACCGGTTTTC 1800
SAUSA300_0648 (USA300-FPR3757)    CATTAGCATATATGAAATTAATGGGTACAACGAATCAAATACCGGTTTTC 1800
SAOUHSC_00668 (NCTC8325)          CATTAGCATATATGAAATTAATGGGTACAACGAATCAAATACCGGTTTTC 1710
NWMN_0631 (Newman)                CATTAGCATATATGAAATTAATGGGTACAACGAATCAAATACCGGTTTTC 1665
SAB0611 (RF122)                   CATTAGCATATATGAAATTAATGGGTACAACGAATCAAATACCGGTTTTC 1800
                                  **************************************************

SaurJH1_0700 (JH1)                ATAGTAATGGGATTATACATTTGTATGTATGCTGTTTTTGCAGTGACGGC 1715
SaurJH9_0685 (JH9)                ATAGTAATGGGATTATACATTTGTATGTATGCTGTTTTTGCAGTGACGGC 1715
SAHV_0659 (Mu3)                   ATAGTAATGGGATTATACATTTGTATGTATGCTGTTTTTGCAGTGACGGC 1715
SAV0662 (Mu50)                    ATAGTAATGGGATTATACATTTGTATGTATGCTGTTTTTGCAGTGACGGC 1850
SA0617 (N315)                     ATAGTAATGGGATTATACATTTGTATGTATGCTGTTTTTGCAGTGACGGC 1850
MW0624 (MW2)                      ATAGTAATGGGATTATACATTTGTATGTATGCTGTTTTTGCAGTGACGGC 1850
SAS0627 (MSSA476)                 ATAGTAATGGGATTATACATTTGTATGTATGCTGTTTTTGCAGTGACGGC 1850
SACOLC720                         ATAGTAATGGGATTATACATTTGTATGTATGCTGTTTTTGCAGTGACGGC 1850
SAUSA300_0648 (USA300-FPR3757)    ATAGTAATGGGATTATACATTTGTATGTATGCTGTTTTTGCAGTGACGGC 1850
SAOUHSC_00668 (NCTC8325)          ATAGTAATGGGATTATACATTTGTATGTATGCTGTTTTTGCAGTGACGGC 1760
NWMN_0631 (Newman)                ATAGTAATGGGATTATACATTTCTATGTATGCTCTTTTTGCACTCACGGC 1715
SAB0611 (RF122)                   ATAGTAATGGGATTATACATTTGTATGTATGCTGTTTTTGCAGTGACGGC 1850
                                  **************************************************

SaurJH1_0700 (JH1)                TTATAATCATTCCAAGCGAACAATTAGACATTCCATATAA 1755
SaurJH9_0685 (JH9)                TTATAATCATTCCAAGCGAACAATTAGACATTCCATATAA 1755
SAHV_0659 (Mu3)                   TTATAATCATTCCAAGCGAACAATTAGACATTCCATATAA 1755
SAV0662 (Mu50)                    TTATAATCATTCCAAGCGAACAATTAGACATTCCATATAA 1890
SA0617 (N315)                     TTATAATCATTCCAAGCGAACAATTAGACATTCCATATAA 1890
MW0624 (MW2)                      TTATAATCATTCCAAGCGAACAATTAGACATTCCATATAA 1890
SAS0627 (MSSA476)                 TTATAATCATTCCAAGCGAACAATTAGACATTCCATATAA 1890
SACOLC720_                        TTATAATCATTCCAAGCGAACAATTAGACATTCCATATAA 1890
SAUSA300_0648 (USA300-FPR3757)    TTATAATCATTCCAAGCGAACAATTAGACATTCCATATAA 1890
SAOUHSC_00668 (NCTC8325)          TTATAATCATTCCAAGCGAACAATTAGACATTCCATATAA 1800
NWMN_0631 (Newman)                TTATAATCATTCCAAGCGAACAATTAGACATTCCATATAA 1755
SAB0611 (RF122)                   TTATAATCATTCCAAGCGAACAATTAGACATTCCATATAA 1890
                                  ****************************************
```

FIG. 12H

Multiple sequence alignment: SACOL0720
Amino acids

```
SACOL0720_                           MTFNEIIFKNFRQNLSHYAIYLFSLIISVVLYFSFVALKYAHKLNMTESY 50
SAUSA300_0648 (USA300-FPR3757)       MTFNEIIFKNFRQNLSHYAIYLFSLIISVVLYFSFVALKYAHKLNMTESY 50
SAOUHSC_00668 (NCTC8325)             ------------------------------MYFSFVALKYAHKLNMTESY 20
NWMN_0631 (Newman)                   ---------------------------------------------MTESY 5
SaurJH1_0700 (JH1)                   ---------------------------------------------MTESY 5
SaurJH9_0685 (JH9)                   ---------------------------------------------MTESY 5
SAHV_0659 (Mu3)                      ---------------------------------------------MTESY 5
SAV0662 (Mu50)                       MTFNEIIFKNFRQNLSHYAIYLFSLIISVVLYFSFVALKYAHKLNMTESY 50
SA0617 (N315)                        MTFNEIIFKNFRQNLSHYAIYLFSLIISVVLYFSFVALKYAHKLNMTESY 50
MW0624 (MW2)                         MTFNEIIFKNFRQNLSHYAIYLFSLIISVVLYFSFVALKYAHKLNMTESY 50
SAS0627 (MSSA476)                    MTFNEIIFKNFRQNLSHYAIYLFSLIISVVLYFSFVALKYAHKLNMTESY 50
SAB0611 (RF122)                      MTFNEIIFKNFRQNLSHYAIYLFSLIISVVLYFSFVALKYAHKLNMTESY 50
                                                                                 *****

SACOL0720_                           PIIKEGSQVGSYFLFFIIIAFLLYANVLFIKRRSYELALYQTLGLSKFNI 100
SAUSA300_0648 (USA300-FPR3757)       PIIKEGSQVGSYFLFFIIIAFLLYANVLFIKRRSYELALYQTLGLSKFNI 100
SAOUHSC_00668 (NCTC8325)             PIIKEGSQVGSYFLFFIIIAFLLYANVLFIKRRSYELALYQTLGLSKFNI 70
NWMN_0631 (Newman)                   PIIKEGSQVGSYFLFFIIIAFLLYANVLFIKRRSYELALYQTLGLSKFNI 55
SaurJH1_0700 (JH1)                   PIIKEGSQVGSYFLFFIIIAFLLYANVLFIKRRSYELALYQTLGLSKFNI 55
SaurJH9_0685 (JH9)                   PIIKEGSQVGSYFLFFIIIAFLLYANVLFIKRRSYELALYQTLGLSKFNI 55
SAHV_0659 (Mu3)                      PIIKEGSQVGSYFLFFIIIAFLLYANVLFIKRRSYELALYQTLGLSKFNI 55
SAV0662 (Mu50)                       PIIKEGSQVGSYFLFFIIIAFLLYANVLFIKRRSYELALYQTLGLSKFNI 100
SA0617 (N315)                        PIIKEGSQVGSYFLFFIIIAFLLYANVLFIKRRSYELALYQTLGLSKFNI 100
MW0624 (MW2)                         PIIKEGSQVGSYFLFFIIIAFLLYANVLFIKRRSYELALYQTLGLSKFNI 100
SAS0627 (MSSA476)                    PIIKEGSQVGSYFLFFIIIAFLLYANVLFIKRRSYELALYQTLGLSKFNI 100
SAB0611 (RF122)                      PIIKEGSQVGSYFLFFIIIAFLLYANVLFIKRRSYELALYQTLGLSKFNI 100
                                     **************************************************

SACOL0720_                           IYILMLEQLLIFIITAILGIIIGIFGSKLLLMIVFTLLGIKEKVPIIFSL 150
SAUSA300_0648 (USA300-FPR3757)       IYILMLEQLLIFIITAILGIIIGIFGSKLLLMIVFTLLGIKEKVPIIFSL 150
SAOUHSC_00668 (NCTC8325)             IYILMLEQLLIFIITAILGIIIGIFGSKLLLMIVFTLLGIKEKVPIIFSL 120
NWMN_0631 (Newman)                   IYILMLEQLLIFIITAILGIIIGIFGSKLLLMIVFTLLGIKEKVPIIFSL 105
SaurJH1_0700 (JH1)                   IYILMLEQLLIFIITAILGIIIGIFGSKLLLMIVFTLLGIKEKVPIIFSL 105
SaurJH9_0685 (JH9)                   IYILMLEQLLIFIITAILGIIIGIFGSKLLLMIVFTLLGIKEKVPIIFSL 105
SAHV_0659 (Mu3)                      IYILMLEQLLIFIITAILGIIIGIFGSKLLLMIVFTLLGIKEKVPIIFSL 105
SAV0662 (Mu50)                       IYILMLEQLLIFIITAILGIIIGIFGSKLLLMIVFTLLGIKEKVPIIFSL 150
SA0617 (N315)                        IYILMLEQLLIFIITAILGIIIGIFGSKLLLMIVFTLLGIKEKVPIIFSL 150
MW0624 (MW2)                         IYILMLEQLLIFIITAILGIIIGIFGSKLLLMIVFTLLGIKEKVPIIFSL 150
SAS0627 (MSSA476)                    IYILMLEQLLIFIITAILGIIIGIFGSKLLLMIVFTLLGIKEKVPIIFSL 150
SAB0611 (RF122)                      IYILMLEQLLIFIITAILGIIIGIFGSKLLLMIVFTLLGIKEKVPIIFSL 150
                                     **************************************************

SACOL0720_                           RAVFETLMLIGVAYFLTSAQNFILVFKQSISQMSKNNQVKETNHNKITFE 200
SAUSA300_0648 (USA300-FPR3757)       RAVFETLMLIGVAYFLTSAQNFILVFKQSISQMSKNNQVKETNHNKITFE 200
SAOUHSC_00668 (NCTC8325)             RAVFETLMLIGVAYFLTSAQNFILVFKQSISQMSKNNQVKETNHNKITFE 170
NWMN_0631 (Newman)                   RAVFETLMLIGVAYFLTSAQNFILVFKQSISQMSKNNQVKETNHNKITFE 155
SaurJH1_0700 (JH1)                   RAVFETLMLIGVAYFLTSAQNFILVFKQSISQMSKNNQVKETNHNKITFE 155
SaurJH9_0685 (JH9)                   RAVFETLMLIGVAYFLTSAQNFILVFKQSISQMSKNNQVKETNHNKITFE 155
SAHV_0659 (Mu3)                      RAVFETLMLIGVAYFLTSAQNFILVFKQSISQMSKNNQVKETNHNKITFE 155
SAV0662 (Mu50)                       RAVFETLMLIGVAYFLTSAQNFILVFKQSISQMSKNNQVKETNHNKITFE 200
SA0617 (N315)                        RAVFETLMLIGVAYFLTSAQNFILVFKQSISQMSKNNQVKETNHNKITFE 200
MW0624 (MW2)                         RAVFETLMLIGVAYFLTSAQNFILVFKQSISQMSKNNQVKETNHNKITFE 200
SAS0627 (MSSA476)                    RAVFETLMLIGVAYFLTSAQNFILVFKQSISQMSKNNQVKETNHNKITFE 200
SAB0611 (RF122)                      RAVFETLMLIGVAYFLTSAQNFILVFKQSISQMSKNNQVKETNHNKITFE 200
                                     **************************************************
```

FIG. 12I

```
SACOL0720_                        EVVLGILGIVLITTGYYLSLNIVQYYDSIGTLMFILLSTVIGAYLFFKSS 250
SAUSA300_0648 (USA300-FPR3757)    EVVLGILGIVLITTGYYLSLNIVQYYDSIGTLMFILLSTVIGAYLFFKSS 250
SAOUHSC_00668 (NCTC8325)          EVVLGILGIVLITTGYYLSLNIVQYYDSIGTLMFILLSTVIGAYLFFKSS 220
NWMN_0631 (Newman)                EVVLGILGIVLITTGYYLSLNIVQYYDSIGTLMFILLSTVIGAYLFFKSS 203
SaurJH1_0700 (JH1)                EVVLGILGIVLITTGYYLSLNIVQYYDSIGTLMFILLSTVIGAYLFFKSS 203
SaurJH9_0685 (JH9)                EVVLGILGIVLITTGYYLSLNIVQYYDSIGTLMFILLSTVIGAYLFFKSS 203
SAHV_0659 (Mu3)                   EVVLGILGIVLITTGYYLSLNIVQYYDSIGTLMFILLSTVIGAYLFFKSS 203
SAV0662 (Mu50)                    EVVLGILGIVLITTGYYLSLNIVQYYDSIGTLMFILLSTVIGAYLFFKSS 250
SA0617 (N315)                     EVVLGILGIVLITTGYYLSLNIVQYYDSIGTLMFILLSTVIGAYLFFKSS 250
MW0624 (MW2)                      EVVLGILGIVLITTGYYLSLNIVQYYDSIGTLMFILLSTVIGAYLFFKSS 250
SAS0627 (MSSA476)                 EVVLGILGIVLITTGYYLSLNIVQYYDSIGTLMFILLSTVIGAYLFFKSS 250
SAB0611 (RF122)                   EVVLGILGIVLITTGYYLSLNIVQYYDSIGTLMFILLSTVIGAYLFFKSS 250
                                  **************************************************

SACOL0720_                        VSLVFKMVKKFRKGVISVNDVMFSSSIMYRIKKNAFSLTVMAIISAITVS 300
SAUSA300_0648 (USA300-FPR3757)    VSLVFKMVKKFRKGVISVNDVMFSSSIMYRIKKNAFSLTVMAIISAITVS 300
SAOUHSC_00668 (NCTC8325)          VSLVFKMVKKFRKGVISVNDVMFSSSIMYRIKKNAFSLTVMAIISAITVS 270
NWMN_0631 (Newman)                VSLVFKMVKKFRKGVISVNDVMFSSSIMYRIKKNAFSLTVMAIISAITVS 253
SaurJH1_0700 (JH1)                VSLVFKMVKKFRKGVISVNDVMFSSSIMYRIKKNAFSLTVMAIISAITVS 253
SaurJH9_0685 (JH9)                VSLVFKMVKKFRKGVISVNDVMFSSSIMYRIKKNAFSLTVMAIISAITVS 253
SAHV_0659 (Mu3)                   VSLVFKMVKKFRKGVISVNDVMFSSSIMYRIKKNAFSLTVMAIISAITVS 253
SAV0662 (Mu50)                    VSLVFKMVKKFRKGVISVNDVMFSSSIMYRIKKNAFSLTVMAIISAITVS 300
SA0617 (N315)                     VSLVFKMVKKFRKGVISVNDVMFSSSIMYRIKKNAFSLTVMAIISAITVS 300
MW0624 (MW2)                      VSLVFKMVKKFRKGVISVNDVMFSSSIMYRIKKNAFSLTVMAIISAITVS 300
SAS0627 (MSSA476)                 VSLVFKMVKKFRKGVISVNDVMFSSSIMYRIKKNAFSLTVMAIISAITVS 300
SAB0611 (RF122)                   VSLVFKMVKKFRKGVISVNDVMFSSSIMYRIKKNAFSLTVMAIISAITVS 300
                                  **************************************************

SACOL0720_                        VLCFAAISRASLSSEIKYTAPHDVTIKDQQKANQLASELNNQKIPHFYNY 350
SAUSA300_0648 (USA300-FPR3757)    VLCFAAISRASLSSEIKYTAPHDVTIKDQQKANQLASELNNQKIPHFYNY 350
SAOUHSC_00668 (NCTC8325)          VLCFAAISRASLSSEIKYTAPHDVTIKDQQKANQLASELNNQKIPHFYNY 320
NWMN_0631 (Newman)                VLCFAAISRASLSSEIKYTAPHDVTIKDQQKANQLASELNNQKIPHFYNY 303
SaurJH1_0700 (JH1)                VLCFAAISRASLSSEIKYTAPHDVTIKDQQKANQLASELNNQKIPHFYNY 303
SaurJH9_0685 (JH9)                VLCFAAISRASLSSEIKYTAPHDVTIKDQQKANQLASELNNQKIPHFYNY 303
SAHV_0659 (Mu3)                   VLCFAAISRASLSSEIKYTAPHDVTIKDQQKANQLASELNNQKIPHFYNY 303
SAV0662 (Mu50)                    VLCFAAISRASLSSEIKYTAPHDVTIKDQQKANQLASELNNQKIPHFYNY 350
SA0617 (N315)                     VLCFAAISRASLSSEIKYTAPHDVTIKDQQKANQLASELNNQKIPHFYNY 350
MW0624 (MW2)                      VLCFAAISRASLSSEIKYTAPHDVTIKDQQKANQLASELNNQKIPHFYNY 350
SAS0627 (MSSA476)                 VLCFAAISRASLSSEIKYTAPHDVTIKDQQKANQLASELNNQKIPHFYNY 350
SAB0611 (RF122)                   VLCFAAISRASLSSEIKYTAPHDVTIKDQQKANQLASELNNQKIPHFYNY 350
                                  **************************************************

SACOL0720_                        KEVIHTKLYKDNLFDVKAKEPYNVTIISDKYIPNTDLKRGQADLFVAEGS 400
SAUSA300_0648 (USA300-FPR3757)    KEVIHTKLYKDNLFDVKAKEPYNVTIISDKYIPNTDLKRGQADLFVAEGS 400
SAOUHSC_00668 (NCTC8325)          KEVIHTKLYKDNLFDVKAKEPYNVTIISDKYIPNTDLKRGQADLFVAEGS 370
NWMN_0631 (Newman)                KEVIHTKLYKDNLFDVKAKEPYNVTIISDKYIPNTDLKRGQADLFVAEGS 353
SaurJH1_0700 (JH1)                KEVIHTKLYKDNLFDVKAKEPYNVTIISDKYIPNTDLKRGQADLFVAEGS 353
SaurJH9_0685 (JH9)                KEVIHTKLYKDNLFDVKAKEPYNVTIISDKYIPNTDLKRGQADLFVAEGS 353
SAHV_0659 (Mu3)                   KEVIHTKLYKDNLFDVKAKEPYNVTIISDKYIPNTDLKRGQADLFVAEGS 353
SAV0662 (Mu50)                    KEVIHTKLYKDNLFDVKAKEPYNVTIISDKYIPNTDLKRGQADLFVAEGS 400
SA0617 (N315)                     KEVIHTKLYKDNLFDVKAKEPYNVTIISDKYIPNTDLKRGQADLFVAEGS 400
MW0624 (MW2)                      KEVIHTKLYKDNLFDVKAKEPYNVTIISDKYIPNTDLKRGQADLFVAEGS 400
SAS0627 (MSSA476)                 KEVIHTKLYKDNLFDVKAKEPYNVTIISDKYIPNTDLKRGQADLFVAEGS 400
SAB0611 (RF122)                   KEVIHTKLYKDNLFDVKSKQPYNVTIISDKYIPSTDLKRGQADLFVAEGS 400
                                  *****************:*:*************.****************

SACOL0720_                        IKDLVKHKKHGKAIIGTKKHHVNIKLRKDINKIYFMTDVDLGGPTFVLND 450
SAUSA300_0648 (USA300-FPR3757)    IKDLVKHKKHGKAIIGTKKHHVNIKLRKDINKIYFMTDVDLGGPTFVLND 450
SAOUHSC_00668 (NCTC8325)          IKDLVKHKKHGKAIIGTKKHHVNIKLRKDINKIYFMTDVDLGGPTFVLND 420
NWMN_0631 (Newman)                IKDLVKHKKHGKAIIGTKKHHVNIKLRKDINKIYFMTDVDLGGPTFVLND 403
SaurJH1_0700 (JH1)                IKDLVKHKKHGKAIIGTKKHHVNIKLRKDINKIYFMTDVDLGGPTFVLND 403
SaurJH9_0685 (JH9)                IKDLVKHKKHGKAIIGTKKHHVNIKLRKDINKIYFMTDVDLGGPTFVLND 403
SAHV_0659 (Mu3)                   IKDLVKHKKHGKAIIGTKKHHVNIKLRKDINKIYFMTDVDLGGPTFVLND 403
SAV0662 (Mu50)                    IKDLVKHKKHGKAIIGTKKHHVNIKLRKDINKIYFMTDVDLGGPTFVLND 450
SA0617 (N315)                     IKDLVKHKKHGKAIIGTKKHHVNIKLRKDINKIYFMTDVDLGGPTFVLND 450
MW0624 (MW2)                      IKDLVKHKKHGKAVIGTKKHHVNIKLRKDINKIYFMTDVDLGGPTFVLND 450
SAS0627 (MSSA476)                 IKDLVKHKKHGKAVIGTKKHHVNIKLRKDINKIYFMTDVDLGGPTFVLND 450
SAB0611 (RF122)                   IKDLVKHKKHGKAVIGTKKHHVNIKLRKDINKIYFMTDVDLGGPTFVLND 450
                                  *************:************************************
```

FIG. 12J

```
SACOL0720_                          KDYQEIRKYTKAKHIVSQFGFDLKHKKDALALEKAKNKVDKSIETRSEAI 500
SAUSA300_0648 (USA300-FPR3757)      KDYQEIRKYTKAKHIVSQFGFDLKHKKDALALEKAKNKVDKSIETRSEAI 500
SAOUHSC_00668 (NCTC8325)            KDYQEIRKYTKAKHIVSQFGFDLKHKKDALALEKAKNKVDKSIETRSEAI 470
NWMN_0631 (Newman)                  KDYQEIRKYTKAKHIVSQFGFDLKHKKDALALEKAKNKVDKSIETRSEAI 455
SaurJH1_0700 (JH1)                  KDYQEIRKYTKAKHIVSQFGFDLKHKKDALALEKVKNKVDKSIKTRSEAI 455
SaurJH9_0685 (JH9)                  KDYQEIRKYTKAKHIVSQFGFDLKHKKDALALEKVKNKVDKSIKTRSEAI 455
SAHV_0659 (Mu3)                     KDYQEIRKYTKAKHIVSQFGFDLKHKKDALALEKVKNKVDKSIKTRSEAI 455
SAV0662 (Mu50)                      KDYQEIRKYTKAKHIVSQFGFDLKHKKDALALEKVKNKVDKSIKTRSEAI 500
SA0617 (N315)                       KDYQEIRKYTKAKHIVSQFGFDLKHKKDALALEKVKNKVDKSIKTRSEAI 500
MW0624 (MW2)                        KDYQEIRKYTKAKHIVSQFGFDLKHKKDALALEKVKNKVDKSIKTRSEAI 500
SAS0627 (MSSA476)                   KDYQEIRKYTKAKHIVSQFGFDLKHKKDALALEKVKNKVDKSIKTRSEAI 500
SAB0611 (RF122)                     KDYQEIRKYTKAKHIVSQFGFDLKHKKDALALEKAKNKVDKSIETRSEAI 500
                                    **********************************.********:******

SACOL0720_                          SSISSLTGILLFVTSFLGITFLIAVCCIIYIKQIDETEDELENYSILRKL 550
SAUSA300_0648 (USA300-FPR3757)      SSISSLTGILLFVTSFLGITFLIAVCCIIYIKQIDETEDELENYSILRKL 550
SAOUHSC_00668 (NCTC8325)            SSISSLTGILLFVTSFLGITFLIAVCCIIYIKQIDETEDELENYSILRKL 520
NWMN_0631 (Newman)                  SSISSLTGILLFVTSFLGITFLIAVCCIIYIKQIDETEDELENYSILRKL 505
SaurJH1_0700 (JH1)                  SSISSLTGILLFVTSFLGITFLIAVCCIIYIKQIDETEDELENYSILRKL 505
SaurJH9_0685 (JH9)                  SSISSLTGILLFVTSFLGITFLIAVCCIIYIKQIDETEDELENYSILRKL 505
SAHV_0659 (Mu3)                     SSISSLTGILLFVTSFLGITFLIAVCCIIYIKQIDETEDELENYSILRKL 505
SAV0662 (Mu50)                      SSISSLTGILLFVTSFLGITFLIAVCCIIYIKQIDETEDELENYSILRKL 550
SA0617 (N315)                       SSISSLTGILLFVTSFLGITFLIAVCCIIYIKQIDETEDELENYSILRKL 550
MW0624 (MW2)                        SSISSLTGILLFVTSFLGITFLIAVCCIIYIKQIDETEDELENYSILRKL 550
SAS0627 (MSSA476)                   SSISSLTGILLFVTSFLGITFLIAVCCIIYIKQIDETEDELENYSILRKL 550
SAB0611 (RF122)                     SSISSLTGILLFVTSFLGITFLIAVCCIIYIKQIDETEDELENYSILRKL 550
                                    **************************************************

SACOL0720_                          GFIQKDMARGLKFKIMFNFGLPLVIALSHAYFTSLAYMKLMGTINQIPVF 600
SAUSA300_0648 (USA300-FPR3757)      GFIQKDMARGLKFKIMFNFGLPLVIALSHAYFTSLAYMKLMGTINQIPVF 600
SAOUHSC_00668 (NCTC8325)            GFIQKDMARGLKFKIMFNFGLPLVIALSHAYFTSLAYMKLMGTINQIPVF 570
NWMN_0631 (Newman)                  GFIQKDMARGLKFKIMFNFGLPLVIALSHAYFTSLAYMKLMGTINQIPVF 555
SaurJH1_0700 (JH1)                  GFIQKDMARGLKFKIMFNFGLPLVIALSHAYFTSLAYMKLMGTINQIPVF 555
SaurJH9_0685 (JH9)                  GFIQKDMARGLKFKIMFNFGLPLVIVLSHAYFTSLAYMKLMGTINQIPVF 555
SAHV_0659 (Mu3)                     GFIQKDMARGLKFKIMFNFGLPLVIALSHAYFTSLAYMKLMGTINQIPVF 555
SAV0662 (Mu50)                      GFIQKDMARGLKFKIMFNFGLPLVIALSHAYFTSLAYMKLMGTINQIPVF 600
SA0617 (N315)                       GFIQKDMARGLKFKIMFNFGLPLVIALSHAYFTSLAYMKLMGTINQIPVF 600
MW0624 (MW2)                        GFIQKDMARGLKFKIMFNFGLPLVIALSHAYFTSLAYMKLMGTINQIPVF 600
SAS0627 (MSSA476)                   GFIQKDMARGLKFKIMFNFGLPLVIALSHAYFTSLAYMKLMGTINQIPVF 600
SAB0611 (RF122)                     GFIQKDMARGLKFKIMFNFGLPLVIALSHAYFTSLAYMKLMGTINQIPVF 600
                                    *************************.************************

SACOL0720_                          IVMGLYICMYAVFAVIAYNHSKRTIRHSI 629
SAUSA300_0648 (USA300-FPR3757)      IVMGLYICMYAVFAVIAYNHSKRTIRHSI 629
SAOUHSC_00668 (NCTC8325)            IVMGLYICMYAVFAVIAYNHSKRTIRHSI 599
NWMN_0631 (Newman)                  IVMGLYICMYAVFAVIAYNHSKRTIRHSI 584
SaurJH1_0700 (JH1)                  IVMGLYICMYAVFAVIAYNHSKRTIRHSI 584
SaurJH9_0685 (JH9)                  IVMGLYICMYAVFAVIAYNHSKRTIRHSI 584
SAHV_0659 (Mu3)                     IVMGLYICMYAVFAVIAYNHSKRTIRHSI 584
SAV0662 (Mu50)                      IVMGLYICMYAVFAVIAYNHSKRTIRHSI 629
SA0617 (N315)                       IVMGLYICMYAVFAVIAYNHSKRTIRHSI 629
MW0624 (MW2)                        IVMGLYICMYAVFAVIAYNHSKRTIRHSI 629
SAS0627 (MSSA476)                   IVMGLYICMYAVFAVIAYNHSKRTIRHSI 629
SAB0611 (RF122)                     IVMGLYICMYAVFAVIAYNHSKRTIRHSI 629
                                    *****************************
```

FIG. 12K

**Description of *S. aureus* sequenced strains (Source: NCBI, The Genome Project)**

| Strain | Description |
|---|---|
| COL | Methicillin-resistant (MRSA) strain that is also resistant to several other antibiotics including penicillin and tetracycline. |
| RF122 | Common strain associated with mastitis in cattle. |
| NCTC 8325 | Prototypical strain originally used as a propagating strain for bacteriophage 47. |
| USA300-FPR3757 | Methicillin resistant strain implicated in outbreaks of skin and soft tissue infections among healthy individuals in U.S., Canada and Europe. |
| N315 | Methicillin-resistant (MRSA) strain isolated in 1982 from a pharyngeal smear of a Japanese patient. |
| Mu50 | Methicillin-resistant (MRSA) strain with vancomycin resistance (VRSA) isolated in 1997 from the pus of a Japanese male baby with a surgical wound infection. |
| JH1 | Vancomycin-intermediate *S. aureus* (VISA) isolate recovered from clinical material in Baltimore, Md. |
| JH9 | Vancomycin-intermediate *S. aureus* (VISA) isolate recovered from clinical material in Baltimore, Md. |
| Mu3 | Heterogeneous vancomycin-intermediate *Staphylococcus aureus* (hVISA). |
| MW2 | Community-acquired methicillin-resistant (MSRA) strain responsible for several fatal infections in the late 1990s. |
| MSSA476 | Hyper-virulent community acquired methicillin-susceptible (MSSA) strain isolated in the United Kingdom. |
| Newman | Isolated from a case of secondarily infected tubercular osteomyelitis in man, great free-coagulase producer. |

FIG. 13

Cellular localization of SACOL0442

Localization Scores:

| | |
|---|---|
| Cytoplasmic | 0.24 |
| CytoplasmicMembrane | 0.01 |
| Cellwall | 0.93 |
| Extracellular | 8.82 |

Final Prediction:

Extracellular 8.82

FIG. 14A

Cellular localization of SACOL0718

Localization Scores:

| | |
|---|---|
| Cytoplasmic | 0.22 |
| CytoplasmicMembrane | 9.49 |
| Cellwall | 0.00 |
| Extracellular | 0.29 |

Final Prediction:

CytoplasmicMembrane 9.49

FIG. 14B

Cellular localization of SACOL0720

Localization Scores:

| | |
|---|---|
| Cytoplasmic | 0.00 |
| CytoplasmicMembrane | 9.99 |
| Cellwall | 0.00 |
| Extracellular | 0.00 |

Final Prediction:

CytoplasmicMembrane 9.99

FIG. 14C

Prediction of the transmembrane helices of protein SACOL0720

```
Number of transmembrane helices: 10
Transmembrane helices: 18-38 59-80 112-135 144-168 202-223 232-255 286-307 509-531
565-588 597-618

     seq  MTFNEIIFKN FRQNLSHYAI YLFSLITSVV LYFSFVALKY AHKLNMTESY    50
     pred IIiiiiiiii iiiiiiiHHH HHHHHHHHHH HHHHHHHHoo oooooooooo

     seq  PIIKEGSQVG SYFLFFIIIA FLLYANVLFI KRRSYELALY QTLGLSKFNI   100
     pred ooooooooHH HHHHHHHHHH HHHHHHHHHH iiiiiiiiii iiiiiIiiii

     seq  IYILMLEQLL IFIITAILGI IIGIFGSKLL LMIVFTLLGI KEKVPIIFSL   150
     pred iiiiiiiiii iHHHHHHHHH HHHHHHHHHH HHHHHooooo oooHHHHHHH

     seq  RAVFETLMLI GVAYFLTSAQ NFILVFKQSI SQMSKNNQVK ETNHNKITFE   200
     pred HHHHHHHHHH HHHHHHHHii iiiiiiiiii iiiIIIiiii iiiiiiiiii

     seq  EVVLGILGIV LITTGYYLSL NIVQYYDSIG TLMFILLSTV IGAYLFFKSS   250
     pred iHHHHHHHHH HHHHHHHHHH HHHooooooo oHHHHHHHHH HHHHHHHHHH

     seq  VSLVFKMVKK FRKGVISVND VMFSSSIMYR IKKNAFSLTV MAIISAITVS   300
     pred HHHHHiiiii iiiiiiiiii iiiiiiiiii iiiiiHHHHH HHHHHHHHHH

     seq  VLCFAAISRA SLSSEIKYTA PHDVTIKDQQ KANQLASELN NQKIPHFYNY   350
     pred HHHHHHHooo oooooooooo ooOOOOOOOO OOOOOOOOOO OOOOOOOOOO

     seq  KEVIHTKLYK DNLFDVKAKE PYNVTITSDK YIPNTDLKRG QADLFVAEGS   400
     pred OOOOOOOOOO OOOOOOOOOO OOOOOOOOOO OOOOOOOOOO OOOOOOOOOO

     seq  IKDLVKHKKH GKAIIGTKKH HVNIKLRKDI NKIYFMTDVD LGGPTFVLND   450
     pred OOOOOOOOOO OOOOOOOOOO OOOOOOOOOO OOOOOOOOOO OOOOOOOOOO

     seq  KDYQEIRKYT KAKHIVSQFG FDLKHKKDAL ALEKAKNKVD KSIETRSEAI   500
     pred OOOOOOOOOO OOOOOOOOOO OOOOOOOOOO OOOOOOOOOO OOOOOOOOOO

     seq  SSISSLTGIL LFVTSFLGIT FLIAVCCIIY IKQIDETEDE LENYSILRKL   550
     pred OOooooooHH HHHHHHHHHH HHHHHHHHHH Hiiiiiiiii iiiiiiIIIi

     seq  GFTQKDMARG LKFKIMFNFG LPLVIALSHA YFTSLAYMKL MGTTNQIPVF   600
     pred iiiiiiiiii iiiiHHHHHH HHHHHHHHHH HHHHHHHHoo ooooooHHHH

     seq  IVMGLYICMY AVFAVTAYNH SKRTIRHSI  629
     pred HHHHHHHHHH HHHHHHHHii iiiiiiiii
```

FIG. 14D

SACOL0720 - IgG2 isotype

SACOL1781 in strain MW2 organism=Staphylococcus aureus subsp. aureus MW2 gene=MW1674

ORFID:MW1674 protein_id=BAB95538.1

MNKHHPKLRSFYSIRKSILGVASVIVSTLFLITSQHQAQAAENTNTSDKISENQNNNATTTQPPKDTNQTQPATQPANTAK
TYPAADESLKDAIKDPALENKEHDIGPREQVNFQLLDKNNETQYYHFFSIKDPADVYYTKKKAEVELDINTASTWKKFEVY
ENNQKLPVRLVSYSPVPEDHAYIRFPVSDGTQELKIVSSTQIDDGEETNYDYTKLVFAKPIYNDPSLVKSDTNDAVVTNDQ
SSSDASNQTNTNTSNQNTSTINNANNQPQATTNMSQPAQPKSSANADQASSQPAHETNSNGNTNDKTNESSNQSDVN
QQYPPADESLQDAIKNPAIIDKEHTADNWRPIDFQMKNDKGERQFYHYASTVEPATVIFTKTGPIIELGLKTASTWKKFEVY
EGDKKLPVELVSYDSDKDYAYIRFPVSNGTREVKIVSSIEYGENIHEDYDYTLMVFAQPITNNPDDYVDEETYNLQKLLAPY
HKAKTLERQVYELEKLQEKLPEKYKAEYKKKLDQTRVELADQVKSAVTEFENVTPTNDQLTDVQEAHFVVFESEENSESV
MDGFVEHPFYTATLNGQKYVVMKTKDDSYWKDLIVEGKRVTTVSKDPKNNSRTLIFPYIPDKAVYNAIVKVVVANIGYEGQ
YHVRIINQDINTKDDDTSQNNTSEPLNVQTGQEGKVADTDVAENSSTATNPKDASDKADVIEPDSDVVKDADNNIDKDVQ
HDVDHLSDMSDNNHFDKYDLKEMDTQIAKDTDRNVDKGADNSVGMSSNVDTDKDSNKNKDKVIQLNHIADKNNHNGKA
AKLDVVKQNYNNTDKVTDKKTTEHLPSDIHKTVDKTVKTKEKAGTPSKENKLSQSKMLPKTGETTSSQSWWGLYALLGM
LALFIPKFRKESK

FIG. 18

SEQUENCE LISTING

```
<160> NUMBER OF SEQ ID NOS: 98

<210> SEQ ID NO 1
<211> LENGTH: 20
<212> TYPE: DNA
<213> ORGANISM: artificial sequence
<220> FEATURE:
<223> OTHER INFORMATION: synthetic PCR primer

<400> SEQUENCE: 1

ggtgctgggc aaatacaagt                                                  20


<210> SEQ ID NO 2
<211> LENGTH: 20
<212> TYPE: DNA
<213> ORGANISM: artificial sequence
<220> FEATURE:
<223> OTHER INFORMATION: synthetic PCR primer

<400> SEQUENCE: 2

tcccacacta aatggtgcaa                                                  20


<210> SEQ ID NO 3
<211> LENGTH: 20
<212> TYPE: DNA
<213> ORGANISM: artificial sequence
<220> FEATURE:
<223> OTHER INFORMATION: synthetic PCR primer

<400> SEQUENCE: 3

aggtcctaga ccagcgcttt                                                  20


<210> SEQ ID NO 4
<211> LENGTH: 19
<212> TYPE: DNA
<213> ORGANISM: artificial sequence
<220> FEATURE:
<223> OTHER INFORMATION: synthetic PCR primer

<400> SEQUENCE: 4

tctctcccat cacttgagc                                                   19


<210> SEQ ID NO 5
<211> LENGTH: 21
```

<212> TYPE: DNA
<213> ORGANISM: artificial sequence
<220> FEATURE:
<223> OTHER INFORMATION: synthetic PCR primer

<400> SEQUENCE: 5
catacacagt tgctggcaga g 21

<210> SEQ ID NO 6
<211> LENGTH: 22
<212> TYPE: DNA
<213> ORGANISM: artificial sequence
<220> FEATURE:
<223> OTHER INFORMATION: synthetic PCR primer

<400> SEQUENCE: 6
caagccatag gaaatatgag ca 22

<210> SEQ ID NO 7
<211> LENGTH: 20
<212> TYPE: DNA
<213> ORGANISM: artificial sequence
<220> FEATURE:
<223> OTHER INFORMATION: synthetic PCR primer

<400> SEQUENCE: 7
gcacaagaag tgttgcgaga 20

<210> SEQ ID NO 8
<211> LENGTH: 20
<212> TYPE: DNA
<213> ORGANISM: artificial sequence
<220> FEATURE:
<223> OTHER INFORMATION: synthetic PCR primer

<400> SEQUENCE: 8
gtcgttttcc cagatccaga 20

<210> SEQ ID NO 9
<211> LENGTH: 26
<212> TYPE: DNA
<213> ORGANISM: artificial sequence
<220> FEATURE:
<223> OTHER INFORMATION: synthetic PCR primer

<400> SEQUENCE: 9
taattaagga aggagtgatt tcaatg 26

<210> SEQ ID NO 10
<211> LENGTH: 26
<212> TYPE: DNA
<213> ORGANISM: artificial sequence
<220> FEATURE:
<223> OTHER INFORMATION: synthetic PCR primer

<400> SEQUENCE: 10
tttttagtga atttgttcac tgtgtc 26

<210> SEQ ID NO 11
<211> LENGTH: 20
<212> TYPE: DNA
<213> ORGANISM: artificial sequence
<220> FEATURE:
<223> OTHER INFORMATION: synthetic PCR primer

<400> SEQUENCE: 11

-continued

```
caatgcatcg cgaaaactta                                              20


<210> SEQ ID NO 12
<211> LENGTH: 20
<212> TYPE: DNA
<213> ORGANISM: artificial sequence
<220> FEATURE:
<223> OTHER INFORMATION: synthetic PCR primer

<400> SEQUENCE: 12

gcttagcttg tgggaactgg                                              20


<210> SEQ ID NO 13
<211> LENGTH: 20
<212> TYPE: DNA
<213> ORGANISM: artificial sequence
<220> FEATURE:
<223> OTHER INFORMATION: synthetic PCR primer

<400> SEQUENCE: 13

catctcggct taggttacgc                                              20


<210> SEQ ID NO 14
<211> LENGTH: 20
<212> TYPE: DNA
<213> ORGANISM: artificial sequence
<220> FEATURE:
<223> OTHER INFORMATION: synthetic PCR primer

<400> SEQUENCE: 14

tttttcggcc taagtttgga                                              20


<210> SEQ ID NO 15
<211> LENGTH: 20
<212> TYPE: DNA
<213> ORGANISM: artificial sequence
<220> FEATURE:
<223> OTHER INFORMATION: synthetic PCR primer

<400> SEQUENCE: 15

ttgcgttagc aaatggagac                                              20


<210> SEQ ID NO 16
<211> LENGTH: 20
<212> TYPE: DNA
<213> ORGANISM: artificial sequence
<220> FEATURE:
<223> OTHER INFORMATION: synthetic PCR primer

<400> SEQUENCE: 16

aatgcgtgca aatacccaag                                              20


<210> SEQ ID NO 17
<211> LENGTH: 14
<212> TYPE: PRT
<213> ORGANISM: Staphylococcus aureus

<400> SEQUENCE: 17

Thr Phe Gly Ile Tyr Pro Lys Ala Asp Ala Ser Thr Gln Asn
1               5                   10


<210> SEQ ID NO 18
<211> LENGTH: 14
<212> TYPE: PRT
<213> ORGANISM: Staphylococcus aureus
```

-continued

<400> SEQUENCE: 18

Lys Asp Thr Ile Asn Gly Lys Ser Asn Lys Ser Arg Asn Trp
1 5 10

<210> SEQ ID NO 19
<211> LENGTH: 15
<212> TYPE: PRT
<213> ORGANISM: Staphylococcus aureus

<400> SEQUENCE: 19

Lys Asp Gly Gly Lys Tyr Thr Leu Glu Ser His Lys Glu Leu Gln
1 5 10 15

<210> SEQ ID NO 20
<211> LENGTH: 14
<212> TYPE: PRT
<213> ORGANISM: Staphylococcus aureus

<400> SEQUENCE: 20

Gln Phe Gly Phe Asp Leu Lys His Lys Lys Asp Ala Leu Ala
1 5 10

<210> SEQ ID NO 21
<211> LENGTH: 13
<212> TYPE: PRT
<213> ORGANISM: Staphylococcus aureus

<400> SEQUENCE: 21

Thr Ile Lys Asp Gln Gln Lys Ala Asn Gln Leu Ala Ser
1 5 10

<210> SEQ ID NO 22
<211> LENGTH: 14
<212> TYPE: PRT
<213> ORGANISM: Staphylococcus aureus

<400> SEQUENCE: 22

Lys Asp Ile Asn Lys Ile Tyr Phe Met Thr Asp Val Asp Leu
1 5 10

<210> SEQ ID NO 23
<211> LENGTH: 13
<212> TYPE: PRT
<213> ORGANISM: Staphylococcus aureus

<400> SEQUENCE: 23

Asp Val Asp Leu Gly Gly Pro Thr Phe Val Leu Asn Asp
1 5 10

<210> SEQ ID NO 24
<211> LENGTH: 612
<212> TYPE: DNA
<213> ORGANISM: Staphylococcus aureus

<400> SEQUENCE: 24
atgttcaaaa aaaatgactc gaaaaattca attctattaa aatctattct atcgctaggt 60
atcatctatg ggggaacatt tggaatatat ccaaaagcag acgcgtcaac acaaaattcc 120
ccaagtgtac aagataaaca attccaaaaa gttgaagaag taccaaataa ttcagaaaaa 180
gctttggtta aaaaacttta cgatagatac agccaaaata caataaacgg aaaatctaat 240
aaatctagga attgggttta ttcagagaga cctttaaatg aaaaccaagt tcgtataaat 300
ttagaaggaa catacagagt tgctgataga gtatatacac ctaagagaaa tattactctt 360
aataaagaag ttgtcacttt aaaggaattg gatcatatca taagatttgc tcatatttct 420
tatggcttat atatgggaga acatttgcct aaaggtaaca tcgtcataaa tacaaaagat 480
ggcggtaaat atacattaga gtcgcataaa gagctacaaa aagataggga aaatgtaaaa 540
attaatacag ccgatataaa aaatgtaact ttcaaacttg tgaaaagtgt taatgacatt 600
gaacaagttt ga 612

<210> SEQ ID NO 25
<211> LENGTH: 612
<212> TYPE: DNA
<213> ORGANISM: Staphylococcus aureus

<400> SEQUENCE: 25
atgttcaaaa aaaatgactc gaaaaattca attctattaa aatctattct atcgctaggt 60
atcatctatg ggggaacatt tggaatatat ccaaaagcag acgcgtcaac acaaaattcc 120
ccaagtgtac aagataaaca attccaaaaa gttgaagaag taccaaataa ttcagaaaaa 180
gctttggtta aaaaacttta cgatagatac agccaaaata caataaacgg aaaatctaat 240
aaatctagga attgggttta ttcagagaga cctttaaatg aaaaccaagt tcgtataaat 300
ttagaaggaa catacagagt tgctgataga gtatatacac ctaagagaaa tattactctt 360
aataaagaag ttgtcacttt aaaggaattg gatcatatca taagatttgc tcatatttct 420
tatggcttat atatgggaga acatttgcct aaaggtaaca tcgtcataaa tacaaaagat 480
ggcggtaaat atacattaga gtcgcataaa gagctacaaa aagataggga aaatgtaaaa 540
attaatacag ccgatataaa aaatgtaact ttcaaacttg tgaaaagtgt taatgacatt 600
gaacaagttt ga 612

<210> SEQ ID NO 26
<211> LENGTH: 612
<212> TYPE: DNA
<213> ORGANISM: Staphylococcus aureus

<400> SEQUENCE: 26
atgttcaaaa aatatgactc aaaaaattca atcgtattaa aatctattct atcgctaggt 60
atcatctatg ggggaacatt tggaatatat ccaaaagcag acgcgtcaac acaaaattcc 120
tcaagtgtac aagataaaca attacaaaaa gttgaagaag taccaaataa ttcagaaaaa 180
gctttggtta aaaaacttta cgatagatac agcaaggata caataaatgg aaaatctaat 240
aaatctagga attgggttta ttcagagaga cctttaaatg aaaaccaagt tcgtatacat 300
ttagaaggaa catacacagt tgctggcaga gtgtatacac ctaagaggaa tattactctt 360
aataaagaag ttgtcacttt aaaagaattg gatcatatca taagatttgc tcatatttcc 420
tatggcttgt atatgggaga acatttgcct aaaggtaaca tcgtcataaa tacaaaagat 480
ggtggtaaat atacattaga gtcgcataaa gagctacaaa aagataggga aaatgtaaaa 540
attaatacag ccgatataaa aaatgtaact ttcaaacttg tgaaaagtgt taatgacatt 600
gaacaagttt ga 612

<210> SEQ ID NO 27
<211> LENGTH: 612
<212> TYPE: DNA
<213> ORGANISM: Staphylococcus aureus

<400> SEQUENCE: 27

```
atgttcaaaa aatatgactc aaaaaattca atcgtattaa aatctattct atcgctaggt     60

atcatctatg ggggaacatt tggaatatat ccaaaagcag acgcgtcaac acaaaattcc    120

tcaagtgtac aagataaaca attacaaaaa gttgaagaag taccaaataa ttcagaaaaa    180

gctttggtta aaaaacttta cgatagatac agcaaggata caataaatgg aaaatctaat    240

aaatctagga attgggttta ttcagagaga cctttaaatg aaaaccaagt tcgtatacat    300

ttagaaggaa catacacagt tgctggcaga gtgtatacac ctaagaggaa tattactctt    360

aataaagaag ttgtcacttt aaaagaattg gatcatatca taagatttgc tcatatttcc    420

tatggcttgt atatgggaga acatttgcct aaaggtaaca tcgtcataaa tacaaaagat    480

ggtggtaaat atacattaga gtcgcataaa gagctacaaa aagataggga aaatgtaaaa    540

attaatacag ccgatataaa aaatgtaact ttcaaacttg tgaaaagtgt taatgacatt    600

gaacaagttt ga                                                        612
```

<210> SEQ ID NO 28
<211> LENGTH: 612
<212> TYPE: DNA
<213> ORGANISM: Staphylococcus aureus

<400> SEQUENCE: 28

```
atgttcaaaa aatatgactc aaaaaattca atcgtattaa aatctattct atcgctaggt     60

atcatctatg ggggaacatt tggaatatat ccaaaagcag acgcgtcaac acaaaattcc    120

tcaagtgtac aagataaaca attacaaaaa gttgaagaag taccaaataa ttcagaaaaa    180

gctttggtta aaaaacttta cgatagatac agcaaggata caataaatgg aaaatctaat    240

aaatctagga attgggttta ttcagagaga cctttaaatg aaaaccaagt tcgtatacat    300

ttagaaggaa catacacagt tgctggcaga gtgtatacac ctaagaggaa tattactctt    360

aataaagaag ttgtcacttt aaaagaattg gatcatatca taagatttgc tcatatttcc    420

tatggcttgt atatgggaga acatttgcct aaaggtaaca tcgtcataaa tacaaaagat    480

ggtggtaaat atacattaga gtcgcataaa gagctacaaa aagataggga aaatgtaaaa    540

attaatacag ccgatataaa aaatgtaact ttcaaacttg tgaaaagtgt taatgacatt    600

gaacaagttt ga                                                        612
```

<210> SEQ ID NO 29
<211> LENGTH: 612
<212> TYPE: DNA
<213> ORGANISM: Staphylococcus aureus

<400> SEQUENCE: 29

```
atgttcaaaa aatatgactc aaaaaattca atcgtattaa aatctattct atcgctaggt     60

atcatctatg ggggaacatt tggaatatat ccaaaagcag acgcgtcaac acaaaattcc    120

tcaagtgtac aagataaaca attacaaaaa gttgaagaag taccaaataa ttcagaaaaa    180

gctttggtta aaaaacttta cgatagatac agcaaggata caataaatgg aaaatctaat    240

aaatctagga attgggttta ttcagagaga cctttaaatg aaaaccaagt tcgtatacat    300

ttagaaggaa catacacagt tgctggcaga gtgtatacac ctaagaggaa tattactctt    360

aataaagaag ttgtcacttt aaaagaattg gatcatatca taagatttgc tcatatttcc    420

tatggcttgt atatgggaga acatttgcct aaaggtaaca tcgtcataaa tacaaaagat    480

ggtggtaaat atacattaga gtcgcataaa gagctacaaa aagataggga aaatgtaaaa    540

attaatacag ccgatataaa aaatgtaact ttcaaacttg tgaaaagtgt taatgacatt    600
```

gaacaagttt ga 612

<210> SEQ ID NO 30
<211> LENGTH: 612
<212> TYPE: DNA
<213> ORGANISM: Staphylococcus aureus

<400> SEQUENCE: 30
atgttcaaaa aatatgactc aaaaaattca atcgtattaa aatctattct atcgctaggt 60
atcatctatg ggggaacatt tggaatatat ccaaaagcag acgcgtcaac acaaaattcc 120
tcaagtgtac aagataaaca attacaaaaa gttgaagaag taccaaataa ttcagaaaaa 180
gctttggtta aaaaacttta cgatagatac agcaaggata caataaatgg aaaatctaat 240
aaatctagga attgggttta ttcagagaga cctttaaatg aaaaccaagt tcgtatacat 300
ttagaaggaa catacacagt tgctgataga gtatatacac ctaagagaaa tattactctt 360
aataaagaag ttgtcacttt aaaggaattg gatcatatca taagatttgc tcatatttct 420
tatggcttat atatgggaga acatttgcct aaaggtaaca tcgtcataaa tacaaaagat 480
ggcggtaaat atacattaga gtcgcataaa gagctacaaa aagataggga aaatgtaaaa 540
attaatacag ccgatataaa aaatgtaact ttcaaacttg tgaaaagtgt taatgacatt 600
gaacaagttt ga 612

<210> SEQ ID NO 31
<211> LENGTH: 612
<212> TYPE: DNA
<213> ORGANISM: Staphylococcus aureus

<400> SEQUENCE: 31
atgttcaaaa aatatgactc aaaaaattca atcgtattaa aatctattct atcgctaggt 60
atcatctatg ggggaacatt tggaatatat ccaaaagcag acgcgtcaac acaaaattcc 120
tcaagtgtac aagataaaca attacaaaaa gttgaagaag taccaaataa ttcagaaaaa 180
gctttggtta aaaaacttta cgatagatac agcaaggata caataaatgg aaaatctaat 240
aaatctagga attgggttta ttcagagaga cctttaaatg aaaaccaagt tcgtatacat 300
ttagaaggaa catacacagt tgctgataga gtatatacac ctaagagaaa tattactctt 360
aataaagaag ttgtcacttt aaaggaattg gatcatatca taagatttgc tcatatttct 420
tatggcttat atatgggaga acatttgcct aaaggtaaca tcgtcataaa tacaaaagat 480
ggcggtaaat atacattaga gtcgcataaa gagctacaaa aagataggga aaatgtaaaa 540
attaatacag ccgatataaa aaatgtaact ttcaaacttg tgaaaagtgt taatgacatt 600
gaacaagttt ga 612

<210> SEQ ID NO 32
<211> LENGTH: 612
<212> TYPE: DNA
<213> ORGANISM: Staphylococcus aureus

<400> SEQUENCE: 32
atgttcaaaa aatatgactc aaaaaattca atcgtattaa aatctattct atcgctaggt 60
atcatctatg ggggaacatt tggaatatat ccaaaagcag acgcgtcaac acaaaattcc 120
tcaagtgtac aagataaaca attacaaaaa gttgaagaag taccaaataa ttcagaaaaa 180
gctttggtta aaaaacttta cgatagatac agcaaggata caataaatgg aaaatctaat 240

```
aaatctagga attgggttta ttcagagaga cctttaaatg aaaaccaagt tcgtatacat    300

ttagaaggaa catacacagt tgctgataga gtatatacac ctaagagaaa tattactctt    360

aataaagaag ttgtcacttt aaaggaattg gatcatatca taagatttgc tcatatttct    420

tatggcttat atatgggaga acatttgcct aaaggtaaca tcgtcataaa tacaaaagat    480

ggcggtaaat atacattaga gtcgcataaa gagctacaaa aagataggga aaatgtaaaa    540

attaatacag ccgatataaa aaatgtaact ttcaaacttg tgaaaagtgt taatgacatt    600

gaacaagttt ga                                                        612
```

```
<210> SEQ ID NO 33
<211> LENGTH: 612
<212> TYPE: DNA
<213> ORGANISM: Staphylococcus aureus

<400> SEQUENCE: 33

atgttcaaaa aatatgactc aaaaaattca atcgtattaa aatctattct atcgctaggt     60

atcatctatg gggaacatt  tggaatatat ccaaaagcag acgcgtcaac acaaaattcc    120

tcaagtgtac aagataaaca attacaaaaa gttgaagaag taccaaataa ttcagaaaaa    180

gctttggtta aaaaacttta cgatagatac agcaaggata caataaatgg aaaatctaat    240

aaatctagga attgggttta ttcagagaga cctttaaatg aaaaccaagt tcgtatacat    300

ttagaaggaa catacacagt tgctgataga gtatatacac ctaagagaaa tattactctt    360

aataaagaag ttgtcacttt aaaggaattg gatcatatca taagatttgc tcatatttct    420

tatggcttat atatgggaga acatttgcct aaaggtaaca tcgtcataaa tacaaaagat    480

ggcggtaaat atacattaga gtcgcataaa gagctacaaa aagataggga aaatgtaaaa    540

attaatacag ccgatataaa aaatgtaact ttcaaacttg tgaaaagtgt taatgacatt    600

gaacaagttt ga                                                        612
```

```
<210> SEQ ID NO 34
<211> LENGTH: 612
<212> TYPE: DNA
<213> ORGANISM: Staphylococcus aureus

<400> SEQUENCE: 34

atgttcaaaa aatatgactc aaaaaattca atcgtattaa aatctattct atcgctaggt     60

atcatctatg gggaacatt  tggaatatat ccaaaagcag acgcgtcaac acaaaattcc    120

tcaagtgtac aagataaaca attacaaaaa gttgaagaag taccaaataa ttcagaaaaa    180

gctttggtta aaaaacttta cgatagatac agcaaggata caataaatgg aaaatctaat    240

aaatctagga attgggttta ttcagagaga cctttaaatg aaaaccaagt tcgtatacat    300

ttagaaggaa catacacagt tgctgataga gtatatacac ctaagagaaa tattactctt    360

aataaagaag ttgtcacttt aaaggaattg gatcatatca taagatttgc tcatatttct    420

tatggcttat atatgggaga acatttgcct aaaggtaaca tcgtcataaa tacaaaagat    480

ggcggtaaat atacattaga gtcgcataaa gagctacaaa aagataggga aaatgtaaaa    540

attaatacag ccgatataaa aaatgtaact ttcaaacttg tgaaaagtgt taatgacatt    600

gaacaagttt ga                                                        612
```

```
<210> SEQ ID NO 35
<211> LENGTH: 612
<212> TYPE: DNA
<213> ORGANISM: Staphylococcus aureus
```

<400> SEQUENCE: 35

```
atgttcaaaa aatatgactc aaaaaattca atcgtattaa aatctattct atcgctaggt     60

atcatctatg ggggaacatt tggaatatat ccaaaagcag acgcgtcaac acaaaattcc    120

tcaagtgtac aagataaaca attccaaaaa gttgaagaag taccaaataa ttcagaaaaa    180

gctttggtta aaaaactgta cgatagatac agccaaaata caataaacgg aaaatctaat    240

aaagctagga attgggttta ttcagagaga cctttaaatg aaaatcaagt tcgcatacat    300

ttagaaggta catacagagt tgctgataga gtgtatacac ctaagaggaa cattactctt    360

aataaagaag ttgtcacttt aaaagaattg gatcatatca taagatttgc tcatatttct    420

tatggcttat atatgggaga acatttgcct aaaggtaaca tcgtcataaa tacaaagaat    480

ggcggtaaat atacattaga gtcgcacaaa gagttacaaa agaataggga aaatgtagaa    540

attaatactg atgatataaa aaatgtaact ttcgaacttg tgaaaagtgt taatgacatt    600

gaacaagttt ga                                                        612
```

<210> SEQ ID NO 36
<211> LENGTH: 612
<212> TYPE: DNA
<213> ORGANISM: Staphylococcus aureus
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (216)..(217)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:

<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (326)..(327)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (477)..(478)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (522)..(523)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (551)..(552)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t

<400> SEQUENCE: 36
atgttcaaaa aanatgactc naaaaattca atnntattaa aatctattct atcgctaggt 60

```
atcatctatg ggggaacatt tggaatatat ccaaaagcag acgcgtcaac acaaaattcc    120

ncaagtgtac aagataaaca attncaaaaa gttgaagaag taccaaataa ttcagaaaaa    180

gctttggtta aaaaactnta cgatagatac agcnannata caataaangg aaaatctaat    240

aaanctagga attgggttta ttcagagaga cctttaaatg aaaancaagt tcgnatanat    300

ttagaaggna catacanagt tgctgnnaga gtntatacac ctaagagnaa nattactctt    360

aataaagaag ttgtcacttt aaangaattg gatcatatca taagatttgc tcatatttcn    420

tatggcttnt atatgggaga acatttgcct aaaggtaaca tcgtcataaa tacaaannat    480

ggnggtaaat atacattaga gtcgcanaaa gagntacaaa annataggga aaatgtanaa    540

attaatacng nngatataaa aaatgtaact ttcnaacttg tgaaaagtgt taatgacatt    600

gaacaagttt ga                                                        612


<210> SEQ ID NO 37
<211> LENGTH: 203
<212> TYPE: PRT
<213> ORGANISM: Staphylococcus aureus

<400> SEQUENCE: 37

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 38
<211> LENGTH: 203
<212> TYPE: PRT
<213> ORGANISM: Staphylococcus aureus

<400> SEQUENCE: 38

Met Phe Lys Lys Tyr Asp Ser Lys Asn Ser Ile Val Leu Lys Ser Ile
1               5                   10                  15
```

```
Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 39
<211> LENGTH: 203
<212> TYPE: PRT
<213> ORGANISM: Staphylococcus aureus

<400> SEQUENCE: 39

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190
```

```
Leu Val Lys Ser Val Asn Asp Ile Glu Gln Val
        195                 200


<210> SEQ ID NO 40
<211> LENGTH: 203
<212> TYPE: PRT
<213> ORGANISM: Staphylococcus aureus

<400> SEQUENCE: 40

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 41
<211> LENGTH: 203
<212> TYPE: PRT
<213> ORGANISM: Staphylococcus aureus

<400> SEQUENCE: 41

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110
```

```
Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 42
<211> LENGTH: 203
<212> TYPE: PRT
<213> ORGANISM: Staphylococcus aureus

<400> SEQUENCE: 42

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 43
<211> LENGTH: 203
<212> TYPE: PRT
<213> ORGANISM: Staphylococcus aureus

<400> SEQUENCE: 43

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30
```

```
Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 44
<211> LENGTH: 203
<212> TYPE: PRT
<213> ORGANISM: Staphylococcus aureus

<400> SEQUENCE: 44

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
```

```
        195                 200


<210> SEQ ID NO 45
<211> LENGTH: 203
<212> TYPE: PRT
<213> ORGANISM: Staphylococcus aureus

<400> SEQUENCE: 45

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 46
<211> LENGTH: 203
<212> TYPE: PRT
<213> ORGANISM: Staphylococcus aureus

<400> SEQUENCE: 46

Met Phe Lys Lys Asn Asp Ser Lys Asn Ser Ile Leu Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Pro Ser Val Gln Asp Lys Gln Phe
        35                  40                  45

Gln Lys Val Glu Glu Val Pro Asn Asn Ser Glu Lys Ala Leu Val Lys
    50                  55                  60

Lys Leu Tyr Asp Arg Tyr Ser Gln Asn Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile Asn Leu Glu Gly Thr Tyr Arg Val Ala Asp Arg Val Tyr
            100                 105                 110

Thr Pro Lys Arg Asn Ile Thr Leu Asn Lys Glu Val Val Thr Leu Lys
```

```
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 47
<211> LENGTH: 203
<212> TYPE: PRT
<213> ORGANISM: Staphylococcus aureus

<400> SEQUENCE: 47

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Ser Val Gln Asp Lys Gln Phe
        35                  40                  45

Gln Lys Val Glu Glu Val Pro Asn Asn Ser Glu Lys Ala Leu Val Lys
    50                  55                  60

Lys Leu Tyr Asp Arg Tyr Ser Gln Asn Thr Ile Asn Gly Lys Ser Asn
65                  70                  75                  80

Lys Ala Arg Asn Trp Val Tyr Ser Glu Arg Pro Leu Asn Glu Asn Gln
                85                  90                  95

Val Arg Ile His Leu Glu Gly Thr Tyr Arg Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asn
145                 150                 155                 160

Gly Gly Lys Tyr Thr Leu Glu Ser His Lys Glu Leu Gln Lys Asn Arg
                165                 170                 175

Glu Asn Val Glu Ile Asn Thr Asp Asp Ile Lys Asn Val Thr Phe Glu
            180                 185                 190

Leu Val Lys Ser Val Asn Asp Ile Glu Gln Val
        195                 200


<210> SEQ ID NO 48
<211> LENGTH: 203
<212> TYPE: PRT
<213> ORGANISM: Staphylococcus aureus
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
```

```
<222> LOCATION: (41)..(41)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid

<400> SEQUENCE: 48

Met Phe Lys Lys Xaa Asp Ser Lys Asn Ser Ile Xaa Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Xaa Ser Val Gln Asp Lys Gln Xaa
        35                  40                  45

Gln Lys Val Glu Glu Val Pro Asn Asn Ser Glu Lys Ala Leu Val Lys
    50                  55                  60

Lys Leu Tyr Asp Arg Tyr Ser Xaa Xaa Thr Ile Asn Gly Lys Ser Asn
65                  70                  75                  80

Lys Xaa Arg Asn Trp Val Tyr Ser Glu Arg Pro Leu Asn Glu Asn Gln
                85                  90                  95

Val Arg Ile Xaa Leu Glu Gly Thr Tyr Xaa Val Ala Xaa Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Xaa
145                 150                 155                 160
```

```
Gly Gly Lys Tyr Thr Leu Glu Ser His Lys Glu Leu Gln Lys Xaa Arg
                165                 170                 175

Glu Asn Val Xaa Ile Asn Thr Xaa Asp Ile Lys Asn Val Thr Phe Xaa
            180                 185                 190

Leu Val Lys Ser Val Asn Asp Ile Glu Gln Val
        195                 200


<210> SEQ ID NO 49
<211> LENGTH: 1755
<212> TYPE: DNA
<213> ORGANISM: Staphylococcus aureus

<400> SEQUENCE: 49

atgacagagt catatccaat tattaaggaa ggctcacaag tcggaagcta ctttctattt      60

ttcatcataa ttgcattttt gttatatgcc aatgtgttat ttattaaacg acgaagttat     120

gagcttgcat tatatcaaac attaggttta tctaaattca acattattta tatactaatg     180

ctcgaacaat tactaatatt tataattacg gcaatattag gtattattat tggtattttt     240

ggttcaaaac tgttattaat gattgtcttt acattattag gaattaaaga aaaggttcca     300

attattttta gtttgagggc ggtatttgaa acattaatgt taatcggtgt cgcttatttt     360

ttaacctctg ctcaaaattt tatattagtg ttcaaacaat ctatttcaca gatgtcaaag     420

aataaccagg ttaaagaaac aaatcataat aaaattacat ttgaagaggt tgttttaggc     480

atcttaggta tagtattgat tatcacagga tactatctat ctttgaacat tgttcaaatat    540

tatgattcta tcggtatact tatgtttatt ttattgtcaa ctgtgattgg ggcatactta     600

ttttttaaaa gctctgtttc tctagttttt aaaatggtga agaagtttag aaaaggtgtt     660

ataagtgtaa atgatgtcat gttctcatca tctattatgt atcgtattaa gaaaaatgct     720

ttttcactta cggtcatggc aatcatttca gcgattactg tttcagttct ttgctttgct     780

gctataagta gagcgtcctt atcaagtgaa ataaaatata ctgcaccaca cgacgttaca     840

attaaagacc aacaaaaagc taatcaatta gcaagtgaat taaacaatca aaaaattcct     900

catttttata attataaaga agtaattcat acgaaattgt ataaagataa tttatttgat     960

gtaaaagcga aagaaccata caatgtaaca attactagtg ataaatatat ccctaatact    1020

gatttgaaac gtggacaagc tgatttgttt gtagcggaag gttctatcaa agatttagtg    1080

aaacataaga agcatggtaa ggcaattata ggaacgaaaa aacatcatgt taatattaag    1140

ttacggaaag atattaataa aatctatttt atgacagatg ttgatttagg tggaccaacg    1200

tttgtcttaa atgacaaaga ctatcaagaa ataagaaagt atacaaaagc aaagcatatc    1260

gtctctcaat ttggattcga tttgaaacat aaaaaagatg ctttagcatt agaaaaagtg    1320

aaaaataaag ttgataaatc tattaaaaca agaagtgaag cgataagctc aatatcaagt    1380

ttaaccggaa tattattatt tgtaacatca tttttaggta ttacattctt gattgctgta    1440

tgttgcatta tatacattaa gcaaatagat gaaaccgaag atgagttaga gaattatagt    1500

atattgagaa agcttggatt tacacaaaaa gatatggcaa ggggactaaa gtttaaaatt    1560

atgtttaatt ttgggttacc tttagttatt gcactatcac atgcatattt tacatcatta    1620

gcatatatga aattaatggg tacaacgaat caaataccgg ttttcatagt aatgggatta    1680

tacatttgta tgtatgctgt ttttgcagtg acggcttata atcattccaa gcgaacaatt    1740

agacattcca tataa                                                     1755


<210> SEQ ID NO 50
```

```
<211> LENGTH: 1755
<212> TYPE: DNA
<213> ORGANISM: Staphylococcus aureus

<400> SEQUENCE: 50

atgacagagt catatccaat tattaaggaa ggctcacaag tcggaagcta ctttctattt     60

ttcatcataa ttgcattttt gttatatgcc aatgtgttat ttattaaacg acgaagttat    120

gagcttgcat tatatcaaac attaggttta tctaaattca acattattta tatactaatg    180

ctcgaacaat tactaatatt tataattacg gcaatattag gtattattat tggtattttt    240

ggttcaaaac tgttattaat gattgtcttt acattattag gaattaaaga aaaggttcca    300

attattttta gtttgagggc ggtatttgaa acattaatgt taatcggtgt cgcttatttt    360

ttaacctctg ctcaaaattt tatattagtg ttcaaacaat ctatttcaca gatgtcaaag    420

aataaccagg ttaaagaaac aaatcataat aaaattacat ttgaagaggt tgttttaggc    480

atcttaggta tagtattgat tatcacagga tactatctat ctttgaacat tgttcaatat    540

tatgattcta tcggtatact tatgtttatt ttattgtcaa ctgtgattgg ggcatactta    600

tttttaaaa gctctgtttc tctagttttt aaaatggtga agaagtttag aaaaggtgtt    660

ataagtgtaa atgatgtcat gttctcatca tctattatgt atcgtattaa gaaaaatgct    720

ttttcactta cggtcatggc aatcatttca gcgattactg tttcagttct ttgctttgct    780

gctataagta gagcgtcctt atcaagtgaa ataaaatata ctgcaccaca cgacgttaca    840

attaaagacc aacaaaaagc taatcaatta gcaagtgaat taaacaatca aaaaattcct    900

catttttata attataaaga agtaattcat acgaaattgt ataaagataa tttatttgat    960

gtaaaagcga aagaaccata caatgtaaca attactagtg ataaatatat ccctaatact   1020

gatttgaaac gtggacaagc tgatttgttt gtagcggaag gttctatcaa agatttagtg   1080

aaacataaga agcatggtaa ggcaattata ggaacgaaaa aacatcatgt taatattaag   1140

ttacggaaag atattaataa aatctatttt atgacagatg ttgatttagg tggaccaacg   1200

tttgtcttaa atgacaaaga ctatcaagaa ataagaaagt atacaaaagc aaagcatatc   1260

gtctctcaat ttggattcga tttgaaacat aaaaaagatg ctttagcatt agaaaaagtg   1320

aaaaataaag ttgataaatc tattaaaaca agaagtgaag cgataagctc aatatcaagt   1380

ttaaccggaa tattattatt tgtaacatca tttttaggta ttacattctt gattgctgta   1440

tgttgcatta tatacattaa gcaaatagat gaaaccgaag atgagttaga gaattatagt   1500

atattgagaa agcttggatt tacacaaaaa gatatggcaa ggggactaaa gtttaaaatt   1560

atgtttaatt ttgggttacc tttagttatt gcactatcac atgcatattt tacatcatta   1620

gcatatatga aattaatggg tacaacgaat caaataccgg ttttcatagt aatgggatta   1680

tacatttgta tgtatgctgt ttttgcagtg acggcttata atcattccaa gcgaacaatt   1740

agacattcca tataa                                                    1755


<210> SEQ ID NO 51
<211> LENGTH: 1755
<212> TYPE: DNA
<213> ORGANISM: Staphylococcus aureus

<400> SEQUENCE: 51

atgacagagt catatccaat tattaaggaa ggctcacaag tcggaagcta ctttctattt     60

ttcatcataa ttgcattttt gttatatgcc aatgtgttat ttattaaacg acgaagttat    120

gagcttgcat tatatcaaac attaggttta tctaaattca acattattta tatactaatg    180
```

```
ctcgaacaat tactaatatt tataattacg gcaatattag gtattattat tggtattttt    240
ggttcaaaac tgttattaat gattgtcttt acattattag gaattaaaga aaaggttcca    300
attattttta gtttgagggc ggtatttgaa acattaatgt taatcggtgt cgcttatttt    360
ttaacctctg ctcaaaattt tatattagtg ttcaaacaat ctatttcaca gatgtcaaag    420
aataaccagg ttaaagaaac aaatcataat aaaattacat ttgaagaggt tgttttaggc    480
atcttaggta tagtattgat taccacagga tactatctat ctttgaacat tgttcaatat    540
tatgattcta tcggtatact tatgtttatt ttattgtcaa ctgtgattgg ggcatactta    600
tttttaaaa gctctgtttc tctagttttt aaaatggtga agaagtttag aaaaggtgtt    660
ataagtgtaa atgatgtcat gttctcatca tctattatgt atcgtattaa gaaaaaatgct    720
ttttcactta cggtcatggc aatcatttca gcgattactg tttcagttct ttgctttgct    780
gctataagta gagcgtcctt atcaagtgaa ataaaatata ctgcaccaca cgacgttaca    840
attaaagacc aacaaaaagc taatcaatta gcaagtgaat taaacaatca aaaaattcct    900
catttttata attataaaga agtaattcat acgaaattgt ataaagataa tttatttgat    960
gtaaaagcga aagaaccata caatgtaaca attactagtg ataaatatat ccctaatact   1020
gatttgaaac gtggacaagc tgatttgttt gtagcggaag gttctatcaa agatttagtg   1080
aaacataaga agcatggtaa ggcaattata ggaacgaaaa aacatcatgt taatattaag   1140
ttacggaaag atattaataa aatctatttt atgacagatg ttgatttagg tggaccaacg   1200
tttgtcttaa atgacaaaga ctatcaagaa ataagaaagt atacaaaagc aaagcatatc   1260
gtctctcaat ttggattcga tttgaaacat aaaaaagatg ctttagcatt agaaaaagtg   1320
aaaaataaag ttgataaatc tattaaaaca agaagtgaag cgataagctc aatatcaagt   1380
ttaaccggaa tattattatt tgtaacatca tttttaggta ttacattctt gattgctgta   1440
tgttgcatta tatacattaa gcaaatagat gaaaccgaag atgagttaga gaattatagt   1500
atattgagaa agcttggatt tacacaaaaa gatatggcaa ggggactaaa gtttaaaatt   1560
atgtttaatt ttgggttacc tttagttatt gcactatcac atgcatattt tacatcatta   1620
gcatatatga aattaatggg tacaacgaat caaataccgg ttttcatagt aatgggatta   1680
tacatttgta tgtatgctgt ttttgcagtg acggcttata atcattccaa gcgaacaatt   1740
agacattcca tataa                                                    1755
```

<210> SEQ ID NO 52
<211> LENGTH: 1890
<212> TYPE: DNA
<213> ORGANISM: Staphylococcus aureus

<400> SEQUENCE: 52

```
atgaccttta acgagataat atttaaaaat ttccgtcaaa atttatcaca ttatgccatc     60
tatcttttt cattaattac gagtgtagta ttgtatttta gctttgtagc attaaaatac    120
gcgcataaac taaacatgac agagtcatat ccaattatta aggaaggctc acaagtcgga    180
agctactttc tatttttcat cataattgca tttttgttat atgccaatgt gttatttatt    240
aaacgacgaa gttatgagct tgcattatat caaacattag gtttatctaa attcaacatt    300
atttatatac taatgctcga acaattacta atatttataa ttacggcaat attaggtatt    360
attattggta tttttggttc aaaactgtta ttaatgattg tctttacatt attaggaatt    420
aaagaaaagg ttccaattat ttttagtttg agggcggtat ttgaaacatt aatgttaatc    480
```

```
ggtgtcgctt atttttaac ctctgctcaa aattttatat tagtgttcaa acaatctatt    540

tcacagatgt caaagaataa ccaggttaaa gaaacaaatc ataataaaat tacatttgaa    600

gaggttgttt taggcatctt aggtatagta ttgattacca caggatacta tctatctttg    660

aacattgttc aatattatga ttctatcggt atacttatgt ttattttatt gtcaactgtg    720

attggggcat acttattttt taaaagctct gtttctctag tttttaaaat ggtgaagaag    780

tttagaaaag gtgttataag tgtaaatgat gtcatgttct catcatctat tatgtatcgt    840

attaagaaaa atgcttttc acttacggtc atggcaatca tttcagcgat tactgtttca    900

gttctttgct ttgctgctat aagtagagcg tccttatcaa gtgaaataaa atatactgca    960

ccacacgacg ttacaattaa agaccaacaa aaagctaatc aattagcaag tgaattaaac   1020

aatcaaaaaa ttcctcattt ttataattat aaagaagtaa ttcatacgaa attgtataaa   1080

gataatttat ttgatgtaaa agcgaaagaa ccatacaatg taacaattac tagtgataaa   1140

tatatcccta atactgattt gaaacgtgga caagctgatt tgtttgtagc ggaaggttct   1200

atcaaagatt tagtgaaaca taagaagcat ggtaaggcaa ttataggaac gaaaaaacat   1260

catgttaata ttaagttacg gaaagatatt aataaaatct attttatgac agatgttgat   1320

ttaggtggac caacgtttgt cttaaatgac aaagactatc aagaaataag aaagtataca   1380

aaagcaaagc atatcgtctc tcaatttgga ttcgatttga aacataaaaa agatgcttta   1440

gcattagaaa aagtgaaaaa taaagttgat aaatctatta aaacaagaag tgaagcgata   1500

agctcaatat caagtttaac cggaatatta ttatttgtaa catcattttt aggtattaca   1560

ttcttgattg ctgtatgttg cattatatac attaagcaaa tagatgaaac cgaagatgag   1620

ttagagaatt atagtatatt gagaaagctt ggatttacac aaaaagatat ggcaagggga   1680

ctaaagttta aaattatgtt taattttggg ttacctttag ttattgcact atcacatgca   1740

tattttacat cattagcata tatgaaatta atgggtacaa cgaatcaaat accggttttc   1800

atagtaatgg gattatacat ttgtatgtat gctgtttttg cagtgacggc ttataatcat   1860

tccaagcgaa caattagaca ttccatataa                                    1890
```

```
<210> SEQ ID NO 53
<211> LENGTH: 1890
<212> TYPE: DNA
<213> ORGANISM: Staphylococcus aureus

<400> SEQUENCE: 53

atgaccttta acgagataat atttaaaaat ttccgtcaaa atttatcaca ttatgccatc     60

tatcttttt cattaattac gagtgtagta ttgtatttta gctttgtagc attaaaatac    120

gcgcataaac taaacatgac agagtcatat ccaattatta aggaaggctc acaagtcgga    180

agctactttc tatttttcat cataattgca tttttgttat atgccaatgt gttatttatt    240

aaacgacgaa gttatgagct tgcattatat caaacattag gtttatctaa attcaacatt    300

atttatatac taatgctcga acaattacta atatttataa ttacggcaat attaggtatt    360

attattggta tttttggttc aaaactgtta ttaatgattg tctttacatt attaggaatt    420

aaagaaaagg ttccaattat ttttagtttg agggcggtat ttgaaacatt aatgttaatc    480

ggtgtcgctt atttttaac ctctgctcaa aattttatat tagtgttcaa acaatctatt    540

tcacagatgt caaagaataa ccaggttaaa gaaacaaatc ataataaaat tacatttgaa    600

gaggttgttt taggcatctt aggtatagta ttgattacca caggatacta tctatctttg    660

aacattgttc aatattatga ttctatcggt atacttatgt ttattttatt gtcaactgtg    720
```

attggggcat acttattttt taaaagctct gtttctctag tttttaaaat ggtgaagaag 780
tttagaaaag gtgttataag tgtaaatgat gtcatgttct catcatctat tatgtatcgt 840
attaagaaaa atgctttttc acttacggtc atggcaatca tttcagcgat tactgtttca 900
gttctttgct ttgctgctat aagtagagcg tccttatcaa gtgaaataaa atatactgca 960
ccacacgacg ttacaattaa agaccaacaa aaagctaatc aattagcaag tgaattaaac 1020
aatcaaaaaa ttcctcattt ttataattat aaagaagtaa ttcatacgaa attgtataaa 1080
gataatttat ttgatgtaaa agcgaaagaa ccatacaatg taacaattac tagtgataaa 1140
tatatcccta atactgattt gaaacgtgga caagctgatt tgtttgtagc ggaaggttct 1200
atcaaagatt tagtgaaaca taagaagcat ggtaaggcaa ttataggaac gaaaaaacat 1260
catgttaata ttaagttacg gaaagatatt aataaaatct attttatgac agatgttgat 1320
ttaggtggac caacgtttgt cttaaatgac aaagactatc aagaaataag aaagtataca 1380
aaagcaaagc atatcgtctc tcaatttgga ttcgatttga aacataaaaa agatgcttta 1440
gcattagaaa aagtgaaaaa taaagttgat aaatctatta aaacaagaag tgaagcgata 1500
agctcaatat caagtttaac cggaatatta ttatttgtaa catcattttt aggtattaca 1560
ttcttgattg ctgtatgttg cattatatac attaagcaaa tagatgaaac cgaagatgag 1620
ttagagaatt atagtatatt gagaaagctt ggatttacac aaaaagatat ggcaagggga 1680
ctaaagttta aaattatgtt taattttggg ttacctttag ttattgcact atcacatgca 1740
tattttacat cattagcata tatgaaatta atgggtacaa cgaatcaaat accggttttc 1800
atagtaatgg gattatacat ttgtatgtat gctgtttttg cagtgacggc ttataatcat 1860
tccaagcgaa caattagaca ttccatataa 1890

<210> SEQ ID NO 54
<211> LENGTH: 1890
<212> TYPE: DNA
<213> ORGANISM: Staphylococcus aureus

<400> SEQUENCE: 54
atgaccttta acgagataat atttaaaaat ttccgtcaaa atttatcaca ttatgccatc 60
tatctttttt cattaattac gagtgtagta ttgtatttta gctttgtagc attaaaatac 120
gcgcataaac taaacatgac agagtcatat ccaattatta aggaaggctc acaagtcgga 180
agctactttc tatttttcat cataattgca tttttgttat atgccaatgt gttatttatt 240
aaacgacgaa gttatgagct tgcattatat caaacattag gtttatctaa attcaacatt 300
atttatatac taatgctcga acaattacta atatttataa ttacggcaat attaggtatt 360
attattggta tttttggttc aaaactgtta ttaatgattg tctttacatt attaggaatt 420
aaagaaaagg ttccaattat ttttagtttg agggcggtat ttgaaacatt aatgttaatc 480
ggtgtcgctt attttttaac ctctgctcaa aattttatat tagtgttcaa acaatctatt 540
tcacagatgt caaagaataa ccaggttaaa gaaacaaatc ataataaaat tacatttgaa 600
gaggttgttt taggcatctt aggtatagta ttgattacca caggatacta tctatctttg 660
aacattgttc aatattatga ttctatcggt atacttatgt ttattttatt gtcaactgtg 720
attggggcat acttattttt taaaagctct gtttctctag tttttaaaat ggtgaagaag 780
tttagaaaag gtgttataag tgtaaatgat gtcatgttct catcatctat tatgtatcgt 840
attaagaaaa atgctttttc acttacggtc atggcaatca tttcagcgat tactgtttca 900

```
gttctttgct ttgctgctat aagtagagcg tccttatcaa gtgaaataaa atatactgca    960

ccacacgacg ttacaattaa agaccaacaa aaagctaatc aattagcaag tgaattaaac   1020

aatcaaaaaa ttcctcattt ttataattat aaagaagtaa ttcatacgaa attgtataaa   1080

gataatttat ttgatgtaaa agcgaaagaa ccatacaatg taacaattac tagtgataaa   1140

tatatcccta atactgattt gaaacgtgga caagctgatt tgtttgtagc ggaaggttct   1200

atcaaagatt tagtgaaaca taagaagcat ggtaaagcag ttataggaac gaaaaaacat   1260

catgttaata ttaagttgcg gaaagatatt aataaaatct attttatgac agatgttgat   1320

ttaggtggac caacgtttgt cttaaatgac aaagactatc aagaaataag aaagtataca   1380

aaagcaaagc atatcgtctc tcaatttgga ttcgatttga aacataaaaa agatgcttta   1440

gcattagaaa aagtgaaaaa taaagttgat aaatctatta aaacaagaag tgaagcgata   1500

agctcaatat caagtttaac cggaatatta ttatttgtaa catcattttt aggtattaca   1560

ttcttgattg ctgtatgttg cattatatac ataaagcaaa tagatgaaac cgaagatgag   1620

ttagagaatt atagtatttt gagaaagctt ggatttacac aaaaagatat ggcaagggga   1680

ctaaagttta aaattatgtt taattttggg ttacctttag ttattgcact atcacatgca   1740

tattttacat cattagcata tatgaaatta atgggtacaa cgaatcaaat accggttttc   1800

atagtaatgg gattatacat ttgtatgtat gctgtttttg cagtgacggc ttataatcat   1860

tccaagcgaa caattagaca ttccatataa                                    1890
```

<210> SEQ ID NO 55
<211> LENGTH: 1890
<212> TYPE: DNA
<213> ORGANISM: Staphylococcus aureus

<400> SEQUENCE: 55

```
atgaccttta acgagataat atttaaaaat ttccgtcaaa atttatcaca ttatgccatc     60

tatctttttt cattaattac gagtgtagta ttgtatttta gctttgtagc attaaaatac    120

gcgcataaac taaacatgac agagtcatat ccaattatta aggaaggctc acaagtcgga    180

agctactttc tatttttcat cataattgca tttttgttat atgccaatgt gttatttatt    240

aaacgacgaa gttatgagct tgcattatat caaacattag gtttatctaa attcaacatt    300

atttatatac taatgctcga acaattacta atatttataa ttacggcaat attaggtatt    360

attattggta tttttggttc aaaactgtta ttaatgattg tctttacatt attaggaatt    420

aaagaaaagg ttccaattat ttttagtttg agggcggtat ttgaaacatt aatgttaatc    480

ggtgtcgctt attttttaac ctctgctcaa aattttatat tagtgttcaa acaatctatt    540

tcacagatgt caaagaataa ccaggttaaa gaaacaaatc ataataaaat tacatttgaa    600

gaggttgttt taggcatctt aggtatagta ttgattacca caggatacta tctatctttg    660

aacattgttc aatattatga ttctatcggt atacttatgt ttattttatt gtcaactgtg    720

attggggcat acttattttt taaaagctct gtttctctag tttttaaaat ggtgaagaag    780

tttagaaaag gtgttataag tgtaaatgat gtcatgttct catcatctat tatgtatcgt    840

attaagaaaa atgctttttc acttacggtc atggcaatca tttcagcgat tactgtttca    900

gttctttgct ttgctgctat aagtagagcg tccttatcaa gtgaaataaa atatactgca    960

ccacacgacg ttacaattaa agaccaacaa aaagctaatc aattagcaag tgaattaaac   1020

aatcaaaaaa ttcctcattt ttataattat aaagaagtaa ttcatacgaa attgtataaa   1080

gataatttat ttgatgtaaa agcgaaagaa ccatacaatg taacaattac tagtgataaa   1140
```

```
tatatcccta atactgattt gaaacgtgga caagctgatt tgtttgtagc ggaaggttct   1200
atcaaagatt tagtgaaaca taagaagcat ggtaaagcag ttataggaac gaaaaaacat   1260
catgttaata ttaagttgcg gaaagatatt aataaaatct attttatgac agatgttgat   1320
ttaggtggac caacgtttgt cttaaatgac aaagactatc aagaaataag aaagtataca   1380
aaagcaaagc atatcgtctc tcaatttgga ttcgatttga aacataaaaa agatgcttta   1440
gcattagaaa aagtgaaaaa taaagttgat aaatctatta aaacaagaag tgaagcgata   1500
agctcaatat caagtttaac cggaatatta ttatttgtaa catcattttt aggtattaca   1560
ttcttgattg ctgtatgttg cattatatac ataaagcaaa tagatgaaac cgaagatgag   1620
ttagagaatt atagtatttt gagaaagctt ggatttacac aaaaagatat ggcaagggga   1680
ctaaagttta aaattatgtt taattttggg ttacctttag ttattgcact atcacatgca   1740
tattttacat cattagcata tatgaaatta atgggtacaa cgaatcaaat accggttttc   1800
atagtaatgg gattatacat ttgtatgtat gctgtttttg cagtgacggc ttataatcat   1860
tccaagcgaa caattagaca ttccatataa                                    1890
```

<210> SEQ ID NO 56
<211> LENGTH: 1890
<212> TYPE: DNA
<213> ORGANISM: Staphylococcus aureus

<400> SEQUENCE: 56

```
atgaccttta acgagataat atttaaaaat ttccgtcaaa atttatcaca ttatgccatc     60
tatctttttt cgttaattac gagtgtagta ttgtatttta gctttgtagc attaaaatac    120
gctcataaac taaacatgac agagtcatat ccaattataa aggaaggctc acaagtcgga    180
agctactttc tatttttcat cataattgca tttttgttat atgccaatgt gttatttatt    240
aaacgacgaa gttatgagct tgcattatat caaacattag gtttatctaa attcaacatt    300
atttatatac taatgctcga acaattacta atatttataa ttacggcaat attaggtatt    360
attattggta tttttggttc gaaactgtta ttaatgattg tctttacatt attaggaatt    420
aaagaaaagg ttccaattat ttttagtttg agggcggtat ttgaaacatt aatgttaatc    480
ggtgtcgctt attttttaac atctgctcaa aattttatat tagtgttcaa acaatctatt    540
tcacagatgt caaagaataa ccaggttaaa gaaacaaatc ataataaaat tacatttgaa    600
gaggttgttt taggcatctt aggtatagta ttgattacca caggatacta tctatctttg    660
aacattgttc aatattatga ttctatcggt acacttatgt ttattttatt gtcaactgtg    720
attggggcat acttattttt taaaagctct gtttctctag tttttaaaat ggtgaagaag    780
tttagaaaag gtgttataag tgtaaatgat gtcatgttct catcatctat tatgtatcgt    840
attaagaaaa atgctttttc acttacggtc atggcaatca tttcagcgat tactgtttca    900
gttctttgct ttgctgctat aagtagagcg tccttatcaa gtgaaataaa atatactgca    960
ccacacgacg ttacaattaa agaccaacaa aaagctaatc aattagcaag tgaattaaac   1020
aatcaaaaaa ttcctcattt ttataattat aaagaagtaa ttcatacgaa attgtataaa   1080
gataatttat ttgatgtaaa agcgaaagaa ccatacaatg taacaattac tagtgataaa   1140
tacatcccta atactgattt gaaacgtggg caagctgatt tatttgtagc ggaaggttct   1200
atcaaagatt tagtgaaaca taagaagcat ggtaaggcaa ttataggaac gaaaaaacat   1260
catgttaata ttaagttacg taaagatatt aataaaatct attttatgac agatgttgat   1320
```

```
ttaggtggac caacgtttgt cttaaatgac aaagactatc aagaaataag aaagtataca   1380

aaggcaaagc atatcgtctc tcaatttgga ttcgatttga aacataaaaa agatgcttta   1440

gcattagaaa aagcgaaaaa taaagttgat aaatctattg aaacaagaag tgaagcgata   1500

agctcaatat caagtttaac cggaatatta ttatttgtaa catcattttt aggtattaca   1560

ttcttgattg ctgtatgttg cattatatac ataaagcaaa tagatgaaac cgaagatgag   1620

ttagagaatt atagtatttt gagaaagctt ggatttacac aaaaagatat ggcaagggga   1680

ctaaagttta aaattatgtt taattttggg ttacctttag ttattgcact atcacatgca   1740

tattttacat cattagcata tatgaaatta atgggtacaa cgaatcaaat accggttttc   1800

atagtaatgg gattatacat ttgtatgtat gctgtttttg cagtgacggc ttataatcat   1860

tccaagcgaa caattagaca ttccatataa                                     1890
```

```
<210> SEQ ID NO 57
<211> LENGTH: 1890
<212> TYPE: DNA
<213> ORGANISM: Staphylococcus aureus

<400> SEQUENCE: 57

atgaccttta acgagataat atttaaaaat ttccgtcaaa atttatcaca ttatgccatc     60

tatctttttt cgttaattac gagtgtagta ttgtatttta gctttgtagc attaaaatac    120

gctcataaac taaacatgac agagtcatat ccaattataa aggaaggctc acaagtcgga    180

agctactttc tatttttcat cataattgca tttttgttat atgccaatgt gttatttatt    240

aaacgacgaa gttatgagct tgcattatat caaacattag gtttatctaa attcaacatt    300

atttatatac taatgctcga acaattacta atatttataa ttacggcaat attaggtatt    360

attattggta tttttggttc gaaactgtta ttaatgattg tctttacatt attaggaatt    420

aaagaaaagg ttccaattat ttttagtttg agggcggtat ttgaaacatt aatgttaatc    480

ggtgtcgctt attttttaac atctgctcaa aattttatat tagtgttcaa acaatctatt    540

tcacagatgt caaagaataa ccaggttaaa gaaacaaatc ataataaaat tacatttgaa    600

gaggttgttt taggcatctt aggtatagta ttgattacca caggatacta tctatctttg    660

aacattgttc aatattatga ttctatcggt acacttatgt ttattttatt gtcaactgtg    720

attggggcat acttattttt taaaagctct gtttctctag tttttaaaat ggtgaagaag    780

tttagaaaag gtgttataag tgtaaatgat gtcatgttct catcatctat tatgtatcgt    840

attaagaaaa atgctttttc acttacggtc atggcaatca tttcagcgat tactgtttca    900

gttctttgct ttgctgctat aagtagagcg tccttatcaa gtgaaataaa atatactgca    960

ccacacgacg ttacaattaa agaccaacaa aaagctaatc aattagcaag tgaattaaac   1020

aatcaaaaaa ttcctcattt ttataattat aaagaagtaa ttcatacgaa attgtataaa   1080

gataatttat ttgatgtaaa agcgaaagaa ccatacaatg taacaattac tagtgataaa   1140

tacatcccta atactgattt gaaacgtggg caagctgatt tatttgtagc ggaaggttct   1200

atcaaagatt tagtgaaaca taagaagcat ggtaaggcaa ttataggaac gaaaaaacat   1260

catgttaata ttaagttacg taaagatatt aataaaatct attttatgac agatgttgat   1320

ttaggtggac caacgtttgt cttaaatgac aaagactatc aagaaataag aaagtataca   1380

aaggcaaagc atatcgtctc tcaatttgga ttcgatttga aacataaaaa agatgcttta   1440

gcattagaaa aagcgaaaaa taaagttgat aaatctattg aaacaagaag tgaagcgata   1500

agctcaatat caagtttaac cggaatatta ttatttgtaa catcattttt aggtattaca   1560
```

```
ttcttgattg ctgtatgttg cattatatac ataaagcaaa tagatgaaac cgaagatgag   1620

ttagagaatt atagtatttt gagaaagctt ggatttacac aaaaagatat ggcaagggga   1680

ctaaagttta aaattatgtt taattttggg ttacctttag ttattgcact atcacatgca   1740

tattttacat cattagcata tatgaaatta atgggtacaa cgaatcaaat accggttttc   1800

atagtaatgg gattatacat ttgtatgtat gctgtttttg cagtgacggc ttataatcat   1860

tccaagcgaa caattagaca ttccatataa                                     1890
```

<210> SEQ ID NO 58
<211> LENGTH: 1800
<212> TYPE: DNA
<213> ORGANISM: Staphylococcus aureus

<400> SEQUENCE: 58

```
ttgtatttta gctttgtagc attaaaatac gctcataaac taaacatgac agagtcatat     60

ccaattataa aggaaggctc acaagtcgga agctactttc tatttttcat cataattgca    120

tttttgttat atgccaatgt gttatttatt aaacgacgaa gttatgagct tgcattatat    180

caaacattag gtttatctaa attcaacatt atttatatac taatgctcga acaattacta    240

atatttataa ttacggcaat attaggtatt attattggta tttttggttc gaaactgtta    300

ttaatgattg tctttacatt attaggaatt aaagaaaagg ttccaattat ttttagtttg    360

agggcggtat ttgaaacatt aatgttaatc ggtgtcgctt attttttaac atctgctcaa    420

aattttatat tagtgttcaa acaatctatt tcacagatgt caaagaataa ccaggttaaa    480

gaaacaaatc ataataaaat tacatttgaa gaggttgttt taggcatctt aggtatagta    540

ttgattacca caggatacta tctatctttg aacattgttc aatattatga ttctatcggt    600

acacttatgt ttattttatt gtcaactgtg attggggcat acttattttt taaaagctct    660

gtttctctag tttttaaaat ggtgaagaag tttagaaaag gtgttataag tgtaaatgat    720

gtcatgttct catcatctat tatgtatcgt attaagaaaa atgctttttc acttacggtc    780

atggcaatca tttcagcgat tactgtttca gttctttgct ttgctgctat aagtagagcg    840

tccttatcaa gtgaaataaa atatactgca ccacacgacg ttacaattaa agaccaacaa    900

aaagctaatc aattagcaag tgaattaaac aatcaaaaaa ttcctcattt ttataattat    960

aaagaagtaa ttcatacgaa attgtataaa gataatttat ttgatgtaaa agcgaaagaa   1020

ccatacaatg taacaattac tagtgataaa tacatcccta atactgattt gaaacgtggg   1080

caagctgatt tatttgtagc ggaaggttct atcaaagatt tagtgaaaca taagaagcat   1140

ggtaaggcaa ttataggaac gaaaaaacat catgttaata ttaagttacg taaagatatt   1200

aataaaatct attttatgac agatgttgat ttaggtggac caacgtttgt cttaaatgac   1260

aaagactatc aagaaataag aaagtataca aaggcaaagc atatcgtctc tcaatttgga   1320

ttcgatttga aacataaaaa agatgcttta gcattagaaa aagcgaaaaa taaagttgat   1380

aaatctattg aaacaagaag tgaagcgata agctcaatat caagtttaac cggaatatta   1440

ttatttgtaa catcattttt aggtattaca ttcttgattg ctgtatgttg cattatatac   1500

ataaagcaaa tagatgaaac cgaagatgag ttagagaatt atagtatttt gagaaagctt   1560

ggatttacac aaaaagatat ggcaagggga ctaaagttta aaattatgtt taattttggg   1620

ttacctttag ttattgcact atcacatgca tattttacat cattagcata tatgaaatta   1680

atgggtacaa cgaatcaaat accggttttc atagtaatgg gattatacat ttgtatgtat   1740
```

```
gctgtttttg cagtgacggc ttataatcat tccaagcgaa caattagaca ttccatataa   1800


<210> SEQ ID NO 59
<211> LENGTH: 1755
<212> TYPE: DNA
<213> ORGANISM: Staphylococcus aureus

<400> SEQUENCE: 59

atgacagagt catatccaat tataaaggaa ggctcacaag tcggaagcta ctttctattt     60

ttcatcataa ttgcattttt gttatatgcc aatgtgttat ttattaaacg acgaagttat    120

gagcttgcat tatatcaaac attaggttta tctaaattca acattattta tatactaatg    180

ctcgaacaat tactaatatt tataattacg gcaatattag gtattattat tggtattttt    240

ggttcgaaac tgttattaat gattgtcttt acattattag gaattaaaga aaaggttcca    300

attattttta gtttgagggc ggtatttgaa acattaatgt taatcggtgt cgcttatttt    360

ttaacatctg ctcaaaattt tatattagtg ttcaaacaat ctatttcaca gatgtcaaag    420

aataaccagg ttaaagaaac aaatcataat aaaattacat ttgaagaggt tgttttaggc    480

atcttaggta tagtattgat taccacagga tactatctat ctttgaacat tgttcaatat    540

tatgattcta tcggtacact tatgtttatt ttattgtcaa ctgtgattgg ggcatactta    600

tttttaaaa gctctgtttc tctagttttt aaaatggtga agaagtttag aaaaggtgtt    660

ataagtgtaa atgatgtcat gttctcatca tctattatgt atcgtattaa gaaaaatgct    720

ttttcactta cggtcatggc aatcatttca gcgattactg tttcagttct ttgctttgct    780

gctataagta gagcgtcctt atcaagtgaa ataaaatata ctgcaccaca cgacgttaca    840

attaaagacc aacaaaaagc taatcaatta gcaagtgaat taaacaatca aaaaattcct    900

catttttata attataaaga agtaattcat acgaaattgt ataaagataa tttatttgat    960

gtaaaagcga aagaaccata caatgtaaca attactagtg ataaatacat ccctaatact   1020

gatttgaaac gtgggcaagc tgatttattt gtagcggaag gttctatcaa agatttagtg   1080

aaacataaga agcatggtaa ggcaattata ggaacgaaaa aacatcatgt taatattaag   1140

ttacgtaaag atattaataa aatctatttt atgacagatg ttgatttagg tggaccaacg   1200

tttgtcttaa atgacaaaga ctatcaagaa ataagaaagt atacaaaggc aaagcatatc   1260

gtctctcaat ttggattcga tttgaaacat aaaaaagatg ctttagcatt agaaaaagcg   1320

aaaaataaag ttgataaatc tattgaaaca agaagtgaag cgataagctc aatatcaagt   1380

ttaaccggaa tattattatt tgtaacatca tttttaggta ttacattctt gattgctgta   1440

tgttgcatta tatacataaa gcaaatagat gaaaccgaag atgagttaga gaattatagt   1500

attttgagaa agcttggatt tacacaaaaa gatatggcaa ggggactaaa gtttaaaatt   1560

atgtttaatt ttgggttacc tttagttatt gcactatcac atgcatattt tacatcatta   1620

gcatatatga aattaatggg tacaacgaat caaataccgg ttttcatagt aatgggatta   1680

tacatttgta tgtatgctgt ttttgcagtg acggcttata atcattccaa gcgaacaatt   1740

agacattcca tataa                                                     1755


<210> SEQ ID NO 60
<211> LENGTH: 1890
<212> TYPE: DNA
<213> ORGANISM: Staphylococcus aureus

<400> SEQUENCE: 60

atgaccttta acgagataat atttaaaaat ttccgtcaaa atttatcaca ttatgccatc     60
```

```
tatctttttt cattaattac gagtgtagta ttgtatttta gctttgtagc attaaaatac    120
gctcataaac taaacatgac agagtcatat ccaattataa aggaaggctc acaagtcgga    180
agctactttc tatttttcat cataattgca tttttgttat atgccaatgt gttatttatt    240
aaacgacgaa gttatgagct tgcattatat caaacattag gtttatctaa attcaacatt    300
atttatatac taatgctcga acaattacta atatttataa ttacggcaat attaggtatt    360
attattggta tttttggttc gaaactgtta ttaatgattg tctttacatt attaggaatt    420
aaagaaaagg ttccaattat ttttagtttg agggcggtat ttgaaacatt aatgttaatc    480
ggtgtcgctt attttttaac atctgctcaa aattttatat tagtgttcaa acaatctatt    540
tcacagatgt caaagaataa ccaggttaaa gaaacaaatc ataataaaat tacatttgaa    600
gaggttgttt taggcatctt aggtatagta ttgattacca caggatacta tctatctttg    660
aacattgttc aatattatga ttctatcggt acacttatgt ttattttatt gtcaactgtg    720
attggggcat acttattttt taaaagctct gtttctctag tttttaaaat ggtgaagaag    780
tttagaaaag gtgttataag tgtaaatgat gtcatgttct catcatctat tatgtatcgt    840
attaagaaaa atgctttttc acttacggtc atggcaatca tttcagcgat tactgtttca    900
gttctttgct ttgctgctat aagtagagcg tccttatcaa gtgaaataaa atatactgca    960
ccacacgacg ttacaattaa agaccaacaa aaagctaatc aattagcaag tgaattaaac   1020
aatcaaaaaa ttcctcattt ttataattat aaagaagtaa ttcatacgaa attgtataaa   1080
gataatttat ttgatgtaaa atcgaaacaa ccatacaatg taacaattac tagtgataaa   1140
tacatcccta gtactgattt gaaacgtggg caagctgatt tgtttgtagc ggaaggttct   1200
atcaaagatt tagtgaaaca taagaagcat ggtaaagcag ttataggaac gaaaaaaacat  1260
catgttaata ttaagttacg taaagatatt aataaaatct attttatgac agatgttgat   1320
ttaggtggac caacgtttgt cttaaatgac aaagactatc aagaaataag aaagtataca   1380
aaggcaaagc atatcgtctc tcaatttgga ttcgatttga aacataaaaa agatgcttta   1440
gcattagaaa aagcgaaaaa taaagttgat aaatctattg agacaagaag tgaagcgata   1500
agctcaatat caagtttaac cggaatatta ttatttgtaa catcattttt aggtattaca   1560
ttcttgattg ctgtatgttg cattatatac attaagcaaa tagatgaaac cgaagatgag   1620
ttagagaatt atagtatatt gagaaagctt ggatttacac aaaaagatat ggcaagggga   1680
ctaaagttta aaattatgtt taattttggg ttacctttag ttattgcact atcacatgca   1740
tattttacat cattagcata tatgaaatta atgggtacaa cgaatcaaat accggttttc   1800
atagtaatgg gattatacat ttgtatgtat gctgtttttg cagtgacggc ttataatcat   1860
tccaagcgaa caattagaca ttccatataa                                    1890
```

```
<210> SEQ ID NO 61
<211> LENGTH: 1755
<212> TYPE: DNA
<213> ORGANISM: Staphylococcus aureus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (503)..(503)
```

<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (973)..(973)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1105)..(1105)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1319)..(1319)
<223> OTHER INFORMATION: n is a, c, g, or t
<220> FEATURE:
<221> NAME/KEY: misc_feature
<222> LOCATION: (1345)..(1345)
<223> OTHER INFORMATION: n is a, c, g, or t
<220> FEATURE:
<221> NAME/KEY: misc_feature
<222> LOCATION: (1347)..(1347)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t
<220> FEATURE:
<221> NAME/KEY: misc_feature
<222> LOCATION: (1503)..(1503)
<223> OTHER INFORMATION: n is a, c, g, or t
<220> FEATURE:
<221> NAME/KEY: misc_feature
<222> LOCATION: (1592)..(1592)
<223> OTHER INFORMATION: n is a, c, g, or t

<400> SEQUENCE: 61
atgacagagt catatccaat tatnaaggaa ggctcacaag tcggaagcta ctttctattt 60
ttcatcataa ttgcattttt gttatatgcc aatgtgttat ttattaaacg acgaagttat 120

```
gagcttgcat tatatcaaac attaggttta tctaaattca acattattta tatactaatg    180

ctcgaacaat tactaatatt tataattacg gcaatattag gtattattat tggtattttt    240

ggttcgaaac tgttattaat gattgtcttt acattattag gaattaaaga aaaggttcca    300

attattttta gtttgagggc ggtatttgaa acattaatgt taatcggtgt cgcttatttt    360

ttaacntctg ctcaaaattt tatattagtg ttcaaacaat ctatttcaca gatgtcaaag    420

aataaccagg ttaaagaaac aaatcataat aaaattacat ttgaagaggt tgttttaggc    480

atcttaggta tagtattgat tancacagga tactatctat ctttgaacat tgttcaatat    540

tatgattcta tcggtanact tatgtttatt ttattgtcaa ctgtgattgg ggcatactta    600

ttttttaaaa gctctgtttc tctagttttt aaaatggtga agaagtttag aaaaggtgtt    660

ataagtgtaa atgatgtcat gttctcatca tctattatgt atcgtattaa gaaaaatgct    720

ttttcactta cggtcatggc aatcatttca gcgattactg tttcagttct ttgctttgct    780

gctataagta gagcgtcctt atcaagtgaa ataaaatata ctgcaccaca cgacgttaca    840

attaaagacc aacaaaaagc taatcaatta gcaagtgaat taaacaatca aaaaattcct    900

catttttata attataaaga agtaattcat acgaaattgt ataaagataa tttatttgat    960

gtaaaancga aanaaccata caatgtaaca attactagtg ataaatanat ccctantact   1020

gatttgaaac gtggncaagc tgatttnttt gtagcggaag gttctatcaa agatttagtg   1080

aaacataaga agcatggtaa ngcanttata ggaacgaaaa aacatcatgt taatattaag   1140

ttncgnaaag atattaataa aatctatttt atgacagatg ttgatttagg tggaccaacg   1200

tttgtcttaa atgacaaaga ctatcaagaa ataagaaagt atacaaangc aaagcatatc   1260

gtctctcaat ttggattcga tttgaaacat aaaaaagatg ctttagcatt agaaaaagng   1320

aaaaataaag ttgataaatc tattnanaca agaagtgaag cgataagctc aatatcaagt   1380

ttaaccggaa tattattatt tgtaacatca tttttaggta ttacattctt gattgctgta   1440

tgttgcatta tatacatnaa gcaaatagat gaaaccgaag atgagttaga gaattatagt   1500

atnttgagaa agcttggatt tacacaaaaa gatatggcaa ggggactaaa gtttaaaatt   1560

atgtttaatt ttgggttacc tttagttatt gnactatcac atgcatattt tacatcatta   1620

gcatatatga aattaatggg tacaacgaat caaataccgg ttttcatagt aatgggatta   1680

tacatttgta tgtatgctgt ttttgcagtg acggcttata atcattccaa gcgaacaatt   1740

agacattcca tataa                                                    1755
```

<210> SEQ ID NO 62
<211> LENGTH: 629
<212> TYPE: PRT
<213> ORGANISM: Staphylococcus aureus

<400> SEQUENCE: 62

```
Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80
```

```
Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Thr Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Ile Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Ala Lys Asn Lys Val Asp Lys Ser Ile Glu Thr Arg
                485                 490                 495
```

```
Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625


<210> SEQ ID NO 63
<211> LENGTH: 629
<212> TYPE: PRT
<213> ORGANISM: Staphylococcus aureus

<400> SEQUENCE: 63

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Thr Leu Met Phe Ile Leu Leu Ser Thr Val
225                 230                 235                 240
```

```
Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Ile Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Ala Lys Asn Lys Val Asp Lys Ser Ile Glu Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625
```

<210> SEQ ID NO 64
<211> LENGTH: 599

```
<212> TYPE: PRT
<213> ORGANISM: Staphylococcus aureus

<400> SEQUENCE: 64

Met Tyr Phe Ser Phe Val Ala Leu Lys Tyr Ala His Lys Leu Asn Met
1               5                   10                  15

Thr Glu Ser Tyr Pro Ile Ile Lys Glu Gly Ser Gln Val Gly Ser Tyr
            20                  25                  30

Phe Leu Phe Phe Ile Ile Ile Ala Phe Leu Leu Tyr Ala Asn Val Leu
        35                  40                  45

Phe Ile Lys Arg Arg Ser Tyr Glu Leu Ala Leu Tyr Gln Thr Leu Gly
    50                  55                  60

Leu Ser Lys Phe Asn Ile Ile Tyr Ile Leu Met Leu Glu Gln Leu Leu
65                  70                  75                  80

Ile Phe Ile Ile Thr Ala Ile Leu Gly Ile Ile Ile Gly Ile Phe Gly
                85                  90                  95

Ser Lys Leu Leu Leu Met Ile Val Phe Thr Leu Leu Gly Ile Lys Glu
            100                 105                 110

Lys Val Pro Ile Ile Phe Ser Leu Arg Ala Val Phe Glu Thr Leu Met
        115                 120                 125

Leu Ile Gly Val Ala Tyr Phe Leu Thr Ser Ala Gln Asn Phe Ile Leu
    130                 135                 140

Val Phe Lys Gln Ser Ile Ser Gln Met Ser Lys Asn Asn Gln Val Lys
145                 150                 155                 160

Glu Thr Asn His Asn Lys Ile Thr Phe Glu Glu Val Val Leu Gly Ile
                165                 170                 175

Leu Gly Ile Val Leu Ile Thr Thr Gly Tyr Tyr Leu Ser Leu Asn Ile
            180                 185                 190

Val Gln Tyr Tyr Asp Ser Ile Gly Thr Leu Met Phe Ile Leu Leu Ser
        195                 200                 205

Thr Val Ile Gly Ala Tyr Leu Phe Phe Lys Ser Ser Val Ser Leu Val
    210                 215                 220

Phe Lys Met Val Lys Lys Phe Arg Lys Gly Val Ile Ser Val Asn Asp
225                 230                 235                 240

Val Met Phe Ser Ser Ser Ile Met Tyr Arg Ile Lys Lys Asn Ala Phe
        245                 250                 255

Ser Leu Thr Val Met Ala Ile Ile Ser Ala Ile Thr Val Ser Val Leu
    260                 265                 270

Cys Phe Ala Ala Ile Ser Arg Ala Ser Leu Ser Ser Glu Ile Lys Tyr
275                 280                 285

Thr Ala Pro His Asp Val Thr Ile Lys Asp Gln Gln Lys Ala Asn Gln
290                 295                 300

Leu Ala Ser Glu Leu Asn Asn Gln Lys Ile Pro His Phe Tyr Asn Tyr
305                 310                 315                 320

Lys Glu Val Ile His Thr Lys Leu Tyr Lys Asp Asn Leu Phe Asp Val
                325                 330                 335

Lys Ala Lys Glu Pro Tyr Asn Val Thr Ile Thr Ser Asp Lys Tyr Ile
            340                 345                 350

Pro Asn Thr Asp Leu Lys Arg Gly Gln Ala Asp Leu Phe Val Ala Glu
        355                 360                 365

Gly Ser Ile Lys Asp Leu Val Lys His Lys Lys His Gly Lys Ala Ile
    370                 375                 380

Ile Gly Thr Lys Lys His His Val Asn Ile Lys Leu Arg Lys Asp Ile
385                 390                 395                 400
```

```
Asn Lys Ile Tyr Phe Met Thr Asp Val Asp Leu Gly Gly Pro Thr Phe
                405                 410                 415

Val Leu Asn Asp Lys Asp Tyr Gln Glu Ile Arg Lys Tyr Thr Lys Ala
            420                 425                 430

Lys His Ile Val Ser Gln Phe Gly Phe Asp Leu Lys His Lys Lys Asp
        435                 440                 445

Ala Leu Ala Leu Glu Lys Ala Lys Asn Lys Val Asp Lys Ser Ile Glu
    450                 455                 460

Thr Arg Ser Glu Ala Ile Ser Ser Ile Ser Ser Leu Thr Gly Ile Leu
465                 470                 475                 480

Leu Phe Val Thr Ser Phe Leu Gly Ile Thr Phe Leu Ile Ala Val Cys
                485                 490                 495

Cys Ile Ile Tyr Ile Lys Gln Ile Asp Glu Thr Glu Asp Glu Leu Glu
            500                 505                 510

Asn Tyr Ser Ile Leu Arg Lys Leu Gly Phe Thr Gln Lys Asp Met Ala
        515                 520                 525

Arg Gly Leu Lys Phe Lys Ile Met Phe Asn Phe Gly Leu Pro Leu Val
    530                 535                 540

Ile Ala Leu Ser His Ala Tyr Phe Thr Ser Leu Ala Tyr Met Lys Leu
545                 550                 555                 560

Met Gly Thr Thr Asn Gln Ile Pro Val Phe Ile Val Met Gly Leu Tyr
                565                 570                 575

Ile Cys Met Tyr Ala Val Phe Ala Val Thr Ala Tyr Asn His Ser Lys
            580                 585                 590

Arg Thr Ile Arg His Ser Ile
        595

<210> SEQ ID NO 65
<211> LENGTH: 584
<212> TYPE: PRT
<213> ORGANISM: Staphylococcus aureus

<400> SEQUENCE: 65

Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
        35                  40                  45

Gly Leu Ser Lys Phe Asn Ile Ile Tyr Ile Leu Met Leu Glu Gln Leu
    50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
    130                 135                 140

Lys Glu Thr Asn His Asn Lys Ile Thr Phe Glu Glu Val Val Leu Gly
145                 150                 155                 160

Ile Leu Gly Ile Val Leu Ile Thr Thr Gly Tyr Tyr Leu Ser Leu Asn
```

```
                165                 170                 175

Ile Val Gln Tyr Tyr Asp Ser Ile Gly Thr Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys Lys His Gly Lys Ala
        355                 360                 365

Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Ala Lys Asn Lys Val Asp Lys Ser Ile
        435                 440                 445

Glu Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Ala Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580
```

<210> SEQ ID NO 66
<211> LENGTH: 584
<212> TYPE: PRT
<213> ORGANISM: Staphylococcus aureus

<400> SEQUENCE: 66

```
Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
        35                  40                  45

Gly Leu Ser Lys Phe Asn Ile Ile Tyr Ile Leu Met Leu Glu Gln Leu
    50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
    130                 135                 140

Lys Glu Thr Asn His Asn Lys Ile Thr Phe Glu Glu Val Val Leu Gly
145                 150                 155                 160

Ile Leu Gly Ile Val Leu Ile Ile Thr Gly Tyr Tyr Leu Ser Leu Asn
                165                 170                 175

Ile Val Gln Tyr Tyr Asp Ser Ile Gly Ile Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys Lys His Gly Lys Ala
        355                 360                 365

Ile Ile Gly Thr Lys Lys His His Val Asn Ile Lys Leu Arg Lys Asp
```

```
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Val Lys Asn Lys Val Asp Lys Ser Ile
        435                 440                 445

Lys Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Ala Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580


<210> SEQ ID NO 67
<211> LENGTH: 584
<212> TYPE: PRT
<213> ORGANISM: Staphylococcus aureus

<400> SEQUENCE: 67

Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
        35                  40                  45

Gly Leu Ser Lys Phe Asn Ile Ile Tyr Ile Leu Met Leu Glu Gln Leu
    50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
    130                 135                 140

Lys Glu Thr Asn His Asn Lys Ile Thr Phe Glu Glu Val Val Leu Gly
145                 150                 155                 160
```

```
Ile Leu Gly Ile Val Leu Ile Ile Thr Gly Tyr Tyr Leu Ser Leu Asn
                165                 170                 175

Ile Val Gln Tyr Tyr Asp Ser Ile Gly Ile Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys Lys His Gly Lys Ala
        355                 360                 365

Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Val Lys Asn Lys Val Asp Lys Ser Ile
        435                 440                 445

Lys Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Val Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
```

580

<210> SEQ ID NO 68
<211> LENGTH: 584
<212> TYPE: PRT
<213> ORGANISM: Staphylococcus aureus

<400> SEQUENCE: 68

```
Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
        35                  40                  45

Gly Leu Ser Lys Phe Asn Ile Ile Tyr Ile Leu Met Leu Glu Gln Leu
    50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
    130                 135                 140

Lys Glu Thr Asn His Asn Lys Ile Thr Phe Glu Glu Val Val Leu Gly
145                 150                 155                 160

Ile Leu Gly Ile Val Leu Ile Thr Thr Gly Tyr Tyr Leu Ser Leu Asn
                165                 170                 175

Ile Val Gln Tyr Tyr Asp Ser Ile Gly Ile Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys Lys His Gly Lys Ala
        355                 360                 365
```

```
Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Val Lys Asn Lys Val Asp Lys Ser Ile
        435                 440                 445

Lys Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Ala Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580


<210> SEQ ID NO 69
<211> LENGTH: 629
<212> TYPE: PRT
<213> ORGANISM: Staphylococcus aureus

<400> SEQUENCE: 69

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160
```

```
Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Ile Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575
```

```
Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625


<210> SEQ ID NO 70
<211> LENGTH: 629
<212> TYPE: PRT
<213> ORGANISM: Staphylococcus aureus

<400> SEQUENCE: 70

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320
```

Pro His Asp Val Thr Ile Lys Asp Gln Gln Lys Ala Asn Gln Leu Ala
325 330 335

Ser Glu Leu Asn Asn Gln Lys Ile Pro His Phe Tyr Asn Tyr Lys Glu
340 345 350

Val Ile His Thr Lys Leu Tyr Lys Asp Asn Leu Phe Asp Val Lys Ala
355 360 365

Lys Glu Pro Tyr Asn Val Thr Ile Thr Ser Asp Lys Tyr Ile Pro Asn
370 375 380

Thr Asp Leu Lys Arg Gly Gln Ala Asp Leu Phe Val Ala Glu Gly Ser
385 390 395 400

Ile Lys Asp Leu Val Lys His Lys Lys His Gly Lys Ala Ile Ile Gly
405 410 415

Thr Lys Lys His His Val Asn Ile Lys Leu Arg Lys Asp Ile Asn Lys
420 425 430

Ile Tyr Phe Met Thr Asp Val Asp Leu Gly Gly Pro Thr Phe Val Leu
435 440 445

Asn Asp Lys Asp Tyr Gln Glu Ile Arg Lys Tyr Thr Lys Ala Lys His
450 455 460

Ile Val Ser Gln Phe Gly Phe Asp Leu Lys His Lys Lys Asp Ala Leu
465 470 475 480

Ala Leu Glu Lys Val Lys Asn Lys Val Asp Lys Ser Ile Lys Thr Arg
485 490 495

Ser Glu Ala Ile Ser Ser Ile Ser Ser Leu Thr Gly Ile Leu Leu Phe
500 505 510

Val Thr Ser Phe Leu Gly Ile Thr Phe Leu Ile Ala Val Cys Cys Ile
515 520 525

Ile Tyr Ile Lys Gln Ile Asp Glu Thr Glu Asp Glu Leu Glu Asn Tyr
530 535 540

Ser Ile Leu Arg Lys Leu Gly Phe Thr Gln Lys Asp Met Ala Arg Gly
545 550 555 560

Leu Lys Phe Lys Ile Met Phe Asn Phe Gly Leu Pro Leu Val Ile Ala
565 570 575

Leu Ser His Ala Tyr Phe Thr Ser Leu Ala Tyr Met Lys Leu Met Gly
580 585 590

Thr Thr Asn Gln Ile Pro Val Phe Ile Val Met Gly Leu Tyr Ile Cys
595 600 605

Met Tyr Ala Val Phe Ala Val Thr Ala Tyr Asn His Ser Lys Arg Thr
610 615 620

Ile Arg His Ser Ile
625

<210> SEQ ID NO 71
<211> LENGTH: 629
<212> TYPE: PRT
<213> ORGANISM: Staphylococcus aureus

<400> SEQUENCE: 71

Met Thr Phe Asn Glu Ile Ile Phe Lys Asn Phe Arg Gln Asn Leu Ser
1 5 10 15

His Tyr Ala Ile Tyr Leu Phe Ser Leu Ile Thr Ser Val Val Leu Tyr
20 25 30

Phe Ser Phe Val Ala Leu Lys Tyr Ala His Lys Leu Asn Met Thr Glu
35 40 45

Ser Tyr Pro Ile Ile Lys Glu Gly Ser Gln Val Gly Ser Tyr Phe Leu

```
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Val Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480
```

```
Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625


<210> SEQ ID NO 72
<211> LENGTH: 629
<212> TYPE: PRT
<213> ORGANISM: Staphylococcus aureus

<400> SEQUENCE: 72

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
```

```
    210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Val Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625
```

<210> SEQ ID NO 73
<211> LENGTH: 629
<212> TYPE: PRT
<213> ORGANISM: Staphylococcus aureus

<400> SEQUENCE: 73

```
Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Thr Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ser
        355                 360                 365

Lys Gln Pro Tyr Asn Val Thr Ile Thr Ser Asp Lys Tyr Ile Pro Ser
```

```
    370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Val Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Ala Lys Asn Lys Val Asp Lys Ser Ile Glu Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
    530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
    610                 615                 620

Ile Arg His Ser Ile
625
```

<210> SEQ ID NO 74
<211> LENGTH: 584
<212> TYPE: PRT
<213> ORGANISM: Staphylococcus aureus
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (369)..(369)
<223> OTHER INFORMATION: Xaa can be any naturally occurring amino acid

```
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (531)..(531)
<223> OTHER INFORMATION: Xaa can be any naturally occurring amino acid

<400> SEQUENCE: 74

Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
        35                  40                  45

Gly Leu Ser Lys Phe Asn Ile Ile Tyr Ile Leu Met Leu Glu Gln Leu
    50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
    130                 135                 140

Lys Glu Thr Asn His Asn Lys Ile Thr Phe Glu Glu Val Val Leu Gly
145                 150                 155                 160

Ile Leu Gly Ile Val Leu Ile Xaa Thr Gly Tyr Tyr Leu Ser Leu Asn
                165                 170                 175

Ile Val Gln Tyr Tyr Asp Ser Ile Gly Xaa Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Xaa Lys Xaa Pro Tyr Asn Val Thr Ile Thr Ser Asp Lys Tyr
                325                 330                 335

Ile Pro Xaa Thr Asp Leu Lys Arg Gly Gln Ala Asp Leu Phe Val Ala
```

```
            340                 345                 350

Glu Gly Ser Ile Lys Asp Leu Val Lys His Lys Lys His Gly Lys Ala
        355                 360                 365

Xaa Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Xaa Lys Asn Lys Val Asp Lys Ser Ile
        435                 440                 445

Xaa Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Xaa Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580


<210> SEQ ID NO 75
<211> LENGTH: 203
<212> TYPE: PRT
<213> ORGANISM: Staphylococcus aureus

<400> SEQUENCE: 75

Met Phe Lys Lys Asn Asp Ser Lys Asn Ser Ile Leu Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Pro Ser Val Gln Asp Lys Gln Phe
        35                  40                  45

Gln Lys Val Glu Glu Val Pro Asn Asn Ser Glu Lys Ala Leu Val Lys
    50                  55                  60

Lys Leu Tyr Asp Arg Tyr Ser Gln Asn Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile Asn Leu Glu Gly Thr Tyr Arg Val Ala Asp Arg Val Tyr
            100                 105                 110

Thr Pro Lys Arg Asn Ile Thr Leu Asn Lys Glu Val Val Thr Leu Lys
        115                 120                 125
```

```
Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200


<210> SEQ ID NO 76
<211> LENGTH: 895
<212> TYPE: PRT
<213> ORGANISM: Staphylococcus aureus

<400> SEQUENCE: 76

Met Asn Lys His His Pro Lys Leu Arg Ser Phe Tyr Ser Ile Arg Lys
1               5                   10                  15

Ser Ile Leu Gly Val Ala Ser Val Ile Val Ser Thr Leu Phe Leu Ile
            20                  25                  30

Thr Ser Gln His Gln Ala Gln Ala Ala Glu Asn Thr Asn Thr Ser Asp
        35                  40                  45

Lys Ile Ser Glu Asn Gln Asn Asn Asn Ala Thr Thr Thr Gln Pro Pro
    50                  55                  60

Lys Asp Thr Asn Gln Thr Gln Pro Ala Thr Gln Pro Ala Asn Thr Ala
65                  70                  75                  80

Lys Thr Tyr Pro Ala Ala Asp Glu Ser Leu Lys Asp Ala Ile Lys Asp
                85                  90                  95

Pro Ala Leu Glu Asn Lys Glu His Asp Ile Gly Pro Arg Glu Gln Val
            100                 105                 110

Asn Phe Gln Leu Leu Asp Lys Asn Asn Glu Thr Gln Tyr Tyr His Phe
        115                 120                 125

Phe Ser Ile Lys Asp Pro Ala Asp Val Tyr Tyr Thr Lys Lys Lys Ala
    130                 135                 140

Glu Val Glu Leu Asp Ile Asn Thr Ala Ser Thr Trp Lys Lys Phe Glu
145                 150                 155                 160

Val Tyr Glu Asn Asn Gln Lys Leu Pro Val Arg Leu Val Ser Tyr Ser
                165                 170                 175

Pro Val Pro Glu Asp His Ala Tyr Ile Arg Phe Pro Val Ser Asp Gly
            180                 185                 190

Thr Gln Glu Leu Lys Ile Val Ser Ser Thr Gln Ile Asp Asp Gly Glu
        195                 200                 205

Glu Thr Asn Tyr Asp Tyr Thr Lys Leu Val Phe Ala Lys Pro Ile Tyr
    210                 215                 220

Asn Asp Pro Ser Leu Val Lys Ser Asp Thr Asn Asp Ala Val Val Thr
225                 230                 235                 240

Asn Asp Gln Ser Ser Ser Asp Ala Ser Asn Gln Thr Asn Thr Asn Thr
                245                 250                 255

Ser Asn Gln Asn Thr Ser Thr Ile Asn Asn Ala Asn Asn Gln Pro Gln
            260                 265                 270

Ala Thr Thr Asn Met Ser Gln Pro Ala Gln Pro Lys Ser Ser Ala Asn
        275                 280                 285

Ala Asp Gln Ala Ser Ser Gln Pro Ala His Glu Thr Asn Ser Asn Gly
    290                 295                 300
```

```
Asn Thr Asn Asp Lys Thr Asn Glu Ser Ser Asn Gln Ser Asp Val Asn
305                 310                 315                 320

Gln Gln Tyr Pro Pro Ala Asp Glu Ser Leu Gln Asp Ala Ile Lys Asn
                325                 330                 335

Pro Ala Ile Ile Asp Lys Glu His Thr Ala Asp Asn Trp Arg Pro Ile
            340                 345                 350

Asp Phe Gln Met Lys Asn Asp Lys Gly Glu Arg Gln Phe Tyr His Tyr
        355                 360                 365

Ala Ser Thr Val Glu Pro Ala Thr Val Ile Phe Thr Lys Thr Gly Pro
    370                 375                 380

Ile Ile Glu Leu Gly Leu Lys Thr Ala Ser Thr Trp Lys Lys Phe Glu
385                 390                 395                 400

Val Tyr Glu Gly Asp Lys Lys Leu Pro Val Glu Leu Val Ser Tyr Asp
                405                 410                 415

Ser Asp Lys Asp Tyr Ala Tyr Ile Arg Phe Pro Val Ser Asn Gly Thr
            420                 425                 430

Arg Glu Val Lys Ile Val Ser Ser Ile Glu Tyr Gly Glu Asn Ile His
        435                 440                 445

Glu Asp Tyr Asp Tyr Thr Leu Met Val Phe Ala Gln Pro Ile Thr Asn
    450                 455                 460

Asn Pro Asp Asp Tyr Val Asp Glu Glu Thr Tyr Asn Leu Gln Lys Leu
465                 470                 475                 480

Leu Ala Pro Tyr His Lys Ala Lys Thr Leu Glu Arg Gln Val Tyr Glu
                485                 490                 495

Leu Glu Lys Leu Gln Glu Lys Leu Pro Glu Lys Tyr Lys Ala Glu Tyr
            500                 505                 510

Lys Lys Lys Leu Asp Gln Thr Arg Val Glu Leu Ala Asp Gln Val Lys
        515                 520                 525

Ser Ala Val Thr Glu Phe Glu Asn Val Thr Pro Thr Asn Asp Gln Leu
    530                 535                 540

Thr Asp Val Gln Glu Ala His Phe Val Val Phe Glu Ser Glu Glu Asn
545                 550                 555                 560

Ser Glu Ser Val Met Asp Gly Phe Val Glu His Pro Phe Tyr Thr Ala
                565                 570                 575

Thr Leu Asn Gly Gln Lys Tyr Val Val Met Lys Thr Lys Asp Asp Ser
            580                 585                 590

Tyr Trp Lys Asp Leu Ile Val Glu Gly Lys Arg Val Thr Thr Val Ser
        595                 600                 605

Lys Asp Pro Lys Asn Asn Ser Arg Thr Leu Ile Phe Pro Tyr Ile Pro
    610                 615                 620

Asp Lys Ala Val Tyr Asn Ala Ile Val Lys Val Val Val Ala Asn Ile
625                 630                 635                 640

Gly Tyr Glu Gly Gln Tyr His Val Arg Ile Ile Asn Gln Asp Ile Asn
                645                 650                 655

Thr Lys Asp Asp Asp Thr Ser Gln Asn Asn Thr Ser Glu Pro Leu Asn
            660                 665                 670

Val Gln Thr Gly Gln Glu Gly Lys Val Ala Asp Thr Asp Val Ala Glu
        675                 680                 685

Asn Ser Ser Thr Ala Thr Asn Pro Lys Asp Ala Ser Asp Lys Ala Asp
    690                 695                 700

Val Ile Glu Pro Asp Ser Asp Val Val Lys Asp Ala Asp Asn Asn Ile
705                 710                 715                 720
```

```
Asp Lys Asp Val Gln His Asp Val Asp His Leu Ser Asp Met Ser Asp
                725                 730                 735

Asn Asn His Phe Asp Lys Tyr Asp Leu Lys Glu Met Asp Thr Gln Ile
            740                 745                 750

Ala Lys Asp Thr Asp Arg Asn Val Asp Lys Gly Ala Asp Asn Ser Val
        755                 760                 765

Gly Met Ser Ser Asn Val Asp Thr Asp Lys Asp Ser Asn Lys Asn Lys
    770                 775                 780

Asp Lys Val Ile Gln Leu Asn His Ile Ala Asp Lys Asn Asn His Asn
785                 790                 795                 800

Gly Lys Ala Ala Lys Leu Asp Val Val Lys Gln Asn Tyr Asn Asn Thr
                805                 810                 815

Asp Lys Val Thr Asp Lys Lys Thr Thr Glu His Leu Pro Ser Asp Ile
            820                 825                 830

His Lys Thr Val Asp Lys Thr Val Lys Thr Lys Glu Lys Ala Gly Thr
        835                 840                 845

Pro Ser Lys Glu Asn Lys Leu Ser Gln Ser Lys Met Leu Pro Lys Thr
    850                 855                 860

Gly Glu Thr Thr Ser Ser Gln Ser Trp Trp Gly Leu Tyr Ala Leu Leu
865                 870                 875                 880

Gly Met Leu Ala Leu Phe Ile Pro Lys Phe Arg Lys Glu Ser Lys
                885                 890                 895


<210> SEQ ID NO 77
<211> LENGTH: 218
<212> TYPE: DNA
<213> ORGANISM: Staphylococcus aureus

<400> SEQUENCE: 77

cattagataa agagaaacac ttaaatatgc tagaatctag agagcaatta tcagtcgaag     60

aatacgaaac attctttaac agatttgata atcaagaatt tgatttcgaa cgtgaattga    120

cacaagatcc atattcaaaa gtatacttat acagtataga agaccatatc agaacatata    180

agatagagaa ataaactagt ggccgattgt gcttgatg                            218


<210> SEQ ID NO 78
<211> LENGTH: 55
<212> TYPE: PRT
<213> ORGANISM: Staphylococcus aureus

<400> SEQUENCE: 78

Met Leu Glu Ser Arg Glu Gln Leu Ser Val Glu Glu Tyr Glu Thr Phe
1               5                   10                  15

Phe Asn Arg Phe Asp Asn Gln Glu Phe Asp Phe Glu Arg Glu Leu Thr
            20                  25                  30

Gln Asp Pro Tyr Ser Lys Val Tyr Leu Tyr Ser Ile Glu Asp His Ile
        35                  40                  45

Arg Thr Tyr Lys Ile Glu Lys
    50                  55


<210> SEQ ID NO 79
<211> LENGTH: 858
<212> TYPE: DNA
<213> ORGANISM: Staphylococcus aureus

<400> SEQUENCE: 79

tattcaaaca ataagtcatc gattattcat gacatttata tatgcacttg ctatgggtat     60
```

```
cgtatacttg attattttca tgtaaaggag cgtaactgat gatagaaatt aataaccttt    120

caaagcgtta ccgtaacaaa cagattttca atcatttaac tatgtccttt gatagtaatc    180

gtttaaccgt attacttggt gataatggtg ctggaaaatc aacattactt cgtatgattg    240

ctggtattga aaaagctaat gatggaacta tcaactattt cggcgaaaaa tggaatcaaa    300

gacaaataca aaatcacatc ggttatgtgc cacaagacat tgcgttattt gaacacatga    360

cagtggctga aaacattaaa ttttttaaat cactttgtaa aaatccaatt aacgatacaa    420

ctatcaacga atatttacag caattaaact ttgatgatac gtctgccaaa gtatctacat    480

tgtccggtgg gaataaacgt aaaattaata tattagtagg tttactaggt caacctcgaa    540

ttctcatttt agatgaaccg acagttggta ttgatttaaa atctagacat gacatccacc    600

aactacttaa catcatgaaa tctaaatgtt taattatatt aactacccat catttagatg    660

aagttgaagc acttgcagat gatatcaagt taattggcca agatcctttt tatcaacatg    720

ttttagagga caaacaatgg acttatacct attattaaaa cgaaaaaatc ccaagctgcg    780

tatgatatcg caacttggga ttttctgtat tatctacttt gcaagtatga cgttgggtct    840

actgcatatt gattaccg                                                  858


<210> SEQ ID NO 80
<211> LENGTH: 219
<212> TYPE: PRT
<213> ORGANISM: Staphylococcus aureus

<400> SEQUENCE: 80

Met Ile Glu Ile Asn Asn Leu Ser Lys Arg Tyr Arg Asn Lys Gln Ile
1               5                   10                  15

Phe Asn His Leu Thr Met Ser Phe Asp Ser Asn Arg Leu Thr Val Leu
            20                  25                  30

Leu Gly Asp Asn Gly Ala Gly Lys Ser Thr Leu Leu Arg Met Ile Ala
        35                  40                  45

Gly Ile Glu Lys Ala Asn Asp Gly Thr Ile Asn Tyr Phe Gly Glu Lys
    50                  55                  60

Trp Asn Gln Arg Gln Ile Gln Asn His Ile Gly Tyr Val Pro Gln Asp
65                  70                  75                  80

Ile Ala Leu Phe Glu His Met Thr Val Ala Glu Asn Ile Lys Phe Phe
                85                  90                  95

Lys Ser Leu Cys Lys Asn Pro Ile Asn Asp Thr Thr Ile Asn Glu Tyr
            100                 105                 110

Leu Gln Gln Leu Asn Phe Asp Asp Thr Ser Ala Lys Val Ser Thr Leu
        115                 120                 125

Ser Gly Gly Asn Lys Arg Lys Ile Asn Ile Leu Val Gly Leu Leu Gly
    130                 135                 140

Gln Pro Arg Ile Leu Ile Leu Asp Glu Pro Thr Val Gly Ile Asp Leu
145                 150                 155                 160

Lys Ser Arg His Asp Ile His Gln Leu Leu Asn Ile Met Lys Ser Lys
                165                 170                 175

Cys Leu Ile Ile Leu Thr Thr His His Leu Asp Glu Val Glu Ala Leu
            180                 185                 190

Ala Asp Asp Ile Lys Leu Ile Gly Gln Asp Pro Phe Tyr Gln His Val
        195                 200                 205

Leu Glu Asp Lys Gln Trp Thr Tyr Thr Tyr Tyr
    210                 215
```

<210> SEQ ID NO 81
<211> LENGTH: 796
<212> TYPE: DNA
<213> ORGANISM: Staphylococcus aureus

<400> SEQUENCE: 81

```
taatcaagag ttaagatgaa tttaattcat gaacacgtct attattttta taattgtagc     60
aaataaagct ttacatcaag gaggtaatta aatatgttca aaaaatatga ctcaaaaaat    120
tcaatcgtat taaaatctat tctatcgcta ggtatcatct atgggggaac atttggaata    180
tatccaaaag cagacgcgtc aacacaaaat tcctcaagtg tacaagataa acaattacaa    240
aaagttgaag aagtaccaaa taattcagaa aaagctttgg ttaaaaaact ttacgataga    300
tacagcaagg atacaataaa tggaaaatct aataaatcta ggaattgggt ttattcagag    360
agacctttaa atgaaaacca agttcgtata catttagaag gaacatacac agttgctggc    420
agagtgtata cacctaagag gaatattact cttaataaag aagttgtcac tttaaaagaa    480
ttggatcata tcataagatt tgctcatatt tcctatggct tgtatatggg agaacatttg    540
cctaaaggta acatcgtcat aaatacaaaa gatggtggta aatatacatt agagtcgcat    600
aaagagctac aaaaagatag ggaaaatgta aaaattaata cagccgatat aaaaaatgta    660
actttcaaac ttgtgaaaag tgttaatgac attgaacaag tttgaaatta agctaaatta    720
gtatatatag tgttttatcg ctaatacttt gaaagttagg tatctaaagg tgcctagctt    780
tctttgttat gattag                                                    796
```

<210> SEQ ID NO 82
<211> LENGTH: 990
<212> TYPE: DNA
<213> ORGANISM: Staphylococcus aureus

<400> SEQUENCE: 82

```
catcaatgca gcttcaacgt tataataaga tagatgttag tcatatgtta aattgaagat     60
acaagtgcca aagcctaaag gaaatgaagt taagataaat tataggagtg ttaaagtggc    120
aattttagaa gtaaaacaat taacaaaaat atatggaact aaaaaaatgg cacaagaagt    180
gttgcgagat atcaatatgt ctattgaaga aggcgagttt attgctatta tgggtccctc    240
tggatctggg aaaacgacat tattaaatgt tttaagttca attgattata tttcacaagg    300
ttctattaca ttaaaaggaa aaaaattaga aaagctttca aacaaggaat tatctgatat    360
acgcaagcat gatattggtt ttatttttca agagtataat ttactgcata cattgactgt    420
taaagaaaac ataatgttac cactaacggt acagaagtta gataaagaac atatgttaaa    480
tcgttatgaa aaagtagcag aagcattaaa tatattggat attagtgata aatatccctc    540
tgaattgtct ggtggacaaa ggcaacgaac atcagctgcc agagcattta taacattgcc    600
ttctattata tttgctgacg aaccaacagg tgcactggat tctaaaagta ctcaagattt    660
attaaaacga ttaacaagaa tgaatgaagc atttaagtct acaattatta tggtaacgca    720
tgatcctgtt gcagcaagct atgcaaatcg agtagtgatg ctaaaagatg gtcaaatttt    780
cactgaatta taccaagggg atgacgataa acatacettt ttcaaagaaa taatacgtgt    840
acaaagtgtt ttaggtggcg ttaattatga cctttaacga gataatattt aaaaatttcc    900
gtcaaaattt atcacattat gccatctatc ttttttcgtt aattacgagt gtagtattgt    960
attttagctt tgtagcatta aaatacgctc                                     990
```

<210> SEQ ID NO 83

<211> LENGTH: 253
<212> TYPE: PRT
<213> ORGANISM: Staphylococcus aureus

<400> SEQUENCE: 83

```
Met Ala Ile Leu Glu Val Lys Gln Leu Thr Lys Ile Tyr Gly Thr Lys
1               5                   10                  15

Lys Met Ala Gln Glu Val Leu Arg Asp Ile Asn Met Ser Ile Glu Glu
            20                  25                  30

Gly Glu Phe Ile Ala Ile Met Gly Pro Ser Gly Ser Gly Lys Thr Thr
        35                  40                  45

Leu Leu Asn Val Leu Ser Ser Ile Asp Tyr Ile Ser Gln Gly Ser Ile
    50                  55                  60

Thr Leu Lys Gly Lys Lys Leu Glu Lys Leu Ser Asn Lys Glu Leu Ser
65                  70                  75                  80

Asp Ile Arg Lys His Asp Ile Gly Phe Ile Phe Gln Glu Tyr Asn Leu
                85                  90                  95

Leu His Thr Leu Thr Val Lys Glu Asn Ile Met Leu Pro Leu Thr Val
            100                 105                 110

Gln Lys Leu Asp Lys Glu His Met Leu Asn Arg Tyr Glu Lys Val Ala
        115                 120                 125

Glu Ala Leu Asn Ile Leu Asp Ile Ser Asp Lys Tyr Pro Ser Glu Leu
    130                 135                 140

Ser Gly Gly Gln Arg Gln Arg Thr Ser Ala Ala Arg Ala Phe Ile Thr
145                 150                 155                 160

Leu Pro Ser Ile Ile Phe Ala Asp Glu Pro Thr Gly Ala Leu Asp Ser
                165                 170                 175

Lys Ser Thr Gln Asp Leu Leu Lys Arg Leu Thr Arg Met Asn Glu Ala
            180                 185                 190

Phe Lys Ser Thr Ile Ile Met Val Thr His Asp Pro Val Ala Ala Ser
        195                 200                 205

Tyr Ala Asn Arg Val Val Met Leu Lys Asp Gly Gln Ile Phe Thr Glu
    210                 215                 220

Leu Tyr Gln Gly Asp Asp Asp Lys His Thr Phe Phe Lys Glu Ile Ile
225                 230                 235                 240

Arg Val Gln Ser Val Leu Gly Gly Val Asn Tyr Asp Leu
                245                 250
```

<210> SEQ ID NO 84
<211> LENGTH: 2456
<212> TYPE: DNA
<213> ORGANISM: Staphylococcus aureus

<400> SEQUENCE: 84

```
agcatttata acattgcctt ctattatatt tgctgacgaa ccaacaggtg cactggattc      60

taaaagtact caagatttat taaaacgatt aacaagaatg aatgaagcat ttaagtctac     120

aattattatg gtaacgcatg atcctgttgc agcaagctat gcaaatcgag tagtgatgct     180

aaaagatggt caaattttca ctgaattata ccaaggggat gacgataaac ataccttttt     240

caaagaaata atacgtgtac aaagtgtttt aggtggcgtt aattatgacc tttaacgaga     300

taatatttaa aaatttccgt caaaatttat cacattatgc catctatctt ttttcgttaa     360

ttacgagtgt agtattgtat tttagctttg tagcattaaa atacgctcat aaactaaaca     420

tgacagagtc atatccaatt ataaaggaag gctcacaagt cggaagctac tttctatttt     480

tcatcataat tgcatttttg ttatatgcca atgtgttatt tattaaacga cgaagttatg     540
```

```
agcttgcatt atatcaaaca ttaggtttat ctaaattcaa cattatttat atactaatgc    600

tcgaacaatt actaatattt ataattacgg caatattagg tattattatt ggtatttttg    660

gttcgaaact gttattaatg attgtcttta cattattagg aattaaagaa aaggttccaa    720

ttatttttag tttgagggcg gtatttgaaa cattaatgtt aatcggtgtc gcttattttt    780

taacatctgc tcaaaatttt atattagtgt tcaaacaatc tatttcacag atgtcaaaga    840

ataaccaggt taaagaaaca aatcataata aaattacatt tgaagaggtt gttttaggca    900

tcttaggtat agtattgatt accacaggat actatctatc tttgaacatt gttcaatatt    960

atgattctat cggtacactt atgtttattt tattgtcaac tgtgattggg gcatacttat   1020

tttttaaaag ctctgtttct ctagttttta aaatggtgaa gaagtttaga aaaggtgtta   1080

taagtgtaaa tgatgtcatg ttctcatcat ctattatgta tcgtattaag aaaaatgctt   1140

tttcacttac ggtcatggca atcatttcag cgattactgt ttcagttctt tgctttgctg   1200

ctataagtag agcgtcctta tcaagtgaaa taaaatatac tgcaccacac gacgttacaa   1260

ttaaagacca acaaaaagct aatcaattag caagtgaatt aaacaatcaa aaaattcctc   1320

atttttataa ttataaagaa gtaattcata cgaaattgta taaagataat ttatttgatg   1380

taaaagcgaa agaaccatac aatgtaacaa ttactagtga taaatacatc cctaatactg   1440

atttgaaacg tgggcaagct gatttatttg tagcggaagg ttctatcaaa gatttagtga   1500

aacataagaa gcatggtaag gcaattatag gaacgaaaaa acatcatgtt aatattaagt   1560

tacgtaaaga tattaataaa atctatttta tgacagatgt tgatttaggt ggaccaacgt   1620

ttgtcttaaa tgacaaagac tatcaagaaa taagaaagta tacaaaggca aagcatatcg   1680

tctctcaatt tggattcgat ttgaaacata aaaaagatgc tttagcatta gaaaaagcga   1740

aaaataaagt tgataaatct attgaaacaa gaagtgaagc gataagctca atatcaagtt   1800

taaccggaat attattattt gtaacatcat ttttaggtat tacattcttg attgctgtat   1860

gttgcattat atacataaag caaatagatg aaaccgaaga tgagttagag aattatagta   1920

ttttgagaaa gcttggattt acacaaaaag atatggcaag ggactaaag tttaaaatta    1980

tgtttaattt tgggttacct ttagttattg cactatcaca tgcatatttt acatcattag   2040

catatatgaa attaatgggt acaacgaatc aaataccggt tttcatagta atgggattat   2100

acatttgtat gtatgctgtt tttgcagtga cggcttataa tcattccaag cgaacaatta   2160

gacattccat ataaaatata cagatggctt tcagtagagt agtggattcg gattcacgaa   2220

ctatactgga agctttttat tataaatgaa gagaagttat atttttagca tgtatagttg   2280

aatactgggt taaaatacca tattaataat gaagtaaagg tatgagtgat tatgaaagtg   2340

ttttgaatga aatatattta attggtgatg cttttaattg aaaagattaa caggattcaa   2400

ctttgtaaat tgtattaaat gtgagaaaat aaaagtatat tcattgagag atatat       2456
```

```
<210> SEQ ID NO 85
<211> LENGTH: 952
<212> TYPE: DNA
<213> ORGANISM: Staphylococcus aureus

<400> SEQUENCE: 85

atacgatttt atatcttcaa caacttcata ttaatttgga tgatattgaa atacaaaaag     60

tctcaattgt tgattcatac ttcaacaata aaaagcaaag gggatctaat tatgatacta    120

agttacttga aaatcgaatt taaagttata atgcgtaaaa aaacaacatt aatattatct    180
```

```
attttatttc ctgttatatt ctatatatta tttacttcga tattggaatt gccggaagat    240

gttaaaccta aattttataa agagtatatg tatagtatga cggtttatag tttgttaagt    300

tttagtttac taacttttcc attagatatt attaatgaaa aacaaaatga atggcgccaa    360

agattaatgg taacaccatt tacttttact agttattata tttcaaaagt agtgaaaact    420

atgctgcaat ttgcaatagc gatattagtt atttttatgg ttggacattt ttataaaggt    480

gttgcaatga gtgcagttca atggttagag tcaggaatat tttatggtt aggtgcgtct     540

ctattaataa cttttggcat attattttct ttgttaaatg atattcaaaa aacaagtgct    600

ttagctaata tcgtaacaat tggtttagca gtattaggtg gattgtggtt tccgataaac    660

acatttccaa attggcttca acatgttgct catgttttac cgagctatca tttgcgtaaa    720

ctaggtgtag atattgcttc aaatcatcat atcaatttaa tatcatttgc tataatactc    780

ttgtatgctt tagggagtat aatagcagta tattgtatta gtcattttaa aagggcggaa    840

taaaatatga aattttttaaa agatacttca attgctgaaa tatcgtctat actttatctg   900

atttttccta ttgccggtat attttttaat gaagtatatg gtcccaaatg gt            952
```

<210> SEQ ID NO 86
<211> LENGTH: 243
<212> TYPE: PRT
<213> ORGANISM: Staphylococcus aureus

<400> SEQUENCE: 86

```
Met Ile Leu Ser Tyr Leu Lys Ile Glu Phe Lys Val Ile Met Arg Lys
1               5                   10                  15

Lys Thr Thr Leu Ile Leu Ser Ile Leu Phe Pro Val Ile Phe Tyr Ile
            20                  25                  30

Leu Phe Thr Ser Ile Leu Glu Leu Pro Glu Asp Val Lys Pro Lys Phe
        35                  40                  45

Tyr Lys Glu Tyr Met Tyr Ser Met Thr Val Tyr Ser Leu Leu Ser Phe
    50                  55                  60

Ser Leu Leu Thr Phe Pro Leu Asp Ile Ile Asn Glu Lys Gln Asn Glu
65                  70                  75                  80

Trp Arg Gln Arg Leu Met Val Thr Pro Phe Thr Phe Thr Ser Tyr Tyr
                85                  90                  95

Ile Ser Lys Val Val Lys Thr Met Leu Gln Phe Ala Ile Ala Ile Leu
            100                 105                 110

Val Ile Phe Met Val Gly His Phe Tyr Lys Gly Val Ala Met Ser Ala
        115                 120                 125

Val Gln Trp Leu Glu Ser Gly Ile Phe Leu Trp Leu Gly Ala Ser Leu
    130                 135                 140

Leu Ile Thr Phe Gly Ile Leu Phe Ser Leu Leu Asn Asp Ile Gln Lys
145                 150                 155                 160

Thr Ser Ala Leu Ala Asn Ile Val Thr Ile Gly Leu Ala Val Leu Gly
                165                 170                 175

Gly Leu Trp Phe Pro Ile Asn Thr Phe Pro Asn Trp Leu Gln His Val
            180                 185                 190

Ala His Val Leu Pro Ser Tyr His Leu Arg Lys Leu Gly Val Asp Ile
        195                 200                 205

Ala Ser Asn His His Ile Asn Leu Ile Ser Phe Ala Ile Ile Leu Leu
    210                 215                 220

Tyr Ala Leu Gly Ser Ile Ile Ala Val Tyr Cys Ile Ser His Phe Lys
225                 230                 235                 240
```

Arg Ala Glu

<210> SEQ ID NO 87
<211> LENGTH: 1081
<212> TYPE: DNA
<213> ORGANISM: Staphylococcus aureus

<400> SEQUENCE: 87

```
gttgttatta tcaatacgat tgctgattta ttaacgttat tacttgatcc gaagcagcgt     60
ttacaattag gaaatccaaa aatcaaaacc aatacaccat tgatatcaga aagtagtgac    120
cgtcatgcat aaaatatttt caaagaataa cctgatattt tttgtattcg ttgcatttat    180
ttttgtggta attgtactgc aattctttgt cagtagtgaa aatgcaacca aagtcaattt    240
atcacaaact tttgaaccta ttagttggtt gcatttatta ggaactgatg attatgggag    300
agatttattt acccgaatta ttatcggtgc acgttcaaca ttgtttgtta ctgttttaac    360
attaatagct atcgttgtca taggtgttac actaggtcta tttgccggat acaaaaaagg    420
gtggattgaa cgattagtgt taaggtttat tgatgttggt ctaagtattc cagaatttat    480
catcatgatt gctttagcaa gtttttttca accatcttta tggaatttag ttatctcaat    540
tacattaata aaatggatga attacacaag gttgactaga agtatagtta atagcgaaat    600
gaataagcct tatataaaaa tggcacaatt atttcatgta ccaacaagaa caatattaat    660
acgtcattta acacctaaaa ttataccggc tattatcgtt ttgatggtcg ttgatttcgg    720
taaaatcatt ctatatataa gttcactatc atttattggg ttaggtgcac aaccgccaac    780
accagagtgg ggcgctatgt tgcaacaagg tcgtgatttt atttcgtctc atccaattat    840
gttgattgca cctgcttcag tcattgctat aactatttta atttttaatt taaccggtga    900
tgcactaaga gatagattgc tgaaacaacg gggtgaatat gatgagtctc attgatatac    960
aaaatttaac aataaagaat actagtgaga aatctcttat taaagggatt gatttgaaaa   1020
tttttagtca acagattaat gccttgattg gagagagcgg cgctggaaaa agtttgattg   1080
c                                                                   1081
```

<210> SEQ ID NO 88
<211> LENGTH: 276
<212> TYPE: PRT
<213> ORGANISM: Staphylococcus aureus

<400> SEQUENCE: 88

```
Met His Lys Ile Phe Ser Lys Asn Asn Leu Ile Phe Phe Val Phe Val
1               5                   10                  15

Ala Phe Ile Phe Val Val Ile Val Leu Gln Phe Phe Val Ser Ser Glu
            20                  25                  30

Asn Ala Thr Lys Val Asn Leu Ser Gln Thr Phe Glu Pro Ile Ser Trp
        35                  40                  45

Leu His Leu Leu Gly Thr Asp Asp Tyr Gly Arg Asp Leu Phe Thr Arg
    50                  55                  60

Ile Ile Ile Gly Ala Arg Ser Thr Leu Phe Val Thr Val Leu Thr Leu
65                  70                  75                  80

Ile Ala Ile Val Val Ile Gly Val Thr Leu Gly Leu Phe Ala Gly Tyr
                85                  90                  95

Lys Lys Gly Trp Ile Glu Arg Leu Val Leu Arg Phe Ile Asp Val Gly
            100                 105                 110

Leu Ser Ile Pro Glu Phe Ile Ile Met Ile Ala Leu Ala Ser Phe Phe
        115                 120                 125
```

```
Gln Pro Ser Leu Trp Asn Leu Val Ile Ser Ile Thr Leu Ile Lys Trp
    130                 135                 140

Met Asn Tyr Thr Arg Leu Thr Arg Ser Ile Val Asn Ser Glu Met Asn
145                 150                 155                 160

Lys Pro Tyr Ile Lys Met Ala Gln Leu Phe His Val Pro Thr Arg Thr
                165                 170                 175

Ile Leu Ile Arg His Leu Thr Pro Lys Ile Ile Pro Ala Ile Ile Val
            180                 185                 190

Leu Met Val Val Asp Phe Gly Lys Ile Ile Leu Tyr Ile Ser Ser Leu
        195                 200                 205

Ser Phe Ile Gly Leu Gly Ala Gln Pro Pro Thr Pro Glu Trp Gly Ala
    210                 215                 220

Met Leu Gln Gln Gly Arg Asp Phe Ile Ser Ser His Pro Ile Met Leu
225                 230                 235                 240

Ile Ala Pro Ala Ser Val Ile Ala Ile Thr Ile Leu Ile Phe Asn Leu
                245                 250                 255

Thr Gly Asp Ala Leu Arg Asp Arg Leu Leu Lys Gln Arg Gly Glu Tyr
            260                 265                 270

Asp Glu Ser His
        275


<210> SEQ ID NO 89
<211> LENGTH: 535
<212> TYPE: DNA
<213> ORGANISM: Staphylococcus aureus

<400> SEQUENCE: 89

cttatgatta caatggctta tcagaaaatg cgaatgaagt ttaaaaaggg agctaatatc      60

aatgaataca aatgatgcta ttaaaatttt aaaagagaac ggtttaaaat atacagataa     120

acgtaaagat atgttagata tttttgtcga agaagataag tatataaacg caaagtatat     180

acaacaagtt atggatgaaa attatcctgg aatttcattc gacacaatat atagaaacct     240

gcacttattt aaagatttag gaattattga aaatacagaa cttgatggtg aaatgaagtt     300

tagaatcgct tgtacaaacc atcatcatca tcattttatc tgtgaaaagt gtggagatac     360

aaaggtaata gattattgtc caatagatca gataaaatta tcactacctg gtgttaatat     420

tcacaaacac aaacttgaag tttatggtgt atgtgagtct tgccaagatt aatataaaga     480

aatgagattt atgcacattt ggtcagatgt atgcataaat ctcatttttt aaatt          535


<210> SEQ ID NO 90
<211> LENGTH: 136
<212> TYPE: PRT
<213> ORGANISM: Staphylococcus aureus

<400> SEQUENCE: 90

Met Asn Thr Asn Asp Ala Ile Lys Ile Leu Lys Glu Asn Gly Leu Lys
1               5                   10                  15

Tyr Thr Asp Lys Arg Lys Asp Met Leu Asp Ile Phe Val Glu Glu Asp
            20                  25                  30

Lys Tyr Ile Asn Ala Lys Tyr Ile Gln Gln Val Met Asp Glu Asn Tyr
        35                  40                  45

Pro Gly Ile Ser Phe Asp Thr Ile Tyr Arg Asn Leu His Leu Phe Lys
    50                  55                  60

Asp Leu Gly Ile Ile Glu Asn Thr Glu Leu Asp Gly Glu Met Lys Phe
65                  70                  75                  80
```

```
Arg Ile Ala Cys Thr Asn His His His His His Phe Ile Cys Glu Lys
                85                  90                  95

Cys Gly Asp Thr Lys Val Ile Asp Tyr Cys Pro Ile Asp Gln Ile Lys
            100                 105                 110

Leu Ser Leu Pro Gly Val Asn Ile His Lys His Lys Leu Glu Val Tyr
        115                 120                 125

Gly Val Cys Glu Ser Cys Gln Asp
    130                 135


<210> SEQ ID NO 91
<211> LENGTH: 912
<212> TYPE: DNA
<213> ORGANISM: Staphylococcus aureus

<400> SEQUENCE: 91

attgaaactc aaattcaaca aacttcaact gaaaaaatag caacagaaaa aacatcgtat     60

ctaataaatt atatgaacgc tgtggcatag aaaggcggcg aaacatgaca cacaaatata    120

tatcaacgca aatgttgatc atttttactg cattaatgat tattgccaat ttttactaca    180

tattttttga aaaaattggc tttttactcg ttctattatt gggatgtgta ttagtttatg    240

taggatatct ttattttcat aaaatacgtg gccttttggc gttttggata ggcgcgctat    300

taattgcatt cacattattg tctaataagt atacaatcat catcttgttc gtctttttat    360

tattacttat tgtgcgttat ttaatacaca agtttaaacc aaaaaaagta gttgcgacgg    420

atgaggttat gacttcacca tcttttatta aacaaaagtg gtttggtgag caacgtacac    480

cagtttatgt atataagtgg gaagatgtac aaattcaaca tggaattggc gacctacata    540

ttgacttaac aaaagctgca aatattaagg aaaataatac cattgttgtt agacacattt    600

taggtaaagt gcaggttata ttgccggtta attacaatat taatttacat gtagctgctt    660

tttatggaag tacttacgtg aatgaaaaat catataaagt tgaaaataac aatattcata    720

ttgaagaaat gatgaaaccg gataactata cagttaatat ctacgtatca acgtttatcg    780

gagacgtaga ggtgatttat cgatgaacca ctacattaga acaattggtt caatgctcat    840

cttagtatat agcatgctag ctgcatttct gttcatcgat aaagtttttg taaatatcat    900

ctattttcaa gg                                                         912


<210> SEQ ID NO 92
<211> LENGTH: 233
<212> TYPE: PRT
<213> ORGANISM: Staphylococcus aureus

<400> SEQUENCE: 92

Met Thr His Lys Tyr Ile Ser Thr Gln Met Leu Ile Ile Phe Thr Ala
1               5                   10                  15

Leu Met Ile Ile Ala Asn Phe Tyr Tyr Ile Phe Phe Glu Lys Ile Gly
            20                  25                  30

Phe Leu Leu Val Leu Leu Leu Gly Cys Val Leu Val Tyr Val Gly Tyr
        35                  40                  45

Leu Tyr Phe His Lys Ile Arg Gly Leu Leu Ala Phe Trp Ile Gly Ala
    50                  55                  60

Leu Leu Ile Ala Phe Thr Leu Leu Ser Asn Lys Tyr Thr Ile Ile Ile
65                  70                  75                  80

Leu Phe Val Phe Leu Leu Leu Leu Ile Val Arg Tyr Leu Ile His Lys
                85                  90                  95
```

```
Phe Lys Pro Lys Lys Val Val Ala Thr Asp Glu Val Met Thr Ser Pro
            100                 105                 110

Ser Phe Ile Lys Gln Lys Trp Phe Gly Glu Gln Arg Thr Pro Val Tyr
        115                 120                 125

Val Tyr Lys Trp Glu Asp Val Gln Ile Gln His Gly Ile Gly Asp Leu
    130                 135                 140

His Ile Asp Leu Thr Lys Ala Ala Asn Ile Lys Glu Asn Asn Thr Ile
145                 150                 155                 160

Val Val Arg His Ile Leu Gly Lys Val Gln Val Ile Leu Pro Val Asn
                165                 170                 175

Tyr Asn Ile Asn Leu His Val Ala Ala Phe Tyr Gly Ser Thr Tyr Val
            180                 185                 190

Asn Glu Lys Ser Tyr Lys Val Glu Asn Asn Asn Ile His Ile Glu Glu
        195                 200                 205

Met Met Lys Pro Asp Asn Tyr Thr Val Asn Ile Tyr Val Ser Thr Phe
    210                 215                 220

Ile Gly Asp Val Glu Val Ile Tyr Arg
225                 230


<210> SEQ ID NO 93
<211> LENGTH: 1017
<212> TYPE: DNA
<213> ORGANISM: Staphylococcus aureus

<400> SEQUENCE: 93

ggcagaaatg cgtaaaaatg aagtgtttta tttatttaaa tagtctgaca attaagggtg      60

ttatgttaat atgattttat gagaagtatg gagtagcaat aaaggggtga cctcgcatgt     120

taattcaatt agatcaaatt gggcgaatga agcaaggaaa aacaatttta aaaaagattt     180

cttggcaaat tgctaaaggt gataaatgga tattatatgg gttgaatggt gctggcaaga     240

caacacttct aaatatttta aatgcgtatg agcctgcaac atctggaact gttaaccttt     300

tcggtaaaat gccaggcaag gtagggtatt ctgcagagac tgtacgacaa catataggtt     360

ttgtatctca tagtttactg gaaaagtttc aagagggtga aagagtaatc gatgtggtga     420

taagcggtgc ctttaaatca attggtgttt atcaagatat tgatgatgag atacgtaatg     480

aagcacatca attacttaaa ttagttggaa tgtctgctaa agcgcaacaa tatattggtt     540

atttatctac cggtgaaaaa caacgagtga tgattgcacg agctttaatg ggcaacccc     600

aggttttaat tttagatgag ccagcagctg gtttagactt tattgcacga gaatcgttgt     660

taagtatact tgactcattg tcagattcat atccaacgct tgcgatgatt tatgtgacgc     720

actttattga agaaataact gctaactttt ccaaaatttt actgctaaaa gatggccaaa     780

gtattcaaca aggcgctgta gaagacatat taacttctga aaacatgtca cgatttttcc     840

agaaaaatgt agcagttcaa agatggaata atcgattttc tatggcaatg ttagagtaaa     900

tattttgcaa ataataagta ataatgacaa aatttaatta agataaaatg gacagtggag     960

ggcaatatag ataacgtaaa agcaatattt ttggacatgg atggaacaat tttacat      1017


<210> SEQ ID NO 94
<211> LENGTH: 260
<212> TYPE: PRT
<213> ORGANISM: Staphylococcus aureus

<400> SEQUENCE: 94

Met Leu Ile Gln Leu Asp Gln Ile Gly Arg Met Lys Gln Gly Lys Thr
1               5                   10                  15
```

```
Ile Leu Lys Lys Ile Ser Trp Gln Ile Ala Lys Gly Asp Lys Trp Ile
            20                  25                  30

Leu Tyr Gly Leu Asn Gly Ala Gly Lys Thr Thr Leu Leu Asn Ile Leu
        35                  40                  45

Asn Ala Tyr Glu Pro Ala Thr Ser Gly Thr Val Asn Leu Phe Gly Lys
    50                  55                  60

Met Pro Gly Lys Val Gly Tyr Ser Ala Glu Thr Val Arg Gln His Ile
65                  70                  75                  80

Gly Phe Val Ser His Ser Leu Leu Glu Lys Phe Gln Glu Gly Glu Arg
                85                  90                  95

Val Ile Asp Val Val Ile Ser Gly Ala Phe Lys Ser Ile Gly Val Tyr
            100                 105                 110

Gln Asp Ile Asp Asp Glu Ile Arg Asn Glu Ala His Gln Leu Leu Lys
        115                 120                 125

Leu Val Gly Met Ser Ala Lys Ala Gln Gln Tyr Ile Gly Tyr Leu Ser
    130                 135                 140

Thr Gly Glu Lys Gln Arg Val Met Ile Ala Arg Ala Leu Met Gly Gln
145                 150                 155                 160

Pro Gln Val Leu Ile Leu Asp Glu Pro Ala Ala Gly Leu Asp Phe Ile
                165                 170                 175

Ala Arg Glu Ser Leu Leu Ser Ile Leu Asp Ser Leu Ser Asp Ser Tyr
            180                 185                 190

Pro Thr Leu Ala Met Ile Tyr Val Thr His Phe Ile Glu Glu Ile Thr
        195                 200                 205

Ala Asn Phe Ser Lys Ile Leu Leu Leu Lys Asp Gly Gln Ser Ile Gln
    210                 215                 220

Gln Gly Ala Val Glu Asp Ile Leu Thr Ser Glu Asn Met Ser Arg Phe
225                 230                 235                 240

Phe Gln Lys Asn Val Ala Val Gln Arg Trp Asn Asn Arg Phe Ser Met
                245                 250                 255

Ala Met Leu Glu
            260
```

```
<210> SEQ ID NO 95
<211> LENGTH: 818
<212> TYPE: DNA
<213> ORGANISM: Staphylococcus aureus

<400> SEQUENCE: 95

gacgtctttg gtaacaagcc atgaaaagat acacatggta gatatgtatt tcaagattat      60

tcaatgaata tcgaattata ggaggagata tgtatgaaaa gattagttac agggttacta     120

gcattatcat tatttttagc tgcatgtggt caagatagtg accaacaaaa agacggtaat     180

aaagaaaaag atgataaagc gaaaactgaa caacaagata aaaaaacaaa tgattcatct     240

aaagataaga aagataataa agatgatagt aaagacgtaa acaaagataa taaagataat     300

agtgcaaacg ataaccagca acaatctaat tcaaatgcaa caaacaatga ccaaaaccaa     360

acaaataata accaatcaag taataaccaa gcgaataata atcaaaaatc aagttacgtt     420

gcaccatatt atggacaaaa tgccgcgccg gttgcacgtc aaatttatcc gtttaatgga     480

aataaaaatc aagctttaca gcaattgcca aatttccaaa cagctttaaa tgcggctaat     540

aatgaagcaa ataaatttgg tagtaataat aaagtgtata atgattattc tattgaagaa     600

cataatggca actataagta tgtgtttagt tttaaagacc caaatgcaaa tggaaaatat     660
```

```
tcaattgtaa cggttgatta tactggacaa gcaatggtta ctgatccaaa ctaccaacaa    720

taatgttaat ataactatga tgcaagttaa aaaataaaac ggtaaactct ataatatgaa    780

ttagggttta ccgtttttg cgtattttaa agtatcaa                             818
```

<210> SEQ ID NO 96
<211> LENGTH: 209
<212> TYPE: PRT
<213> ORGANISM: Staphylococcus aureus

<400> SEQUENCE: 96

```
Met Lys Arg Leu Val Thr Gly Leu Leu Ala Leu Ser Leu Phe Leu Ala
1               5                   10                  15

Ala Cys Gly Gln Asp Ser Asp Gln Gln Lys Asp Gly Asn Lys Glu Lys
            20                  25                  30

Asp Asp Lys Ala Lys Thr Glu Gln Gln Asp Lys Lys Thr Asn Asp Ser
        35                  40                  45

Ser Lys Asp Lys Lys Asp Asn Lys Asp Asp Ser Lys Asp Val Asn Lys
    50                  55                  60

Asp Asn Lys Asp Asn Ser Ala Asn Asp Asn Gln Gln Gln Ser Asn Ser
65                  70                  75                  80

Asn Ala Thr Asn Asn Asp Gln Asn Gln Thr Asn Asn Asn Gln Ser Ser
                85                  90                  95

Asn Asn Gln Ala Asn Asn Asn Gln Lys Ser Ser Tyr Val Ala Pro Tyr
            100                 105                 110

Tyr Gly Gln Asn Ala Ala Pro Val Ala Arg Gln Ile Tyr Pro Phe Asn
        115                 120                 125

Gly Asn Lys Asn Gln Ala Leu Gln Gln Leu Pro Asn Phe Gln Thr Ala
    130                 135                 140

Leu Asn Ala Ala Asn Asn Glu Ala Asn Lys Phe Gly Ser Asn Asn Lys
145                 150                 155                 160

Val Tyr Asn Asp Tyr Ser Ile Glu Glu His Asn Gly Asn Tyr Lys Tyr
                165                 170                 175

Val Phe Ser Phe Lys Asp Pro Asn Ala Asn Gly Lys Tyr Ser Ile Val
            180                 185                 190

Thr Val Asp Tyr Thr Gly Gln Ala Met Val Thr Asp Pro Asn Tyr Gln
        195                 200                 205

Gln
```

<210> SEQ ID NO 97
<211> LENGTH: 1716
<212> TYPE: DNA
<213> ORGANISM: Staphylococcus aureus

<400> SEQUENCE: 97

```
gttgaaaatg ataatgccaa attatgctat atctataaat ttagagcgcg atttgcagta     60

cttgcacatc ttttaacaca gcgggaaggc ttaccagcta aacaagatgt cattgaaaat    120

tatcaaaaaa atcaaatgta tttagatgat tattcatgtt gtgaagtgtc atgcacatgt    180

tagaagtgaa atatgatatg agaactgggc attatacgcc catacctaat gaacctcatt    240

atttggttat tagtcatgcg gataaactta ccgcaacaga aaaagcgaaa ttaagattat    300

taatcataaa acagaaatta gatatttcat tggcagaaag tgtagtttct tcgcctatag    360

cgagtgaaca tgtgatagaa caattgacac tatttcaaca tgagcgacga catttaagac    420

ctaaaataag tgcgacattt ttagcctggt tgttgatatt tttaatgttt gcattgccaa    480
```

```
tcggtatcgc ttatcaattt tcagattggt ttcaaaatca gtatgtgtca gcatggatag    540

aatatttaac tcaaacaaca ttgctcaatc acgatatatt acagcatata ttatttggtg    600

attatggtgt gctatcactt ggaacatatt cgctcgtatg ggcattgccg gttgtaatat    660

tgattagttt atcaactgct ataattgatc aaacaggact caaatcatgg atgatatggg    720

caattgaacc gtcaatgtta tggataggat tacaaggtaa tgatatcgtg ccactattag    780

aagggtttgg atgtaatgca gcagctattt cacaagcagc acaccaatgc catacctgca    840

cgaagacaca gtgtatgagt ttaataagct ttggtagttc ttgtagttat caaataggtg    900

cgacattatc tatttttagt gtagctggaa agtcatggct atttatgccg tacttaatat    960

tagtactttt aggtggcatc ttacataata ggatatggtt gaaaaagaat gatcaacaac   1020

ttagcgttcc gctaccttat gataggcaat tacatatgcc aaatatacgt caaatgttgc   1080

tacaaatgtg gcaaaatata caaatgttta tcgttcaagc gctacctatt tttatcacaa   1140

tctgtcttat tgttagtatt ttatcactaa cgccaatttt gaatgtttta tcacaaatat   1200

ttacacctat attatcgtta ttaggcatct cgtcagaatt gtcaccaggg attttatttt   1260

caatgattcg aaaagacggc atgctcttgt ttaatttgca tcagggcgcc ttattacaag   1320

gaatgacagc aacacagtta ctactacttg tgttttttag ttcaacattt acagcgtgct   1380

cggtcacaat gacgatgctt ttgaaacatt taggtggtca gtcagcacta aaattaattg   1440

gaaagcaaat ggtgacatca ttgtctttag ttattggtgt aggcatcatt gttaaaatag   1500

taatgctgat tatttaaaaa aaatgaacta taactgaata tagagtcatg tcagtcaata   1560

ggagatctat cttggaatat gctattcata tgaagtataa gaggagagtc gcagatgaaa   1620

atagttatta taggtgggtt tttaggtggc ggtaaaacga ctgtcttaaa tcatttgctc   1680

gctgaatcat taaaggaatc gctgaaacca gcagtc                               1716
```

<210> SEQ ID NO 98
<211> LENGTH: 439
<212> TYPE: PRT
<213> ORGANISM: Staphylococcus aureus

<400> SEQUENCE: 98

```
Met Arg Thr Gly His Tyr Thr Pro Ile Pro Asn Glu Pro His Tyr Leu
1               5                   10                  15

Val Ile Ser His Ala Asp Lys Leu Thr Ala Thr Glu Lys Ala Lys Leu
            20                  25                  30

Arg Leu Leu Ile Ile Lys Gln Lys Leu Asp Ile Ser Leu Ala Glu Ser
        35                  40                  45

Val Val Ser Ser Pro Ile Ala Ser Glu His Val Ile Glu Gln Leu Thr
    50                  55                  60

Leu Phe Gln His Glu Arg Arg His Leu Arg Pro Lys Ile Ser Ala Thr
65                  70                  75                  80

Phe Leu Ala Trp Leu Leu Ile Phe Leu Met Phe Ala Leu Pro Ile Gly
                85                  90                  95

Ile Ala Tyr Gln Phe Ser Asp Trp Phe Gln Asn Gln Tyr Val Ser Ala
            100                 105                 110

Trp Ile Glu Tyr Leu Thr Gln Thr Thr Leu Leu Asn His Asp Ile Leu
        115                 120                 125

Gln His Ile Leu Phe Gly Asp Tyr Gly Val Leu Ser Leu Gly Thr Tyr
    130                 135                 140

Ser Leu Val Trp Ala Leu Pro Val Val Ile Leu Ile Ser Leu Ser Thr
145                 150                 155                 160
```

```
Ala Ile Ile Asp Gln Thr Gly Leu Lys Ser Trp Met Ile Trp Ala Ile
                165                 170                 175

Glu Pro Ser Met Leu Trp Ile Gly Leu Gln Gly Asn Asp Ile Val Pro
            180                 185                 190

Leu Leu Glu Gly Phe Gly Cys Asn Ala Ala Ala Ile Ser Gln Ala Ala
        195                 200                 205

His Gln Cys His Thr Cys Thr Lys Thr Gln Cys Met Ser Leu Ile Ser
    210                 215                 220

Phe Gly Ser Ser Cys Ser Tyr Gln Ile Gly Ala Thr Leu Ser Ile Phe
225                 230                 235                 240

Ser Val Ala Gly Lys Ser Trp Leu Phe Met Pro Tyr Leu Ile Leu Val
                245                 250                 255

Leu Leu Gly Gly Ile Leu His Asn Arg Ile Trp Leu Lys Lys Asn Asp
            260                 265                 270

Gln Gln Leu Ser Val Pro Leu Pro Tyr Asp Arg Gln Leu His Met Pro
        275                 280                 285

Asn Ile Arg Gln Met Leu Leu Gln Met Trp Gln Asn Ile Gln Met Phe
    290                 295                 300

Ile Val Gln Ala Leu Pro Ile Phe Ile Thr Ile Cys Leu Ile Val Ser
305                 310                 315                 320

Ile Leu Ser Leu Thr Pro Ile Leu Asn Val Leu Ser Gln Ile Phe Thr
                325                 330                 335

Pro Ile Leu Ser Leu Leu Gly Ile Ser Ser Glu Leu Ser Pro Gly Ile
            340                 345                 350

Leu Phe Ser Met Ile Arg Lys Asp Gly Met Leu Leu Phe Asn Leu His
        355                 360                 365

Gln Gly Ala Leu Leu Gln Gly Met Thr Ala Thr Gln Leu Leu Leu Leu
    370                 375                 380

Val Phe Phe Ser Ser Thr Phe Thr Ala Cys Ser Val Thr Met Thr Met
385                 390                 395                 400

Leu Leu Lys His Leu Gly Gly Gln Ser Ala Leu Lys Leu Ile Gly Lys
                405                 410                 415

Gln Met Val Thr Ser Leu Ser Leu Val Ile Gly Val Gly Ile Ile Val
            420                 425                 430

Lys Ile Val Met Leu Ile Ile
        435
```

BACTERIAL VACCINE COMPONENTS FROM *STAPHYLOCOCCUS AUREUS* AND USES THEREOF

CROSS-REFERENCE TO RELATED APPLICATIONS

This application is a National Entry Application of PCT application no. PCT/CA2011/050145* filed on Mar. 17, 2011 and published in English under PCT Article 21(2), which itself claims benefit of U.S. provisional application Ser. No. 61/314,670, filed on Mar. 17, 2010. All documents above are incorporated herein in their entirety by reference.

STATEMENT REGARDING FEDERALLY SPONSORED RESEARCH OR DEVELOPMENT

Not applicable.

FIELD OF THE INVENTION

The present invention relates to novel vaccine targets and components. More specifically, the present invention is concerned with novel antigens which represent vaccine components, processes of manufacturing same, methods using same, and methods of preventing and treating microbial infections involving the administration of same.

REFERENCE TO SEQUENCE LISTING

Pursuant to 37 C.F.R. 1.821(c), a sequence listing is submitted herewith as an ASCII compliant text file named 14692 28-Sequence listing, created on Feb. 13, 2014 and having a size of ~190 kilobytes. The content of the aforementioned file is hereby incorporated by reference in its entirety.

BACKGROUND OF THE INVENTION

Bovine mastitis is the most frequent and costly disease for dairy producers and *Staphylococcus aureus* is considered to be the transmittable bacterium that is the most often responsible for the development of the disease (Sears et al., 2003). Staphylococcal intramammary infections (IMI), which may lead to mastitis, are difficult to treat and frequent relapses are common (Sandholm et al., 1990). Bacterial susceptibility to antibiotics in vitro is a poor predictor of therapeutic efficacy in chronically infected cows (Owens et al., 1997). Although infections that follow treatment of mastitis can be due to newly acquired strains, they are often the result of the persistence of the original infective organism (Sandholm et al., 1990; Myllys et al., 1997). Existing therapies thus often fail to eliminate the infection and it would be highly desirable to find novel approaches to prevent or treat staphylococcal IMI.

A lack of vaccine efficacy and protective ability has been noted for commercially available *S. aureus* vaccines (Middleton, 2008). A number of additional Staphylococci vaccines and vaccine components have been described and proposed. The use of milk or low-iron media as surrogate systems for exploring *S. aureus* genes that are expressed during IMI do not fully replicate the actual mammalian host environment that may vary in nutrient composition, in interactions with host cells and in immune response components, to name just a few differences. Hence, the *S. aureus* components currently proposed as vaccine are not necessarily the components that are expressed during IMI at multiple points in time, by multiple strains (including chronic strains) and in multiple hosts. Thus it would be highly desirable to identify *S. aureus* genes that are expressed during IMI at multiple points in time, by multiple strains, and in multiple hosts, so that a selection of genes and gene-encoded products (e.g., proteins) can be used either alone or in combination for protection against IMI and mastitis.

The present invention seeks to meet these and other needs.

The present description refers to a number of documents, the content of which is herein incorporated by reference in their entirety.

SUMMARY OF THE INVENTION

In an aspect, the present invention provides a method for preventing and/or treating Staphylococcal intramammary infection (IMI) in a mammal, said method comprising administrating to said mammal an effective amount of at least one agent, wherein said agent is: (a) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e).

In another aspect, the present invention provides a use of an agent, wherein said agent is: (a) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599 based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e), for preventing and/or treating Staphylococcal intramammary infection (IMI) in a mammal.

In another aspect, the present invention provides a use of an agent, wherein said agent is: (a) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599 based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e), for the preparation of a medicament for preventing and/or treating Staphylococcal intramammary infection (IMI) in a mammal.

In another aspect, the present invention provides a pharmaceutical composition for preventing and/or treating Staphylococcal intramammary infection (IMI) in a mammal, said composition comprising: (a) at least one agent, wherein said agent is (i) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599 based on the gene nomenclature from the *Sta-*

*phylococcus aureus* COL (SACOL) genome set forth in NCBI Reference Sequence NC__002951.2; (ii) a polypeptide encoded by a gene from a same operon as one of the genes of (i); (iii) an immunogenic fragment of (i) or (ii); (iv) an immunogenic variant of any one of (i) to (iii); (v) a nucleic acid encoding the polypeptide of any one of (i) to (iv); or (vi) any combination of (i) to (v). It may optionally comprise (b) a pharmaceutically acceptable excipient.

In another aspect, the present invention provides a pharmaceutical composition comprising: (a) at least one agent, wherein said agent is: (i) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2; (ii) a polypeptide encoded by a gene from a same operon as one of the genes of (a); (iii) an immunogenic fragment of (i) or (ii); (iv) an immunogenic variant of any one of (i) to (iii); (v) a nucleic acid encoding the polypeptide of any one of (i) to (iv); or (vi) any combination of (i) to (v); and (b) a pharmaceutically acceptable excipient.

In another aspect, the present invention provides a kit for the prevention and/or treatment of Staphylococcal IMI, comprising (a) at least one agent, wherein said agent is: (i) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2; (ii) a polypeptide encoded by a gene from a same operon as one of the genes of (a); (iii) an immunogenic fragment of (i) or (ii); (iv) an immunogenic variant of any one of (i) to (iii); (v) a nucleic acid encoding the polypeptide of any one of (i) to (iv); or (vi) any combination of (i) to (v); and (b) instructions to use the kit for the prevention and/or treatment of Staphylococcal IMI.

In another aspect, the present invention provides a method of diagnosing Staphylococcal IMI in a mammal, said method comprising: determining a level of expression of at least one gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, or the level of activity of a polypeptide encoded by said one or more genes, in a biological sample from said mammal; and comparing said level of expression or activity to a reference level of expression or activity; wherein a higher expression or activity in said biological sample relative to said reference expression or activity is indicative that said mammal has staphylococcal IMI.

In another aspect, the present invention provides a kit for the diagnosis of Staphylococcal IMI, comprising (a) at least one ligand, wherein said at least one ligand binds to: (i) a polypeptide encoded by a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2; (ii) a polypeptide encoded by a gene from a same operon as one of the genes of (a); (iii) an immunogenic fragment of (i) or (ii); (iv) an immunogenic variant of any one of (i) to (iii); (v) a nucleic acid encoding the polypeptide of any one of (i) to (iv); or (vi) any combination of (i) to (v); and (b) instructions to use the kit for the diagnosis of Staphylococcal IMI.

In another aspect, the present invention provides a method for preventing and/or treating Staphylococcal intramammary infection (IMI) in a mammal, said method comprising administrating to said mammal an effective amount of at least one agent, wherein said agent is a live attenuated form of *Staphyloccocus aureus* comprising a mutation in a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2, and wherein the mutation is a deletion or an insertion.

In another aspect, the present invention provides a use of an agent, wherein said agent is a live attenuated form of *Staphyloccocus aureus* comprising a mutation in a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2, and wherein the mutation is a deletion, an insertion or a substitution of one or more nucleotides, for preventing and/or treating Staphylococcal intramammary infection (IMI) in a mammal or for the preparation of a medicament for preventing and/or treating Staphylococcal intramammary infection (IMI) in a mammal.

In another aspect, the present invention provides a pharmaceutical composition for preventing and/or treating Staphylococcal intramammary infection (IMI) in a mammal, said composition comprising an agent, wherein said agent is a live attenuated form of *Staphyloccocus aureus* comprising a mutation in a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2, and wherein the mutation is a deletion, an insertion or a substitution of one or more nucleotides.

In another aspect, the present invention provides a kit for the prevention and/or treatment of Staphylococcal IMI, comprising at least one agent, wherein said agent is a live attenuated form of *Staphyloccocus aureus* comprising a mutation in a gene, wherein said gene is SACOL0029, SACOL0264, SACOL0442, SACOL0718, SACOL0720, SACOL1353, SACOL1416, SACOL1611, SACOL1944, SACOL2144, SACOL2365 or SACOL2599, based on the gene nomenclature from the *Staphylococcus aureus* COL (SACOL) genome set forth in NCBI Reference Sequence NC__002951.2, and wherein the mutation is a deletion, an insertion or a substitution of one or more nucleotides.

In an embodiment, the above-mentioned gene from the same operon as one of the genes of (a) is SACOL0720, and wherein said one or more genes of (a) is SACOL0718.

In an embodiment, the above-mentioned one or more genes is SACOL0442, SACOL0718, SACOL0720 or any combination thereof. In a further embodiment, the above-mentioned one or more genes is SACOL0442, SACOL0720 or both.

In another embodiment, the above-mentioned methods, uses, pharmaceutical compositions or kits comprise a combination of agents. In a further embodiment, the above-mentioned combination of agents comprises: (i) a first agent, wherein said first agent is (a) a polypeptide encoded by SACOL0442, (b) an immunogenic fragment of (a); (c) an immunogenic variant of (a) or (b); (d) a nucleic acid encoding the polypeptide of any one of (a) to (c); or (e) any combination of (a) to (d): and (ii) a second agent, wherein said second agent is (a) a polypeptide encoded by SACOL0720, (b) an immunogenic fragment of (a); (c) an immunogenic variant of (a) or (b); (d) a nucleic acid encoding the polypeptide of any one of (a) to (c); or (e) any combination of (a) to (d).

In an embodiment, the above-mentioned gene is SACOL0442 and the immunogenic fragment comprises one or more of the following amino acid sequences: TFGIYPKADASTQN (SEQ ID NO: 17), KDTINGKSNKSRNW (SEQ ID NO: 18) or KDGGKYTLESHKELQ (SEQ ID NO: 19).

In another embodiment, the above-mentioned gene is SACOL0720 and the immunogenic fragment comprises one or more of the following amino acid sequences: QFGFDLKHKKDALA (SEQ ID NO: 20), TIKDQQKANQLAS (SEQ ID NO: 21), KDINKIYFMTDVDL (SEQ ID NO: 22) or DVDLGGPTFVLND (SEQ ID NO: 23).

In an embodiment, the above-mentioned Staphylococcal intramammary infection is caused by one or more *Staphylococcus aureus* strains.

In an embodiment, the above-mentioned methods, uses, pharmaceutical compositions or kits further comprise an adjuvant. In a further embodiment, the above-mentioned adjuvant is alum, Emulsigen™ D, cyclic-diguanosine-5'-monophosphate (c-di-GMP), polyphosphasine or pathogen-associated molecular patterns (PAMPS). In yet a further embodiment, the above-mentionedPAMPS is unmethylated dinucleotides (CpG) or microbial polysaccharides.

In an embodiment, the above-mentioned (i) agent, (ii) adjuvant, or both (i) and (ii) are comprised in a pharmaceutical composition.

In an embodiment, the above-mentioned pharmaceutical composition further comprises one or more pharmaceutically acceptable excipients.

In an embodiment, the above-mentioned mammal is a cow.

In an embodiment, the above-mentioned IMI is associated with bovine mastitis.

In an embodiment, the above-mentioned reference expression or activity is a level of expression or activity determined in a corresponding biological sample from a mammal known to not having staphylococcal IMI.

In another embodiment, the above-mentioned level of expression is determined by measuring the level of expression of a mRNA transcribed from said one or more genes. In another embodiment, said level of expression is determined by measuring the level of expression of a polypeptide encoded by said one or more genes.

In an embodiment, the above-mentioned biological sample is milk.

In an embodiment, the above-mentioned kit comprises a combination of ligands.

In an embodiment, the above-mentioned combination of ligands comprises ligands which bind to: (i) a first agent, wherein said first agent is (a) a polypeptide encoded by SACOL0442, (b) an immunogenic fragment of (a); (c) an immunogenic variant of (a) or (b); (d) a nucleic acid encoding the polypeptide of any one of (a) to (c); or (e) any combination of (a) to (d): and (ii) a second agent, wherein said second agent is (a) a polypeptide encoded by SACOL0720, (b) an immunogenic fragment of (a); (c) an immunogenic variant of (a) or (b); (d) a nucleic acid encoding the polypeptide of any one of (a) to (c); or (e) any combination of (a) to (d).

BRIEF DESCRIPTION OF THE DRAWINGS

In the appended drawings:

FIG. 5 shows experimental infection profiles caused by chronic strains #3, #557 and #1290 and by a strain isolated from a typical mastitis case SHY97-3906 in cows reported as a function of bacterial (CFU) (left Y axis) or somatic cell counts (SCC) (right Y axis) over the infection period.

FIG. 10 shows the growth kinetics of the *S. aureus* strain ATCC 29213 and the isogenic three mutants ATCC 29213ΔSACOL0442a (Δ442a), ATCC 29213ΔSACOL0442b (Δ442b) and ATCC29213 ΔSACOL0720 (Δ720). Mutants for genes SACOL0442 and SACOL0720 were produced by gene replacement (Δ442a) or by intron insertion (Δ442b and Δ720). Prior to experimental bovine IMI, the relative growth of the parental strain and the mutants was evaluated in vitro in freshly collected milk (FIG. 10A).

FIGS. 11A-11D show a nucleic acid (FIGS. 11A-C) and amino acid (FIG. 11D) sequence alignment of SACOL0442 from various *Staphylococcus aureus* strains (nucleic acid sequences: MW0345 (MW2) (SEQ ID NO: 24); SAS0347 (MSSA476) (SEQ ID NO: 25); SACOL0442 (Col) (SEQ ID NO: 26); SAOUHSC__00354 (nctc8325) (SEQ ID NO: 27); NWMN__0362 (NEWMAN) (SEQ ID NO: 28); SAUSA300__0370 (USA300-FPR3757) (SEQ ID NO: 29); SaurJH1__0429 (JH1) (SEQ ID NO: 30); SAHV__0367 (Mu3) (SEQ ID NO: 31); SaurJH9__0419 (JH9) (SEQ ID NO: 32); SAV0370 (Mu50) (SEQ ID NO: 33); SA0357 (N315) (SEQ ID NO: 34); SAB0321 (RF122) (SEQ ID NO: 35); and consensus (SEQ ID NO: 36); amino acid sequences: SACOL0442 (Col) (SEQ ID NO: 37); SAOUHSC__00354 (nctc8325) (SEQ ID NO: 38); NWMN__0362 (NEWMAN) (SEQ ID NO: 39); SAUSA300__0370 (USA300-FPR3757) (SEQ ID NO: 40); SaurJH1__0429 (JH1) (SEQ ID NO: 41); SAHV__0367 (Mu3) (SEQ ID NO: 42); SaurJH9__0419 (JH9) (SEQ ID NO: 43); SAV0370 (Mu50) (SEQ ID NO: 44); SA0357 (N315) (SEQ ID NO: 45); SAS0347 (MSSA476) (SEQ ID NO: 46); SAB0321 (RF122) (SEQ ID NO: 47); and consensus (SEQ ID NO: 48). Alignments are based on the sequences available from multiple *Staphylococcus aureus* strains, including the bovine mastitis isolate RF122. The amino acid sequence of MW0345 (MW2) (SEQ ID NO: 75) is not included in the alignment. The characteristics of the compared strains are provided in FIG. 13. Under each alignment, an asterisk (*) indicates a 100% match of nucleotide or amino acid between all strains compared; a double-dot (:) indicates that conserved substitutions have been observed and a single dot (•) means that semi-conserved substitutions are observed.

FIGS. 12A-12K show a nucleic acid (FIGS. 12A-H) and amino acid (FIG. 121-K) sequence alignment of SACOL0720 from various *Staphylococcus aureus* strains. (nucleic acid sequences: SaurJH1__0700 (JH1) (SEQ ID NO: 49); SaurJH9__0685 (JH9) (SEQ ID NO: 50); SAHV__0659 (Mu3) (SEQ ID NO: 51); SAV0662 (Mu50) (SEQ ID NO: 52); SA0617 (N315) (SEQ ID NO: 53); MW0624 (MW2) (SEQ ID NO:54); SAS0627 (MSSA476) (SEQ ID NO: 55); SACOL0720 (SEQ ID NO: 56); SAUSA300__0648 (USA300-FPR3757) (SEQ ID NO: 57); SAOUHSC__00668 (NCTC8325) (SEQ ID NO: 58); NWMN__0631 (Newman) (SEQ ID NO: 59); SAB0611 (RF122) (SEQ ID NO: 60); consensus (SEQ ID NO: 61); amino acid sequence: SACOL0720 (SEQ ID NO: 62); SAUSA300__0648 (USA300-FPR3757) (SEQ ID NO: 63); SAOUHSC__00668 (NCTC8325) (SEQ ID NO: 64); NWMN__0631 (Newman) (SEQ ID NO: 65); SaurJH10700 (JH1) (SEQ ID NO: 66); SaurJH9__0685 (JH9) (SEQ ID NO: 67); SAHV__0659 (Mu3) (SEQ ID NO: 68); SAV0662 (Mu50) (SEQ ID NO: 69); SA0617 (N315) (SEQ ID NO: 70); MW0624 (MW2) (SEQ ID NO: 71); SAS0627 (MSSA476) (SEQ ID NO: 72); SAB0611 (RF122) (SEQ ID NO: 73); consensus (SEQ ID NO: 74). Alignments are based on the sequences available from multiple *Staphylococcus aureus* strains, including the bovine mastitis isolate RF122. The characteristics of the compared strains are provided in FIG. 13. Under each alignment, an asterisk (*) indicates a 100% match of nucleotide or amino acid between all strains compared; a double-dot (:) indicates that conserved substitutions have been observed and a single dot (•) means that semi-conserved substitutions are observed.

FIG. 13 shows the characteristics of the *Staphylococcus aureus* strains whose sequences are aligned at FIGS. 11A-D and 12A-K.

FIG. 14A-14C show the predicted cellular localization of proteins SACOL0442 (FIG. 14A), SACOL0718 (FIG. 14B) and SACOL0720 (FIG. 14C), and FIG. 14D shows the predicted transmembrane helices of protein SACOL0720 (SEQ ID NO: 62). In FIG. 14D, "I" and "i" represent intracellular amino acids, "H" and "h" represent amino acids part of helix and are localized in the membrane, "O" and "o" represent amino acids that are extracellular, i.e., localized outside the cytoplasmic membrane (capital letters indicate a stronger prediction relative to lower case letters). The highlighted and boxed sequence is the longest extracellular sequence of the protein that was used as a vaccine component in Example 7. Cellular localization was determined using the web site: http://psort.org/index.html (Gardy J. L. et al., Bioinformatics 2005 21(5):617-623; doi:10.1093/bioinformatics/bti057) and amino acid composition at the web site: http://www.expasy.ch/tools/protparam.html (Gasteiger E. et al., The Proteomics Protocols Handbook, Humana Press (2005), pp. 571-607). The localization of the transmembrane helix was provided by the server ExPASy™ proteomic server: http://www.enzim.hu/hmmtop/index.html (G. E Tusnády and I. Simon (2001), Bioinformatics 17, 849-850).

FIG. 18 shows the amino acid (SEQ ID NO: 76) sequence of SACOL01781 from *S. aureus* MW2 strain.

DESCRIPTION OF ILLUSTRATIVE EMBODIMENTS

Figure 1:
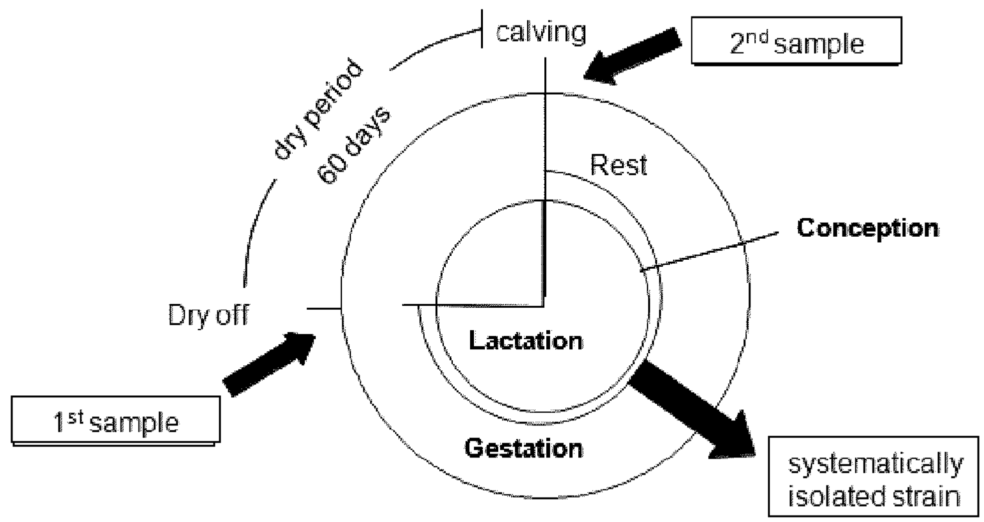
FIG. 1 shows the types of *Staphylococcus aureus* strains isolated from cows: chronic and systematically isolated strains from cows with clinical symptoms. Chronic isolates were isolated from cows shedding a genetically identical *S. aureus* strain >55 days apart, between dry off and calving as illustrated ($1^{st}$ and $2^{nd}$ samples). Systematically isolated strains were taken at calving or in the lactation period from cows shedding high somatic cell counts (SCC) in milk or having signs of inflammation (mastitis). Somatic cells are leukocytes (white blood cells). The SCC is an indicator of the quality of milk. The number of somatic cells increases in response to pathogenic bacteria like *S. aureus*.

In a first aspect, the present invention provides a method for preventing and/or treating Staphylococcal intramammary infection (IMI) in a mammal, said method comprising administrating to said mammal an effective amount of an agent, wherein said agent is: (a) a polypeptide encoded by a gene, wherein said gene is SACOL0029, SACOL0100, SACOL0101, SACOL0105, SACOL0148, SACOL0154, SACOL0204, SACOL0205, SACOL0264, SACOL0442, SACOL0461, SACOL0608, SACOL0660, SACOL0688, SACOL0690, SACOL0704, SACOL0718, SACOL0720, SACOL0829, SACOL1054, SACOL1142, SACOL1145, SACOL1320, SACOL1353, SACOL1416, SACOL1611, SACOL1637, SACOL1680, SACOL1781, SACOL1812, SACOL1867, SACOL1912, SACOL1944, SACOL2092, SACOL2144, SACOL2169, SACOL2171, SACOL2321, SACOL2325, SACOL2342, SACOL2365, SACOL2379, SACOL2385 or SACOL2599, based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e).

In another aspect, the present invention provides a use of an agent, wherein said agent is: (a) a polypeptide encoded by a gene, wherein said gene is SACOL0029, SACOL0100, SACOL0101, SACOL0105, SACOL0148, SACOL0154, SACOL0204, SACOL0205, SACOL0264, SACOL0442, SACOL0461, SACOL0608, SACOL0660, SACOL0688, SACOL0690, SACOL0704, SACOL0718, SACOL0720, SACOL0829, SACOL1054, SACOL1142, SACOL1145, SACOL1320, SACOL1353, SACOL1416, SACOL1611, SACOL1637, SACOL1680, SACOL1781, SACOL1812, SACOL1867, SACOL1912, SACOL1944, SACOL2092, SACOL2144, SACOL2169, SACOL2171, SACOL2321, SACOL2325, SACOL2342, SACOL2365, SACOL2379, SACOL2385 or SACOL2599, based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any of (a) to (c); (e) a nucleic acid encoding the polypeptide of any one of (a) to (d); or (f) any combination of (a) to (e), for preventing and/or treating a Staphylococcal intramammary infection (IMI) in a mammal.

In another aspect, the present invention provides a use of an agent, wherein said agent is: (a) a polypeptide encoded by a gene, wherein said agent is SACOL0029, SACOL0100, SACOL0101, SACOL0105, SACOL0148, SACOL0154, SACOL0204, SACOL0205, SACOL0264, SACOL0442, SACOL0461, SACOL0608, SACOL0660, SACOL0688, SACOL0690, SACOL0704, SACOL0718, SACOL0720, SACOL0829, SACOL1054, SACOL1142, SACOL1145, SACOL1320, SACOL1353, SACOL1416, SACOL1611, SACOL1637, SACOL1680, SACOL1781, SACOL1812, SACOL1867, SACOL1912, SACOL1944, SACOL2092, SACOL2144, SACOL2169, SACOL2171, SACOL2321, SACOL2325, SACOL2342, SACOL2365, SACOL2379, SACOL2385 or SACOL2599, based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e), for the preparation of a medicament for preventing and/or treating Staphylococcal intramammary infection (IMI) in a mammal.

In another aspect, the present invention provides a pharmaceutical composition (e.g., a vaccine) for preventing and/or treating Staphylococcal intramammary infection (IMI) in a mammal, said composition comprising an agent, wherein said agent is: (a) a polypeptide encoded by a gene, wherein said gene is SACOL0029, SACOL0100, SACOL0101, SACOL0105, SACOL0148, SACOL0154, SACOL0204, SACOL0205, SACOL0264, SACOL0442, SACOL0461, SACOL0608, SACOL0660, SACOL0688, SACOL0690, SACOL0704, SACOL0718, SACOL0720, SACOL0829, SACOL1054, SACOL1142, SACOL1145, SACOL1320, SACOL1353, SACOL1416, SACOL1611, SACOL1637, SACOL1680, SACOL1781, SACOL1812, SACOL1867, SACOL1912, SACOL1944, SACOL2092, SACOL2144, SACOL2169, SACOL2171, SACOL2321, SACOL2325, SACOL2342, SACOL2365, SACOL2379, SACOL2385 or SACOL2599, based on the gene nomenclature from the *Staphylococcus aureus* COL (SACOL) genome set forth in NCBI Reference Sequence NC_002951.2; (b) a polypeptide encoded by a gene from a same operon as one of the genes of (a); (c) an immunogenic fragment of (a) or (b); (d) an immunogenic variant of any one of (a) to (c); (e) a nucleic acid encoding the polypeptide of any one of (a) to (d); or (f) any combination of (a) to (e), and optionally one or more pharmaceutically acceptable excipients/carriers.

The Genbank accession numbers for the above-mentioned *S. aureus* genes and encoded polypeptides are depicted in Table I below:

TABLE I

Genbank accession numbers for the IMI-associated *S. aureus* genes and encoded polypeptides described herein.

| Gene name | GenBank Gene ID No. | GenBank protein No. |
|---|---|---|
| SACOL0029 | 3236748 (SEQ ID NO: 77) | YP_184940.1 (SEQ ID NO: 78) |
| SACOL0100 | 3236858 | YP_185004.1 |
| SACOL0101 | 3236840 | YP_185005.1 |
| SACOL0105 | 3236844 | YP_185009.1 |
| SACOL0148 | 3236734 | YP_185048.1 |
| SACOL0154 | 3238707 | YP_185054.1 |
| SACOL0204 | 3236774 | YP_185103.1 |
| SACOL0205 | 3236775 | YP_185104.1 |
| SACOL0264 | 3236683 (SEQ ID NO: 79) | YP_185159.1 (SEQ ID NO: 80) |
| SACOL0442 | 3236485 (SEQ ID NO: 81) | YP_185332.1 (SEQ ID NO: 37) |
| SACOL0461 | 3236475 | YP_185351.1 |
| SACOL0608 | 3236353 | YP_185493.1 |
| SACOL0660 | 3238251 | YP_185544.1 |
| SACOL0688 | 3236721 | YP_185570.1 |
| SACOL0690 | 3236723 | YP_185572.1 |
| SACOL0704 | 3236241 | YP_185586.1 |
| SACOL0718 | 3236599 (SEQ ID NO: 82) | YP_185600.1 (SEQ ID NO: 83) |
| SACOL0720 | 3236600 (SEQ ID NO: 84) | YP_185601.1 (SEQ ID NO: 62) |

TABLE I-continued

Genbank accession numbers for the IMI-associated *S. aureus* genes and encoded polypeptides described herein.

| Gene name | GenBank Gene ID No. | GenBank protein No. |
|---|---|---|
| SACOL0829 | 3238649 | YP_185703.1 |
| SACOL1054 | 3236163 | YP_185919.1 |
| SACOL1142 | 3236098 | YP_186005.1 |
| SACOL1145 | 3237661 | YP_186008.1 |
| SACOL1320 | 3236394 | YP_186175.1 |
| SACOL1353 | 3236077 (SEQ ID NO: 85) | YP_186206.1 (SEQ ID NO: 86) |
| SACOL1416 | 3236563 (SEQ ID NO: 87) | YP_186268.1 (SEQ ID NO: 88) |
| SACOL1611 | 3236575 (SEQ ID NO: 89) | YP_186451.1 (SEQ ID NO: 90) |
| SACOL1637 | 3238018 | YP_186477.1 |
| SACOL1680 | 3238476 | YP_186520.1 |
| SACOL1781 | 3236594 | YP_186614.1 |
| SACOL1812 | 3238705 | YP_186645.1 |
| SACOL1867 | 3236101 | YP_186695.1 |
| SACOL1912 | 3236086 | YP_186737.1 |
| SACOL1944 | 3237515 (SEQ ID NO: 91) | YP_186769.1 (SEQ ID NO: 92) |
| SACOL2092 | 3238693 | YP_186907.1 |
| SACOL2144 | 3237436 (SEQ ID NO: 93) | YP_186957.1 (SEQ ID NO: 94) |
| SACOL2169 | 3237416 | YP_186981.1 |
| SACOL2171 | 3237418 | YP_186983.1 |
| SACOL2321 | 3238070 | YP_187128.1 |
| SACOL2325 | 3238483 | YP_187132.1 |
| SACOL2342 | 3235997 | YP_187148.1 |
| SACOL2365 | 3238203 (SEQ ID NO: 95) | YP_187170.1 (SEQ ID NO: 96) |
| SACOL2379 | 3237628 | YP_187183.1 |
| SACOL2385 | 3238646 | YP_187189.1 |
| SACOL2599 | 3237186 (SEQ ID NO: 97) | YP_187390.1 (SEQ ID NO: 98) |

In an embodiment, the above-mentioned gene is SACOL0029, SACOL0264, SACOL0442, SACOL0718, SACOL0720, SACOL1353, SACOL1416, SACOL1611, SACOL1944, SACOL2144, SACOL2365 or SACOL2599.

As used herein, the term "vaccine" refers to any compound/agent ("vaccine component"), or combinations thereof, capable of inducing/eliciting an immune response in a host and which permits to treat and/or prevent an infection and/or a disease. Therefore, non-limiting examples of such agent include proteins, polypeptides, protein/polypeptide fragments, immunogens, antigens, peptide epitopes, epitopes, mixtures of proteins, peptides or epitopes as well as nucleic acids, genes or portions of genes (encoding a polypeptide or protein of interest or a fragment thereof) added separately or in a contiguous sequence such as in nucleic acid vaccines, and the like.

An immunogenic fragment of a protein/polypeptide is defined as a part of a protein/polypeptide which is capable of inducing/eliciting an immune response in a host. In an embodiment, the immunogenic fragment is capable of eliciting the same immune response in kind, albeit not necessarily in amount, as the protein/polypeptide. An immunogenic fragment of a protein/polypeptide preferably comprises one or more epitopes of said protein/polypeptide. An epitope of a protein/polypeptide is defined as a fragment of said protein/polypeptide of at least about 4 or 5 amino acids in length, capable of eliciting a specific antibody and/or an immune cell (e.g., a T cell or B cell) bearing a receptor capable of specifically binding said epitope. Two different kinds of epitopes exist: linear epitopes and conformational epitopes. A linear epitope comprises a stretch of consecutive amino acids. A conformational epitope is typically formed by several stretches of consecutive amino acids that are folded in position and together form an epitope in a properly folded protein. An immunogenic fragment as used herein refers to either one, or both, of said types of epitopes. In an embodiment, the immunogenic fragment of a protein/polypeptide comprises at least 4 or 5 amino acid residues. In a further embodiment, the immunogenic fragment comprises at least 6, 7, 8, 9, 10, 13, 14, 15, 20, 25, 30, 50 or 100 consecutive amino acids of the native protein/polypeptide.

As will be understood by the person of ordinary skill, agents (proteins/polypeptides, fragments thereof) having non-naturally occurring modifications (e.g., immunogenic variants) and which are capable of inducing an immune response specific for the unmodified agent (e.g., capable of inducing the production of antibodies capable of recognizing the unmodified agent) are also within the scope of the term “vaccine component”. For example, the vaccine components of the present invention can be modified to enhance their activity, stability, and/or bioavailability, and/or to reduce their toxicity. Conservative amino acid substitutions may be made, like for example replacement of an amino acid comprising an acidic side chain by another amino acid comprising an acidic side chain, replacement of a bulky amino acid by another bulky amino acid, replacement of an amino acid comprising a basic side chain by another amino acid comprising a basic side chain, and the like. A person skilled in the art is well able to generate variants of a protein/polypeptide. This is for instance done through screening of a peptide library or by peptide changing programs. An immunogenic variant according to the invention has essentially the same immunogenic properties of said protein in kind, not necessarily in amount. An immunogenic variant of a protein/polypeptide of the invention may for instance comprise a fusion protein and/or chimeric protein. For example, the biological function of protein SACOL0442 identified herein is predicted to be an exotoxin, enterotoxin or superantigen and it could potentially interfere with the mammalian immune system and antibody production, and/or show some toxicity in the host. Although such interference was not observed when the SACOL0442 polypeptide was used in combination with for example SACOL0720 during immunization (FIG. 15), it may be useful to modify the protein or polypeptide used for vaccination so that the biological activity of the exotoxin is decreased. For such a purpose, it is possible to inactivate the exotoxin with chemicals (e.g., formaldehyde). It is also possible to use molecular biology techniques to delete or mutate the putative region(s) involved in exotoxin activity without loosing immunogenicity (Chang et al., 2008). Another example is the conjugation or mixture of amino acid-based components with nucleic acids (e.g., genes or portions of genes added separately or in a contiguous sequence) carbohydrates such as those found in microbial polysaccharide capsules or biofilms.

In an embodiment, the above-mentioned polypeptide is a polypeptide normally secreted or expressed at the surface of the bacteria (e.g., *Staphylococcus aureus*).

In another embodiment, the above-mentioned polypeptide, or a polypeptide substantially identical to said polypeptide, is expressed in at least two different strains of *Staphylococcus aureus*. Substantially identical as used herein refers to polypeptides having at least 60% of similarity, in embodiments at least 65%, 70%, 75%, 80%, 85%, 90%, 91%, 92%, 93%, 94%, 95%, 96%, 97%, 98% or 99% A of similarity in their amino acid sequences. In further embodiments, the polypeptides have at least 60%, 70%, 75%, 80%, 85%, 90%, 91%, 92%, 93%, 94%, 95%, 96%, 97%, 98% or 99% of identity in their amino acid sequences.

In an embodiment, the above-mentioned immunogenic fragment comprises a sequence that is conserved (i.e. identical) in at least two different strains of *Staphylococcus aureus*. In further embodiments, the above-mentioned immunogenic fragment comprises a sequence that is conserved (i.e. identical) in at least 3, 4, 5, 6, 7, 8, 9 or 10 different strains of *Staphylococcus aureus*. In another embodiment, the above-mentioned strains of *Staphylococcus aureus* are COL, RF122, NCTC 8325, JH1, JH9, Newman, Mu3, Mu50, USA300-FPR3757, N315, MW2 or MSSA476. In an embodiment, the above-mentioned strains of *Staphylococcus aureus* is associated with bovine mastitis (e.g., RF122).

The similarity and identity between amino acid or nucleotide sequences can be determined by comparing each position in the aligned sequences. Optimal alignment of sequences for comparisons of similarity and/or identity may be conducted using a variety of algorithms, for example using a multiple sequence alignment program/software well known in the art such as ClustalW™, SAGA™, UGENE™ or T-coffee™. Examples of multiple sequence alignments are described in the examples below and depicted in FIGS. 11A-D and FIGS. 12A-K.

Also within the context of the present invention is the in vivo administration of a nucleic acid of the invention to a mammal so that one or more proteins/polypeptides (or a fragment thereof) of interest is/are expressed in the mammal (e.g., nucleic acid vaccine, DNA or RNA vaccine).

The nucleic acid of the present invention preferably comprises a nucleotide sequence that encodes one or more proteins/polypeptides noted above (or fragments thereof) operably linked to regulatory elements needed for gene expression, such as a promoter, an initiation codon, a stop codon, enhancers, and a polyadenylation signal. Regulatory elements are preferably selected that are operable in the species to which they are to be administered.

The nucleic acid of the present vaccine can be “naked” DNA or can be operably incorporated in a vector. Nucleic acids may be delivered to cells in vivo using methods well known in the art such as direct injection of DNA, receptor-mediated DNA uptake, viral-mediated transfection or non-viral transfection and lipid-based transfection, all of which may involve the use of vectors. Direct injection has been used to introduce naked DNA into cells in vivo (see e.g., Acsadi et al. (1991) Nature 332:815-818; Wolff et al. (1990) *Science* 247:1465-1468). A delivery apparatus (e.g., a “gene gun”) for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90:2122-2126).

Useful delivery vectors include biodegradable microcapsules, immuno-stimulating complexes (ISCOMs) or liposomes, and genetically engineered attenuated live vectors such as viruses or bacteria. Examples of suitable attenuated live bacterial vectors include *Salmonella typhimurium, Salmonella typhi, Shigella, Bacillus, Lactobacillus*, Bacille Calmette-Guerin (BCG), *Escherichia coli, Vibrio cholerae,*

*Campylobacter*, or any other suitable bacterial vector, as is known in the art. Methods of transforming live bacterial vectors with an exogenous DNA construct are well described in the art. See, for example, Joseph Sambrook and David W. Russell, Molecular Cloning, A Laboratory Manual, 3rd Ed., Cold Spring Harbor Laboratory Press, Cold Spring Harbor, N.Y. (2001).

Preferred viral vectors include Bacteriophages, Herpes virus, Adenovirus, Polio virus, Vaccinia virus, defective retroviruses, adeno-associated virus (MV) and Avipox. Methods of transforming viral vector with an exogenous DNA construct are also well described in the art. See Sambrook and Russell, above.

Liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., Biochemistry 27:3917 3925 (1988); and H. Eibl, et al., Biophysical Chemistry 10:261 271 (1979). Alternatively, a microsphere such as a polylactide-coglycolide biodegradable microsphere can be utilized. A nucleic acid construct is encapsulated or otherwise complexed with the liposome or microsphere for delivery of the nucleic acid to a tissue, as is known in the art.

Alternatively, the nucleic acid (e.g., DNA or RNA) may be incorporated in a cell in vitro or ex vivo by transfection or transformation, and the transfected or transformed cell (e.g., an immune cell such as a dendritic cell), which expresses the protein or polypeptide of interest (or a fragment thereof), may be administered to the host. Following administration, the cell will express the protein or polypeptide of interest (or a fragment thereof) in the host, which will in turn lead to the induction of an immune response directed against the protein, polypeptide or fragment thereof.

Also encompassed by the methods, uses, pharmaceutical compositions and kits of the present invention is passive immunization, which is the injection of antibodies or antiserum, previously generated against the pathogen, in order to protect or cure a recipient animal of an infection or future infection. Protection fades over the course of a few weeks during which time the active immunization with protein and/or DNA (as described above) will have time to generate a lasting protective response. Serum for passive immunization can be generated by immunization of donor animals using the *S. aureus* antigens (proteins, polypeptides or nucleic acids), as described above. This serum, which contains antibodies against the antigens, can be used immediately or stored under appropriate conditions. It can be used to combat acute infections (IMI) or as a prophylactic (Tuchscherr et al., 2008). Use of antibodies or serums in a passive immunization can be combined with other agents such as an antibiotic to increase the cure rate of an infection currently in progress or to increase protection against an imminent infection.

Also encompassed by the methods, uses, pharmaceutical compositions and kits of the present invention is immunization with the *Staphylococcus aureus* bacteria in attenuated live or inactivated form (e.g., *S. aureus* having at least one of the genes of the present invention mutated (e.g., Δ442a, Δ442b and Δ720 of SACOL442 and SACOL720, as described in Example 6). Mutation as used herein includes a substitution, a deletion and/or an insertion of one or more nucleotides that prevents expression of the polypeptide encoded by a gene of the present invention or that prevents expression of a functional polypeptide. In a preferred embodiment, the mutation prevents expression of the polypeptide (e.g., Δ442a, Δ442b and Δ720 of SACOL442 and SACOL720, as described in Example 6). In another specific embodiment, the mutation is a deletion or an insertion. It is expected that a mutated strain of *S. aureus* having a mutation at any position of one of the genes of the present invention that prevents expression of the polypeptide can be used as an attenuated live vaccine in accordance with the present invention. Attenuated live vaccines, i.e. vaccines comprising the bacterium according to the invention in a live attenuated form, have the advantage over inactivated vaccines that they best mimic the natural way of infection. In addition, their replicating abilities allow vaccination with low amounts of bacteria; their number will automatically increase until it reaches the trigger level of the immune system. From that moment on, the immune system will be triggered and will finally eliminate the bacteria. A minor disadvantage of the use of live attenuated bacteria however might be that inherently there is a certain level of virulence left. This need not be a real disadvantage as long as the level of virulence is acceptable, i.e. as long as the vaccine at least decreases the mammal IMI symptoms. Of course, the lower the rest virulence of the live attenuated vaccine is, the less influence the vaccination has on weight gain during/after vaccination.

The components identified in accordance with the teachings of the present invention have a prophylactic and/or therapeutic value such as they can be used to raise an immune response to prevent and/or combat diseases or conditions, and more particularly diseases or conditions related to microbial infections.

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in the severity of the disease (e.g., a reduction or inhibition of infection), a decrease/reduction in symptoms and disease-related effects, an amelioration of symptoms and disease-related effects, and an increased survival time of the affected host animal, following administration of the at least one agent (or of a composition comprising the agent). In accordance with the invention, a prophylactic effect may comprise a complete or partial avoidance/inhibition or a delay of infection, and an increased survival time of the affected host animal, following administration of the at least one agent (or of a composition comprising the agent).

As used herein, the term "pharmaceutically acceptable" refers to vaccine components (e.g., excipients, carriers) and compositions that are physiologically tolerable and do not typically produce an allergic or similar untoward reaction, such as gastric upset, dizziness and the like, when administered to a subject. Preferably, as used herein, the term "pharmaceutically acceptable" means approved by regulatory agency of the federal or state government or listed in the U.S. Pharmacopeia or other generally recognized pharmacopeia for use in animals, and in humans. The term "excipient" refers to a diluent, carrier, or vehicle with which the vaccine components of the present invention may be administered. Sterile water or aqueous saline solutions and aqueous dextrose and glycerol solutions may be employed as carriers, particularly for injectable solutions.

In an embodiment, the agent of the present invention is administered in combination with an adjuvant or immunostimulant. Suitable adjuvant or immunostimulant that may improve the efficacy of components to raise an immune response include but is not limited to oils (e.g., mineral oils, emulsified oil such as EMULSIGENT™-D), metallic salts (e.g., alum, aluminum hydroxide or aluminum phosphate), natural and artificial microbial components (e.g., bacterial liposaccharides, Freund's adjuvants, muramyl dipeptide (MDP), cyclic-diguanosine-5'-monophosphate (c-di-GMP), pathogen-associated molecular patterns (PAMPS)), plant components (e.g., Quil A), and/or one or more substances that have a carrier effect (e.g., bentonite, latex particles, liposomes, ISCOM™ and polyphosphazine (PCPP) copolymers). Immunization with synthetic nanoparticles (such as those made from a biodegradable synthetic polymer like poly (D,L-lacticco-glycolic acid)) containing antigens plus ligands that signal through TLR to stimulate proinflammatory cytokines is also possible (Kasturi et al, 2011).

Vaccine components of the invention may be administered in a pharmaceutical composition. Pharmaceutical compositions may be administered in unit dosage form. Any appropriate route of administration may be employed, for example, parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation); transdermal (topical); transmucosal, and rectal administration.

Conventional pharmaceutical practice may be employed to provide suitable formulations or compositions to administer such vaccine components with or without adjuvants to subjects. Methods well known in the art for making pharmaceutical compositions and formulations are found in, for example, Remington: The Science and Practice of Pharmacy, (20th ed.) ed. A. R. Gennaro A R., 2000, Lippincott: Philadelphia. Formulations for parenteral administration may, for example, contain excipients, sterile water, or saline, polyalkylene glycols such as polyethylene glycol, miglyol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. Formulations for inhalation or intramammary injection may contain excipients, or example, lactose, or may be aqueous solutions containing, for example, polyoxyethylene-9-lauryl ether, miglyol, glycocholate and deoxycholate, or may be oily solutions (e.g., paraffin oil) for administration in the form of nasal drops, or as a gel.

Therapeutic formulations may be in the form of liquid solutions or suspension; for oral administration, formulations may be in the form of tablets or capsules; and for intranasal formulations, in the form of powders, nasal drops, or aerosols. Solutions or suspensions used for parenteral, intradermal, intramammary or subcutaneous application can include the following components: a sterile diluent such as water for injection, saline solution, fixed oils (e.g., paraffin oil), polyethylene glycols, glycerine, propylene glycol, miglyol or other synthetic solvents; antibacterial agents such as benzyl alcohol or methyl parabens; antioxidants such as ascorbic acid or sodium bisulfite; chelating agents such as ethylenediaminetetraacetic acid; reducing agents such dithiothreitol, buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous or intramammary administration, suitable carriers include physiological saline, bacteriostatic water, Cremophor™ ELTM (BASF, Parsippany, N.J.) or phosphate buffered saline (PBS).

Oral compositions generally include an inert diluent or an edible carrier. They can be enclosed in gelatin capsules or compressed into tablets or feed. For the purpose of oral vaccine administration, the active components can be incorporated with excipients and used in the form of tablets, troches, capsules or in feed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the vaccine components are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Liposomal suspensions (including liposomes targeted to specific cell types) can also be used as pharmaceutically acceptable carriers.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. They may also contain other therapeutically valuable agents.

Intravenous, intramuscular, intramammary or oral administration is a preferred form of use. The dosages in which the components of the present invention are administered in effective amounts depend on the nature of the specific active ingredient, the host and the requirements of the subject and the mode of application. In general, an amount of about 0.01 mg-500 mg per dose, come into consideration.

Toxicity or efficacy of vaccine components to elicit an immune response can be determined by standard procedures in cell cultures or experimental animals. The dose ratio between toxic and immune stimulatory effects can be measured. Components that exhibit large ratios are preferred. While components that exhibit toxic side effects may be used, care should be taken to design a delivery system in order to minimize potential damage to cells and, thereby, reduce side effects.

Data obtained from cell culture assays and laboratory animal studies can be used in formulating a range of dosage for use in large animals and humans. The dosage of such components lies preferably within a range of administered concentrations that include efficacy with little or no toxicity. The dosage may vary within this range depending upon the dosage form employed and the route of administration utilized.

The skilled artisan will appreciate that certain factors may influence the dosage required to effectively raise an immune response in a subject. Moreover, the therapeutically effective amount of a component of the present invention may require a series of doses.

The present invention also encompasses kits comprising the components of the present invention. For example, the kit can comprise one or more components. The components can be packaged in a suitable container and device for administration. The kit can further comprise instructions for using the kit.

The present invention also provides a method of diagnosing Staphylococcal IMI in a mammal, said method comprising: determining a level of expression of at least one gene, wherein said gene is SACOL0029, SACOL0100, SACOL0101, SACOL0105, SACOL0148, SACOL0154, SACOL0204, SACOL0205, SACOL0264, SACOL0442, SACOL0461, SACOL0608, SACOL0660, SACOL0688, SACOL0690, SACOL0704, SACOL0718, SACOL0720, SACOL0829, SACOL1054, SACOL1142, SACOL1145, SACOL1320, SACOL1353, SACOL1416, SACOL1611, SACOL1637, SACOL1680, SACOL1781, SACOL1812, SACOL1867, SACOL1912, SACOL1944, SACOL2092, SACOL2144, SACOL2169, SACOL2171, SACOL2321, SACOL2325, SACOL2342, SACOL2365, SACOL2379, SACOL2385 or SACOL2599, based on the gene nomenclature from the *Staphylococcus aureus* COL (SACOL) genome set forth in NCBI Reference Sequence NC_002951.2, or the level of activity of a polypeptide encoded by said one or more genes (at least one gene), in a biological sample from said mammal; and comparing said level of expression or activity to a reference level of expression or activity; wherein a higher expression or activity in said biological sample relative to said reference expression or activity is indicative that said mammal has staphylococcal IMI.

In an embodiment, the above-mentioned reference expression or activity is a level of expression or activity determined in a corresponding biological sample from a mammal known to not having staphylococcal IMI. Such reference expression or activity may be an expression or activity corresponding to an average or median expression or activity calculated based on measurements made in several subjects not suffering from the condition (e.g., known to not having staphylococcal IMI). The reference expression or activity may be adjusted or normalized for age, gender, race, or other parameters.

In an embodiment, the above-mentioned at least one gene is SACOL0029, SACOL0264, SACOL0442, SACOL0718, SACOL0720, SACOL1353, SACOL1416, SACOL1611, SACOL1944, SACOL2144, SACOL2365 or SACOL2599.

"Sample" or "biological sample" refers to any solid or liquid sample isolated from a live being. In a particular embodiment, it refers to any solid (e.g., tissue sample) or liquid sample isolated from a mammal, such as milk, a biopsy material (e.g., solid tissue sample), blood (e.g., plasma, serum or whole blood), saliva, synovial fluid, urine, amniotic fluid and cerebrospinal fluid. Such sample may be, for example, fresh, fixed (e.g., formalin-, alcohol- or acetone-fixed), paraffin-embedded or frozen prior to analysis of the infectious agent's expression level.

In an embodiment, the above-mentioned biological sample is milk.

In an embodiment, the above-mentioned mammal is a cow.

In an embodiment, the above-mentioned level of expression is determined by measuring the level of expression of a polypeptide/protein encoded by said one or more genes. Methods to measure the amount/level of selected polypeptides/proteins of this invention (one or more of the polypeptides noted above) are well known in the art. Protein/polypeptide levels may be detected either directly using affinity reagents, such as an antibody or a fragment thereof (for methods, see for example Harlow, E. and Lane, D (1988) Antibodies: A Laboratory Manual, Cold Spring Harbor Laboratory Press, Cold Spring Harbor, N.Y.), or a ligand (natural or synthetic) which binds the protein. Protein/polypeptide levels may be detected based on other properties, for example by measurement of the protein's activity, which may entail enzymatic activity to produce a detectable product (e.g., with altered spectroscopic properties) or a detectable phenotype (e.g., alterations in cell growth/function).

Examples of methods to measure the amount/level of selected proteins/polypeptides include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, flow cytometry, and assays based on a property of the protein including but not limited to DNA binding, ligand binding, interaction with other protein partners or enzymatic activity.

In an embodiment, the amount of the polypeptide/protein within the methods of the present invention is detected using antibodies that are directed specifically against the polypeptide/protein. The term "antibody" as used herein encompasses monoclonal antibodies, polyclonal antibodies, multispecific antibodies (e.g., bispecific antibodies), and antibody fragments, so long as they exhibit the desired biological activity or specificity. "Antibody fragments" comprise a portion of a full-length antibody, generally the antigen binding or variable region thereof. Interactions between antibodies and a target polypeptide are detected by radiometric, colorimetric, or fluorometric means. Detection of antigen-antibody complexes may be accomplished by addition of a secondary antibody that is coupled to a detectable tag, such as for example, an enzyme, fluorophore, or chromophore.

Methods for making antibodies are well known in the art. Polyclonal antibodies can be prepared by immunizing a suitable subject (e.g., rabbit, goat, mouse, or other mammal) with the polypeptide/protein of interest or a fragment thereof as an immunogen. A polypeptide/protein "fragment" "portion" or "segment" is a stretch of amino acid residues of at least about 5, 7, 10, 14, 15, 20, 21 or more amino acids of the polypeptide noted above. The antibody titer in the immunized subject can be monitored over time by standard techniques, such as with an enzyme linked immunosorbent assay (ELISA) using immobilized exosomal marker polypeptide or a fragment thereof. At an appropriate time after immunization, e.g., when the antibody titers are highest, antibody-producing cells can be obtained from the animal, usually a mouse, and can be used to prepare monoclonal antibodies by standard techniques, such as the hybridoma technique originally described by Kohler and Milstein (1975) Nature 256: 495-497, the human B cell hybridoma technique (Kozbor et al. (1983) Immunol. Today 4: 72), the EBV-hybridoma technique (Cole et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan et al., eds. (1994) Current Protocols in Immunology, John Wiley & Sons, Inc., New York, N.Y.).

Alternatively to preparing monoclonal antibody-secreting hybridomas, a monoclonal antibody can be identified and isolated by screening a recombinant combinatorial immunoglobulin library (e.g., an antibody phage display library) with a polypeptide or a fragment thereof to thereby isolate immunoglobulin library members that bind the polypeptide. Kits for generating and screening phage display libraries are commercially available (e.g., the Pharmacia Recombinant Phage Antibody System™, Catalog No. 27-9400-01; and the Stratagene SurfZAP™ Phage Display Kit, Catalog No. 240612).

Furthermore, antibodies directed against one or more of the polypeptides/proteins described herein may be obtained from commercial sources.

The use of immobilized antibodies specific for the polypeptides/proteins is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality (2 or more) of polypeptides/proteins may be carried out separately or simultaneously with one test sample. Several polypeptides/proteins may be combined into one test for efficient processing of a multiple of samples.

The analysis of polypeptides/proteins could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340, 2002) and capillary devices.

In an embodiment, the above-mentioned level of expression is determined by measuring the level of expression of a mRNA transcribed from said one or more genes.

Methods to determine nucleic acid (mRNA) levels are known in the art, and include for example polymerase chain reaction (PCR), reverse transcriptase-PCR (RT-PCR), SAGE, quantitative PCR (q-PCR), Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the nucleic acids encoding the protein/polypeptide of this invention; amplification of mRNA expressed from one or more of the nucleic acids encoding the proteins/polypeptides of this invention using specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the biological sample, which is then labeled and used to probe cDNAs or oligonucleotides encoding all or part of the nucleic acids encoding the proteins/polypeptides of this invention, arrayed on any of a variety of surfaces.

The present invention also provides a kit or package comprising reagents useful for determining the amount/level of one or more proteins/polypeptides of the present invention, for example a ligand that specifically bind to proteins/polypeptides, such as a specific antibody, or to a nucleic acid encoding proteins/polypeptides, such as an oligonucleotide (e.g., primer or probe). Such kit may further comprise, for example, instructions for the diagnosis of Staphylococcal IMI, control samples (e.g., samples to which the test sample may be compared to establish the diagnostic), containers, reagents useful for performing the methods (e.g., buffers, enzymes, immunodetection reagents, etc). The kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like. The present invention also provides a kit or package comprising one or more agents of the present invention for treating and/or preventing Staphyloccocal IMI. Such kit may further comprise, for example, instructions for the prevention and/or treatment of IMI in a mammal.

The use of the word "a" or "an" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

MODE(S) FOR CARRYING OUT THE INVENTION

The present invention is illustrated in further details by the following non-limiting examples.

Example 1

Materials and Methods

*Staphylococcus aureus* strains. Two types of *Staphylococcus aureus* isolates from cows were used in this study: chronic and systematically isolated strains (i.e. strains isolated from bovine mastitis with clinical signs (high somatic cell counts (SCC) in milk or signs of inflammation). Chronic isolates were from cows shedding a genetically identical *S. aureus* strain >55 days apart, between dry off and calving as illustrated in FIG. 1 ($1^{st}$ and $2^{nd}$ samples). Systematically isolated strains were taken at calving or in the lactation period from cows shedding high somatic cell counts (SCC) in milk or signs of inflammation (mastitis). For the experimental infections described further below, 3 chronic strains were used (#3, #557 and #1290) and were compared to SHY97-3906, a previously described strain isolated from a typical mastitis case with clinical signs (Diarra et al., 2002) and of a known in vitro transcriptome (Allard et al., 2006). The collection of isolates used in this study is shown in Table II below.

TABLE II

*Staphylococcus aureus* mastitis isolates used in the studies described herein

| Isolate | Type | Date | Interval (days) | Herd | Cow | Quarter |
|---|---|---|---|---|---|---|
| 3 | Chr | 20 oct 05 | — | 3 | 37 | 1 |
| 151 | Chr | 04 jan 06 | 77 | 3 | 37 | 1 |
| 54 | Chr | 18 nov 05 | — | 2 | 147 | 4 |
| 353 | Chr | 10 feb 06 | 85 | 2 | 147 | 4 |
| 140 | Chr | 1 jan 06 | — | 8 | 46 | 3 |
| 552 | Chr | 3 apr 06 | 93 | 8 | 46 | 3 |
| 205 | Chr | 31 jan 06 | — | 8 | 40 | 4 |
| 996 | Chr | 20 may 07 | 110 | 8 | 40 | 4 |
| 557 | Chr | 03 apr 06 | — | 3 | 16 | 1 |
| 1429 | Chr | 29 jun 06 | 88 | 3 | 16 | 1 |
| 2099 | Chr | 25 aug 06 | — | 2 | 96 | 3 |
| 3992 | Chr | 17 nov 06 | 85 | 2 | 96 | 3 |
| 1290 | Chr | 16 jul 06 | — | 1 | 83 | 4 |
| 2483 | Chr | 08 sep 06 | 55 | 1 | 83 | 4 |
| 2484 | Chr | 15 sep 06 | — | 4 | 39 | 1 |
| 4210 | Chr | 08 dec 06 | 85 | 4 | 39 | 1 |
| 3237 | Chr | 29 sep 06 | — | 4 | 36 | 4 |
| 4334 | Chr | 22 dec 06 | 85 | 4 | 36 | 4 |
| G3 | R | 15 mar 06 | — | 12 | 19 | C |
| G6 | R | 16 mar 06 | — | 11 | 249 | C |
| G7 | R | 16 mar 06 | — | 11 | 156 | C |
| G11 | R | 22 mar 06 | — | 5 | 28 | C |
| G17 | R | 03 apr 06 | — | 10 | 106 | C |
| G18 | R | 24 mar 06 | — | 7 | 15 | C |
| G23 | R | NA | — | NA | NA | NA |
| G26 | R | 06 apr 06 | — | 6 | 135 | C |
| G28 | R | 13 apr 06 | — | 5 | 32 | C |
| G51 | R | 16 nov 05 | — | 5 | 13 | C |
| 275 | R | NA | — | NA | NA | NA |
| SHY97-3906 | R | From mastitis; Diarra, MS et al., 2002; Allard et al., 2006 | | | | NA |
| Newbould | R | From mastitis; Prasad and Newbould, 1968 (ATCC 29740) | | | | NA |
| ATCC 49775 | — | Reference strain from human | | | | — |
| ATCC 51811 | — | Reference strain from human | | | | — |
| MRSA COL | — | Reference MRSA strain from human | | | | — |
| N315 | — | Reference MRSA strain from human | | | | — |

Chr, chronic;
R, random;
C, mix of all quarters;
NA, not available

Comparative Genomic Hybridization of *S. aureus* Isolates.

Figure 2:
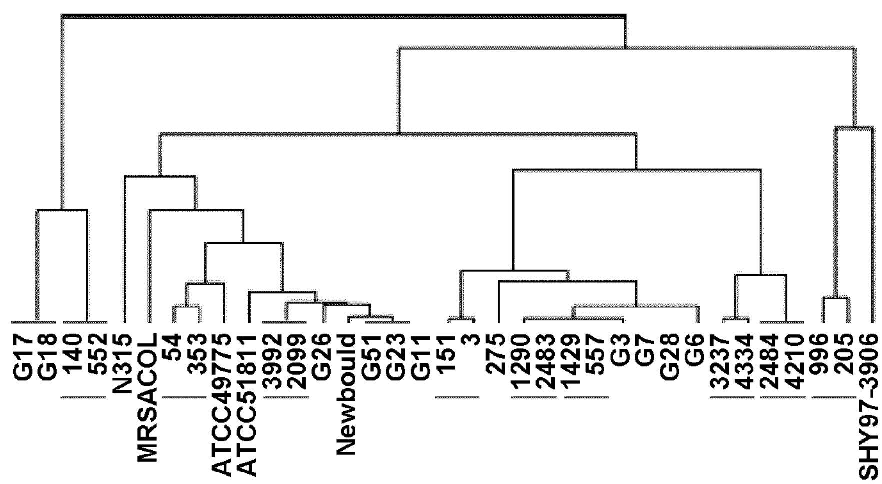
FIG. 2 shows the genetic relatedness of the *S. aureus* isolates used in the studies described herein as determined by comparative genomic DNA hybridization data obtained for 530 genes printed on DNA arrays. Underlined isolates are chronic strains. Unrelated reference strains and isolates randomly/systematically picked from bovine mastitis cases with clinical symptoms during lactation are shown for comparison.

The genetic relatedness of *S. aureus* isolates was determined by comparative genomic DNA hybridization data obtained for 530 genes printed on arrays as described previously (Atalla et al., 2008) and is shown in FIG. 2.

Production of biofilms by *S. aureus* isolates. Biofilm formation was evaluated by spectrophotometry in microplates using crystal violet staining, as previously described with a few modifications (Brouillette et al., 2005). Briefly, strains were cultured from frozen stocks onto BHI agar plates and incubated overnight at 35° C. Three colonies were then inoculated into 7 ml of BHI containing 0.25% of supplemental glucose and incubated at 35° C. for 18 h with shaking at 225 rpm. This culture was then diluted to 0.5 McFarland in BHI 0.25% glucose and transferred into wells of a flat-bottom polystyrene microtiter plate half full of the same medium. The plates were then incubated at 35° C. for 24 or 48 h. The supernatant was then discarded and the wells were delicately washed three times with 200 μl of PBS. The plates were dried, stained for 30 min with crystal violet, washed twice with 200 μl of water and allowed to dry again. A volume of 200 μl of 95% ethanol was added to each well and plates were incubated at room temperature for 1 h with frequent agitation. The absorbance of each well was then measured at 560 nm using a plate reader (Bio-Tek Instruments). The results were collected from at least three independent experiments in which the biofilm formation of each culture tested was evaluated in four replicates.

In Vitro Culture Conditions.

For bacterial growth in low and high iron concentrations, bacteria were first grown in Mueller-Hinton broth (MHB, Becton Dickinson Sparks, Md., USA) in an orbital shaker (225 RPM) at 35° C. At an $A_{600\ nm}$ of 0.6 (approx. $1\times10^8$ CFU/ml), the culture was divided in two pre-warmed sterile flasks. Iron limitation was induced by addition of 2,2-dipyridyl (Sigma Chemicals, St-Louis, Mo.) at 600 μM to one culture, whereas $FeCl_3$ was added to the other culture at 10 μM. The growth rate of *S. aureus* in the presence of supplemental 2,2-dipyridyl or $FeCl_3$ was equivalent in both test conditions and these supplements did not affect the exponential growth during the one-hour treatment period. After 1 h, the cultures reached an $A_{600\ nm}$ of 1.0 (approx. $10^9$ CFU/ml) and 5 ml of each culture were treated with RNAprotect™ (QIAgen, Mississauga, ON, Canada) for 10 min before harvesting the cells by centrifugation. For bacterial growth in freshly collected non-mastitic milk, *S. aureus* SHY97-3906, #3, #557 and #1290 were first grown overnight in MHB in an orbital shaker (225 RPM) at 35° C. In the morning, 250 ml of fresh milk was inoculated with bacteria from the overnight culture to obtain a bacterial concentration of approximately $10^4$ CFU/ml. Bacterial growth was allowed for 7 h in an orbital shaker (225 RPM) at 35° C. before isolating the bacteria from milk as described below. For bacterial growth destined to the qPCR amplification of icaC and hld genes, *S. aureus* was grown in brain heart infusion (BHI) broth (BD, ON, Canada) until the cultures reached an $A_{600\ nm}$ of 0.6.

Animals.

All animal experiments were approved by local institutional animal care committees and conducted in accordance with the guidelines of the Canadian Council on Animal Care. Animals were kept in a level 2 confinement barn for the entire duration of each trial. Eight Multiparous Holstein cows in mid lactation were housed at the Dairy and Swine Research and Development Centre of Agriculture and Agri-Food Canada in Sherbrooke, QC, Canada. Cows were selected as not infected before the experiment by bacterial analysis of aseptic milk samples and somatic cell count (SCC) determination.

Experimental Infections.

Before the animal trials, the relation between the absorbance of bacterial cultures ($A_{600\ nm}$) and CFU was determined as previously described (Petitclerc et al., 2007). The morning of the challenge, a volume of the overnight culture of *S. aureus* in MHB was transferred to 200 ml of fresh MHB to obtain an $A_{600\ nm}$ of 0.1 and grown at 35° C. without shaking until the $A_{600\ nm}$ reached a value corresponding to $10^8$ CFU/ml in the exponential phase of growth. Bacteria were then diluted in sterile physiological saline (Baxter Healthcare Corporation, Deerfield, Ill.) to obtain 50 CFU in 3 ml. Intramammary (IM) infusions were performed the same day immediately after the late evening milking. Each individual mammary gland quarter was infused with 3 ml of a bacterial suspension. Each of the 8 cows was infused with the four different *S. aureus* strains and the position of each strain in the four quarters alternated between the animals. Infusion of mammary quarters with bacteria was performed according to the procedure described by Nickerson et al. (1999) with few modifications. All infusions were performed after milking. Before inoculation, the teat end of each quarter was thoroughly wiped to remove gross contamination and dipped in a solution of iodine. After a minimum of 30 second contact time, teats were wiped dry and subsequently scrubbed with gauzes soaked in 70% ethanol. Teats were allowed to air-dry. Foremilk was then discarded and the IM infusion was performed. Immediately afterwards, all quarters were thoroughly massaged and teats dipped again with an iodine solution. Disposable gloves were worn throughout the procedure and changed before proceeding to the next animal.

Milk Samples.

Milk samples were always aseptically collected before milking the experimentally infected cows using the procedure suggested by the National Mastitis Council (1996). After foremilk was discarded, a 10 ml milk sample was collected for each individual quarter in a 50 ml sterile vial. Milk samples were serially diluted and 200 µl plated on TSA and on mannitol salt agar plates (MSA; Becton Dickinson Sparks, Md., USA) for *S. aureus* identification. Plates were then incubated for 24 h at 35° C. before colony counting. The dilution that showed between 30 and 300 colonies was the one considered for the calculation of bacterial concentration. Considering the wide range of dilutions plated and the great number of samples to be tested, only one plate per sample was considered. Samples that showed 0 colonies for the undiluted milk was considered to have a concentration of ≤5 CFU/ml. The concentration of lactose, protein, fat and SCC in milk which indicates the presence of leukocytes in response to an infection were determined in a commercial laboratory (Valacta Inc., Step-Anne-de-Bellevue, QC, Canada). This was done every two days over the 18-day period of experimental infections.

Milk Collection for Bacterial Isolation.

Milk was collected from each quarter of each cow every 2-4 days in the morning for a total of 18 days. Milk was harvested using individual quarter milking units. Prior to milking, the four reservoirs were disinfected with 70% ethanol. A maximum of one liter of milk was collected for centrifugation and isolation of bacteria.

Bacterial Isolation from Milk.

Mastitic milk from experimentally infected cows or freshly collected milk from non-infected cows used for bacterial growth in vitro was treated with 200 µg/ml of protease from bovine pancreas (Sigma) for 10 min in an orbital shaker (100 RPM) at 35° C. After the treatment, the milk was centrifuged 15 minutes at 4000 g. The supernatant was discarded and the pellet was washed with PBS and centrifuged. The supernatant was discarded and the bacterial cell pellet was suspended in 1 ml PBS and treated with RNAprotect™ for 10 min before harvesting the cells by centrifugation. The cell pellet was then stored frozen at −86° C.

RNA Extraction and Purification.

Bacterial pellets from in vitro and in vivo growth conditions were suspended in 200 µl of TE buffer containing 200 µg/ml Lysostaphin™ (Sigma). Cell lysis was allowed for 1 h at room temperature before RNA extraction with the TRIzol™ Max bacterial RNA isolation Kit (Invitrogen, Carlsbad, Calif., USA) followed by a DNase treatment with TURBO™ DNase (Ambion, Austin, Tex., USA). RNA from bacteria isolated from the milk of infected cows underwent an additional purification step using the MICROBEnrich™ Kit from Ambion followed by a second round of DNase treatment with TURBO™ DNase (Ambion). The RNA concentration in samples was determined by an $A_{260\ nm}$ reading and the samples were stored at −86° C. until used.

cDNA probe synthesis. Fluorescent probes for hybridization to DNA arrays were generated through an aminoallyl cDNA labelling procedure. Briefly, 2.5-5 µg of total RNA was mixed with 5 µg of random hexamers (Amersham Biosciences, Piscataway, N.J., USA). This mixture was denatured at 70° C. for 10 min. Reverse transcription was carried out in the presence of RT buffer (Invitrogen), 10 mM DDT, dNTP mix (final concentration: 500 µM dATP, dCTP, dGTP, 300 µM dTTP and 200 µM 5-[3-Amioally]-2-dUTP (Sigma)) and 400 U of Superscript™ II RT was added to the RNA preparation and the reaction was allowed to occur for 2 h at 42° C. The RNA was hydrolyzed after transcription with 200 mM NaOH and 100 mM EDTA at 65° C. for 15 min. The reaction was neutralized with 333 µM HEPES pH 7.5. The cDNAs were purified before fluorescent labeling through three passages on a Microcon™ YM30 (Millipore). The resulting aadUTP-cDNA was coupled with NHS-Cy5 (Fluorolink™ Cy5 monoreactive pack, Amersham Biosciences) in the presence of 100 µM $NaHCO_3$, pH 9.0 for 1 h at room temperature. The reactions were quenched with 1.25 µM hydroxylamine for 15 min at room temperature. The fluorescent cDNAs were purified by using a QIAquick™ PCR purification kit (QIAgen), including three washing steps with buffer PE, before eluting in water.

DNA Arrays.

Arrays were previously described (Allard et al., 2006; Moisan et al., 2006) and contained a selection of 530 known or putative genes implicated in iron/cation-transport and acquisition systems, virulence (biofilm genes, adhesins, toxins and homologs of such genes), secretion, general stress responses, sensory/regulator systems, antibiotic resistance and various biosynthesis and metabolism genes. Genes were first amplified by PCR using Sigma Genosys™ (Oakville, ON, Canada) primers based on the published genome sequence of the *S. aureus* COL genome as well as other primers that were designed using the Primer3™ software (primer3_www.cgi v 0.2). PCR products were then purified using the QIAquick™ PCR purification kit, precipitated, suspended at a concentration of 150 ng/µl in 50% DMSO and printed in triplicate on Corning™ GAPS II slides (Corning, Corning, N.Y., USA) with the help of the Microarray printing platform of the Biotechnology Research Institute of Montreal (Montreal, QC, Canada). Control spots were from the Lucidea Universal Scorecard (Amersham, Piscataway, N.J.).

Hybridization to DNA arrays and analysis. The probes were suspended in 16.5 µl of hybridization buffer (5×SSC, 0.1% SDS, 25% formamide). The prehybridization, hybridization and washing steps were done as prescribed for Corning™ Gaps II Slides. Hybridization signals for each spot were quantified with the ScanArrayExpress™ Microarray Scanner and the ScanArrayExpress™ software V 2.2.0.0022 (Perkin Elmer, Wellesley, Mass., USA). A mean intensity value was calculated as the: Σ(intensity of every spots)/number of genes on array=100%. Only genes with a Cy5 signal intensity of ≥100%, i.e., greater or equal to the mean Cy5 intensity of the entire array were analyzed. Thus, this report identifies only genes that were strongly expressed in vivo during mastitis because their signal intensities on arrays were higher than average.

Quantitative PCR (qPCR).

Additional RNA preparations were obtained for qPCR analyses. Bacteria were collected from broth cultures (low-iron and iron-rich) as well as from milk (in vitro and in vivo) as described above. Also, RNA was extracted as mentioned earlier. Total RNA (2-5 µg) was reversed transcribed with 0.5 mM dNTP, 50 ng random hexamers and 200 U of Invitrogen Superscript™ II Reverse Transcriptase according to the manufacturer recommendations. RNA was denatured and the cDNAs were purified with QIAquick™ PCR purification kit. One µl of cDNA was amplified on the Stratagene™ MX3000P Real-Time PCR (Sratagene, LaJolla, Calif. USA) with a master mix composed of 6 mM Tris-HCI pH 8.3, 25 mM KCl, 4 mM MgCl2, 75 mM trehalose, 0.1% (v/v) Tween™ 20, 0.1 mg/ml nonacetylated BSA, 0.07×SYBR green (Invitrogen), 125 nM dNTPs and 0.5 U JumpStart™ Taq DNA Polymerase (Sigma), and 100 nM of the primers listed in Table III below. Reaction mixtures were denatured for 10 min at 95° C., followed by 40 cycles of 1 min at 60° C., 1 min at 72° C. and finished with a dissociation ramp from 55° C. to 95° C. The level of expression of each gene was calculated by using the Ct of the in vitro experiments as the calibrator (expression fold=$2^{-\Delta}$Ct, where ΔCt represents the difference between the Ct of the in vitro and in vivo conditions). The fold expression of genes from each experiment was then normalized with their respective gyrB expression level. The gyrB gene was found to be constitutively expressed during growth up to the early stationary phase (Goerke et al., 2000), which is well within the boundaries of the growth experiments described herein. Also, it was found that the expression of gyrB in the in vitro as well as in the in vivo conditions was not significantly modulated.

obtained from the Comprehensive Microbial Resource (CMR) of the J. Craig Venter™ Institute at http://cmr-.jcvi.org/tigr-scripts/CMR/cmrHomePage.cgi (Peterson, J. D., et al., *Nucleic Acids Res.* 2001 29(1): 123-5). The sequences were submitted to a multiple sequence alignment program for DNA or proteins, ClustalW2™, available online for free from the European Bioinformatics Institute (www.e-bi.ac.uk; Larkin M. A. et al., 2007. Bioinformatics 23(21): 2947-2948).

Purification of Proteins Encoded by *S. aureus* Genes Expressed during IMI.

Genes or part of the genes were cloned into the vector pQE-30 (Qiagen) downstream to a polyhistidine signal to allow protein expression in *Escherichia coli* and purification of the expressed his-tagged polypeptides using a nickel affinity column (Qiagen Ni-NTA 1018244). Expression of the recombinant proteins and their purification was performed according to the manufacturer's recommendations (Qiagen).

Immunization of Mammalian Species and Measurement of Antibody Titers.

Mice were immunized with the antigens (purified recombinant proteins, polypeptides or epitopes of interest, alone or in combination). For example, each animal group composed of ten mice received a different antigen (100 µg per injection), a combination of antigens (100 µg of each per injection) or saline (i.e. the control non-immunized group). Mice were immunized twice 3 weeks apart. The antigens or saline was combined with the adjuvant Emulsigen®-D (MVP Technologies, Omaha, USA). Injections were performed subcutaneously in 400 µl on the back of the mice. Blood samples were performed in the mandibular vein before each injection and, 3 weeks after the second injection, mice were euthanized and

TABLE III

Sequence of primers used for quantitative PCR (qPCR).

| ORF | Gene | Description | Forward sequence | Reverse sequence |
|---|---|---|---|---|
| SACOL0005 | gyrB | DNA gyrase, B subuni | GGTGCTGGGCAAATACAAGT (SEQ ID NO: 1) | TCCCACACTAAATGGTGCAA (SEQ ID NO: 2) |
| SACOL0148 | cap M | Capsular polysaccharide biosynthesis | AGGTCCTAGACCAGCGCTTT (SEQ ID NO: 3) | TCTCTCCCATCACTTGAGC (SEQ ID NO: 4) |
| SACOL0442 | | Exotoxin, putative | CATACACAGTTGCTGGCAGAG (SEQ ID NO: 5) | CAAGCCATAGGAAATATGAGCA (SEQ ID NO: 6) |
| SACOL0718 | | ABC transporter, unknown function | GCACAAGAAGTGTTGCGAGA (SEQ ID NO: 7) | GTCGTTTTCCCAGATCCAGA (SEQ ID NO: 8) |
| SACOL2022 | hld | Delta-hemolysin, RNA III | TAATTAAGGAAGGAGTGATTTCAATG (SEQ ID NO: 9) | TTTTTAGTGAATTTGTTCACTGTGTC (SEQ ID NO: 10) |
| SACOL2171 | | Unknown function, possibly iron-related | CAATGCATCGCGAAAACTTA (SEQ ID NO: 11) | GCTTAGCTTGTGGGAACTGG (SEQ ID NO: 12) |
| SACOL2325 | | Transcriptional regulator, LysR family | CATCTCGGCTTAGGTTACGC (SEQ ID NO: 13) | TTTTTCGGCCTAAGTTTGGA (SEQ ID NO: 14) |
| SACOL269 | icaA | Biosynthesis of polysaccharides, biofilms | TTGCGTTAGCAAATGGAGAC (SEQ ID NO: 15) | AATGCGTGCAAATACCCAAG (SEQ ID NO: 16) |

Sequence Alignments.

Nucleic acid and amino acid sequences of *S. aureus* genes (including SACOL0442 and SACOL0720, as well as other genes) and encoded proteins from *Staphylococcus aureus* strains COL, RF122, NCTC 8325, JH1, JH9, Newman, Mu3, Mu50, USA300-FPR3757, N315, MW2 or MSSA476 were maximum blood was sampled. The levels of specific antibodies against the immunizing antigens were determined. Levels of antibodies were evaluated using standard ELISA methodology (Loiselle et al., 2009). Briefly 96-well plates were coated with individual purified antigen and then saturated with non-specific protein. After incubation with serial dilutions of the serums and washes, a secondary antibody conjugated to an enzyme (HRP) was added and the presence of antibodies was detected with a colorimetric reaction.

Immunization in Cows.

Each animal group composed of 5 cows receives a different antigen (300 μg per injection), a combination of antigens (300 μg of each per injection) or saline (i.e. the control non-immunized group). The antigens or saline is combined with the adjuvant Emulsigen®-D. After blood samplings for the determination of pre-immune levels of antibodies, a final volume of 3 ml per dose of antigens or saline is injected subcutaneously in the neck of the cows. Blood samplings is performed every 2 weeks. Ten weeks after the first injection, the second injection is performed subcutaneously in the neck on the other side of the animals. The levels of the specific antibodies is determined as described for the mice immunization.

Evaluation of Antibody Binding on Bacterial Surface.

Bacteria were incubated at 4° C., under gentle agitation, with a solution of PBS-2% BSA containing a 1/500 dilution of rabbit serum to block staphylococcal protein A, which can bind non specifically the Fc fragment of immunoglobulins. After 2 washes with PBS-2% BSA-0.02% tween20™, bacteria were incubated at 4° C., under gentle agitation, in PBS-2% PBS containing 10 μl of bovine pre immune or immune serum against the antigen of interest. After 2 washes with PBS-2% BSA-0.02% tween20™, bacteria were incubated for one hour at 4° C., under gentle agitation, in PBS-2% PBS containing a 1/1000 dilution of FITC-conjugated goat anti-bovine IgG. After 3 washes with PBS-2% BSA-0.02% tween20™ bacteria were suspended in PBS with 1% formaldehyde. Surface labeling was then analyzed by flow cytometry using a BD FACSCalibur™ instrument and the CellQuest™ Pro software.

Identification of B cell epitopes. With a combination of prediction software including BCPred Predictions (EL-Manzalawy et al., 2008a), AAP Predictions (Chen J et al., 2007), FBCPred Prediction (EL-Manzalawy et al., 2008b) and ABCPred (Saha, S, and Raghava G. P. S., 2006), available at http://bioinfo.bgu.ac.il/bsu/immunology/epitope_pred/index.htm, http://ailab.cs.iastate.edu/bcpreds/index.html and elsewhere, B cell epitopes, i.e., short amino acid sequences that will be recognized by B cells, thus inducing the production of antibodies by B cells, were determined for several vaccine components.

Identification of T Cell Epitopes.

Computer driven algorithms can also be used to facilitate identification of T cell epitopes i.e., short amino acid sequences that will bind MHC molecules (MHC class I and/or II) and be recognized by T cells, thus inducing a cellular immune response. The antigens may be subjected to analysis by the Epimatrix™ System (http://www.epivax.com/platform/) to identify putative T cell epitopes. This in-silico technique divides the total sequence of the antigen into fragments of 9 amino acids overlapping by 8 amino acids. This pool of 9-mer peptides is then screened for predicted affinity against a group of known MHC class I and class II alleles. The resulting scores can be used to rate putative epitopes on a common scale which can then be tested in vitro. The technique is applicable to any animal for which a sufficient knowledge of MHC sequences is available. (De Groot et al., 2008).

Example 2

Validation of Chronic *S. aureus* Strains

Comparative genomic hybridization data for the members of chronic isolate pairs collected from cows >55 days apart between dry-off and calving (FIG. 2, underlined isolates), show a high genetic relatedness. Unrelated reference strains (*S. aureus* N315, MRSACOL, Newbould, ATCC 49775, ATCC 51811 and SHY97-3906) and isolates randomly or systematically picked from bovine mastitis cases with clinical symptoms during lactation (annoted "R" in Table I above) are also shown in FIG. 2 for comparison. This analysis confirmed that the isolates that were collected from the same cow and the same quarter >55 days apart, were genetically identical. It is clear that the chronic isolates #3, #557, and #1290 used in the studies described herein have the ability to cause an IMI and persist in the mammary gland for a long period of time (i.e., are able to cause a chronic IMI).

Figure 3:
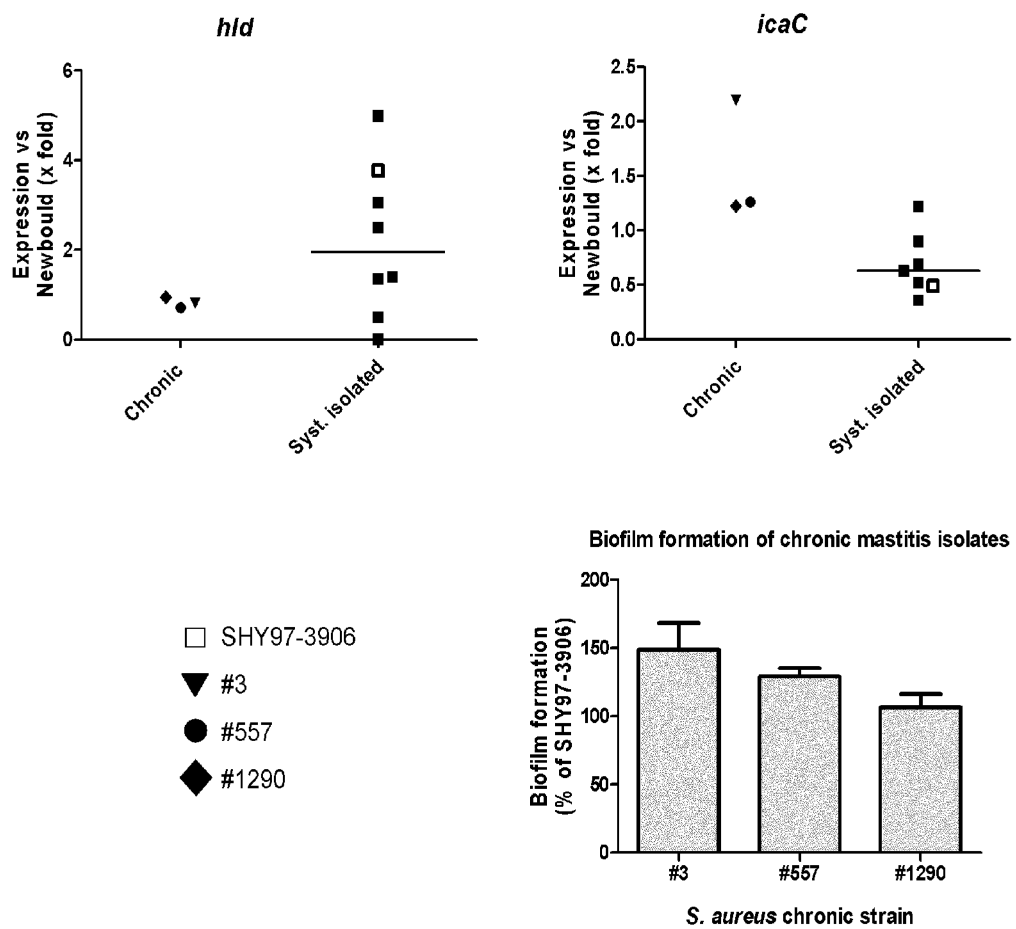
FIG. 3 shows Q-PCR analyses reporting the relative level of gene expression for indicators of virulence: hld (Agr-dependent exotoxin production), icaC (ica-dependent biofilm production) and overall biofilm production (measured by a spectrophotometric method with crystal violet) in *S. aureus* isolates grown in a cultivation medium in vitro. Chronic isolates #3 (black inverted triangle), #557 (black circle) and #1290 (black diamond) are compared to a collection of systematically isolated strains from bovine mastitis with clinical signs (black squares, where isolate SHY97-3906, a previously described strain isolated from a typical mastitis case with clinical signs, is represented as the open square). Q-PCR results are presented as fold-expression compared to the reference strain Newbould (ATCC 29740) and biofilm production is reported as a percentage of that produced by strain SHY97-3906. All Q-PCR results are normalized using the level of expression of gyr.

FIG. 3 shows Q-PCR analyses reporting the relative level of gene expression for indicators of virulence such as hld (Agr-dependent exotoxin production), icaC (ica-dependent biofilm production) and overall biofilm production (measured by a spectrophotometric method with crystal violet) for *S. aureus* isolates grown in a cultivation medium in vitro. Chronic isolates (#3, 557, 1290) were compared to a collection of systematically isolated strains from bovine mastitis with clinical signs (where isolate SHY97-3906 is represented as the open square). Q-PCR results are presented as fold-expression relative to the reference strain Newbould (ATCC 29740) and biofilm production is reported as a percentage of that produced by strain SHY97-3906. All Q-PCR results were normalized based on the level of expression of gyrA. The primers used for the analysis are shown in Table II above. This analysis confirmed that the chronic isolates used in the Examples described herein substantially differ in their basal level of gene expression for known virulence determinants and for biofilm production compared with the population of systematically collected isolates from clinical mastitis cases during lactation. These characteristics described for the chronic isolates resemble those reported for *S. aureus* strains isolated from persistent bovine IMI (Melchior et al., 2009).

Example 3

Figure 4:
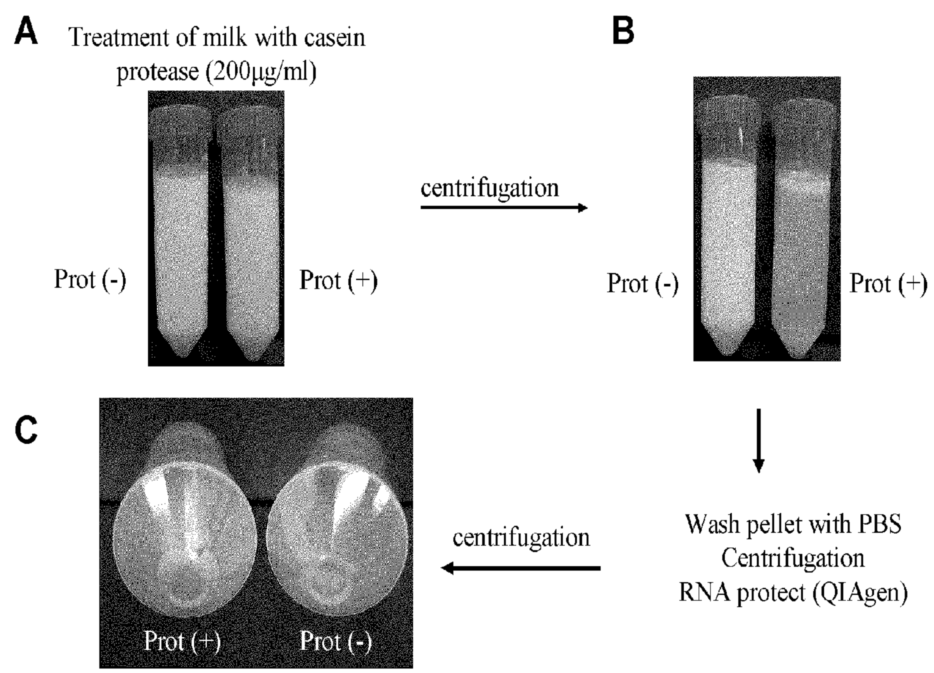
FIG. 4 shows the description of the method used for isolating bacteria from mastitis milk samples. (A) Milk before first centrifugation with (Prot (+)) or without (Prot (−)) casein protease. (B) After first centrifugation. (C) After "RNA Protect" treatment and centrifugation (last step). A large bacterial pellet is recovered from milk treated with casein protease.

Efficient Isolation of Bacteria from the Milk of Experimentally Infected Cows The method used for isolating bacteria from mastitis milk samples is illustrated in FIG. 4. The bacterial pellet recovered from milk treated with proteases (prot+, FIG. 4) was much larger and allowed greater amounts of microbial RNA to be isolated for DNA microarray and qPCR experiments compared to that obtained from the untreated bacterial pellet (prot−, FIG. 4). A DNA microarray experiment comparing the transcriptional profiles of *S. aureus* grown in vitro in milk treated with casein protease to that of *S. aureus* cells grown in untreated milk did not show significant gene modulation. Quantitative PCR analysis for 4 genes expressed in *S. aureus* grown in an iron-restricted medium in vitro and under iron-rich conditions show that a 2-hour delay before RNA extraction (time period between milking and RNA extraction) did not affect the observed modulations in expression of iron-regulated genes (isdB, ferritin and SACOL2170) and did not affect expression of the housekeeping gene gyrB. The integrity of bacterial messenger RNA directly isolated from mastitis milk should therefore not be affected by the time required for isolation of bacteria after milking of the infected cow.

Example 4

Experimental Infection Profiles in Cows

Figure 5A:
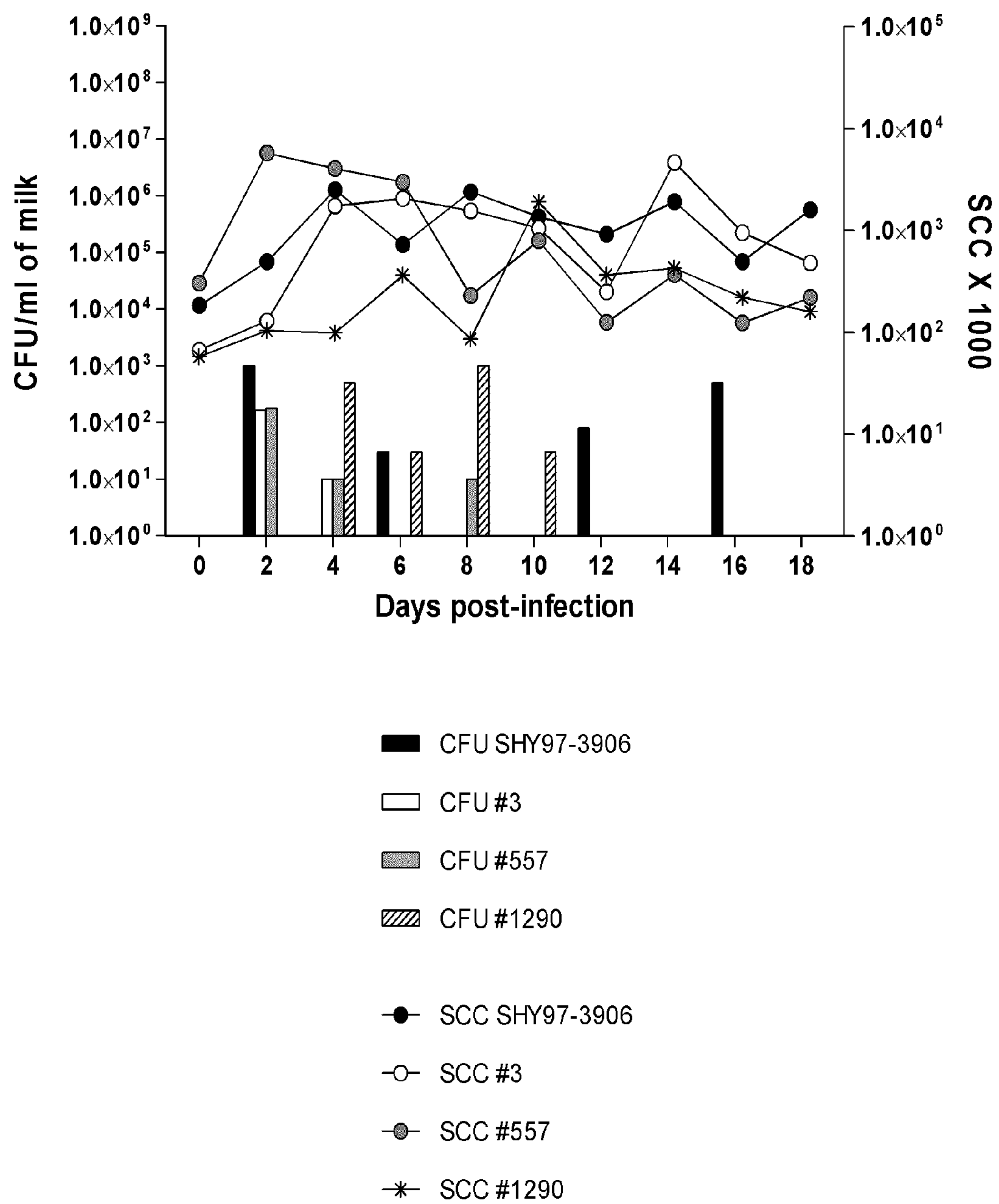
FIGS. 5A, 5B and 5C represent cows #313, cow #307 and cow #5325, respectively. The four different *S. aureus* strains used in this study are represented as black bars and dots (SHY97-3906), white bars and dots (chronic isolate #3), grey bars and dots (chronic isolate #557) and shaded bars and star-shaped dots (chronic isolate #1290). Cow #5325 was euthanized at day 15.
Figure 5B:
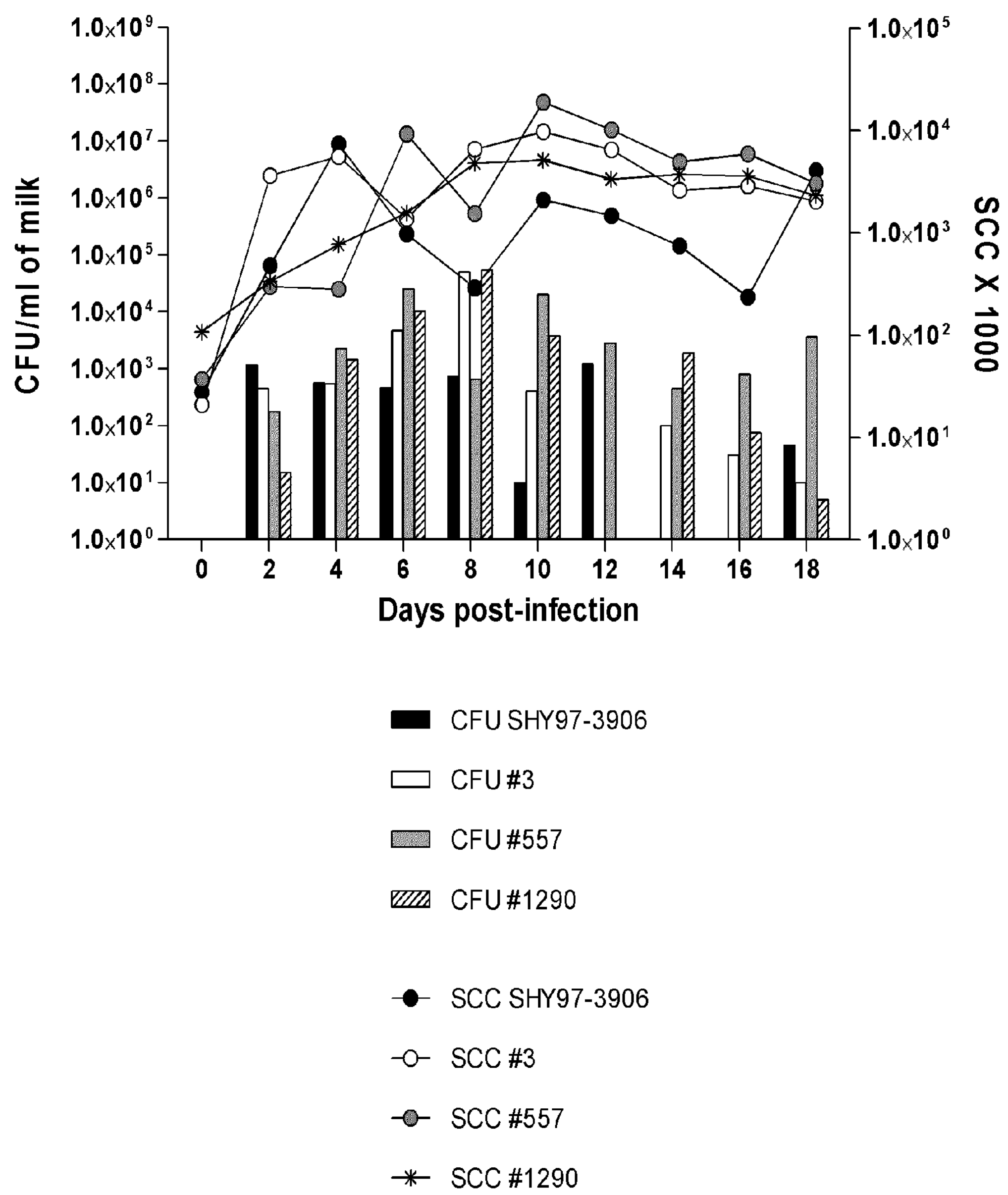
Figure 5C:
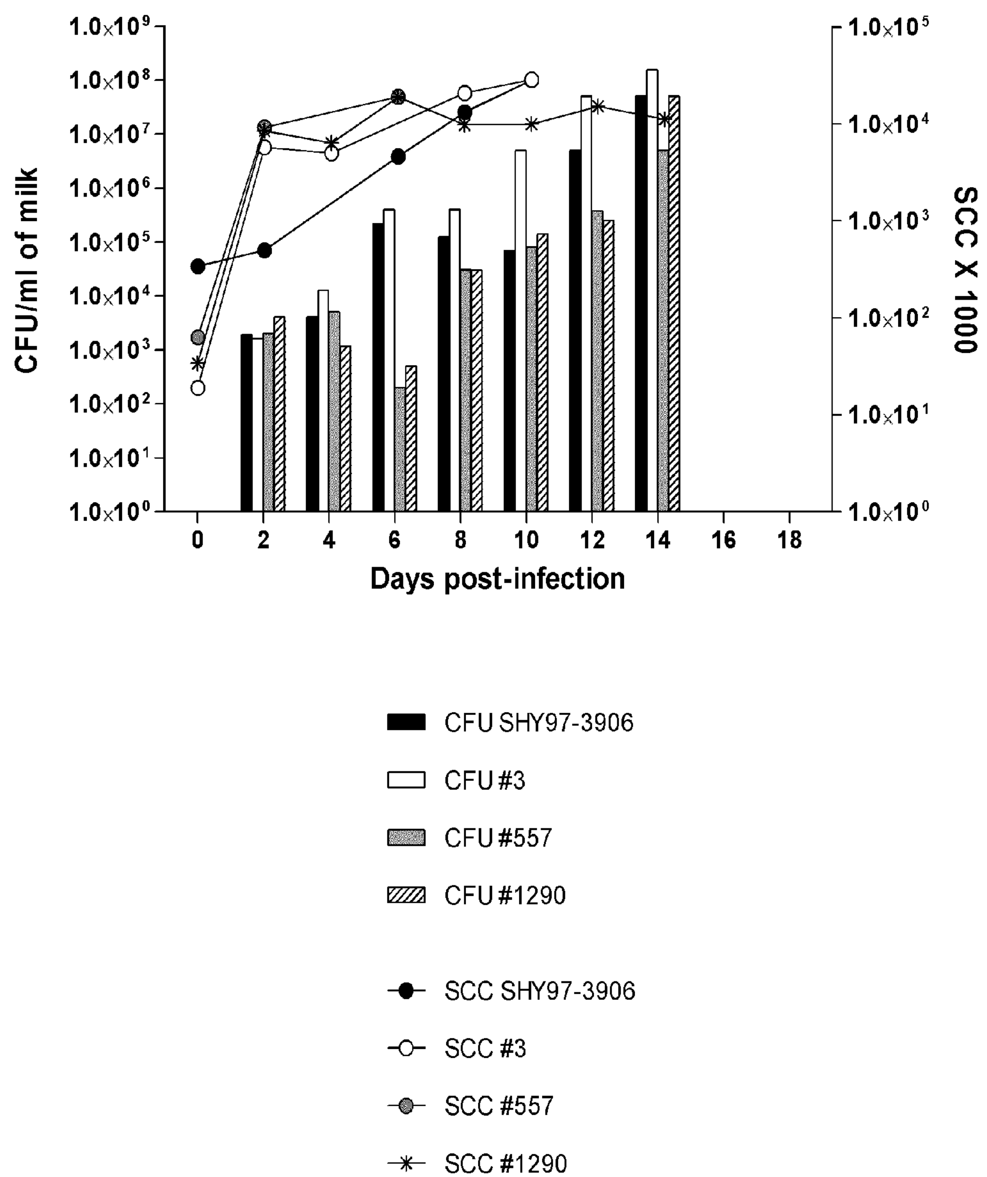

Experimental infection profiles for strain SHY97-3906 and the 3 chronic strains (#3, 557, 1290) in 3 different cows are reported in FIG. 5 as a function of bacterial (left Y axis) or somatic cell counts (right Y axis) over the infection period. Data show that all bacterial isolates are able to establish an intra-mammary infection in cows although the host (cow) seems to influence the level of bacterial counts, cow #313 showing low bacterial counts vs. cow #5325 showing high counts for all tested isolates. Milk samples with high bacterial counts (obtained from cows #307 and 5325) were thereafter used for transcriptional analyses.

Example 5

*S. aureus* Genes Expressed During IMI in Cows

Figure 6:
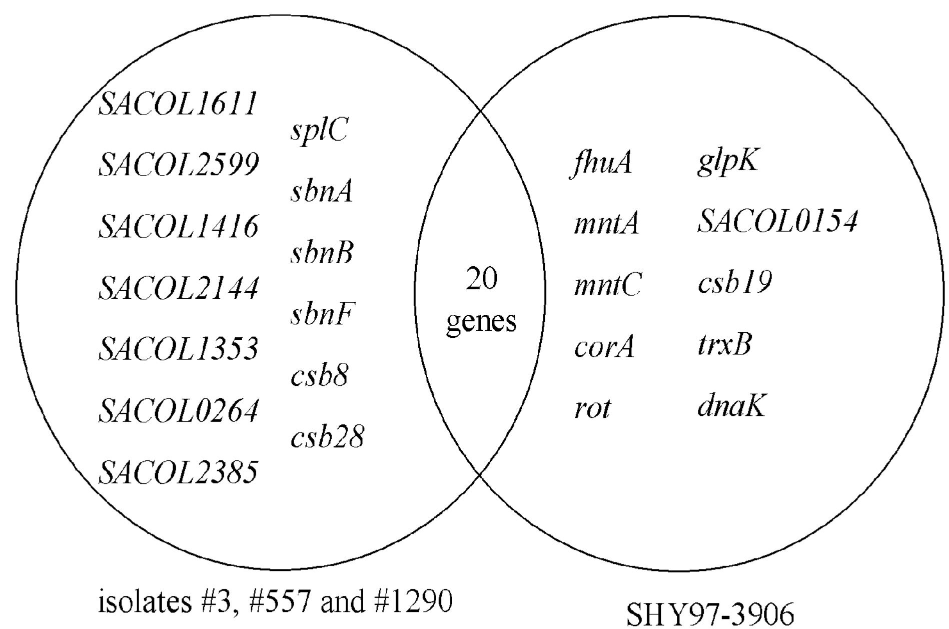
FIG. 6 shows a Venn diagram of the genes differentially expressed in the chronic strains taken all together (isolates #3, #557 and #1290) versus SHY97-3906 isolated from a typical mastitis case with clinical signs.

The transcriptional profile of *S. aureus* strains infecting the mammary glands of cows was determined by DNA microarray experiments. The relative levels of expression of the differentially expressed genes and the genes expressed by both of the two groups of isolates (i.e., from chronic or acute mastitis) are reported in Table IV below. FIG. 6 shows the Venn diagram of the genes differentially expressed in the chronic strains taken all together (isolates #3, #557 and #1290) versus SHY97-3906 isolated from a typical mastitis case with clinical signs (acute mastitis). This analysis shows that the two types of isolates (chronic vs. typical mastitis isolate (acute)) present different gene expression profiles and that specific genes may be more strongly expressed in each group. These specific sub-groups of genes constitute therapeutic or vaccine targets to treat specific clinical cases. Also of interest are the genes commonly expressed by both types of isolates (20 genes in this case, identified by a plus [+] sign in Table IV below), which may be used to treat acute and/or chronic cases.

Figure 7:
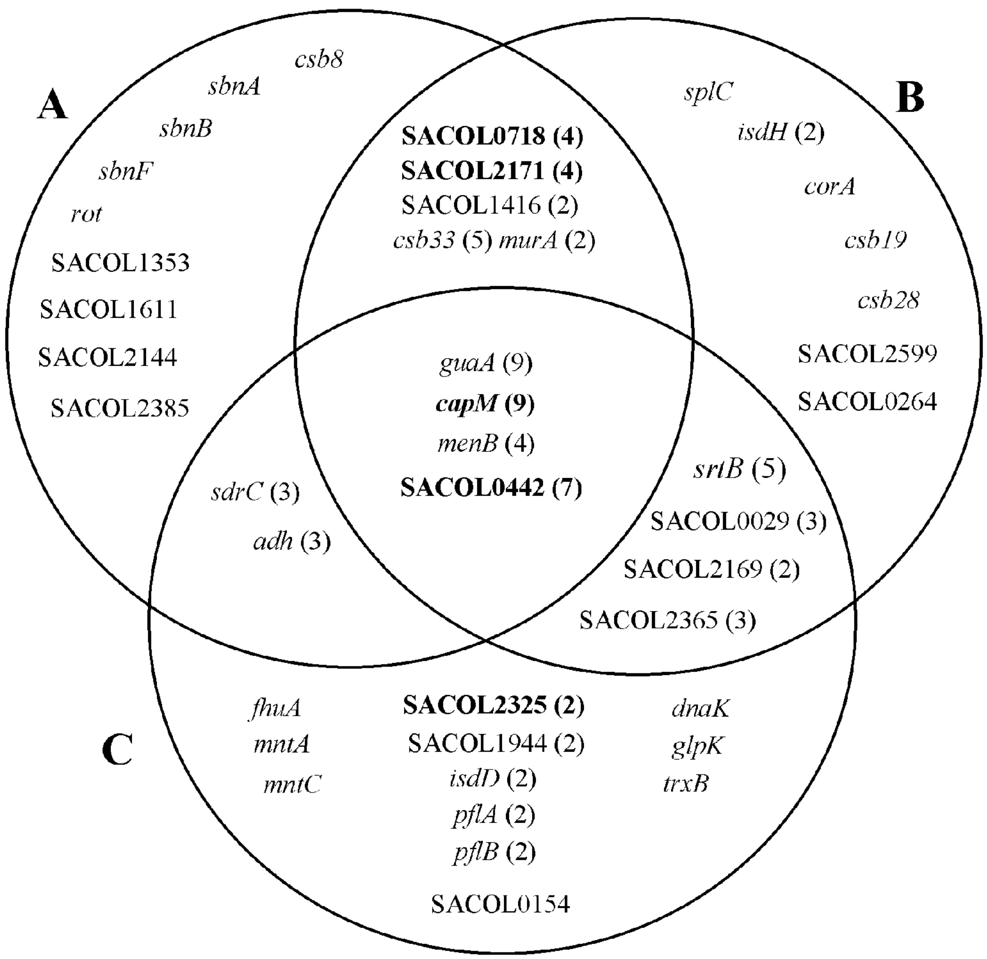
FIG. 7 shows a Venn diagram of the 43 genes found to be strongly expressed in microarray experiments using bacterial samples from cow #307 at day 8 (A) and day 10 (B) of infection, and in cow #5325 at day 10 of infection (C). The number of bacterial samples in which the genes were shown to be expressed is indicated in parenthesis and the gene names in bold characters were selected for Q-PCR analyses (see FIG. 8).
Figure 8:
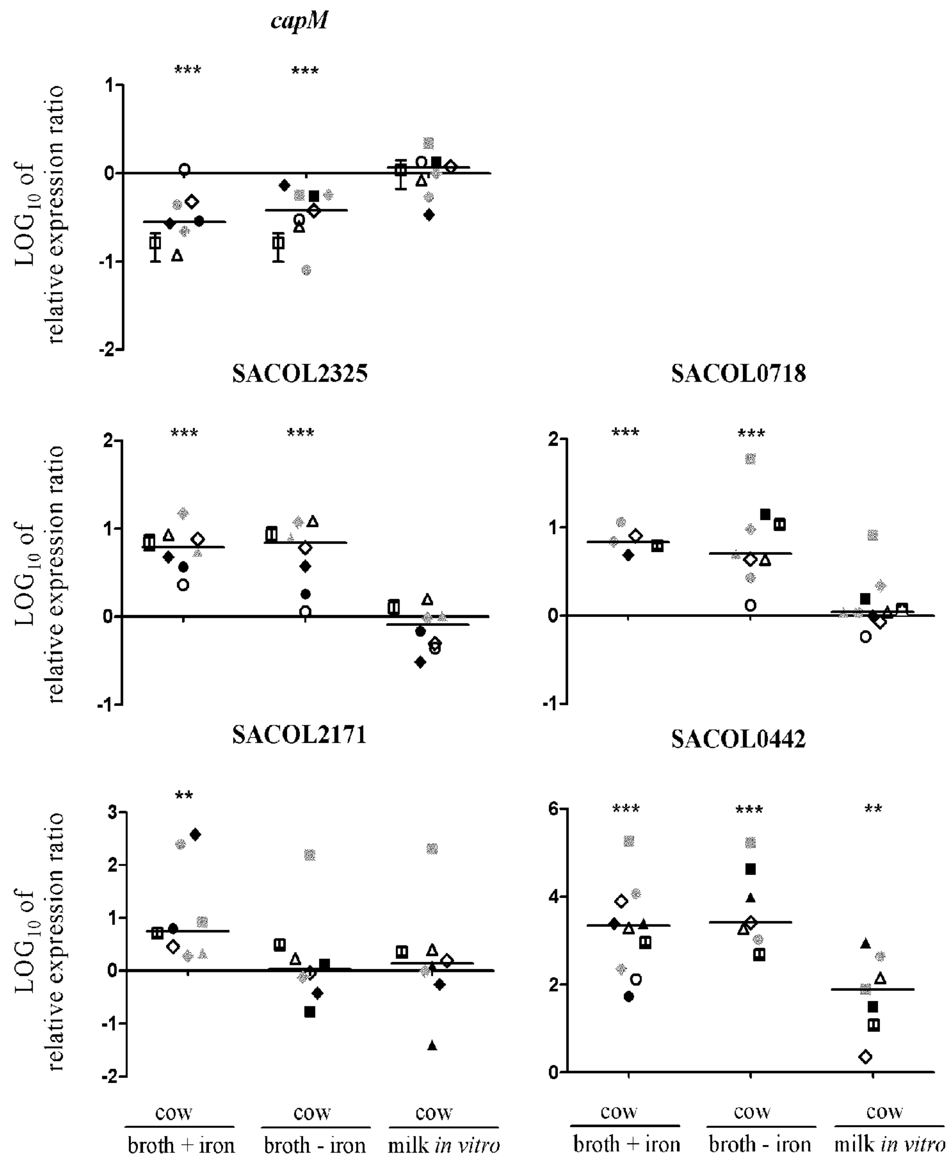
FIG. 8 shows quantitative PCR analyses of genes found to be strongly expressed by *S. aureus* collected from cow's IMI (cow). Gene expression was compared to that measured in *S. aureus* cultivated in vitro in Mueller-Hinton broth supplemented with iron (broth+iron), in iron-restricted broth (broth−iron), and in freshly collected non-mastitis milk in vitro (milk in vitro). All results are normalized using the level of expression of gyrB and are presented as Log 10 values of the relative expression ratios. The horizontal bar represents the median ratio value of all samples. Significant differences between the median and a ratio of zero (representing no change in the expression of the gene) are shown (*=P<0.05; =P<0.01; *=P<0.005; unpaired t-test). RNA samples from *S. aureus* grown in two different animals were analyzed: cow #5325 at day 10 of infection with isolates SHY97-3906 (○), #3 (Δ), #557 (◇), and #1290 (□), cow 307 at day 8 of infection (same symbol shapes, black symbols) and cow #307 at day 14 of infection (same symbol shapes, grey symbols). For the sample collected from strain #1290 in cow #5325 at day 10 of infection (□), the error bars are shown. Relative gene expression is shown for a capsular biosynthesis gene (capM), a gene of unknown function (SACOL2171), a transcriptional regulator of unknown function (SACOL2325), an ABC transporter of unknown function (SACOL0718) and a chromosomally encoded gene not previously characterized (SACOL0442).

FIG. 7 shows the Venn diagram of the 43 genes found to be strongly expressed in microarray experiments (Table IV below) using bacterial samples from cow #307 at day 8 (A) and day 10 (B) of infection, and in cow #5325 at day 10 of infection (C). The number of bacterial samples in which the genes were shown to be expressed is indicated in parenthesis and the gene names that are represented in bold characters were chosen for qPCR analyses (FIG. 8). This analysis allows identification of genes that are expressed by one or more isolates in one or more cows at one or more time points during the infection.

Several genes shown in FIG. 7 were thus expressed in one of the following situations: (i) expressed in more than one strain, (ii) observed in more than one cow and/or (iii) at more than one time point. The expression of 5 such interesting *S. aureus* genes in 5 to 12 independent samples collected from cows with IMI was thus verified and confirmed by qPCR (FIG. 8). These included the capsular biosynthesis gene (cap), a gene of unknown function (SACOL2171), a transcriptional regulator of unknown function (SACOL2325), an ABC transporter of unknown function (SACOL0718) and a chromosomally encoded gene not previously characterized (SACOL0442). In parallel, gene expression was compared to that measured in *S. aureus* cultivated in vitro in Muller-Hinton broth supplemented with iron (broth+iron), in iron-restricted broth (broth−iron), and in freshly collected non-mastitic milk in vitro (milk in vitro) in order to identify the environmental stimuli involved in gene expression (FIG. 8).

It was observed (i) that the expression of capM was reduced in cows and in milk compared to that seen in vitro, (ii) that gene SACOL2171 was up-regulated by iron restriction either in cows, in milk or in iron-restricted broth in vitro, (iii) that the expression of SACOL0718 and SACOL2325 were specifically induced by the milk environment (i.e. up-regulated in cows compared to any broth in vitro but equivalent to that seen in fresh milk) and (iv) that gene SACOL0442 was exclusively expressed during infection in the cow, i.e., more expressed in cows compared to any other environment. The summary of the expression profile determined by DNA array and qPCR analyses for genes SACOL0442 and SACOL0718 in different strains, cows and time points during infection is reported in Table V below. As seen, SACOL442 and SACOL0718 are representative examples of *S. aureus* genes that exhibit sustained expression during IMI and this independently of individual *S. aureus* strains. Table VI below lists 11 genes (i.e. SACOL442, SACOL0718 and 9 other genes) for which expression had never been reported before, when *S. aureus* was grown in "other" mammalian environments (i.e. different from the bovine mammary gland environment, as used herein) (Allard et al., 2006; Burlak et al., 2007; Goerke et al., 2000; Garzoni et al., 2007) or in surrogate cultivation media such as in human neutrophils in vitro (Voyich et al., 2005), an iron-restricted medium in vitro (Allard et al., 2006; Maresso et al., 2006), in milk in vitro (Lammers et al., 2000) or when *S. aureus* mastitis isolates were grown in vitro (Taverna et al., 2007). The genes depicted in Table VI thus represent excellent targets for prevention and/or treatment of *S. aureus* IMI, for example as components for a vaccine composition aimed at preventing *S. aureus* IMI. Also, reports of *S. aureus* genes expressed in surrogate media or in mammalian environment other than the mammary gland can actually lead away from what is reported here for *S. aureus* genes expressed during bovine IMI. For example, the gene capM (SACOL0148) was reported to be expressed in a mastitis isolate grown on a blood agar plate in vitro (Taverna et al., 2007) but is shown here to be less expressed during bovine IMI than that measured after growth in vitro (FIG. 8). It has been previously demonstrated that the genes capM, csb33, csb28, pflB, glpK, and SACOL0154 (listed in Table III above) were all less expressed during growth of *S. aureus* in tissue cages implanted in the peritoneal cavity of mice than when measured in vitro (Allard et al., 2006), whereas a strong expression of all these genes during bovine IMI is shown in the instant studies. Indeed, the host defense barriers and immune response, the infected mammary gland tissue and tissue damage, as well as the altered composition and low oxygen tension of the mastitis milk of cows suffering from IMI all create a unique and complex environment that would be difficult to mimic in other animal models of infection, in surrogate systems or other cultivation media (Mayer et al., 1988; Park et al., 2007).

Figure 9:
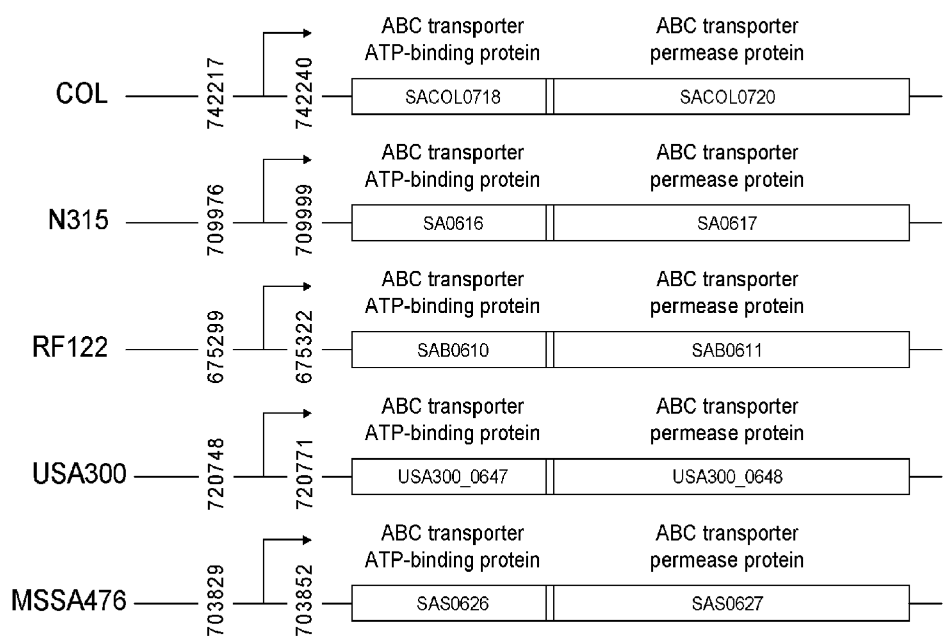
FIG. 9 shows the organization of the SACOL0718-720 predicted operon in *S. aureus* strains COL, N315, RF122, USA300 and MSSA476. The two genes overlap by 10 nucleotides. The arrow indicates the direction of transcription. The genome position of the predicted −10 and −35 boxes of the promoter region is also indicated.

Gene SACOL0718 identified in Tables III and V is part of an operon comprising genes SACOL0718-SACOL0720 as illustrated in FIG. 9 and as determined by programs known by those in the field (Prediction of operon: www.microbesonline.org, Dehal P. S. et al., *Nucleic Acids Res.* 2010 January; 38(Database issue): D396-400. Epub 2009 Nov. 11; Promoter search: www.softberry.com, Srivastava S et al., Bioinformation 2008; 3(4):173-6. Epub 2008 Dec. 6). The predicted function of these genes is the formation of an ABC transporter composed of an ATP-binding protein and a permease (Table V below). SACOL0720 was not detected in the microarray experiments (Table III above) because it was not included in the composition of the DNA array (Allard et al., 2006). However, it is well known that genes from operons are expressed from the same promoter sequence and are translated into proteins from the same messenger RNA. Therefore, given that expression of SACOL0718 is detected during IMI, it may be predicted that expression of SACOL0720 certainly also occurs and thus that both SACOL0718 and SACOL720 represent targets for prevention and/or treatment of *S. aureus* IMI.

Table IV:

*S. aureus* genes (43 genes) with significant levels of expression (intensity >100%) during bovine IMI as determined in microarray experiments. Genes are listed by name (if attributed) as well as by open reading frame (ORF) numbers for three different *S. aureus* strains for which the genome is sequenced (MRSA COL, N315 and the mastitis isolate RF122). Such genes are also reported in the Venn diagrams of FIGS. 6 and 7. The 20 genes expressed by both chronic strains as well as by strain SHY97-3906 (common) are indicated by a plus (+) sign.

TABLE IV

| | ORF | ORF | ORF | | Com- | Cow 307, Day 8 | | | | Cow 307, Day 10 | | | | Cow 5325, Day 10 | |
|---|---|---|---|---|---|---|---|---|---|---|---|---|---|---|---|
| Gene | COL | RF122 | N315 | Description | mon | SHY97 | #3 | #557 | #1290 | SHY97 | #3 | #557 | #1290 | SHY97 | #3 |
| | 0029 | — | 35 | Biosynthesis of cofactors | + | | | | | 106.6 | | | | 195.4 | 356.4 |
| sbnA | 0100 | 55 | 112 | Staphylobactin biosynthesis | | | | | 440.5 | | | | | | |
| sbnB | 0101 | 56 | 113 | Staphylobactin biosynthesis | | | | 559.4 | | | | | | | |
| sbnF | 0105 | 60 | 117 | Staphylobactin biosynthesis | | | | | 395.7 | | | | | | |
| capM | 0148 | 102 | 156 | Capsular polysaccharide biosynthesis | – | 1187.2 | 291.6 | 592.3 | 568.2 | 177.9 | | 347.7 | 181.0 | 208.7 | 351.9 |
| | 0154 | 108 | 162 | Aldehyde dehydrogenase | | | | | | | | | | 136.8 | |
| pflB | 0204 | 164 | 218 | Formate acetyltransferase | – | | | | | | | | | 1825.5 | 465.6 |
| pflA | 0205 | 165 | 219 | Formate-lyase activating enzyme | + | | | | | | | | | 1300.8 | 231.8 |
| | 0264 | 216c | 266 | ABC transporter, unknown function | | | | | | | 111.8 | | | | |
| | 0442 | 321 | 357 | Exotoxin, putative | + | 383.8 | 115.3 | | 201.3 | 123.5 | | 227.2 | 145.1 | | 115.8 |
| guaA | 0461 | 341 | 376 | GMP synthase | + | 396.3 | 213.0 | 720.5 | 555.2 | 331.7 | 335.6 | 135.6 | 156.5 | | 209.8 |
| sdrC | 0608 | 513 | 519 | Virulence adhesin | + | | | 132.3 | | | | | | 173.6 | 312.1 |
| adh | 0660 | 557 | 562 | Alcool deshydrogenase, Zn containing | + | | | 110.5 | | | | | | 2228.3 | 168.2 |
| mntC | 0688 | 581c | 587 | Manganese ABC transporter | | | | | | | | | | 273.8 | |
| mntA | 0690 | 583c | 589 | Manganese ABC transporter | | | | | | | | | | 168.8 | |
| fhuA | 0704 | 596 | 602 | Ferrichrome transport ATP-binding protein | | | | | | | | | | 162.1 | |
| | 0718 | 610 | 616 | ABC transporter, unknown function | + | 116.8 | | 171.5 | | 108.7 | 110.6 | | | | |
| trxB | 0829 | 717 | 719 | Thioredoxin reductase | | | | | | | | | | 258.3 | |
| menB | 1054 | 912 | 898 | Enoyl-CoA hydratase/isomerase family | + | | | 132.2 | | 115.0 | 112.8 | | | 222.6 | |
| isdD | 1142 | 996 | 979 | Iron transport from heme | + | | | | | | | | | 142.5 | 200.0 |
| srtB | 1145 | 999 | 982 | Sortase B | + | | | | | 107.4 | 109.3 | 125.2 | | 434.1 | 672.1 |
| glpK | 1320 | 1161 | 1141 | Glycerol kinase | | | | | | | | | | 163.2 | |
| | 1353 | — | 1157 | ABC transporter, unknown function | | | | 115.5 | | | | | | | |
| | 1416 | 1236c | 1213 | ABC transporter, unknown function | | | | 103.9 | | | 117.1 | | | | |
| | 1611 | 1426c | 1383 | Transcription regulator homolog | | | | 118.0 | | | | | | | |
| dnaK | 1637 | 1452c | 1409 | Chaperone protein | | | | | | | | | | 264.1 | |
| csb8 | 1680 | — | 1452 | Conserved protein | | | | 120.9 | | | | | | | |
| isdH | 1781 | 1590c | 1552 | Iron transport from heme | + | | | | | 120.1 | 117.2 | | | | |
| rot | 1812 | 1622c | 1583 | Regulator of toxin, Rot | | 116.2 | | | | | | | | | |
| splC | 1867 | 1671c | 1629 | Serine protease | | | | | | | 111.0 | | | | |
| csb33 | 1912 | 1788c | 1671 | Glucosamine-6-phosphate isomerase | + | 110.8 | | | | 186.8 | 176.5 | 158.2 | 220.9 | | |
| | 1944 | 1818c | 1702 | Hypothetical protein | + | | | | | | | | | 138.0 | 277.4 |
| murA | 2092 | 1984c | 1902 | UDP-NAcGlc-1-carboxyvinyltransferase | + | 104.2 | | | | | 116.4 | | | | |
| | 2144 | 2033c | 1958 | ABC transporter, unknown function | | | | 377.6 | | | | | | | |
| | 2169 | 2060c | 1981 | Siderophore biosynthesis, putative | + | | | | | | 112.8 | | | 177.3 | |
| | 2171 | 2062 | 1983 | Siderophore biosynthesis, putative | + | 100.4 | | 114.0 | | 144.0 | 128.4 | | | | |
| csb28 | 2321 | 2205c | 2119 | Oxidoreductase dehydrogenase/reductase | | | | | | | 129.9 | | | | |
| | 2325 | 2209 | 2123 | Transcriptional regulator, LysR family | + | | | | | | | | | 242.1 | 364.9 |

TABLE IV-continued

| Gene | ORF COL | ORF RF122 | ORF N315 | Description | Common | Cow 307, Day 8 SHY97 | #3 | #557 | #1290 | Cow 307, Day 10 SHY97 | #3 | #557 | #1290 | Cow 5325, Day 10 SHY97 | #3 |
|---|---|---|---|---|---|---|---|---|---|---|---|---|---|---|---|
| corA | 2342 | 2226c | 2137 | Magnesium and cobalt transport protein | | | | | | 106.9 | | | | | |
| | 2365 | 2248c | 2158 | Hypothetical protein | + | | | | | 106.9 | | | | 124.7 | 198.0 |
| csb19 | 2379 | 2261 | 2170 | Conserved protein | | | | | | 116.2 | | | | | |
| | 2385 | 2266 | 2175 | HSP20 family protein | | | | 123.7 | | | | | | | |
| | 2599 | 2457c | 2369 | Homolog to FeoB, Fe2+ transport protein | | | | | | | 101.8 | | | | |
| Proportion of genes (%) with significant level of expression (intensity >100%) on arrays | | | | | | 6.6 | 5.4 | 7.5 | 5.9 | 16.7 | 16.7 | 16.1 | 15.4 | 7.6 | 8.3 |

TABLE V

Mastitic milk samples in which the expression of SACOL0442 (upper panel) or SACOL0718 (lower panel) was detected on DNA array or by qPCR for 4 different *S. aureus* strains at 3 different time points in two cows.

| Cow | Day of infection | *S. aureus* strains SHY97-3609 | 3 | 557 | 1290 |
|---|---|---|---|---|---|
| Gene SACOL0442 | | | | | |
| 307 | 8 | ● | ● | ● | ● |
| 307 | 10 | ● | ND | ● | ● |
| 307 | 14 | ● | ● | ● | ● |
| 5325 | 10 | ● | ● | ● | ● |
| Gene | | | | | |

TABLE V-continued

Mastitic milk samples in which the expression of SACOL0442 (upper panel) or SACOL0718 (lower panel) was detected on DNA array or by qPCR for 4 different *S. aureus* strains at 3 different time points in two cows.

| Cow | Day of infection | *S. aureus* strains SHY97-3609 | 3 | 557 | 1290 |
|---|---|---|---|---|---|
| SACOL0718 | | | | | |
| 307 | 8 | ● | ● | ● | ● |
| 307 | 10 | ● | ● | ND | ND |
| 307 | 14 | ● | ● | ● | ● |
| 5325 | 10 | ● | ● | ● | ● |

ND, not detected.

TABLE VI

Names and annotations for a selection of 11 genes or operons taken from the 43 genes found to be strongly expressed in microarray experiments (Table III above) and for which expression had never been reported when *S. aureus* was grown in a different mammalian environment or in surrogate cultivation media such as in human neutrophils in vitro, in iron-restricted media or in milk in vitro or when *S. aureus* mastitis isolates were grown in vitro. Annotations are compared for representatives of the *S. aureus* sequenced genomes (MRSA COL, N315, RF122 [a mastitis isolate], USA300, MSSA476).

| Gene SACOL | COL | N315 | RF122 | USA300 | MSSA476 |
|---|---|---|---|---|---|
| 0442 | enterotoxin, putative | similar to exotoxin 2 | hypothetical protein | enterotoxin, putative | putative exported protein |
| 0718-0720 | ABC transporter, ATP-binding protein and permease | ABC transporter, ATP-binding protein and permease | ABC transporter, ATP-binding protein and permease | ABC transporter, ATP-binding protein and permease | putative ABC transporter protein and permease |
| 2365 | lipoprotein, putative | hypothetical protein, similar to TpgX protein | lipoprotein, putative | lipoprotein, putative | lipoprotein, putative |
| 0029 | HMG-CoA synthase, truncation | probable HMG-CoA synthase | — | conserved hypothetical protein | — |
| 1416 | peptide ABC transporter, permease protein, putative | oligopeptide transporter membrane permease domain (opp2c) | probable oligopeptide membrane, permease | peptide ABC transporter, permease protein | putative oligopeptide transport system permease |
| 1944 | conserved hypothetical protein | conserved hypothetical protein | conserved hypothetical protein | conserved hypothetical protein | putative membrane protein |
| 1611 | transcriptional regulator, Fur family | ferric uptake regulator homolog | zinc-specific metalloregulator (zur) | ferric uptake regulation protein (fur) | zinc-specific metalloregulatory protein |
| 2599 | conserved domain protein | hypothetical protein, similar to ferrous iron transporter | probable membrane protein | transporter gate domain protein | putative membrane protein |
| 2144 | ABC transporter, ATP-binding protein | ABC transporter, ATP-binding protein | ABC transporter, ATP-binding protein | ABC transporter, ATP-binding protein | ABC transporter, ATP-binding protein |
| 1353 | ABC transporter, permease protein, putative | hypothetical protein, similar to ABC transporter integral | — | ABC transporter, permease protein | putative membrane protein |

TABLE VI-continued

Names and annotations for a selection of 11 genes or operons taken from the 43 genes found to be strongly expressed in microarray experiments (Table III above) and for which expression had never been reported when *S. aureus* was grown in a different mammalian environment or in surrogate cultivation media such as in human neutrophils in vitro, in iron-restricted media or in milk in vitro or when *S. aureus* mastitis isolates were grown in vitro. Annotations are compared for representatives of the *S. aureus* sequenced genomes (MRSA COL, N315, RF122 [a mastitis isolate], USA300, MSSA476).

| Gene SACOL | COL | N315 | RF122 | USA300 | MSSA476 |
|---|---|---|---|---|---|
| 0264 | ABC transporter, ATP-binding protein | conserved hypothetical protein | probable ABC transporter ATP binding protein | ABC transporter, ATP-binding protein | putative ABC transporter ATP-binding protein |

Example 6

Attenuation of *S. aureus* Virulence

Figure 10A:
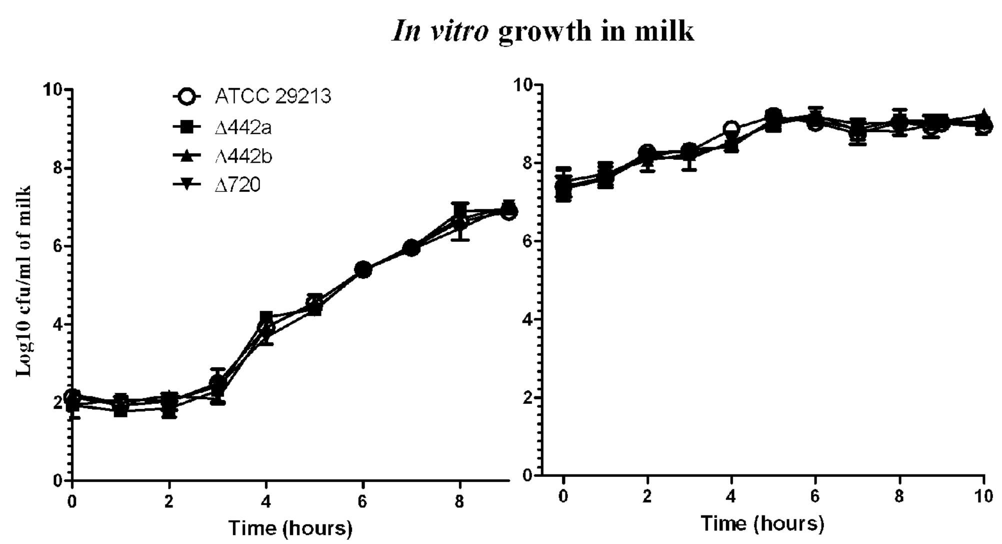
In FIG. 10A, the mean CFU/ml (log 10) for the 4 strains is represented over time following a small or large inoculum (left and right panels, respectively).
Figure 10B:
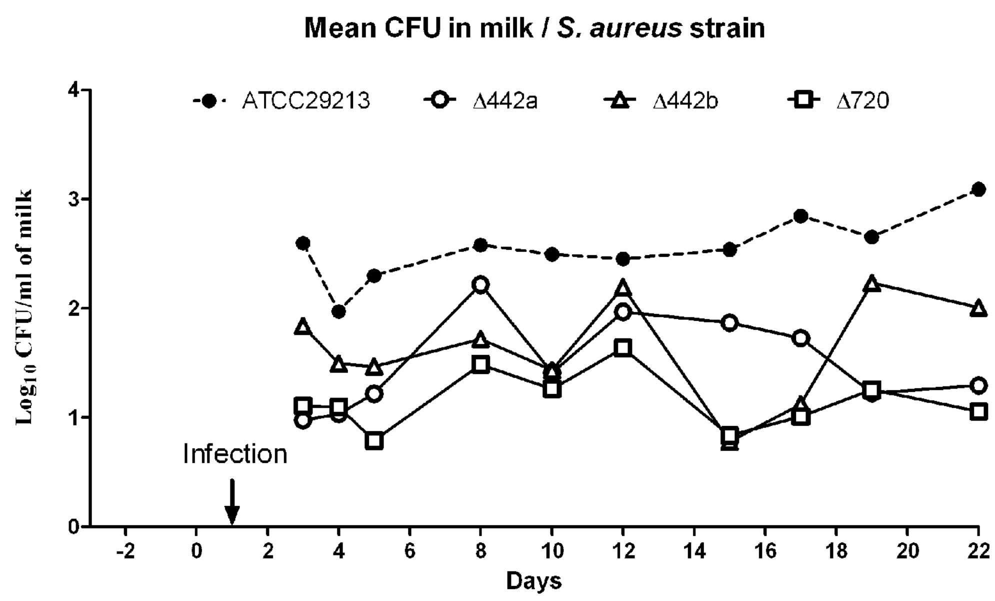
FIG. 10B shows the mean bacterial counts recovered from the milk of eight (8) experimentally infected multiparous Holstein cows in mid lactation as a function of time. Each of the 8 cows was infused intramammary with the four *S. aureus* strains (ATCC 29213 and mutants Δ442a, Δ442b, and Δ720) and the position of each strain in each of the four mammary gland quarters alternated between the animals. The infections were carried out for 21 days. Milk of the infected quarters was collected and the determination of viable bacterial counts was performed. Solid circles and open line represent growth of the parent strain and the open symbols and solid lines the growth of the three mutants as indicated on the graph.

Mutants for genes SACOL0442 and SACOL0720 were produced by gene replacement for mutant Δ442a, (Mitchell et al., 2008) and by intron insertion for mutants Δ442b and Δ720 (TargeTron Gene Knockout System, Sigma Aldrich (Chen et al., 2007)). The mutants were carried out in the *S. aureus* parental strain ATCC 29213 that could be easily transformed by electroporation. For creating mutant Δ442a, a 223-pb fragment of gene SACOL0442 in strain ATCC 29213 was deleted and replaced by insertion of the 1300-bp erythromycin resistance gene ermA between positions 188 and 411 of the nucleotide sequence of SACOL0442. For creating mutants Δ442b and Δ720, the Group II intron (fragment size of approx. 2 Kb) from the TargeTron Gene Knockout System inserted itself into the target chromosomal gene between nucleotide positions 45 and 46 for gene SACOL0442 and between positions 803 and 804 for gene SACOL0720, respectively. Prior to experimental IMI with the mutants, their growth, compared to the parental strain, was evaluated in vitro in freshly collected milk (FIG. 10A). No difference between the growth of the 3 mutants and the parental strain was observed. Eight healthy lactating cows were then inoculated intramammary with 25-250 CFU of the parental strain and of the three mutants and the infection was followed for 21 days. Each of the 8 cows was infused with the four *S. aureus* strains and the position of each strain in the four quarters alternated between the animals. Milk of the infected quarters was collected and the determination of viable bacterial counts was performed. Each of the three mutants showed a significant reduction of bacterial counts in milk compared to the parental strain (FIG. 10B). The virulence of each of the mutants is thus attenuated compared to the parental strain. These results demonstrate the importance of the expression of genes SACOL0442 and SACOL0718-720 for the infection process. Antibodies directed toward their gene products should greatly impair the ability of *S. aureus* to cause bovine IMI (see Examples 8-11). Besides, attenuated bacterial strains have been used as live vaccines (for example, PRIORIX® is a combined measles, mumps and rubella, live, attenuated vaccine; VARILRIX®, is a varicella virus vaccine, live, attenuated (Oka-strain); BCG, is a vaccine for tuberculosis using the attenuated live bacteria *Mycobacterium bovis*) and thus, the use of the mutants described herein (e.g., Δ442a, Δ442b and Δ720 mutants) for immunization of cows is another approach to stimulate immunity and to protect the animal against a future infection by a fully virulent strain. Hence, a mutation/deletion of any of the genes identified here as being expressed by *S. aureus* during bovine IMI may attenuate virulence and such resulting attenuated mutants could be used in a live attenuated vaccine method for immunization.

Example 7

Relatedness of Some *S. aureus* Genes and Proteins

FIG. 11 shows the nucleic acid (FIGS. 11A-11C) and amino acid (FIG. 11D) alignments of vaccine components SACOL0442 and SACOL0720 of all *Staphylococcus aureus* sequenced strains, including the strain RF122 isolated from bovine mastitis. The sequences for SACOL0442 and SACOL0720 show a similarity of about 94 to 100% among the compared strains and are thus considered as highly conserved among these representative *S. aureus* strains. The fact that these genes/proteins could be found in strains isolated from multiple sources strengthens their potential as targets (e.g., vaccine candidates) as it would target most *S. aureus* udder infections (IMI infections).

Similarly, Table VII below shows the percentage of similarity and identity of the amino acid sequences corresponding to some of the *S. aureus* genes expressed in vivo during bovine IMI (Table VI above) for some representatives of the sequenced *S. aureus* genomes. Again, a high degree of similarity and identity was observed (>92.7%), confirming that these genes and encoded proteins represent good target for protection against multiple *S. aureus* strains. There is also about 40% identity and about 60% similarity between the amino acid sequence of SACOL0442 and that of other putative exotoxins such as SACOL0469, SACOL0470, SACOL0472 and SACOL0473 (also known as SA0383 exotoxin 7 [set7], SA0384 exotoxin 8 [set8], SA0385 exotoxin 9 [set9] and SA0389 exotoxin 13 [set13] in strain N315, respectively) (www.jcvi.org). Although these components are not the same genes or proteins, it is possible to find common protein regions, fragments or epitopes for use in vaccines with broader applications and thus aim at the prevention and control of many types of *S. aureus* infections in addition to IMI. Some genetically related bacterial species or genus such as *Staphylococcus epidermidis, Streptococcocus, Listeria* and others may also have homologs of these genes or proteins. Thus it may also be possible to find common protein regions, fragments or epitopes for use in vaccines with broader applications aimed at the prevention and control of many types of bacterial infections. For example, the *S. aureus* gene SACOL1416 shows about 30% sequence homology to *Streptococcus agalactiae* gene SAJ1496 and *Listeria* gene LWE0119 and the *S. aureus* gene SACOL0718 shows about 40-50% sequence homologies to *Streptococcus agalactiae* gene SAJ1013 and *Listeria* gene LWE1764 (www.jcvi.org). Noteworthy, *Streptococcus agalactiae* is also a pathogen involved in IMI and *Listeria* is a pathogen often contaminating milk products (Bradley, 2002; Jayarao et al., 2001).

TABLE VII

Percentage similarity (% sim) and identity (% ide) of the amino acid sequences corresponding to some of the *S. aureus* genes expressed in vivo during bovine IMI (Table IV above) for some representatives of the sequenced *Staphylococcus aureus* genomes (strains N315, RF122, USA300-FPR3757 and MSSA476 compared to the MRSA COL strain).

| Gene | COL | | N315 | | RF122 | | USA300 | | MSSA476 | |
|---|---|---|---|---|---|---|---|---|---|---|
| SACOL | % ide | % sim | % ide | % sim | % ide | % sim | % ide | % sim | % ide | % sim |
| 0442 | 100 | 100 | 99.5 | 99.5 | 94.6 | 98 | 100 | 100 | 95.6 | 98.0 |
| 0718 | 100 | 100 | 99.6 | 100 | 99.6 | 100 | 99.6 | 100 | 99.6 | 100 |
| 0720 | 100 | 100 | 99.4 | 99.7 | 99.4 | 100 | 100 | 100 | 99.4 | 99.7 |
| 2365 | 100 | 100 | 98.5 | 98.5 | 97.1 | 98.1 | 100 | 100 | 99.0 | 99.0 |
| 0029 | 100 | 100 | 100 | 100 | — | — | 100 | 100 | — | — |
| 1416 | 100 | 100 | 99.6 | 100 | 98.2 | 99.6 | 100 | 100 | 100 | 100 |
| 1944 | 100 | 100 | 100 | 100 | 99.6 | 99.6 | 100 | 100 | 100 | 100 |
| 1611 | 100 | 100 | 100 | 100 | 100 | 100 | 100 | 100 | 100 | 100 |
| 2599 | 100 | 100 | 99.8 | 100 | 99.1 | 99.8 | 100 | 100 | 99.8 | 99.8 |
| 2144 | 100 | 100 | 94.6 | 98.5 | 92.7 | 96.2 | 99.6 | 99.6 | 96.2 | 99.2 |
| 1353 | 100 | 100 | 99.6 | 99.6 | — | — | 100 | 100 | 99.6 | 100 |
| 0264 | 100 | 100 | 99.5 | 99.5 | 99.1 | 99.5 | 100 | 100 | 99.1 | 99.1 |

Example 8

Preparation of Vaccines

Bioinformatic software provided sequence and structural information on proteins SACOL0718, SACOL0720 and SALCOL0442 that were useful for preparing such proteins in vaccine compositions (FIG. 14). For example, protein SACOL0442 was determined to be extracellular (secreted bacterial protein). The cellular localization of protein SACOL0718 and its amino acid composition showing 45% of hydrophobic amino acids suggest that it is associated with the bacterial cytoplasmic membrane. Protein SACOL0720 was also predicted to be associated with the bacterial cytoplasmic membrane. Protein SACOL0720 contains 10 transmembrane helices and it was possible to identify a region exposed at the surface of the bacterium.

For vaccine preparation, most of the SACOL0442 protein was used (polypeptide comprising amino acids 44 to 159 in the sequence depicted at FIG. 11D (the full sequence of SACOL0442 is set forth in SEQ ID NO: 37)) and as such, excluded its transport signal (amino acids 1 to 35). The predicted extracellular region of protein SACOL0720 (o-annotated amino acids 309 to 508 in the sequence depicted at FIG. 14D (the full sequence of SACOL0720 is set forth in SEQ ID NO: 62)) was also used in a vaccine composition. In the same way, the extracellular region of the SACOL1781 protein (polypeptide comprising amino acids 41 to 895 of protein IsdH (the full sequence of SACOL1781 is set forth in SEQ ID NO: 76), see also FIG. 18); (www.jcvi.org)) was used as an additional vaccine component.

Example 9

Immunogenicity of Vaccine of the Present Invention in Mice

Figure 15:
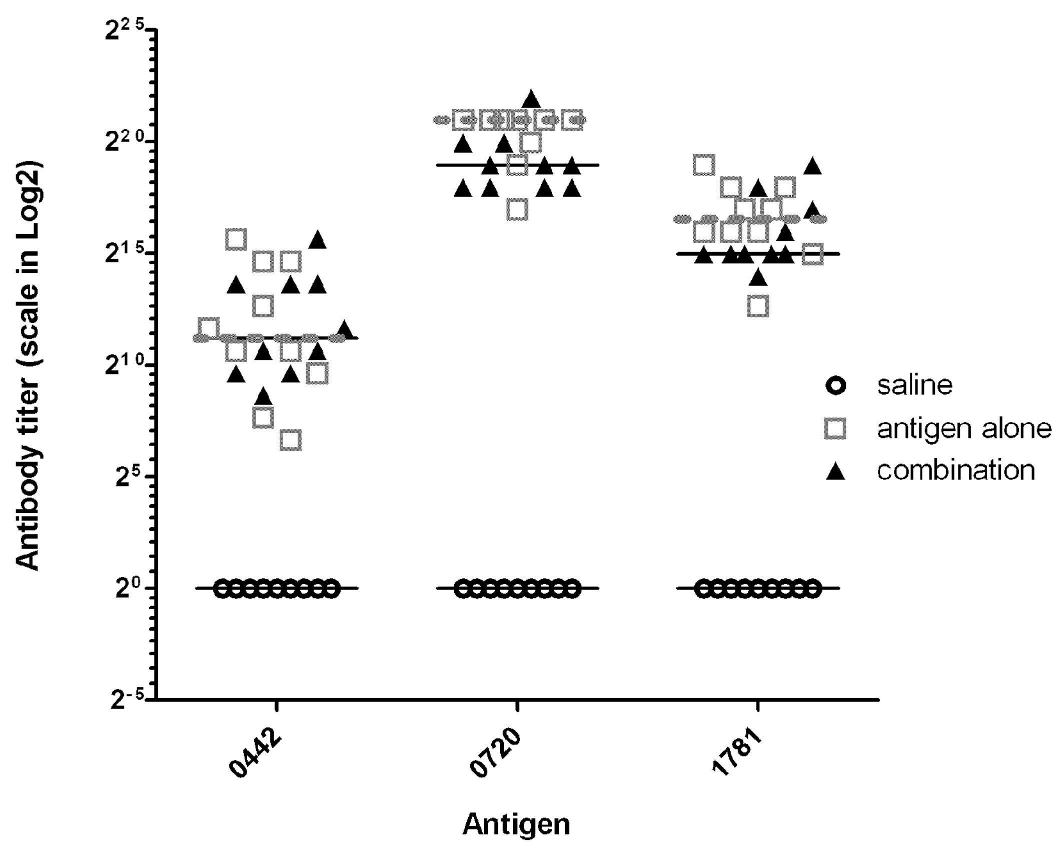
FIG. 15 shows total IgG titers in serums of mice vaccinated with SACOL0442 and SACOL0720. Antibody titers were determined by ELISA. One group of animals (10 mice per group) received two injections of saline, one group received 2 injections of 100 μg of polypeptide SACOL0442, one group received 2 injections of 100 μg of polypeptide SACOL720, one group received 2 injections of 100 μg of polypeptide SACOL1781, and one group received 2 injections of 100 μg of each of all three polypeptides premixed together (SACOL0442, SACOL0720, and SACOL1781). The 2 injections were performed 3 weeks apart. Three weeks after the second immunization, mice were euthanized and blood collected for the determination of total IgG titers by ELISA. Each dot represents the serum titer of one mouse. Horizontal bars are the means for each group (dotted grey lines, antigens injected individually; solid black lines, antigens injected in combination).

Each of the purified polypeptides derived from SACOL0442, SACOL0720 and SACOL1781, independently or all together in combination, were tested for antibody production in mice. Antibody titers in sera of mice vaccinated with SACOL0442, SACOL0720 and SACOL1781 (in the presence of the adjuvant Emulsigen®-D) are shown in FIG. 15. One group of animals (10 animals per group) twice received saline, one received 2 injections of 100 μg of polypeptide SACOL0442, one group received 2 injections of 100 μg of polypeptide SACOL0720, one group received 2 injections of 100 μg of polypeptide SACOL1781, and one group received 2 injections of 100 μg of each three polypeptides SACOL0442, SACOL0720 and SACOL1781 premixed together in a combination. The 2 injections were performed 3 weeks apart, and 3 weeks after the second immunization mice were euthanized and blood collected for the determination of antibody titers by ELISA. Results from FIG. 15 show that the polypeptides used for immunization were indeed immunogenic (i.e., able to stimulate an immune response and antibody production). Results also show that the combination of polypeptides SACOL0442 and SACOL0720 to another antigen such as SACOL1781 did not reduce or alter antibody production compared to that measured when SACOL0442 and SACOL0720 were injected independently. Such a vaccine composition (SACOL0442 and/or SACOL0720 with or without other antigens) is thus a practical useful approach for raising antibodies against multiple antigens of interest. Such a combination vaccine could then provide protection against bovine IMI as well as protection against other diseases that may require other vaccine components for immunization.

Example 10

Immunogenicity of Vaccine of the Present Invention in Cows

Figure 16:
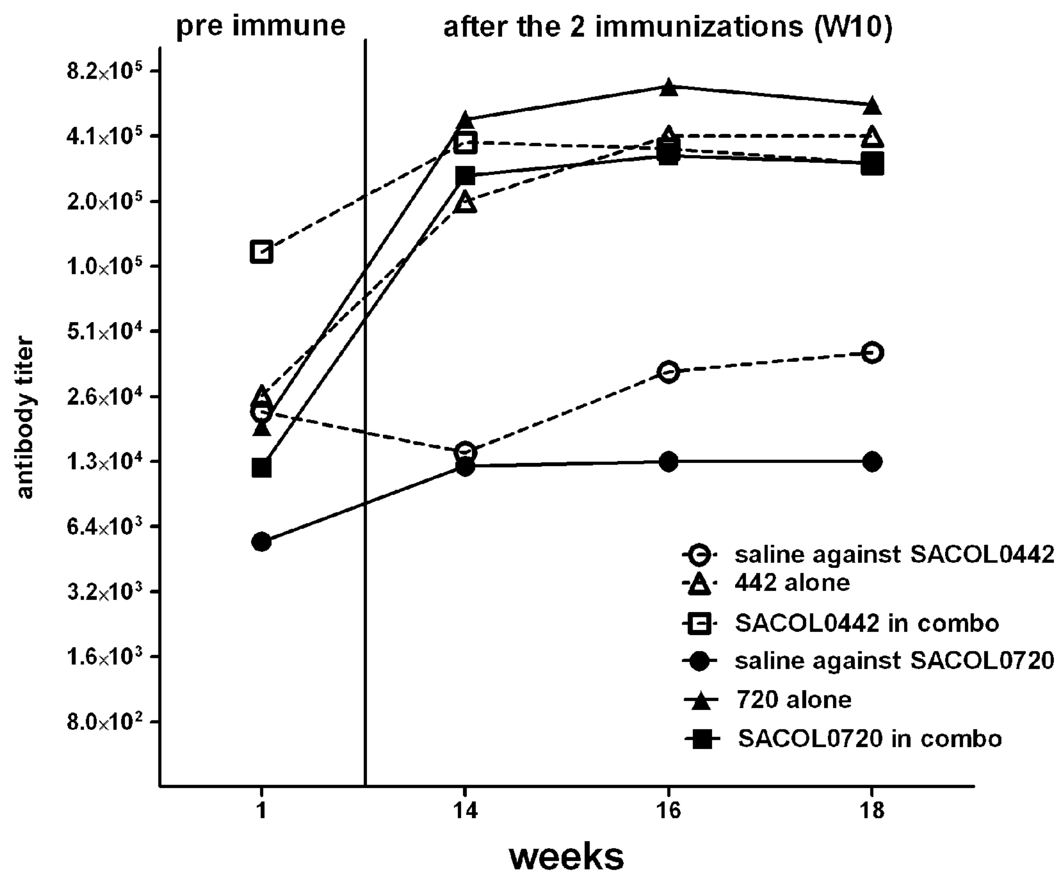
FIG. 16 shows total IgG antibody titers in serums of dairy cows vaccinated with SACOL0442 and SACOL0720. One group of animals (5 cows per group) received two injections of saline, one group received 2 injections of 300 μg of polypeptide SACOL0442, one group received 2 injections of 300 μg of polypeptide SACOL720 and one group received 2 injections of 300 μg of each of the two polypeptides premixed together (SACOL0442, SACOL0720). The 2 injections were performed 10 weeks apart. Blood was collected every two weeks for the determination of the total IgG antibody titers by ELISA. Data represent the mean of each group. Solid lines and solid symbols represent total IgG antibody titer against SACOL0720 and open lines and open symbols present total IgG antibody titers against SACOL0442. Circles (solid for SACOL0720 and open for SACOL0442) represent the antibody titers for the group that received saline. Triangles (solid for SACOL0720 and open for SACOL0442) represent the antibody titers for the two groups that received each one of the two polypeptides. Squares (solid for SACOL0720 and open for SACOL0442) represent the antibody titers for the group that received both polypeptides.
Figure 17A:
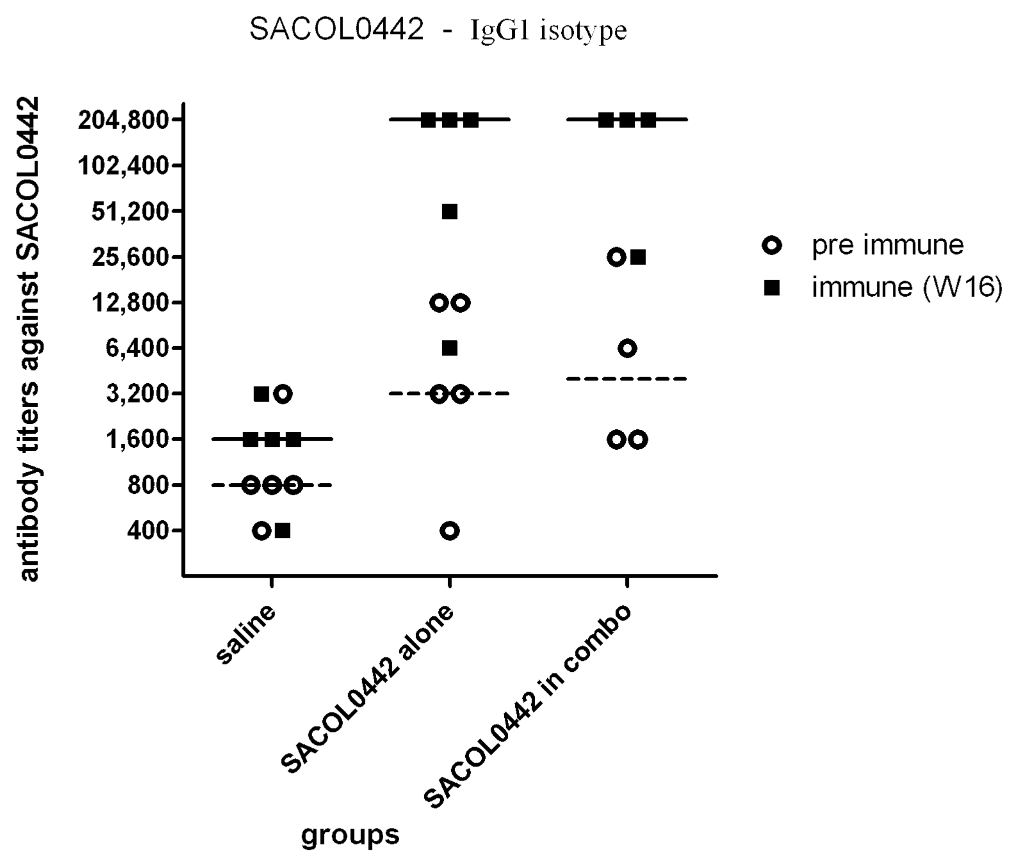
FIGS. 17A and B show IgG1 and IgG2 isotypes titers, respectively against polypeptide SACOL0442, FIGS. 17C and D show IgG1 and IgG2 isotypes titers, respectively against polypeptide SACOL0720. Each dot on the graphs represents the serum titer of one cow (black squares, week 16; open circles, pre-immune titers before immunization). Horizontal bars are the medians for each group (solid lines, immune serums at week 16; open lines, pre-immune serums before immunizations).
Figure 17B:
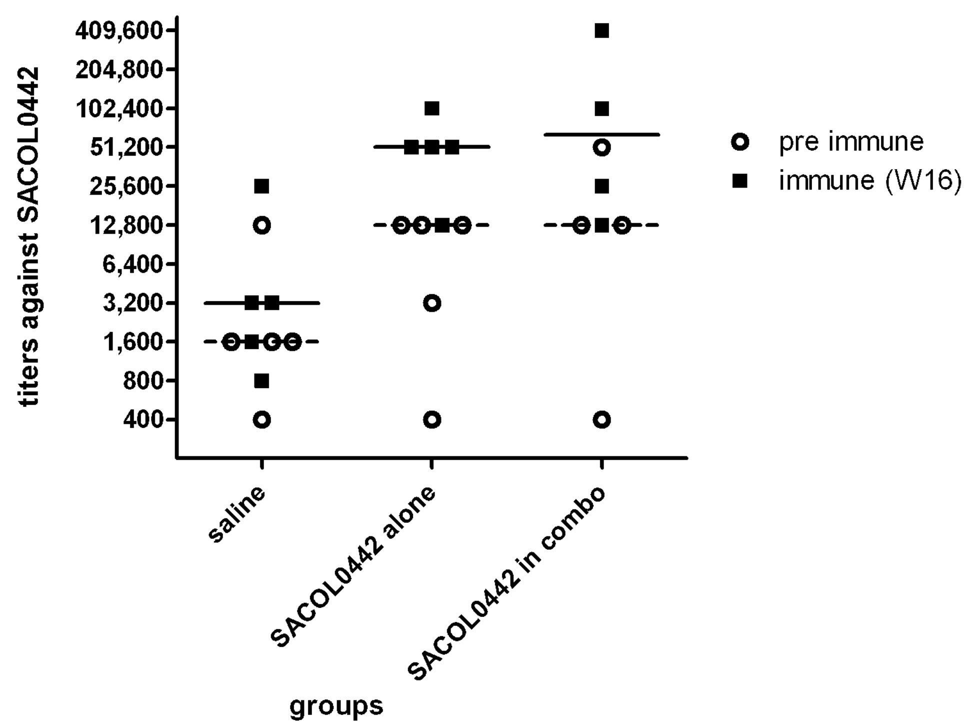
FIG. 17 shows IgG1 and IgG2 antibody titers at week 16, in serums of dairy cows vaccinated with SACOL0442 and SACOL0720 (total IgG titers from the same samples at week 16 were shown in FIG. 16). As described in FIG. 16, one group of animals (5 cows per group) received two injections of saline, one group received 2 injections of 300 μg of polypeptide SACOL0442, one group received 2 injections of 300 μg of polypeptide SACOL720 and one group received 2 injections of 300 μg of each of the two polypeptides premixed together (SACOL0442, SACOL0720). The 2 injections were performed 10 weeks apart. Blood was collected at week 16 for the determination of IgG1 and IgG2 antibody titers by ELISA.
Figure 17C:
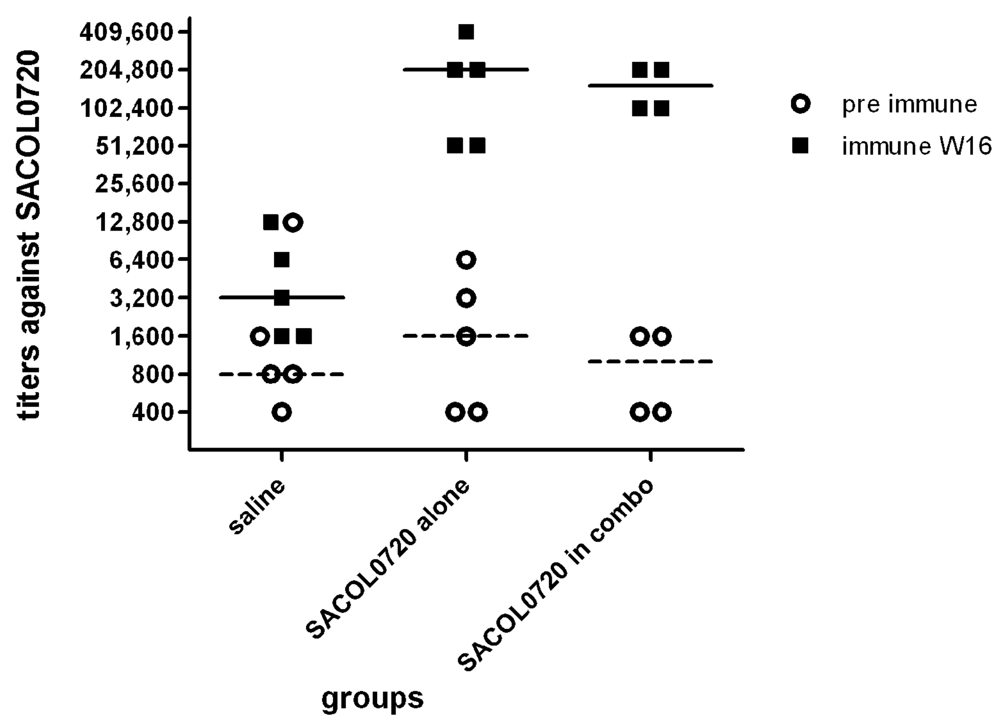
Figure 17D:
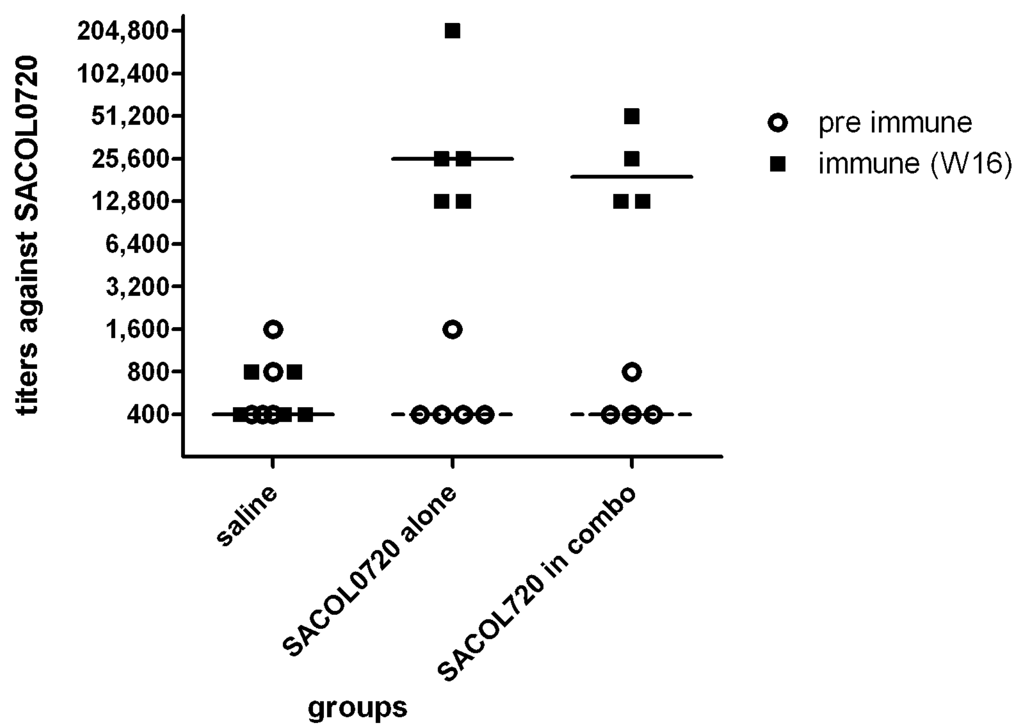

Immunizations were also performed in dairy cows. Antibody titers in sera of cows vaccinated with the polypeptide fragments of SACOL0442, SACOL0720 described in Example 8 (in the presence of the adjuvant Emulsigen®-D) are shown in FIG. 16. One group of animals (5 animals per group) received 2 injections of saline, one group received 2 injections of 300 μg of polypeptide SACOL0442, one group received 2 injections of 300 μg of polypeptide SACOL0720 and one group received 2 injections of 300 μg of each of the two polypeptides SACOL0442 and SACOL0720 premixed together in a combination. The 2 injections were performed 10 weeks apart, and blood was collected for the determination of total IgG antibody titers by ELISA. Results from FIG. 16 show that the polypeptides used for immunization were also highly immunogenic in cows and that combining the antigens for immunization also does not significantly modify the immune response compared to that obtained using individual antigens. The determination of the isotypes is presented in FIG. 17. Immunization of cows leads to the induction of an immune response with the presence of both IgG1 and IgG2. Isotype IgG2 is known to be helpful for opsonization of *S. aureus* and to increase bovine neutrophil functions (Guidry et al., 1993; Barrio et al., 2003). It is known that using different types of adjuvant and/or vaccine administration vehicles or routes can modulate the resulting balance of IgG1 and IgG2 for specific needs (Spickler and Roth, 2003). The capacity of bovine antibodies induced by immunization to bind their target proteins (e.g., SACOL0720) at the bacterial surface was evaluated. Bacteria grown for 8 hours in freshly collected milk were used for this assay as this condition was shown to allow expression of SACOL0718-720 as measured by qPCR (FIG. 8). Evaluation of antibody binding on the bacterial surface was done using flow cytometry as described in "Example 1 materials and methods". It was found that 22.2% more bacteria were bound by labeled antibodies in the presence of the bovine immune serum raised against SACOL0720 in comparison to the labeling obtained in presence of the control pre-immune serum. This demonstrates that bovine antibodies induced against SACOL0720 are able to bind to the protein at the surface of the bacteria. Such antibody binding (opsonization) is known to help neutrophils phagocytic and killing activity (Guidry et al., 1993; Barrio et al., 2003).

Example 11

Epitopes of Interest

As an alternative of using the entire proteins or a long region of the polypeptides of interest for vaccination, it is also possible to specifically used small peptide regions predicted to be recognized by the B or T cells from the mammalian immune system. Identification of the B cell epitopes (that is to say short amino acid sequences that will be recognized by the immune system and able to induce the production of antibodies by the B cells) among some of the proteins of interest such as SACOL0442 and SACOL0720 are shown in Table VIII below. For each protein, the predicted B cell epitopes are presented with their position in the protein sequence. The score was obtained from 4 distinct programs: BCPred Predictions, AAP Predictions, FBCPred Predictions and ABCPred.

Similarly, computer driven algorithms can also be used to facilitate the identification of T cell epitopes (that is to say short amino acid sequences that will be recognized by the immune system and able to induce a cellular response by T cells) for use as vaccines against *Staphylococcus aureus* infection. The proteins of interest can be subjected to analysis by the Epimatrix™ system to identify putative T cell epitopes. This in-silico technique divides the total sequence of the antigen into fragments of 9 amino acids overlapping by 8 amino acids. This pool of 9-mer is screened for predicted affinity against a group of known MHC class I and class II alleles. The resulting scores can be used to rate putative epitopes on a common scale which can then be tested in vitro. The technique is applicable to any animal for which a sufficient knowledge of MHC sequences is available. (De Groot et al., 2008)

The B or T cell epitopes can therefore be used in vaccine compositions alone or in combination with an assemblage of proteins, peptides or other epitopes. In addition, any B or T cell epitopes as well as any other epitopes can be presented in a contiguous sequence (such as in a protein fusion approach) by using genetic and protein engineering methods.

TABLE VIII

Identification of B cell epitopes among some of the proteins of interest. (A) SACOL0442 and (B) SACOL0720. For each protein, the predicted B cell epitopes are presented with their position in the protein sequence and the prediction score they obtained using 4 distinct softwares: BCPred Predictions, AAP Predictions, FBCPred Predictions and ABCPred.

| Potential B cell epitope | Position into the sequence | score |
|---|---|---|
| (A) SACOL0442 | | |
| TFGIYPKADASTQN (SEQ ID NO: 17) | 26 | 0.840 |
| KDTINGKSNKSRNW (SEQ ID NO: 18) | 72 | 0.848 |
| KDGGKYTLESHKELQ (SEQ ID NO: 19) | 159 | 1.000 |
| (B) SACOL0720 | | |
| QFGFDLKHKKDALA (SEQ ID NO: 20) | 468 | 0.981 |
| TIKDQQKANQLAS (SEQ ID NO: 21) | 325 | 0.898 |
| KDINKIYFMTDVDL (SEQ ID NO: 22) | 428 | 0.890 |
| DVDLGGPTFVLND (SEQ ID NO: 23) | 436 | 0.993 |

Example 12

Use of *S. aureus* Genes Expressed During IMI as Diagnostic Tools

The diagnosis of *S. aureus* IMI is difficult and requires time. Traditionally, milk samples are taken and shipped to a microbiology laboratory where cultivation of *S. aureus* is achieved using various artificial growth media. Following growth and if growth occur (usually 24 h after sample arrival), the microorganism need to be identified as *S. aureus* among other possible pathogens by a variety of biochemical tests which could take up an additional 24 h. For milk producers, this delay represents a serious economic loss as cows suspected to have acquired an IMI need to be removed from the milk production herd while cows not tested for *S. aureus* but that have subclinical IMI may continue to contaminate the bulk milk tank. It would thus be highly desirable to develop a novel tool for rapid detection of *S. aureus* in milk to permit a rapid intervention by milk producers or veterinarians.

As an alternative of using traditional microbial cultures to identify *S. aureus* in milk samples of cows with or without clinical signs of IMI and mastitis, the products of the *S. aureus* genes identified as expressed during IMI (either the messenger RNA, the protein or the metabolic product subsequent to the protein activity) may be used as diagnostic tools. Indeed, the detection of such specific products, for example in milk, blood or biopsies, would indicate the presence of *S. aureus*. Since such products are strongly expressed during IMI, their detection would also strongly correlate with this specific type of infection.

For example, detection of the putative exotoxin SACOL0442 that is secreted in the extracellular milieu, i.e., in milk during mastitis, would be a strong indication that the cow is infected by *S. aureus* since the gene is only expressed during IMI. The detection of the putative exotoxin SACOL0442 can be easily achieved by the use of a specific antibody and an ELISA technique or a dip stick approach or the like and the signal of detection can be easily amplified by a variety of signal amplification techniques. Such techniques could rapidly be performed by the microbiology laboratory or even on-farm by the milk producer himself, hence gaining valuable time. Alternatively, detection of messenger RNA (mRNA) from the genes expressed during IMI would also indicate the presence of *S. aureus* in milk. Detection of mRNA is possible after its release from bacteria by a cell lysis step, copying mRNA into complementary DNA by reverse transcription and by PCR amplification.

REFERENCES

Allard, M., H. Moisan, E. Brouillette, A. L. Gervais, M. Jacques, P. Lacasse, M. S. Diarra, and F. Malouin. 2006. Transcriptional modulation of some *Staphylococcus aureus* iron-regulated genes during growth in vitro and in a tissue cage model in vivo. Microbes Infect. 7:1679-1690.

Allard, M., C. Ster, L. St-James, P. Lacasse, M. S. Diarra, C. L. Jacob, and F. Malouin. 2008. Transcriptional Analysis of In Vivo-Expressed Genes in *Staphylococcus aureus* During Bovine Mastitis. American Society for Microbiology General Meeting. Boston, USA. Jun. 1-5, 2008 (Poster)

Atalla, H., C. Gyles, C. L. Jacob, H. Moisan, F. Malouin, and B. Mallard. 2008. Characterization of a *Staphylococcus aureus* small colony variant (SCV) associated with persistent bovine mastitis. Foodborne Pathog 5:785-799.

Barkema, H. W., Y. H. Schukken, and R. N. Zadoks. 2006. Invited Review: The role of cow, pathogen, and treatment regimen in the therapeutic success of bovine *Staphylococcus aureus* mastitis. J Dairy Sci. 89:1877-1895.

Bradley, A. 2002. Bovine mastitis: an evolving disease. Vet J. 164:116-128.

Barrio, M. B., P. Rainard, F. B. Gilbert, B. Poutrel. 2003. Assessment of the opsonic activity of purified bovine sIgA following intramammary immunization of cows with *Staphylococcus aureus. J. Dairy Sci.* 86:2884-2894.

Brouillette, E., M. Hyodo, Y. Hayakawa, D. K. Karaolis, and F. Malouin. 2005. 3',5'-cyclic diguanylic acid reduces the virulence of biofilm-forming *Staphylococcus aureus* strains in a mouse model of mastitis infection. Antimicrob. Agents Chemother. 49:3109-3113.

Burlak, C., C. H. Hammer, M. A. Robinson, A. R. Whitney, M. J. McGavin, B. N. Kreiswirth, and F. R. Deleo. 2007. Global analysis of community-associated methicillin-resistant *Staphylococcus aureus* exoproteins reveals molecules produced in vitro and during infection. Cell Microbiol. 9:1172-1190

Chang, B. S., J. S. Moon, H. M. Kang, Y. I. Kim, H. K. Lee, J. D. Kim, B. S. Lee, H. C. Koo, Y. H. Park. 2008. Protective effects of recombinant staphylococcal enterotoxin type C mutant vaccine against experimental bovine infection by a strain of *Staphylococcus aureus* isolated from subclinical mastitis in dairy cattle. Vaccine. 26:2081-2091.

Chen J., H Liu., J. Yang, K. Chou. 2007. Prediction of linear B-cell epitopes using amino acid pair antigenicity scale. Amino Acids 33: 423-428

Chen Y., L. Caruso, B. McClane, D. Fisher, P. Gupta. 2007. Disruption of a toxin by introduction of a foreign gene into the chromosome of *Clostridium perfringens* using targetron induced mutagenesis. Plasmid. 58:182-189.

De Groot, A. S., J. McMurry, and L. Moise. 2008. Prediction of immunogenicity: in silico paradigms, ex vivo and in vivo correlates. Curr Opinion in Pharmacol. 8:620-626.

Dehal P S, Joachimiak M P, Price M N, Bates J T, Baumohl J K, Chivian D, Friedland G D, Huang K H, Keller K, Novichkov P S, Dubchak I L, Alm E J, Arkin A P. MicrobesOnline: an integrated portal for comparative and functional genomics. Nucleic Acids Res. 2010 January; 38(Database issue): D396-400. Epub 2009 Nov. 11.

Diarra, M. S., D. Petitclerc, and P. Lacasse. 2002. Response of *Staphylococcus aureus* isolates from bovine mastitis to exogenous iron sources. J. Dairy Sci. 85:2141-2148.

EL-Manzalawy Y, Dobbs D, Honavar V. 2008a. Predicting linear B-cell epitopes using string kernels. J Mol Recognit 21: 243-255.

EL-Manzalawy Y, Dobbs D, Honavar V. 2008b. Predicting flexible length linear B-cell epitopes. Th International Conference on Computational Systems Bioinformatics, Stanford, Calif. pp. 121-131

Eng, N. F., S. Garlapati, V. Gerdts, A. Potter, L. A. Babiuk, and G. K. Mutwiri. 2010. The Potential of Polyphosphazenes for Delivery of Vaccine Antigens and Immunotherapeutic Agents. Curr Drug Deliv. 7(1):13-30.

Gardy, J. L., M. R. Laird, F. Chen, S. Rey, C. J. Walsh, M. Ester and F. S. L. Brinkman. 2005. PSORTb v.2.0: Expanded prediction of bacterial protein subcellular localization and insights gained from comparative proteome analysis. Bioinformatics 21(5):617-623; doi:10.1093/bioinformatics/bti057

Garzoni, C., P. Francois, A. Huyghe, S. Couzinet, C. Tapparel, Y. Charbonnier, A. Renzoni, S. Lucchini, D. P. Lew, P. Vaudaux, W, L. Kelley, and J. Schrenzel. 2007. A global view of *Staphylococcus aureus* whole genome expression upon internalization in human epithelial cells. BMC Genomics. 8:171.

Gasteiger E., Hoogland C., Gattiker A., Duvaud S., Wilkins M. R., Appel R. D., Bairoch A. Protein Identification and Analysis Tools on the ExPASy Server; (In) John M. Walker (ed): The Proteomics Protocols Handbook, Humana Press (2005), pp. 571-607

Goerke, C., S. Campana, M. G. Bayer, G. Döring, K. Botzenhart, and C. Wolz. 2000. Direct quantitative transcript analysis of the agr regulon of *Staphylococcus aureus* during human infection in comparison to the expression profile in vitro. Infect Immun. 68:1304-1311.

Guidry, A. J., L. M. Berning, C. N. Hambleton. 1993. Opsonization of *Staphylococcus aureus* by bovine immunoglobulin isotypes. *J. of Dairy Sci.* 76:1285-1289.

Haveri, M., A. Roslöf, L. Rantala, and S. Pyörälä. 2007. Virulence genes of bovine *Staphylococcus aureus* from persistent and nonpersistent intramammary infections with different clinical characteristics. J Appl Microbiol. 103: 993-1000.

Hogarth, C. J., J. L. Fitzpatrick, A. M. Nolan, F. J. Young, A. Pitt, and P. D. Eckersall. 2004. Differential protein composition of bovine whey: a comparison of whey from healthy animals and from those with clinical mastitis. Proteomics. 4:2094-2100.

Jayarao, B. M., D. R. Henning. 2001. Prevalence of foodborne pathogens in bulk tank milk. J Dairy Sci. 84:2157-2162.

Karaolis, D. K., T. K. Means, D. Yang, M. Takahashi, T. Yoshimura, E. Muraille, D. Philpott, J. T. Schroeder, M. Hyodo, Y. Hayakawa, B. G. Talbot, E. Brouillette, and F.

Malouin. 2007. Bacterial c-di-GMP is an immunostimulatory molecule. J. Immunol. 178:2171-2181.

Kasturi, S. P. et al. 2011. Programming the magnitude and persistence of antibody responses with innate immunity. Nature 470:543-547.

Lammers, A., E. Kruijt, K. C. van de, P. J. Nuijten, and H. E. Smith. 2000. Identification of *Staphylococcus aureus* genes expressed during growth in milk: a useful model for selection of genes important in bovine mastitis? Microbiology. 146:981-987.

Larkin M. A., Blackshields G., Brown N. P., Chenna R., McGettigan P. A., McWilliam H.*, Valentin F.*, Wallace I. M., Wilm A., Lopez R., Thompson J. D., Gibson T. J. and Higgins D. G. 2007. ClustalW and ClustalX version 2. Bioinformatics 2007 23(21): 2947-2948.

Linghua, Z., T. Xingshan, Z. Fengzhen. 2006. The efficacy of CpG oligodinucleotides, in combination with conventional adjuvants, as immunological adjuvants to swine streptococcic septicemia vaccine in piglets in vivo. Int Immunopharmacol. 6:1267-76.

Loiselle, M. C., C. Ster, B. G. Talbot, X. Zhao, G. F. Wagner, Y. R. Boisclair, and P. Lacasse. 2009. Impact of postpartum milking frequency on the immune system and the blood metabolite concentration of dairy cows. J Dairy Sci. 92:1900-1912.

Lowe, A. M., D. T. Beattie, and R. L. Deresiewicz. 1998. Identification of novel staphylococcal virulence genes by in vivo expression technology. Mol. Microbiol. 27:967-976.

Maresso, A. W., and O. Schneewind. 2006. Iron acquisition and transport in *Staphylococcus aureus*. Biometals. 19:193-203.

Mayer, S. J., A. E. Waterman, P. M. Keen, N. Craven, and F. J. Bourne. 1988. Oxygen concentration in milk of healthy and mastitic cows and implications of low oxygen tension for the killing of *Staphylococcus aureus* by bovine neutrophils. J Dairy Res 55:513-519.

Melchior, M. B., M. H. vanOsch, R. M. Graat, E. van Duijkeren, D. J. Mevius, N. Nielen, W. Gaastra, J. Fink-Gremmels. 2009. Biofilm formation and genotyping of *Staphylococcus aureus* bovine mastitis isolates: evidence for lack of penicillin-resistance in Agr-type II strains. Vet. Microbiol. 137:83-89.

Middleton, J. R. 2008. *Staphylococcus aureus* antigens and challenges in vaccine development. Expert Rev Vaccines. 7:805-815.

Moisan, H., E. Brouillette, C. L. Jacob, P. Langlois-Bégin, S. Michaud, and F. Malouin. 2006. Transcription of virulence factors in *Staphylococcus aureus* small-colony variants isolated from cystic fibrosis patients is influenced by SigB. J. Bacteriol. 188:64-76.

Mitchell, G., C. A. Lamontagne, E. Brouillette, G. Grondin, B. G. Talbot, M. Grandbois, F. Malouin. 2008. *Staphylococcus aureus* SigB activity promotes a strong fibronectin-bacterium interaction which may sustain host tissue colonization by small-colony variants isolated from cystic fibrosis patients. Mol Microbiol 70:1540-1555.

Myllys, V., J. Ridell, J. Bjorkroth, I. Biese, and S. Pyorala. 1997. Persistence in bovine mastitis of *Staphylococcus aureus* clones as assessed by random amplified polymorphic DNA analysis, ribotyping and biotyping. Vet Microbiol. 57:245-251.

National Mastitis Council. 1996. Current Concept of Bovine Mastitis. 4 ed. National Mastitis Council, Madison, Wis.

Nickerson, S. C., W. E. Owens, L. K. Fox, C. C. Scheifinger, T. R. Shryock, and T. E. Spike. 1999. Comparison of tilmicosin and cephapirin as therapeutics for *Staphylococcus aureus* mastitis at dry-off. J Dairy Sci. 82:696-703.

Owens, W. E., C. H. Ray, J. L. Watts, and R. J. Yancey. 1997. Comparison of success of antibiotic therapy during lactation and results of antimicrobial susceptibility tests for bovine mastitis. J Dairy Sci. 80:313-317.

Park, Y. K., H. C. Koo, S. H. Kim, S. Y. Hwang, W. K. Jung, J. Kim, S. Shin, R. Kim, and Y. Park. 2007. The analysis of milk components and pathogenic bacteria isolated from bovine raw milk in Korea. J Dairy Sci. 90:5405-5414.

Peles, F., M. Wagner, L. Varga, I. Hein, P. Rieck, K. Gutser, P. Keresztúri, G. Kardos, I. Turcsányi, B. Béri, and A. Szabó. 2007. Characterization of *Staphylococcus aureus* strains isolated from bovine milk in Hungary. Int J Food Microbiol. 118:186-93.

Peterson, J. D., Umayam, L. A., Dickinson, T., Hickey, E. K., White, O. 2001. The Comprehensive Microbial Resource. Nucleic Acids Res. 29(1): 123-5.

Petitclerc, D., K. Lauzon, A. Cochu, C. Ster, M. S. Diarra, and P. Lacasse. 2007. Efficacy of a lactoferrin-penicillin combination to treat {beta}-lactam-resistant *Staphylococcus aureus* mastitis. J Dairy Sci. 90:2778-2787.

Pragman, A. A., and P. M. Schlievert. 2004. Virulence regulation in *Staphylococcus aureus*: the need for in vivo analysis of virulence factor regulation. FEMS Immunol Med. Microbiol. 42:147-154.

Saha. S and Raghava G. P. S. BcePred: Prediction of Continuous B-Cell Epitopes in Antigenic Sequences Using Physico-chemical Properties. In G. Nicosia, V. Cutello, P. J. Bentley and J. Timis (Eds.) ICARIS 2004, LNCS 3239, 197-204, Springer, 2004.

Saha, S and Raghava G. P. S., (2006) Prediction of Continuous B-cell Epitopes in an Antigen Using Recurrent Neural Network. Proteins, 65(1), 40-48.

Sandholm, M., L. Kaartinen, and S. Pyorala. 1990. Bovine mastitis—why does antibiotic therapy not always work? An overview. J Vet Phamacol Therap. 13:248-260.

Schaffer, A. C., and J. C. Lee. 2009. Staphylococcal vaccines and immunotherapies. Infect Dis Clin North Am. 23:153-171.

Sears, P. M. and McCarthy, K. K. 2003. Management and treatment of staphylococcal mastitis. Vet Clin North Am Food Anim Pract 19:171-185.

Sibbald, M. J., A. K. Ziebandt, S. Engelmann, M. Hecker, A. de Jong, H. J. Harmsen, G. C. Raangs, I. Stokroos, J. P. Arends, J. Y. Dubois, and J. M. van Dijl. 2006. Mapping the pathways to staphylococcal pathogenesis by comparative secretomics. Microbiol. Mol Biol Rev. 70:755-788.

Silanikove, N., F. Shapiro, and G. Leitner. 2007. Posttranslational ruling of xanthine oxidase activity in bovine milk by its substrates. Biochem Biophys Res Commun. 363:561-565.

Somerville, G. A., and R. A. Proctor. 2009. At the crossroads of bacterial metabolism and virulence factor synthesis in Staphylococci. Microbiol. Mol Biol Rev. 73:233-248.

Sprickler A. R. and J. A. Roth. Adjuvants in veterinary vaccines: mode of action and adverse effects. 2003. 17:273-281.

Srinivasan, V., A. A. Sawant, B. E. Gillespie, S. J. Headrick, L. Ceasaris, and S. P. Oliver. 2006. Prevalence of enterotoxin and toxic shock syndrome toxin genes in *Staphylococcus aureus* isolated from milk of cows with mastitis. Foodborne Pathog Dis. 3:274-83.

Srivastava S, Singh V, Kumar V, Verma P C, Srivastava R, Basu V, Gupta V, Rawat A K. Identification of regulatory elements in 16S rRNA gene of *Acinetobacter* species isolated from water sample. Bioinformation. 2008; 3(4):173-6. Epub 2008 Dec. 6.

Taverna, F., A. Negri, R. Piccinini, A. Zecconi, S, Nonnis, S. Ronchi, and G. Tedeschi. 2007. Characterization of cell wall associated proteins of a *Staphylococcus aureus* isolated from bovine mastitis case by a proteomic approach. Vet Microbiol. 119:240-247

Tollersrud, T., A. H. Kampen, and K. Kenny. 2006. *Staphylococcus aureus* enterotoxin D is secreted in milk and stimulates specific antibody responses in cows in the course of experimental intramammary infection. Infect Immun. 74:3507-3512.

Tuchscherr, L. P., F. R. Buzzola, L. P. Alvarez, J. C. Lee, and D. O, Sordelli. 2008. Antibodies to capsular polysaccharide and clumping factor A prevent mastitis and the emergence of unencapsulated and small-colony variants of *Staphylococcus aureus* in mice. Infect Immun. 76:5738-5744.

Tusnády, G. E. and Simon, I. 2001. The HMMTOP transmembrane topology prediction server" *Bioinformatics* 17, 849-850

Voyich, J. M., K. R. Braughton, D. E. Sturdevant, A. R. Whitney, B. Saïd-Salim, S. F. Porcella, R. D. Long, D. W. Dorward, D. J. Gardner, B. N. Kreiswirth, J. M. Musser, and F. R. DeLeo. 2005. Insights into mechanisms used by *Staphylococcus aureus* to avoid destruction by human neutrophils. J. Immunol. 175:3907-3919.

WO/2003/091279

WO/2004/043405

WO/2008/152447

WO/2005/007683

WO/2006/059846

Ziebandt, A. K., H. Kusch, M. Degner, S. Jaglitz, M. J. Sibbald, J. P. Arends, M. A. Chlebowicz, D. Albrecht, R. Pantucek, J. Doškar, W. Ziebuhr, B. M. Bröker, M. Hecker, J. M. van Dijl, and S. Engelmann. 2010. Proteomics uncovers extreme heterogeneity in the *Staphylococcus aureus* exoproteome due to genomic plasticity and variant gene regulation. Proteomics 285(47)36794-36803.

The invention claimed is:

1. A method of immunizing a mammal against a Staphylococcal intramammary infection (IMI), said method comprising administering to said mammal an effective amount of a composition comprising an emulsified oil and a polypeptide which is:

(a) a polypeptide comprising the amino acid sequence of SEQ ID NO: 78; and/or (b) a polypeptide comprising an amino acid sequence at least 95% identical overall to SEQ ID NO: 78.

2. The method of claim 1, wherein said Staphylococcal intramammary infection is caused by one or more *Staphylococcus aureus* strains.

3. The method of claim 1, further comprising administering to said mammal an effective amount of an adjuvant.

4. The method of claim 3, wherein said adjuvant is alum, cyclic-diguanosine-5'-monophosphate (c-di-GMP), polyphosphasine or pathogen-associated molecular patterns (PAMPS).

5. The method of claim 4, wherein said PAMPS is unmethylated dinucleotides (CpG) or microbial polysaccharides.

6. The method of claim 3, wherein said (i) polypeptide, (ii) adjuvant, or both (i) and (ii) are comprised in said composition.

7. The method of claim 6, wherein said composition is a pharmaceutical composition comprising further one or more pharmaceutically acceptable excipients.

8. The method of claim 1, wherein said mammal is a cow.

9. The method of claim 8, wherein said IMI is associated with bovine mastitis.

10. The method of claim 1, wherein said method further comprises administering to said mammal an effective amount of at least one additional polypeptide, wherein said at least one additional polypeptide is:

(a) a polypeptide comprising the amino acid sequence of SEQ ID NO: 80, SEQ ID NO: 37, SEQ ID NO: 48, SEQ ID NO: 83, SEQ ID NO: 62, SEQ ID NO: 74, SEQ ID NO: 86, SEQ ID NO: 88, SEQ ID NO: 90, SEQ ID NO: 92, SEQ ID NO: 94, SEQ ID NO: 96 and/or SEQ ID NO: 98; and/or (b) a polypeptide comprising an amino acid sequence at least 95% identical overall to the amino acid sequence of SEQ ID NO: 80, SEQ ID NO: 37, SEQ ID NO: 48. SEQ ID NO: 83, SEQ ID NO: 62, SEQ ID NO: 74, SEQ ID NO: 86. SEQ ID NO: 88, SEQ ID NO: 90, SEQ ID NO: 92, SEQ ID NO: 94, SEQ ID NO: 96 and/or SEQ ID NO: 98.

11. The method of claim 10, wherein said at least one additional polypeptide is:

(a) a polypeptide comprising the amino acid sequence of SEQ ID NO: 37;

(b) a polypeptide comprising the amino acid sequence of SEQ ID NO: 62; and/or (c) a polypeptide comprising an amino acid sequence at least 95% identical overall to the amino acid sequence of SEQ ID NO: 37 or SEQ ID NO: 62.

12. The method of claim 1, wherein said method further comprises administering to said mammal an effective amount of at least one additional agent, wherein said at least one additional agent is a polypeptide comprising the amino acid sequence of any one of SEQ ID NOs: 17, 18 and 20-23.

13. The method of claim 8, wherein said Staphylococcal intramammary infection is caused by one or more *Staphylococcus aureus* strains.

14. The method of claim 8, further comprising administering to said mammal an effective amount of an adjuvant.

15. The method of claim 8, wherein said adjuvant is alum, cyclic-diguanosine-5'-monophosphate (c-di-GMP), polyphosphasine or pathogen-associated molecular patterns (PAMPS).

16. The method of claim 4, wherein said PAMPS is unmethylated dinucleotides (CpG) or microbial polysaccharides.

17. The method of claim 8, wherein said method further comprises administering to said mammal an effective amount of at least one additional polypeptide, wherein said at least one additional polypeptide is:

(a) a polypeptide comprising the amino acid sequence of SEQ ID NO: 80, SEQ ID NO: 37, SEQ ID NO: 48, SEQ ID NO: 83, SEQ ID NO: 62, SEQ ID NO: 74, SEQ ID NO: 86, SEQ ID NO: 88, SEQ ID NO: 90, SEQ ID NO: 92, SEQ ID NO: 94, SEQ ID NO: 96 and/or SEQ ID NO: 98; and/or (b) a polypeptide comprising an amino acid sequence at least 95% identical overall to the amino acid sequence of SEQ ID NO: 80, SEQ ID NO: 37, SEQ ID NO: 48, SEQ ID NO: 83, SEQ ID NO: 62, SEQ ID NO: 74, SEQ ID NO: 86, SEQ ID NO: 88, SEQ ID NO: 90, SEQ ID NO: 92, SEQ ID NO: 94, SEQ ID NO: 96 and/or SEQ ID NO: 98.

18. The method of claim 17, wherein said at least one additional polypeptide is:

(a) a polypeptide comprising the amino acid sequence of SEQ ID NO: 37;

(b) a polypeptide comprising the amino acid sequence of SEQ ID NO: 62; and/or (c) a polypeptide comprising an amino acid sequence at least 95% identical overall to the amino acid sequence of SEQ ID NO: 37 or SEQ ID NO: 62.

19. The method of claim 8, wherein said method further comprises administering to said mammal an effective amount of at least one additional polypeptide, wherein said at least one additional polypeptide is a polypeptide comprising the amino acid sequence of any one of SEQ ID NOs: 17, 18 and 20-23.

* * * * *